US012201427B2

(12) United States Patent
Connor

(10) Patent No.: US 12,201,427 B2
(45) Date of Patent: Jan. 21, 2025

(54) HEADBAND WITH BRAIN ACTIVITY SENSORS

(71) Applicant: Robert A. Connor, Wyoming, MN (US)

(72) Inventor: Robert A. Connor, Wyoming, MN (US)

(73) Assignee: Medibotics LLC, Ham Lake, MN (US)

( * ) Notice: Subject to any disclaimer, the term of this patent is extended or adjusted under 35 U.S.C. 154(b) by 0 days.

(21) Appl. No.: 18/748,059

(22) Filed: Jun. 19, 2024

(65) Prior Publication Data

US 2024/0341652 A1 Oct. 17, 2024

Related U.S. Application Data

(63) Continuation-in-part of application No. 18/411,540, filed on Jan. 12, 2024, which is a continuation-in-part of application No. 18/219,684, filed on Jul. 9, 2023, which is a continuation-in-part of application No. 17/714,988, filed on Apr. 6, 2022, now Pat. No. 11,850,052, which is a continuation-in-part of application No. 17/665,086, filed on Feb. 4, 2022, now Pat. No. 11,662,819, and a continuation-in-part of application No. 17/136,117, filed on Dec. 29, 2020, now abandoned, said application No. 17/665,086 is a continuation-in-part of application No. 17/136,117, filed on Dec. 29, 2020, now abandoned, which is a continuation-in-part of application No. 16/838,541,
(Continued)

(51) Int. Cl.
    A61B 5/256 (2021.01)
    A61B 5/245 (2021.01)
    A61B 5/369 (2021.01)

(52) U.S. Cl.
    CPC ............. *A61B 5/256* (2021.01); *A61B 5/245* (2021.01); *A61B 5/369* (2021.01)

(58) Field of Classification Search
    CPC ......... A61B 5/256; A61B 5/245; A61B 5/369; A61B 5/291; A61B 5/6803; A61B 5/0006; G06F 3/015; G02C 3/003
    See application file for complete search history.

(56) References Cited

U.S. PATENT DOCUMENTS 4,941,477 A * 7/1990 Farwell ................. A61B 5/377
                                                       600/544
D565,735 S * 4/2008 Washbon ..................... D24/187
(Continued)

OTHER PUBLICATIONS (Acar, 2019), "Wearable and Flexible Textile Electrodes for Biopotential Signal Monitoring: A Review," Electronics, 2019, 8(5), 479.
(Continued)

*Primary Examiner* — Jacqueline Cheng
*Assistant Examiner* — Tho Q Tran

(57) ABSTRACT

This invention is a head-worn device (e.g. headband, halo, or headset) with sensors (e.g. electrodes) which record brain activity. In an example, the device can be undulating with concave undulations which rest on the tops of a person's ears. In an example, the device can further comprise right side and left side ear prongs (e.g. arms, segments, or portions) which curve around the posterior and upper surfaces of a person's right and left ears.

1 Claim, 35 Drawing Sheets

Related U.S. Application Data filed on Apr. 2, 2020, now abandoned, said application No. 18/219,684 is a continuation-in-part of application No. 16/838,541, filed on Apr. 2, 2020, now abandoned, said application No. 17/136,117 is a continuation-in-part of application No. 16/737,052, filed on Jan. 8, 2020, now Pat. No. 11,754,542, which is a continuation-in-part of application No. 16/568,580, filed on Sep. 12, 2019, now Pat. No. 11,478,158, said application No. 17/136,117 is a continuation-in-part of application No. 16/568,580, filed on Sep. 12, 2019, now Pat. No. 11,478,158, said application No. 17/665,086 is a continuation-in-part of application No. 16/554,029, filed on Aug. 28, 2019, now abandoned, said application No. 17/714,988 is a continuation-in-part of application No. 16/554,029, filed on Aug. 28, 2019, now abandoned, said application No. 16/838,541 is a continuation-in-part of application No. 16/554,029, filed on Aug. 28, 2019, now abandoned, said application No. 17/136,117 is a continuation-in-part of application No. 16/554,029, filed on Aug. 28, 2019, now abandoned, which is a continuation-in-part of application No. 16/022,987, filed on Jun. 29, 2018, now Pat. No. 11,172,859, said application No. 16/737,052 is a continuation-in-part of application No. 15/963,061, filed on Apr. 25, 2018, now Pat. No. 10,772,559, said application No. 16/568,580 is a continuation-in-part of application No. 15/963,061, filed on Apr. 25, 2018, now Pat. No. 10,772,559, which is a continuation-in-part of application No. 15/464,349, filed on Mar. 21, 2017, now Pat. No. 9,968,297, said application No. 16/838,541 is a continuation-in-part of application No. 15/236,401, filed on Aug. 13, 2016, now abandoned, said application No. 15/464,349 is a continuation-in-part of application No. 15/136,948, filed on Apr. 24, 2016, now Pat. No. 10,234,942, said application No. 16/022,987 is a continuation-in-part of application No. 15/136,948, filed on Apr. 24, 2016, now Pat. No. 10,234,942, said application No. 15/236,401 is a continuation-in-part of application No. 15/136,948, filed on Apr. 24, 2016, now Pat. No. 10,234,942, which is a continuation-in-part of application No. 14/599,522, filed on Jan. 18, 2015, now Pat. No. 9,814,426, said application No. 15/236,401 is a continuation-in-part of application No. 14/599,522, filed on Jan. 18, 2015, now Pat. No. 9,814,426, said application No. 15/464,349 is a continuation-in-part of application No. 14/562,719, filed on Dec. 7, 2014, now Pat. No. 10,130,277, said application No. 14/599,522 is a continuation-in-part of application No. 14/562,719, filed on Dec. 7, 2014, now Pat. No. 10,130,277, said application No. 15/464,349 is a continuation-in-part of application No. 14/330,649, filed on Jul. 14, 2014, now abandoned, which is a continuation-in-part of application No. 13/797,955, filed on Mar. 12, 2013, now Pat. No. 9,456,916, said application No. 14/330,649 is a continuation-in-part of application No. 13/523,739, filed on Jun. 14, 2012, now Pat. No. 9,042,596.

(60) Provisional application No. 62/972,692, filed on Feb. 11, 2020, provisional application No. 62/851,904, filed on May 23, 2019, provisional application No. 62/796,901, filed on Jan. 25, 2019, provisional application No. 62/791,838, filed on Jan. 13, 2019, provisional application No. 62/430,667, filed on Dec. 6, 2016, provisional application No. 62/322,594, filed on Apr. 14, 2016, provisional application No. 62/303,126, filed on Mar. 3, 2016, provisional application No. 62/169,661, filed on Jun. 2, 2015, provisional application No. 62/160,172, filed on May 12, 2015, provisional application No. 62/089,696, filed on Dec. 9, 2014, provisional application No. 62/017,615, filed on Jun. 26, 2014, provisional application No. 61/939,244, filed on Feb. 12, 2014, provisional application No. 61/932,517, filed on Jan. 28, 2014, provisional application No. 61/729,494, filed on Nov. 23, 2012.

(56) References Cited

U.S. PATENT DOCUMENTS

| | | |
|---|---|---|
| 8,798,710 B2 | 8/2014 | Chi |
| 9,204,796 B2 | 12/2015 | Tran |
| 9,314,183 B2 | 4/2016 | Chi et al. |
| 9,320,885 B2 | 4/2016 | Vasapollo |
| 9,474,461 B2 | 10/2016 | Fisher et al. |
| 9,820,670 B2 | 11/2017 | Parvizi et al. |
| 10,285,646 B1 | 5/2019 | Grant et al. |
| 10,433,756 B1 | 10/2019 | Bachelder et al. |
| 10,452,144 B2 | 10/2019 | Aimone et al. |
| 10,512,770 B2 | 12/2019 | Wingeier et al. |
| 10,535,278 B2 | 1/2020 | Chahine |
| 10,564,717 B1 | 2/2020 | Shahmohammadi et al. |
| 10,656,710 B1 | 5/2020 | Shahmohammadi et al. |
| 10,809,796 B2 | 10/2020 | Armstrong-Muntner et al. |
| 10,842,404 B2 | 11/2020 | Mercier et al. |
| 10,856,032 B2 | 12/2020 | Aimone et al. |
| 10,860,097 B2 | 12/2020 | Chae |
| 10,867,720 B2 | 12/2020 | Mallires et al. |
| 10,888,240 B2 | 1/2021 | Parvizi et al. |
| 10,962,789 B1 | 3/2021 | Lewis |
| 10,980,480 B2 | 4/2021 | Grant et al. |
| 10,990,175 B2 | 4/2021 | Forsland et al. |
| 11,209,654 B1 | 12/2021 | Lewis |
| 11,241,183 B2 | 2/2022 | Leuthardt et al. |
| 11,272,870 B2 | 3/2022 | Katnani et al. |
| 11,301,044 B1 | 4/2022 | Chevillet et al. |
| 11,357,434 B2 | 6/2022 | Bachelder et al. |
| 11,360,559 B2 | 6/2022 | Keller et al. |
| 11,363,980 B2 | 6/2022 | Dauguet et al. |
| 11,471,088 B1 | 10/2022 | Parvizi et al. |
| 11,540,759 B2 | 1/2023 | Flood et al. |
| 11,583,231 B2 | 2/2023 | Yee et al. |
| 11,612,331 B2 | 3/2023 | Wyeth et al. |
| 11,617,897 B2 | 4/2023 | Wingren |
| 11,622,709 B2 | 4/2023 | Gunasekar et al. |
| 11,642,081 B2 | 5/2023 | Kentin et al. |
| 11,740,696 B2 | 8/2023 | Keller et al. |
| 11,744,504 B2 | 9/2023 | Kele et al. |
| 11,747,903 B2 | 9/2023 | Keller et al. |
| 11,749,426 B2 | 9/2023 | Futashima et al. |
| 11,751,796 B2 | 9/2023 | Han et al. |
| 11,850,055 B2 | 12/2023 | Hiratsuka |
| 11,852,901 B2 | 12/2023 | Howell et al. |
| 2006/0252978 A1 | 11/2006 | Vesely et al. |
| 2006/0252979 A1 | 11/2006 | Vesely et al. |
| 2007/0019279 A1 | 1/2007 | Goodall et al. |
| 2007/0106172 A1 | 5/2007 | Abreu |
| 2007/0235716 A1* | 10/2007 | Delic .......... A61B 5/6803 257/13 |
| 2009/0134887 A1 | 5/2009 | Hu et al. |
| 2010/0041962 A1* | 2/2010 | Causevic .......... A61B 5/38 600/383 |
| 2011/0298706 A1 | 12/2011 | Mann |
| 2013/0056010 A1 | 3/2013 | Walker et al. |
| 2013/0102874 A1 | 4/2013 | Chi |
| 2013/0242262 A1 | 9/2013 | Lewis |
| 2013/0274583 A1 | 10/2013 | Heck |

(56) References Cited

U.S. PATENT DOCUMENTS

| | | |
|---|---|---|
| 2014/0023999 A1 | 1/2014 | Greder |
| 2014/0024912 A1 | 1/2014 | Dalke |
| 2014/0107458 A1 | 4/2014 | Op De Beeck et al. |
| 2014/0148872 A1 | 5/2014 | Goldwasser et al. |
| 2014/0223462 A1 | 8/2014 | Aimone et al. |
| 2014/0288406 A1 | 9/2014 | Chai |
| 2014/0316230 A1 | 10/2014 | Denison et al. |
| 2014/0347265 A1 | 11/2014 | Aimone et al. |
| 2015/0065838 A1 | 3/2015 | Wingeier et al. |
| 2015/0088224 A1 | 3/2015 | Goldwasser et al. |
| 2015/0141788 A1 | 5/2015 | Chi et al. |
| 2015/0199010 A1 | 7/2015 | Coleman et al. |
| 2015/0265176 A1 | 9/2015 | Dalke |
| 2015/0379896 A1 | 12/2015 | Yang |
| 2016/0070122 A1 | 3/2016 | Sales |
| 2016/0089045 A1 | 3/2016 | Sadeghian-Motahar et al. |
| 2016/0143554 A1 | 5/2016 | Lim et al. |
| 2016/0174859 A1 | 6/2016 | Oudenhoven et al. |
| 2016/0256086 A1 | 9/2016 | Byrd et al. |
| 2016/0287173 A1 | 10/2016 | Abreu |
| 2016/0367189 A1 | 12/2016 | Aimone et al. |
| 2017/0112444 A1 | 4/2017 | Lin et al. |
| 2017/0135597 A1 | 5/2017 | Mann |
| 2017/0150925 A1 | 6/2017 | Jung |
| 2017/0164857 A1 | 6/2017 | Soulet De Brugiere et al. |
| 2017/0164903 A1 | 6/2017 | Soulet De Brugiere et al. |
| 2017/0172447 A1 | 6/2017 | Mitra et al. |
| 2017/0215759 A1 | 8/2017 | Dudek et al. |
| 2017/0224990 A1 | 8/2017 | Goldwasser et al. |
| 2017/0258353 A1 | 9/2017 | Jovanovic et al. |
| 2017/0258400 A1 | 9/2017 | Jovanovic et al. |
| 2017/0258410 A1 | 9/2017 | Gras |
| 2017/0281036 A1 | 10/2017 | Parvizi et al. |
| 2017/0340855 A1 | 11/2017 | Soulet De Brugiere et al. |
| 2018/0049639 A1 | 2/2018 | Tian |
| 2018/0049661 A1 | 2/2018 | Parvizi et al. |
| 2018/0078206 A1 | 3/2018 | Aimone et al. |
| 2018/0103894 A1 | 4/2018 | Tzvieli |
| 2018/0153470 A1 | 6/2018 | Gunasekar et al. |
| 2018/0192906 A1 | 7/2018 | Soulet De Brugiere et al. |
| 2018/0204276 A1 | 7/2018 | Tumey |
| 2018/0221620 A1 | 8/2018 | Metzger |
| 2018/0235499 A1 | 8/2018 | Zorman et al. |
| 2018/0235500 A1 | 8/2018 | Lee et al. |
| 2018/0236232 A1 | 8/2018 | Soulet De Brugiere et al. |
| 2018/0278984 A1 | 9/2018 | Aimone et al. |
| 2018/0321173 A1 | 11/2018 | Hanein et al. |
| 2018/0344171 A1 | 12/2018 | Straka et al. |
| 2018/0348863 A1 | 12/2018 | Aimone et al. |
| 2018/0353096 A1 | 12/2018 | Mercier et al. |
| 2018/0353725 A1 | 12/2018 | Mercier et al. |
| 2018/0368717 A1 | 12/2018 | Soulet De Brugiere et al. |
| 2019/0000338 A1 | 1/2019 | Van Den Ende et al. |
| 2019/0073605 A1 | 3/2019 | Keller |
| 2019/0101977 A1 | 4/2019 | Armstrong-Muntner et al. |
| 2019/0113973 A1 | 4/2019 | Coleman et al. |
| 2019/0200925 A1 | 7/2019 | Aimone et al. |
| 2019/0239807 A1 | 8/2019 | Watson et al. |
| 2019/0246977 A1 | 8/2019 | Miller et al. |
| 2019/0255313 A1 | 8/2019 | Wingeier et al. |
| 2019/0328261 A1 | 10/2019 | Shakour et al. |
| 2019/0336765 A1 | 11/2019 | Charlesworth et al. |
| 2019/0343462 A1 | 11/2019 | Grant et al. |
| 2019/0365270 A1 | 12/2019 | Bachelder et al. |
| 2019/0374766 A1 | 12/2019 | Wingeier et al. |
| 2019/0384392 A1 | 12/2019 | Aimone et al. |
| 2020/0019243 A1 | 1/2020 | Aimone et al. |
| 2020/0060571 A1 | 2/2020 | Dauguet et al. |
| 2020/0069206 A1 | 3/2020 | Zaliasl et al. |
| 2020/0081247 A1 | 3/2020 | Khaderi et al. |
| 2020/0094054 A1 | 3/2020 | Sharma et al. |
| 2020/0133393 A1 | 4/2020 | Forsland et al. |
| 2020/0159324 A1 | 5/2020 | Keller et al. |
| 2020/0237249 A1 | 7/2020 | Gunasekar et al. |
| 2020/0264454 A1 | 8/2020 | Mackenzie et al. |
| 2020/0268296 A1 | 8/2020 | Alcaide et al. |
| 2020/0281527 A1 | 9/2020 | Gunasekar et al. |
| 2020/0305786 A1 | 10/2020 | Grant et al. |
| 2020/0316370 A1 | 10/2020 | Hanein et al. |
| 2020/0337653 A1 | 10/2020 | Alcaide et al. |
| 2020/0367789 A1 | 11/2020 | Moffat et al. |
| 2020/0375524 A1 | 12/2020 | Aminifar et al. |
| 2021/0000347 A1 | 1/2021 | Stump |
| 2021/0038106 A1 | 2/2021 | Ramakrishnan et al. |
| 2021/0085235 A1 | 3/2021 | Kamousi et al. |
| 2021/0109594 A1 | 4/2021 | Keller et al. |
| 2021/0121115 A1 | 4/2021 | Chiang |
| 2021/0124422 A1 | 4/2021 | Forsland |
| 2021/0128044 A1 | 5/2021 | Parvizi et al. |
| 2021/0200313 A1 | 7/2021 | Aimone et al. |
| 2021/0223864 A1 | 7/2021 | Forsland et al. |
| 2021/0267539 A1 | 9/2021 | Grant et al. |
| 2021/0282695 A1 | 9/2021 | Goldstein et al. |
| 2021/0338128 A1 | 11/2021 | Le Lous et al. |
| 2021/0353200 A1 | 11/2021 | Xu et al. |
| 2021/0361235 A1 | 11/2021 | Li et al. |
| 2022/0000407 A1 | 1/2022 | Ludwig et al. |
| 2022/0004257 A1 | 1/2022 | Keller et al. |
| 2022/0015701 A1 | 1/2022 | Gunasekar et al. |
| 2022/0022813 A1 | 1/2022 | Gunasekar et al. |
| 2022/0031217 A1 | 2/2022 | Kidmose et al. |
| 2022/0031248 A1 | 2/2022 | Grant et al. |
| 2022/0117535 A1 | 4/2022 | Parvizi et al. |
| 2022/0117536 A1 | 4/2022 | Parvizi et al. |
| 2022/0211313 A1 | 7/2022 | Lee |
| 2022/0233123 A1 | 7/2022 | Telfer et al. |
| 2022/0276707 A1 | 9/2022 | Barascud et al. |
| 2022/0308668 A1 | 9/2022 | Keller et al. |
| 2023/0000416 A1 | 1/2023 | Bachelder et al. |
| 2023/0014065 A1 | 1/2023 | Hanein et al. |
| 2023/0018247 A1 | 1/2023 | Elias |
| 2023/0031613 A1 | 2/2023 | Fleury |
| 2023/0043938 A1 | 2/2023 | Kele |
| 2023/0165503 A1 | 6/2023 | Coyle |
| 2023/0172468 A1 | 6/2023 | Kaplan et al. |
| 2023/0320669 A1 | 10/2023 | Desai et al. |
| 2024/0108263 A1* | 4/2024 | Pickett ............... A61B 5/1455 |
| 2024/0138745 A1 | 5/2024 | Yonce et al. |

OTHER PUBLICATIONS (Casson, 2019), "Wearable EEG and Beyond," Biomedical Engineering Letters, Jan. 2019, 9(1), 53-71.
(Chen, 2014), "Soft, Comfortable Polymer Dry Electrodes for High Quality ECG and EEG Recording," Sensors, Dec. 10, 2014, 14(12), 23758-80.
(Chen, 2016), "Polymer-Based Dry Electrodes for Biopotential Measurements," Thesis, Arenberg Doctoral School, 2016.
(Chi, 2010), "Dry-Contact and Noncontact Biopotential Electrodes: Methodological Review," IEEE Reviews in Biomedical Engineering, 2010, 3, 106-119.
(Chlaihawi, 2018), "Development of Printed and Flexible Dry ECG Electrodes," Sensing and Bio-Sensing Research, 2018, 20, 9-15.
(Flumeri, 2019), "The Dry Revolution: Evaluation of Three Different EEG Dry Electrode Types in Terms of Signal Spectral Features, Mental States Classification and Usability," Sensors, Mar. 19, 2019, 19(6) 1365.
(Fu, 2020), "Dry Electrodes for Human Bioelectrical Signal Monitoring," Sensors, Jun. 29, 2020, 20(13), 3651.
(Gao, 2018), "Soft Pin-Shaped Dry Electrode with Bristles for EEG Signal Measurements," Sensors and Actuators, 2018, vol. 283, 348-361.
(Hsu, 2014), "Developing Barbed Microtip-Based Electrode Arrays for Biopotential Measurement," Sensors, 2014, 14(7), 12370-12386.
(Kocturova, 2019), "Comparison of Dry Electrodes for Mobile EEG System," 2019.
(Krachunov, 2016), "3D Printed Dry EEG Electrodes," Sensors, 2016, 16(10), 1635.
(Lau-Zhu, 2019), "Mobile EEG in Research on Neurodevelopmental Disorders: Opportunities and Challenges," Developmental Cognitive Neuroscience, 2019, vol. 36.

(56) References Cited

OTHER PUBLICATIONS (Lee, 2015), "Reverse-Curve-Arch-Shaped Dry EEG Electrode for Increased Skin-Electrode Contact Area on Hairy Scalps," Electronics Letters, Oct. 1, 2015.
(Lopez-Gordo, 2014), "Dry EEG Electrodes," Sensors, Jul. 18, 2014, 14(7), 12847-70.
(Mota, 2013), "Development of a Quasi-Dry Electrode for EEG Recording," Sensors and Actuators, 2013, vol. 199, 310-317.
(Olesen, 2020), "Development and Assessment of Electrodes and Instrumentation for Plantar Skin Impedance Measurements," Thesis, Master in Electronics, Informatics and Technology, University of Oslo Autumn 2020.
(Ouyang, 2021), "Application of Intrinsically Conducting Polymers in Flexible Electronics," SmartMat, Aug. 18, 2021, 2.
(Ruffini, 2008), "First Human Trials of a Dry Electrophysiology Sensor Using a Carbon Nanotube Array Interface," Sensors and Actuators, Jun. 15, 2008, 144.
(Shad, 2020), "Impedance and Noise of Passive and Active Dry EEG Electrodes: A Review," IEEE Sensors Journal, Jul. 27, 2020.
(Sunwoo, 2020), "Advances in Soft Bioelectronics for Brain Research and Clinical Neuroengineering," Matter, 2020, 3(6) 1923-1947.
(Zhang, 2020), "Fully Organic Compliant Dry Electrodes Self-Adhesive to Skin for Long-Term Motion-Robust Epidermal Biopotential Monitoring," Nature Communications, 2020, 11, 4683.

\* cited by examiner

HEADBAND WITH BRAIN ACTIVITY SENSORS

CROSS-REFERENCE TO RELATED APPLICATIONS

This patent application is a continuation-in-part of U.S. patent application Ser. No. 18/411,540 filed on 2024 Jan. 12. This patent application is a continuation-in-part of U.S. patent application Ser. No. 18/219,684 filed on 2023 Jul. 9. U.S. patent application Ser. No. 18/411,540 was a continuation-in-part of U.S. patent application Ser. No. 18/219,684 filed on 2023 Jul. 9. U.S. patent application Ser. No. 18/219,684 was a continuation-in-part of U.S. patent application Ser. No. 17/714,988 filed on 2022 Apr. 6. U.S. patent application Ser. No. 18/219,684 was a continuation-in-part of U.S. patent application Ser. No. 16/838,541 filed on 2020 Apr. 2.

U.S. patent application Ser. No. 17/714,988 was a continuation-in-part of U.S. patent application Ser. No. 17/665,086 filed on 2022 Feb. 4. U.S. patent application Ser. No. 17/714,988 was a continuation-in-part of U.S. patent application Ser. No. 17/136,117 filed on 2020 Dec. 29. U.S. patent application Ser. No. 17/714,988 was a continuation-in-part of U.S. patent application Ser. No. 16/554,029 filed on 2019 Aug. 28. U.S. patent application Ser. No. 17/665,086 was a continuation-in-part of U.S. patent application Ser. No. 17/136,117 filed on 2020 Dec. 29. U.S. patent application Ser. No. 17/665,086 was a continuation-in-part of U.S. patent application Ser. No. 16/554,029 filed on 2019 Aug. 28.

U.S. patent application Ser. No. 17/136,117 was a continuation-in-part of U.S. patent application Ser. No. 16/838,541 filed on 2020 Apr. 2. U.S. patent application Ser. No. 17/136,117 claimed the priority benefit of U.S. provisional patent application 62/972,692 filed on 2020 Feb. 11. U.S. patent application Ser. No. 17/136,117 was a continuation-in-part of U.S. patent application Ser. No. 16/737,052 filed on 2020 Jan. 8. U.S. patent application Ser. No. 17/136,117 was a continuation-in-part of U.S. patent application Ser. No. 16/568,580 filed on 2019 Sep. 12. U.S. patent application Ser. No. 17/136,117 was a continuation-in-part of U.S. patent application Ser. No. 16/554,029 filed on 2019 Aug. 28.

U.S. patent application Ser. No. 16/838,541 claimed the priority benefit of U.S. provisional patent application 62/972,692 filed on 2020 Feb. 11. U.S. patent application Ser. No. 16/838,541 was a continuation-in-part of U.S. patent application Ser. No. 16/554,029 filed on 2019 Aug. 28. U.S. patent application Ser. No. 16/838,541 claimed the priority benefit of U.S. provisional patent application 62/851,917 filed on 2019 May 23. U.S. patent application Ser. No. 16/838,541 claimed the priority benefit of U.S. provisional patent application 62/837,712 filed on 2019 Apr. 23. U.S. patent application Ser. No. 16/838,541 was a continuation-in-part of U.S. patent application Ser. No. 15/236,401 filed on 2016 Aug. 13. U.S. patent application Ser. No. 16/737,052 was a continuation-in-part of U.S. patent application Ser. No. 16/568,580 filed on 2019 Sep. 12. U.S. patent application Ser. No. 16/737,052 was a continuation-in-part of U.S. patent application Ser. No. 15/963,061 filed on 2018 Apr. 25. U.S. patent application Ser. No. 16/568,580 was a continuation-in-part of U.S. patent application Ser. No. 15/963,061 filed on 2018 Apr. 25.

U.S. patent application Ser. No. 16/554,029 claimed the priority benefit of U.S. provisional patent application 62/851,904 filed on 2019 May 23. U.S. patent application Ser. No. 16/554,029 claimed the priority benefit of U.S. provisional patent application 62/796,901 filed on 2019 Jan. 25. U.S. patent application Ser. No. 16/554,029 claimed the priority benefit of U.S. provisional patent application 62/791,838 filed on 2019 Jan. 13. U.S. patent application Ser. No. 16/554,029 was a continuation-in-part of U.S. patent application Ser. No. 16/022,987 filed on 2018 Jun. 29. U.S. patent application Ser. No. 16/022,987 was a continuation-in-part of U.S. patent application Ser. No. 15/136,948 filed on 2016 Apr. 24. U.S. patent application Ser. No. 15/963,061 was a continuation-in-part of U.S. patent application Ser. No. 15/464,349 filed on 2017 Mar. 21.

U.S. patent application Ser. No. 15/464,349 claimed the priority benefit of U.S. provisional patent application 62/430,667 filed on 2016 Dec. 6. U.S. patent application Ser. No. 15/464,349 was a continuation-in-part of U.S. patent application Ser. No. 15/136,948 filed on 2016 Apr. 24. U.S. patent application Ser. No. 15/464,349 was a continuation-in-part of U.S. patent application Ser. No. 14/562,719 filed on 2014 Dec. 7. U.S. patent application Ser. No. 15/464,349 was a continuation-in-part of U.S. patent application Ser. No. 14/330,649 filed on 2014 Jul. 14. U.S. patent application Ser. No. 15/236,401 was a continuation-in-part of U.S. patent application Ser. No. 15/136,948 filed on 2016 Apr. 24. U.S. patent application Ser. No. 15/236,401 was a continuation-in-part of U.S. patent application Ser. No. 14/599,522 filed on 2015 Jan. 18.

U.S. patent application Ser. No. 15/136,948 claimed the priority benefit of U.S. provisional patent application 62/322,594 filed on 2016 Apr. 14. U.S. patent application Ser. No. 15/136,948 claimed the priority benefit of U.S. provisional patent application 62/303,126 filed on 2016 Mar. 3. U.S. patent application Ser. No. 15/136,948 claimed the priority benefit of U.S. provisional patent application 62/169,661 filed on 2015 Jun. 2. U.S. patent application Ser. No. 15/136,948 claimed the priority benefit of U.S. provisional patent application 62/160,172 filed on 2015 May 12. U.S. patent application Ser. No. 15/136,948 was a continuation-in-part of U.S. patent application Ser. No. 14/599,522 filed on 2015 Jan. 18.

U.S. patent application Ser. No. 14/599,522 claimed the priority benefit of U.S. provisional patent application 62/089,696 filed on 2014 Dec. 9. U.S. patent application Ser. No. 14/599,522 was a continuation-in-part of U.S. patent application Ser. No. 14/562,719 filed on 2014 Dec. 7. U.S. patent application Ser. No. 14/599,522 claimed the priority benefit of U.S. provisional patent application 62/017,615 filed on 2014 Jun. 26. U.S. patent application Ser. No. 14/599,522 claimed the priority benefit of U.S. provisional patent application 61/939,244 filed on 2014 Feb. 12. U.S. patent application Ser. No. 14/599,522 claimed the priority benefit of U.S. provisional patent application 61/932,517 filed on 2014 Jan. 28.

U.S. patent application Ser. No. 14/562,719 claimed the priority benefit of U.S. provisional patent application 61/932,517 filed on 2014 Jan. 28. U.S. patent application Ser. No. 14/330,649 was a continuation-in-part of U.S. patent application Ser. No. 13/797,955 filed on 2013 Mar. 12. U.S. patent application Ser. No. 14/330,649 was a continuation-in-part of U.S. patent application Ser. No. 13/523,739 filed on 2012 Jun. 14. U.S. patent application Ser. No. 13/797,955 claimed the priority benefit of U.S. provisional patent application 61/729,494 filed on 2012 Nov. 23.

The entire contents of these applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to wearable devices with brain activity sensors.

INTRODUCTION

Headbands, halos, or other head-worn devices with sensors (e.g. electrodes) for recording brain activity (e.g. electroencephalographic data) can be used to predict and/or detect health events (e.g. seizure, stroke, or heart attack) or function as a BCI (Brain-to-Computer Interface) for communication.

REVIEW OF THE RELEVANT ART

In the patent literature, U.S. patent applications 20060252978 (Vesely et al., Nov. 9, 2006, "Biofeedback Eyewear System") and 20060252979 (Vesely et al., Nov. 9, 2006, "Biofeedback Eyewear System") disclose a biofeedback eyewear system comprising stereo lenses, binaural audio and plurality of electrodes for biofeedback devices. U.S. patent application 20070019279 (Goodall et al., Jan. 25, 2007, "Adjustable Lens System with Neural-Based Control") discloses methods and systems for modifying or enhancing vision via analysis of neural or neuromuscular activity. U.S. patent application 20070106172 (Abreu, May 10, 2007, "Apparatus and Method for Measuring Biologic Parameters") discloses support structures for positioning sensors on a physiologic tunnel for measuring physical, chemical and biological parameters of the body and to produce an action according to the measured value of the parameters.

U.S. patent application 20090134887 (Hu et al., May 28, 2009, "Contact Sensor") discloses a contact sensor wherein a conductor has an arc shape. U.S. patent applications 20110298706 (Mann, Dec. 8, 2011, "Brainwave Actuated Apparatus") and 20170135597 (Mann, May 18, 2017, "Brainwave Actuated Apparatus") disclose a brainwave actuated apparatus with a brainwave sensor for outputting a brainwave signal, an effector responsive to an input signal, and a controller operatively connected to an output of said brainwave sensor and a control input to said effector. U.S. patent application 20130056010 (Walker et al., Mar. 7, 2013, "Autonomous Positive Airway Pressure System") discloses an apparatus, such as in the form of eyeglasses or goggles comprising dual lenses configured to serve as a gas chamber, or as headgear where the chamber is contoured to fit on the user's head and includes all components required to operate APAP, or the device may be configured to be placed on other locations such as the arm, torso, back, or leg.

U.S. patent application 20130102874 (Chi, Apr. 25, 2013, "Apparatuses, Systems and Methods for Biopotential Sensing with Dry Electrodes") and U.S. Pat. No. 8,798,710 (Chi, Aug. 5, 2014, "Apparatuses, Systems and Methods for Biopotential Sensing with Dry Electrodes") disclose an electrode with an electrical conductor, a membrane selectively permeable to ionic conduction, and a conductive medium. U.S. patent application 20130242262 (Lewis, Sep. 19, 2013, "Enhanced Optical and Perceptual Digital Eyewear") discloses wearable optics with a frame member, a lens, and circuitry within the frame member for enhancing the use of the wearable optics. U.S. patent application 20130274583 (Heck, Oct. 17, 2013, "Electrodes Adapted for Transmitting or Measuring Voltages Through Hair") discloses an electrode to measure and/or deliver voltages through skin covered with hair.

U.S. patent application 20140023999 (Greder, Jan. 23, 2014, "Detection and Feedback of Information Associated with Executive Function") discloses a neurosensing and feedback device to detect mental states and alert a wearer, such as in real-time. U.S. patent application 20140024912 (Dalke, Jan. 23, 2014, "Neurophysiological Dry Sensor") and U.S. patent application 20150265176 (Dalke, Sep. 24, 2015, "Neurophysiological Dry Sensor") disclose a sensor assembly of conductive spires. U.S. patent application 20140107458 (Op De Beeck et al., Apr. 17, 2014, "Resilient Sensor for Biopotential Measurements") discloses a sensor with a cavity wherein an electrical contacting unit is partially secured and a means for maintaining the electrical contacting unit in a resiliently deformed state when it is in contact with skin.

U.S. patent applications 20140148872 (Goldwasser et al., May 29, 2014, "Wearable Transdermal Electrical Stimulation Devices and Methods of Using Them") and 20150088224 (Goldwasser et al., Mar. 26, 2015, "Wearable Transdermal Electrical Stimulation Devices and Methods of Using Them") disclose devices, systems, and methods for transdermal electrical stimulation. U.S. patent application 20140223462 (Aimone et al., Aug. 7, 2014, "System and Method for Enhancing Content Using Brain-State Data") discloses a computer system or method for modulating content based on a person's brainwave data, including modifying presentation of digital content at least one computing device.

U.S. patent application 20140288406 (Chai, Sep. 25, 2014, "Line-Contact Dry Electrode") discloses an electrode with a plurality of elastic conductive branches which form a comb-like electrode. U.S. patent application 20140316230 (Denison et al., Oct. 23, 2014, "Methods and Devices for Brain Activity Monitoring Supporting Mental State Development and Training") discloses a method for receiving electroencephalography (EEG) data related to a user. U.S. patent application 20140347265 (Aimone et al., Nov. 27, 2014, "Wearable Computing Apparatus and Method") discloses a method performed by a wearable computing device comprising at least one bio-signal measuring sensor, the at least one bio-signal measuring sensor including at least one brainwave sensor.

U.S. patent application 20150065838 (Wingeier et al., Mar. 5, 2015, "Electrode System for Electrical Stimulation") and U.S. patent application 20190374766 (Wingeier et al., Dec. 12, 2019, "Electrode System for Electrical Stimulation") disclose a system with an array of protrusions for electrically stimulating and/or detecting a person's bioelectrical signals. U.S. patent application 20150141788 (Chi et al., May 21, 2015, "Transducer Assemblies for Dry Applications of Transducers") and U.S. Pat. No. 9,314,183 (Chi et al., Apr. 19, 2016, "Transducer Assemblies for Dry Applications of Transducers") disclose at least one probe extending from a support terminal which penetrate and slide through patches of hair.

U.S. patent application 20150199010 (Coleman et al., Jul. 16, 2015, "Systems and Methods for Collecting, Analyzing, and Sharing Bio-Signal and Non-Bio-Signal Data") and U.S. patent application 20190113973 (Coleman et al., Apr. 18, 2019, "Systems and Methods for Collecting, Analyzing, and Sharing Bio-Signal and Non-Bio-Signal Data") disclose a system that: captures bio-signal data and non-bio-signal data; and extracts one or more features related to a person interacting with a biofeedback computer system. U.S. Pat. No. 9,204,796 (Tran, Dec. 8, 2015, "Personal Emergency Response (PER) System") discloses one or more sensors to detect activities of a mobile object and a processor coupled to the sensor and the wireless transceiver to classify sequences of motions into groups of similar postures each represented by a model and to apply the models to identify an activity of the object.

U.S. patent application 20150379896 (Yang, Dec. 31, 2015, "Intelligent Eyewear and Control Method Thereof") discloses intelligent eyewear including an eyeglass, an eyeglass frame, and a leg with a brainwave recognizer. U.S. patent application 20160070122 (Sales, Mar. 10, 2016, "Computerized Replacement Temple for Standard Eyewear") discloses a computerized eyewear retrofit kit comprising a replacement temple. U.S. patent application 20160089045 (Sadeghian-Motahar et al., Mar. 31, 2016, "Bio-Potential Sensing Materials as Dry Electrodes and Devices") discloses a dry electrode made with an electrically-conductive solid material.

U.S. Pat. No. 9,320,885 (Vasapollo, Apr. 26, 2016, "Dual-Purpose Sleep-Wearable Headgear for Monitoring and Stimulating the Brain of a Sleeping Person") discloses headgear for monitoring and stimulating the brain of a sleeping person. U.S. patent application 20160143554 (Lim et al., May 26, 2016, "Apparatus for Measuring Bioelectrical Signals") discloses using tapered electrodes to measure bioelectrical signals. U.S. patent application 20160174859 (Oudenhoven et al., Jun. 23, 2016, "Electrode for Biopotential Sensing") discloses a plurality of contact pins protruding from a sensor base.

U.S. patent application 20160256086 (Byrd et al., Sep. 8, 2016, "Non-Invasive, Bioelectric Lifestyle Management Device") discloses techniques to ascertain a biological condition such as blood glucose level, a heart rate, a blood ketone level, a blood alcohol content, a hydration level, a blood albumin level, and/or a blood electrolyte level. U.S. patent application 20160287173 (Abreu, Oct. 6, 2016, "Apparatus Configured to Support a Device on a Head") discloses apparatuses support by at least a portion of a forehead in combination with at least one of a nose, an ear, and a head, or present an adjustable apparatus to provide improved fit of a head-positioned apparatus.

U.S. Pat. No. 9,474,461 (Fisher et al., Oct. 25, 2016, "Miniature Wireless Biomedical Telemetry Device") discloses a miniature wireless biomedical telemetry device to record physiological signals from rats, mice and birds, as well as humans. U.S. patent application 20160367189 (Aimone et al., Dec. 22, 2016, "Wearable Apparatus for Brain Sensors") discloses a wearable apparatus with an outer band member comprising outer band ends joined by a curved outer band portion of a curve generally shaped to correspond to a user's forehead. U.S. patent application 20170112444 (Lin et al., Apr. 27, 2017, "Bio-Signal Sensor") discloses a dry electrode with a plurality of probes.

U.S. patent application 20170150925 (Jung, Jun. 1, 2017, "EEG Hair Band") discloses an EEG-monitoring hair band. U.S. patent application 20170164903 (Soulet De Brugiere et al., Jun. 15, 2017, "Autonomous Bioelectric Physiological Signal Acquisition Device") discloses a method for physiological signal acquisition that includes selecting an amplification factor. U.S. patent application 20170164857 (Soulet De Brugiere et al., Jun. 15, 2017, "Method and Device for Bioelectric Physiological Signal Acquisition and Processing") discloses a method for bioelectric physiological signal acquisition and processing which includes converting the analog signals.

U.S. patent application 20170172447 (Mitra et al., Jun. 22, 2017, "Sensor, System, and Holder Arrangement for Biosignal Activity Measurement") discloses an electrode base and a plurality of pins protruding from the base. U.S. patent application 20170215759 (Dudek et al., Aug. 3, 2017, "Self-Contained EEG Recording System") discloses a electroencephalogram sensor comprising a first electrode and a second electrode, wherein the first and second electrodes cooperate to measure a skin-electrode impedance. U.S. patent application 20170224990 (Goldwasser et al., Aug. 10, 2017, "Apparatuses and Methods for Neuromodulation") discloses devices and methods for transdermal electrical stimulation.

U.S. patent application 20170258353 (Jovanovic et al., Sep. 14, 2017, "Headsets and Electrodes for Gathering Electroencephalographic Data") and U.S. patent application 20170258400 (Jovanovic et al., Sep. 14, 2017, "Headsets and Electrodes for Gathering Electroencephalographic Data") disclose an electrode with a ring in an opening and an arm, wherein the arm has a portion extending outward from the opening. U.S. patent application 20170258410 (Gras, Sep. 14, 2017, "Method and Apparatus for Prediction of Epileptic Seizures") discloses a system for predicting epileptic seizures including sensors operable to record a wearer's brain activity.

U.S. patent application 20170281036 (Parvizi et al., Oct. 5, 2017, "Methods and Apparatus for Electrode Placement and Tracking"), U.S. Pat. No. 9,820,670 (Parvizi et al., Nov. 21, 2017, "Methods and Apparatus for Electrode Placement and Tracking"), U.S. patent application 20180049661 (Parvizi et al., Feb. 22, 2018, "Methods and Apparatus for Electrode Placement and Tracking"), U.S. patent Ser. No. 10/888,240 (Parvizi et al., Jan. 12, 2021, "Methods and Apparatus for Electrode Placement and Tracking"), U.S. patent application 20210128044 (Parvizi et al., May 6, 2021, "Methods and Apparatus for Electrode Placement and Tracking"), U.S. patent application 20220117535 (Parvizi et al., Apr. 21, 2022, "Methods and Apparatus for Electrode Placement and Tracking"), and U.S. patent application 20220117536 (Parvizi et al., Apr. 21, 2022, "Methods and Apparatus for Electrode Placement and Tracking") disclose tubular members extending out from an electrode body and a reservoir containing a conductive fluid or gel.

U.S. patent application 20170340855 (Soulet De Brugiere et al., Nov. 30, 2017, "Device and Method for Stimulating Slow Brain Waves") discloses a device for stimulating slow brain waves. U.S. patent application 20180049639 (Tian, Feb. 22, 2018, "Dry Electrode, Its Manufacturing Method and Bio-Electromagnetic Wave Detecting Device and Sensor Element Comprising the Dry Electrode") discloses a dry electrode with a flexible substrate and protruding structures arranged on the substrate. U.S. patent application 20180078206 (Aimone et al., Mar. 22, 2018, "Wearable Apparatus for Brain Sensors") discloses an apparatus with an outer band, a flexible inner band, and at least one brainwave sensor disposed inwardly along the inner band. U.S. patent application 20180103894 (Tzvieli, Apr. 19, 2018, "Neurofeedback Eyeglasses") discloses using forehead thermal measurements in brain-related treatments such as neurofeedback.

U.S. patent application 20180153470 (Gunasekar et al., Jun. 7, 2018, "Electroencephalography Headset and System for Collecting Biosignal Data"), U.S. patent application 20200281527 (Gunasekar et al., Sep. 10, 2020, "Electroencephalography Headset and System for Collecting Biosignal Data"), U.S. patent application 20220015701 (Gunasekar et al., Jan. 20, 2022, "Electroencephalography Headset and System for Collecting Biosignal Data"), and U.S. patent application 20220022813 (Gunasekar et al., Jan. 27, 2022, "Electroencephalography Headset and System for Collecting Biosignal Data") disclose a system for collecting biosignal data including: a left junction; a right junction; a first band spanning the left and right junctions; and a first band adjuster which adjusts a length of the first band between the left and right junctions.

U.S. patent application 20180192906 (Soulet De Brugiere et al., Jul. 12, 2018, "Polymer Composition and Electrode for a Device for the Non-Invasive Measurement of Biological Electrical Signals") discloses electrodes with a polymer matrix in which there are carbon nanotubes and adsorbent elements such as activated carbon particles or graphene nanoplatelets. U.S. patent application 20180204276 (Tumey, Jul. 19, 2018, "Brain Actuated Control of an E-Commerce Application") discloses a brain-to-computer interface providing brain actuated control of a 3D virtual/augmented/mixed reality e-commerce application, effected by releasably attaching a plurality of high-impedance dry silver-based electrodes to selected locations on a human user's scalp.

U.S. patent application 20180221620 (Metzger, Aug. 9, 2018, "Modulation of Brainwave Activity Using Non-Invasive Stimulation of Sensory Pathways") discloses modulation of the central nervous system (e.g. brain oscillatory activity) via non-invasive stimuli. U.S. patent application 20180235500 (Lee et al., Aug. 23, 2018, "Dry Electrode for Detecting Biosignal and Method for Manufacturing Same") discloses a dry electrode with a protrusion is made from conductive silicone and coated with Ag, AgCl, and, optionally, 3-aminopropyltriethoxysilane. U.S. patent application 20180235499 (Zorman et al., Aug. 23, 2018, "Method for Measuring an Electrophysiological Parameter by Means of a Capacitive Electrode Sensor of Controlled Capacitance") discloses a sensor with a plurality of protrusions projecting from it.

U.S. patent application 20180236232 (Soulet De Brugiere et al., Aug. 23, 2018, "Methods and Systems for Acoustic Stimulation of Brain Waves") discloses an personalized acoustic stimulation device. U.S. patent application 20180278984 (Aimone et al., Sep. 27, 2018, "System and Method for Enhancing Content Using Brain-State Data") discloses a computer system or method for modulating content based on a person's brainwave data. U.S. patent application 20180321173 (Hanein et al., Nov. 8, 2018, "Sensing Electrode and Method of Fabricating the Same") discloses a method comprising placing on the surface a flexible sensing device having an array of coated electrodes, wherein at least one electrode of the array is metallic and coated by a polymer.

U.S. patent application 20180344171 (Straka et al., Dec. 6, 2018, "Sensor Band for Multimodal Sensing of Biometric Data") discloses a pair of ECG sensors coupled to an interior surface of a band. U.S. patent application 20180348863 (Aimone et al., Dec. 6, 2018, "Wearable Computing Device With Electrophysiological Sensors") and U.S. patent Ser. No. 10/452,144 (Aimone et al., Oct. 22, 2019, "Wearable Computing Device with Electrophysiological Sensors") disclose a wearable device with bio-signal sensors and a feedback module which provides a user with an interactive mediated reality environment.

U.S. patent application 20180353096 (Mercier et al., Dec. 13, 2018, "Electrode, Wearable Assembly and System") and U.S. patent Ser. No. 10/842,404 (Mercier et al., Nov. 24, 2020, "Electrode, Wearable Assembly and System") disclose an electrode with a base and a plurality of legs extending from the base. U.S. patent application 20180353725 (Mercier et al., Dec. 13, 2018, "Method and System for Commanding The Production of an Acoustic Waveform Based on a Physiological Control Signal, and Associated Computer Program") discloses a method for producing an acoustic waveform based on a physiological control signal. U.S. patent application 20180368717 (Soulet De Brugiere et al., Dec. 27, 2018, "Method and System for Recovering Operating Data of a Device for Measuring Brain Waves") discloses a method for retrieving operating data from measuring device measuring brain waves.

U.S. patent application 20190000338 (Van Den Ende et al., Jan. 3, 2019, "Method and System for Obtaining Signals from Dry EEG Electrodes") discloses an electroencephalography system with actuators which move electrodes in at least two dimensions. U.S. patent application 20190073605 (Keller, Mar. 7, 2019, "Systems and Methods for Real-Time Neural Command Classification and Task Execution") discloses a system for transmitting context commands based on biosignals. U.S. patent application 20200081247 (Khaderi et al., Mar. 15, 2019, "Modular Display and Sensor System for Attaching to Eyeglass Frames and Capturing Physiological Data") discloses a modular device with EOG sensors that is integrated with eyeglasses.

U.S. patent application 20190101977 (Armstrong-Muntner et al., Apr. 4, 2019, "Monitoring a User of a Head-Wearable Electronic Device") and U.S. patent Ser. No. 10/809,796 (Armstrong-Muntner et al., Oct. 20, 2020, "Monitoring a User of a Head-Wearable Electronic Device") disclose an eye frame, a right light-emitting component, a left light-emitting component, and a processor to analyze light data indicative of the sensed right light and the sensed left light and determine a head gesture of the user based on the analyzed light data.

U.S. patent Ser. No. 10/285,646 (Grant et al., May 14, 2019, "Connection Quality Assessment for EEG Electrode Arrays"), U.S. patent application 20190343462 (Grant et al., Nov. 14, 2019, "Connection Quality Assessment for EEG Electrode Arrays"), U.S. patent Ser. No. 10/980,480 (Grant et al., Apr. 20, 2021, "Connection Quality Assessment for EEG Electrode Arrays"), and U.S. patent application 20220031248 (Grant et al., Feb. 3, 2022, "Connection Quality Assessment for EEG Electrode Arrays") disclose devices and methods to assess connection quality between electrodes and a subject's body.

U.S. patent application 20190200925 (Aimone et al., Jul. 4, 2019, "Wearable Computing Device") discloses a wearable device to wear on a head of a user including a flexible band generally shaped to correspond to the user's head, the band having at least a front portion to contact at least part of a frontal region of the user's head, a rear portion to contact at least part of an occipital region of the user's head, and at least one side portion extending between the front portion and the rear portion to contact at least part of an auricular region of the user's head. U.S. patent application 20190239807 (Watson et al., Aug. 8, 2019, "Hair Ratcheting Electroencephalogram Sensors") discloses a locking mechanism in an EEG sensor which permits one-way axial motion of a thread.

U.S. patent application 20190246977 (Miller et al., Aug. 15, 2019, "Optical Sensor for Wearable Devices") discloses methods, systems, apparatuses, and/or devices for taking optical measurements. U.S. patent application 20190255313 (Wingeier et al., Aug. 22, 2019, "Electrode Positioning System and Method") discloses a system and method for stimulating a person's brain. U.S. patent Ser. No. 10/433,756 (Bachelder et al., Oct. 8, 2019, "Adjustable Geometry Wearable Electrodes"), U.S. patent application 20190365270 (Bachelder et al., Dec. 5, 2019, "Adjustable Geometry Wearable Electrodes"), U.S. patent Ser. No. 11/357,434 (Bachelder et al., Jun. 14, 2022, "Adjustable Geometry Wearable Electrodes"), and U.S. patent application 20230000416 (Bachelder et al., Jan. 5, 2023, "Adjustable Geometry Wearable Electrodes") disclose collapsing, compressing, and/or telescoping electrodes.

U.S. patent application 20190328261 (Shakour et al., Oct. 31, 2019, "Brush Electrode") discloses a brush electrode wherein a plurality of strand electrodes extend outward from the electrode base. U.S. patent application 20190336765 (Charlesworth et al., Nov. 7, 2019, "Apparatuses and Methods for Transdermal Electrical Stimulation of Nerves to Modify or Induce a Cognitive State") discloses Transdermal Electrical Stimulation (TES) applicators for modifying a subject's cognitive state by applying stimulation. U.S. patent application 20190384392 (Aimone et al., Dec. 19, 2019, "Wearable Computing Apparatus and Method") discloses a method which includes acquiring a brainwave state measurement from a person using a bio-signal measuring sensor and processing the brainwave state measurement in accordance with the person's profile.

U.S. patent Ser. No. 10/512,770 (Wingeier et al., Dec. 24, 2019, "System for Electrical Stimulation") discloses electrodes with hydrophilic and conductive layers. U.S. patent Ser. No. 10/535,278 (Chahine, Jan. 14, 2020, "Garment with Stretch Sensors") discloses a knitted or woven garment with electrical connectors which support the receipt and transmission of electrical signals between a controller and sensors. U.S. patent applications 20200019243 (Aimone et al., Jan. 16, 2020, "Wearable Computing Device with Electrophysiological Sensors") and 20210200313 (Aimone et al., Jul. 1, 2021, "Wearable Computing Device with Electrophysiological Sensors") disclose a wearable computing device with bio-signal sensors and feedback providing an interactive mediated reality ("VR") environment.

U.S. patent Ser. No. 10/564,717 (Shahmohammadi et al., Feb. 18, 2020, "Apparatus, Systems, and Methods for Sensing Biopotential Signals") and 10656710 (Shahmohammadi et al., May 19, 2020, "Apparatus, Systems, and Methods for Sensing Biopotential Signals Via Compliant Electrodes") disclose a head-mounted-display device with electrodes which measures an EOG or EMG signal. U.S. patent application 20200060571 (Dauguet et al., Feb. 27, 2020, "Device for Measuring and/or Stimulating Brain Activity") discloses an EEG device with means for transmitting and/or detecting physiological signals produced by the brain of an individual, and a support for the transmission and/or detection means, wherein the support is configured to extend over the top of the individual's head.

U.S. patent application 20200069206 (Zaliasl et al., Mar. 5, 2020, "System and a Method for Acquiring an Electrical Signal and a Wearable Device") discloses a plurality of electrodes and signal quality detectors, wherein each detector detects a signal from a pair of electrodes and each detector comprises an analog-to-digital converter. U.S. patent application 20200094054 (Sharma et al., Mar. 26, 2020, "Auricular Nerve Stimulation to Address Patient Disorders, and Associated Systems and Methods") discloses auricular nerve stimulation techniques for addressing patient disorders.

U.S. patent applications 20200133393 (Forsland et al., Apr. 30, 2020, "Brain Computer Interface for Augmented Reality") and 20210223864 (Forsland et al., Jul. 22, 2021, "Brain Computer Interface for Augmented Reality") disclose a brain computer interface in a headset with an augmented reality display, one or more sensors, a processing module, at least one biofeedback device, and a battery. U.S. patent application 20200159324 (Keller et al., May 21, 2020, "Headware for Computer Control"), U.S. patent application 20210109594 (Keller et al., Apr. 15, 2021, "Headware for Computer Control"), U.S. patent Ser. No. 11/360, 559 (Keller et al., Jun. 14, 2022, "Headware for Computer Control"), U.S. patent application 20220308668 (Keller et al., Sep. 29, 2022, "Headware for Computer Control"), and U.S. patent Ser. No. 11/740,696 (Keller et al., Aug. 29, 2023, "Headware for Computer Control") disclose a head-worn device with an inner layer including a first surface and a second surface, an outer layer on the first surface, and at least one sensor on the second surface.

U.S. patent application 20200237249 (Gunasekar et al., Jul. 30, 2020, "Headset and Electrodes for Sensing Bioelectrical Potential and Methods of Operation Thereof") discloses medical devices for sensing bioelectrical potential including an electroencephalography (EEG) headset with electrodes. U.S. patent application 20200264454 (Mackenzie et al., Aug. 20, 2020, "Eyeglasses with Bio-Signal Sensors") discloses eyeglasses with a front portion for holding two lenses, an assembly for attaching to a signal pod, side arms connected to the front portion, a nose assembly connected to the front portion, and nose contacts for supporting the front portion.

U.S. patent applications 20200268296 (Alcaide et al., Aug. 27, 2020, "Brain-Computer Interface with Adaptations for High-Speed, Accurate, and Intuitive User Interactions") and 20200337653 (Alcaide et al., Oct. 29, 2020, "Brain-Computer Interface with Adaptations for High-Speed, Accurate, and Intuitive User Interactions") disclose a Brain-to-Computer Interface (BCI) that combines real-time eye-movement tracking and brain activity tracking. U.S. patent application 20200305786 (Grant et al., Oct. 1, 2020, "Systems and Methods for Processing Sonified Brain Signals") and U.S. patent application 20210267539 (Grant et al., Sep. 2, 2021, "Systems and Methods for Processing Sonified Brain Signals") disclose systems and methods for sonifying EEG signals from a person.

U.S. patent application 20200316370 (Hanein et al., Oct. 8, 2020, "Device and Method for Neurostimulation") discloses a nanoscale semiconducting optoelectronic system. U.S. patent Ser. No. 10/809,796 (Armstrong-Muntner et al., Oct. 20, 2020, "Monitoring a User of a Head-Wearable Electronic Device") discloses systems, methods, and computer-readable media for monitoring a person via a light-sensing head-wearable electronic device. U.S. patent application 20200367789 (Moffat et al., Nov. 26, 2020, "Wearable Computing Apparatus with Movement Sensors and Methods Therefor") discloses a wearable system for determining at least one movement property.

U.S. patent Ser. No. 10/856,032 (Aimone et al., Dec. 1, 2020, "System and Method for Enhancing Content Using Brain-State Data") discloses a computer system or method for modulating content based on a person's brainwave data, including modifying presentation of digital content at least one computing device. U.S. patent application 20200375524 (Aminifar et al, Dec. 3, 2020, "A Wearable System for Real-Time Detection of Epileptic Seizures") by the École polytechnique fédérale de Lausanne discloses an innovative wearable system for epileptic seizure detection. This system comprises an eyeglasses frame with a left arm and a right arm configured to rest over the ears of an intended person wearing the eyeglasses, a first pair of electrodes located in the left arm, and a second pair of electrodes located in the right arm.

U.S. patent Ser. No. 10/860,097 (Chae, Dec. 8, 2020, "Eye-Brain Interface (EBI) System and Method for Controlling Same") discloses methods and systems for calibrating an eye-brain interface (EBI) system controlled on the basis of eye movements and brain waves. U.S. patent Ser. No. 10/867,720 (Mallires et al, Dec. 15, 2020, "Impregnation of a Non-Conductive Material with an Intrinsically Conductive Polymer") discloses composite materials made by impregnating a non-conductive material with a conducting monomer to form a monomer-impregnated non-conductive material. U.S. patent application 20210000347 (Stump, Jan. 7, 2021, "Enhanced Physiological Monitoring Devices and Computer-Implemented Systems and Methods of Remote Physiological Monitoring of Subjects") discloses physiological sign monitoring devices, and systems and computer-implemented methods of remote physiological monitoring of people.

U.S. patent application 20210038106 (Ramakrishnan et al., Feb. 11, 2021, "Mobile, Wearable EEG Device With High Quality Sensors") discloses sensors with conductive segments in a flexible sensing layer material. U.S. patent application 20210085235 (Kamousi et al., Mar. 25, 2021, "Systems and Methods for Seizure Prediction and Detection") discloses a method for seizure detection. U.S. patent Ser. No. 10/962,789 (Lewis, Mar. 30, 2021, "Digital Eyewear System and Method for the Treatment and Prevention of Migraines and Photophobia") and U.S. Pat. No. 11,209,654 (Lewis, Dec. 28, 2021, "Digital Eyewear System and Method for the Treatment and Prevention of Migraines and Photophobia") disclose digital eyewear for monitoring, detecting, and predicting, treating, and training patients for self-care of migraines and/or photophobia.

U.S. patent Ser. No. 10/990,175 (Forsland et al., Apr. 27, 2021, "Brain Computer Interface for Augmented Reality") discloses a brain computer interface (BCI) in a headset which includes an augmented reality (AR) display. U.S. patent application 20210121115 (Chiang, Apr. 29, 2021, "EEG Signal Monitoring Adapter Device Configurable on Eyewear") discloses an EEG adapter device for eyewear which can be worn invisibly and continuously. U.S. patent application 20210124422 (Forsland, Apr. 29, 2021, "Nonverbal Multi-Input and Feedback Devices for User Intended Computer Control and Communication of Text, Graphics and Audio") discloses sensors which detect a person inputting gestures.

U.S. patent application 20210282695 (Goldstein et al., Sep. 16, 2021, "Personal Apparatus for Conducting Electroencephalography") discloses an apparatus for conducting electroencephalography while allowing for secure and easy application to a person's forehead. U.S. patent application 20210338128 (Le Lous et al., Nov. 4, 2021, "Sensor for Measuring a Biological Potential") discloses a measurement electrode comprising a base and at least one leg. U.S. patent application 20210353200 (Xu et al., Nov. 18, 2021, "Electrode for Potential Acquisition of a Surface and Manufacturing Method Thereof") discloses an electrode with at least two pins.

U.S. patent application 20210361235 (Li et al., Nov. 25, 2021, "Electroencephalogram Electrode Cap") discloses an electroencephalogram electrode cap. U.S. patent application 20220000407 (Ludwig et al., Jan. 6, 2022, "Dry Electrodes") discloses dry electrodes comprising electrically conductive particles with points that protrude from a supporting layer. U.S. patent application 20220004257 (Keller et al., Jan. 6, 2022, "Headware for Computer Control") and U.S. patent Ser. No. 11/747,903 (Keller et al., Sep. 5, 2023, "Headware for Computer Control") disclose a head-worn device with a first arm that is pivotally coupled to a body portion and a second arm that is pivotally coupled to the body portion. U.S. patent application 20220031217 (Kidmose et al., Feb. 3, 2022, "Electrode for Detecting Bioelectrical Signals") discloses an electrode with a coating of iridium oxide.

U.S. patent Ser. No. 11/241,183 (Leuthardt et al., Feb. 8, 2022, "EEG Headsets with Precise and Consistent Electrode Positioning") discloses EEG headset designs which improve upon prior art headsets. U.S. patent Ser. No. 11/272,870 (Katnani et al., Mar. 15, 2022, "Non-Invasive Systems and Methods for Detecting Mental Impairment") discloses a non-invasive mental impairment detection system and method. U.S. patent Ser. No. 11/301,044 (Chevillet et al., Apr. 12, 2022, "Wearable Brain Computer Interface") discloses a Brain Computer Interface (BCI) with a light source subsystem.

U.S. patent Ser. No. 11/363,980 (Dauguet et al., Jun. 21, 2022, "Device for Measuring and/or Stimulating Brain Activity") discloses a device for measuring and/or stimulating brain activity which includes a removable support which extends over the top of a person's head. U.S. patent application 20220211313 (Lee, Jul. 7, 2022, "Dry Electroencephalographic Electrode") discloses a dry electrode with a plurality of protrusions distributed in a comb shape. U.S. patent application 20220233123 (Telfer et al., Jul. 28, 2022, "Method and Apparatus for Motion Dampening for Biosignal Sensing and Influencing") discloses motion dampening electroencephalography (EEG), electrocardiogram (EKG), photoplethysmography (PPG), electromyography (EMG), and temperature devices for measuring bio-activity signals from a body.

U.S. patent application 20220276707 (Barascud et al., Sep. 1, 2022, "Brain-Computer Interface") discloses an adaptive calibration method in a brain-computer interface. U.S. patent Ser. No. 11/471,088 (Parvizi et al., Oct. 18, 2022, "Handheld or Wearable Device for Recording or Sonifying Brain Signals") discloses a handheld device for sonifying electrical signals from a person. U.S. patent Ser. No. 11/540,759 (Flood et al., Jan. 3, 2023, "Biosignal Headphones") discloses headphones with electrodes. U.S. patent application 20230018247 (Elias, Jan. 19, 2023, "Brain-Activity Actuated Extended-Reality Device") discloses the use of quantum sensors in an extended reality device. U.S. patent application 20230014065 (Hanein et al., Jan. 19, 2023, "System and Method for Mapping Muscular Activation") discloses a system for determining muscle activation using a set of electrode adhered to a person's skin.

U.S. patent application 20230031613 (Fleury, Feb. 2, 2023, "Wearable Device") discloses a wearable device with a flexible and extendable body which encircles a portion of a person's body. U.S. patent application 20230043938 (Kele, Feb. 9, 2023, "Flexible Electroencephalography Headset") and U.S. patent Ser. No. 11/744,504 (Kele et al., Sep. 5, 2023, "Flexible Electroencephalography Headset") discloses electrode bodies which are elastically interconnected by spring elements. U.S. patent Ser. No. 11/583,231 (Yee et al., Feb. 21, 2023, "Adjustable Electrode Headset") discloses an electroencephalography headset with straps which adjust the size and shape of the headset.

U.S. patent Ser. No. 11/612,331 (Wyeth et al., Mar. 28, 2023, "Headset Device for Detecting Fluid in Cranium Via Time Varying Magnetic Field Phase Shifts and Harmonics of Fundamental Frequencies") discloses a diagnostic method for monitoring changes in a fluid medium in a person's head. U.S. patent Ser. No. 11/617,897 (Wingren, Apr. 4, 2023, "Head Worn Electronic Device") discloses a frame with first and second light emitters which is worn on a person's head. U.S. patent Ser. No. 11/622,709 (Gunasekar et al., Apr. 11, 2023, "Headset and Electrodes for Sensing Bioelectrical Potential and Methods of Operation Thereof") discloses a headset with a left junction, a right junction, a plurality of length-adjustable bands connecting the left and the right junctions, and electrodes.

U.S. patent Ser. No. 11/642,081 (Kentin et al., May 9, 2023, "Electrode Headset") discloses a head covering with holes and an electrode assembly which aligns with the holes. U.S. patent application 20230165503 (Coyle, Jun. 1, 2023, "Flexible Electrical Measurement Apparatus") discloses an electrode with a central portion and a plurality of legs which extend radially outwards from the central portion. U.S. patent application 20230172468 (Kaplan et al., Jun. 8, 2023, "PPG and ECG Sensors for Smart Glasses") discloses smart glasses with photoplethysmography and electrocardiogram sensors.

U.S. patent Ser. No. 11/749,426 (Futashima et al., Sep. 5, 2023, "Method for Producing Bioelectrode") discloses a method for producing a bioelectrode comprising silicone rubber and a silver powder. U.S. patent Ser. No. 11/751,796 (Han et al., Sep. 12, 2023, "Systems and Methods for Neuro-Feedback Training Using Video Games") discloses a method for neurofeedback training including determining a brainwave signal frequency distribution. U.S. patent application 20230320669 (Desai et al., Oct. 12, 2023, "Real-Time In-Ear Electroencephalography Signal Verification") discloses a real-time in-ear EEG signal verification system.

U.S. patent Ser. No. 11/850,055 (Hiratsuka, Dec. 26, 2023, "Electroencephalographic Data Analysis System, Information Processing Terminal, Electronic Device, and Method of Presenting Information for Dementia Examination") discloses an electronic device to acquire and analyze electroencephalogram data for examination of cognitive function. U.S. patent Ser. No. 11/852,901 (Howell et al., Dec. 26, 2023, "Wireless Headset Supporting Messages and Hearing Enhancement") discloses an eyeglass frame with a circuit board and electrical components. U.S. patent application 20240138745 (Yonce et al., May 2, 2024, "Fieldable EEG System, Architecture, and Method") discloses a fieldable EEG signal monitoring device, system, and method which is configured to receive and analyze EEG signals.

There is also relevant art in the non-patent literature. (Acar, 2019), "Wearable and Flexible Textile Electrodes for Biopotential Signal Monitoring: A Review," Electronics, 2019, 8(5), 479, presents a systematic review of wearable textile electrodes for physiological signal monitoring. (Casson, 2019), "Wearable EEG and Beyond," Biomedical Engineering Letters, January, 2019, 9(1), 53-71, reviews recent progress on electrodes used to make connections to the head and the physical EEG hardware. (Chen, 2014), "Soft, Comfortable Polymer Dry Electrodes for High Quality ECG and EEG Recording," Sensors, Dec. 10, 2014, 14(12), 23758-80, discloses dry electrodes fabricated from EPDM rubber containing various additives for optimum conductivity, flexibility and ease of fabrication.

(Chen, 2016), "Polymer-Based Dry Electrodes for Biopotential Measurements," Thesis, Arenberg Doctoral School, 2016, investigates the mechanical properties of the polymer dry electrodes with compression tests for elastic modulus and compliance characterization. (Chi, 2010), "Dry-Contact and Noncontact Biopotential Electrodes: Methodological Review," IEEE Reviews in Biomedical Engineering, 2010, 3, 106-119, explores the use of dry/noncontact electrodes for clinical use by explaining the electrical models for dry, insulated and noncontact electrodes and showing performance limits, along with measured data. (Chlaihawi, 2018), "Development of Printed and Flexible Dry ECG Electrodes," Sensing and Bio-Sensing Research, 2018, 20, 9-15, discloses printed, flexible and wearable dry electrodes for monitoring electrocardiogram (ECG) signals without any skin preparation or wet gel.

(Flumeri, 2019), "The Dry Revolution: Evaluation of Three Different EEG Dry Electrode Types in Terms of Signal Spectral Features, Mental States Classification and Usability," Sensors, Mar. 19, 2019, 19(6), 1365, compares three different dry electrode types: gold-coated single pin, multiple pins and solid-gel. (Fu, 2020), "Dry Electrodes for Human Bioelectrical Signal Monitoring," Sensors, Jun. 29, 2020, 20(13), 3651, gives a retrospective overview of the development of dry electrodes used for monitoring bioelectrical signals, including sensing principles, material selection, device preparation, and measurement performance. (Gao, 2018), "Soft Pin-Shaped Dry Electrode with Bristles for EEG Signal Measurements," Sensors and Actuators, 2018, Vol. 283, 348-361, presents a novel soft pin-shaped dry electrode for electroencephalography recording.

(Hsu, 2014), "Developing Barbed Microtip-Based Electrode Arrays for Biopotential Measurement," Sensors, 2014, 14(7), 12370-12386, discloses the fabrication of barbed microtip-based electrode arrays via silicon wet etching. (Kocturova, 2019), "Comparison of Dry Electrodes for Mobile EEG System," 2019, evaluates two types of comb electrodes: one based on a Ag—AgCl alloy and one based on a flexible conductive polymer. (Krachunov, 2016), "3D Printed Dry EEG Electrodes," Sensors, 2016, 16(10), 1635, presents a novel methodology for the design and manufacture of dry electrodes using low cost desktop 3D printers.

(Lau-Zhu, 2019), "Mobile EEG in Research on Neurodevelopmental Disorders: Opportunities and Challenges," Developmental Cognitive Neuroscience, 2019, Vol. 36, presents a brief overview of recent developments in mobile EEG technologies. (Lee, 2015), "Reverse-Curve-Arch-Shaped Dry EEG Electrode for Increased Skin-Electrode Contact Area on Hairy Scalps," Electronics Letters, Oct. 1, 2015, discloses reverse-curve-arch-shaped dry EEG electrodes for use in increasing the skin-electrode contact area on hairy scalps. (Lopez-Gordo, 2014), "Dry EEG Electrodes," Sensors, Jul. 18, 2014, 14(7), 12847-70, reviews current approaches to developing dry EEG electrodes for clinical and other applications.

(Mota, 2013), "Development of a Quasi-Dry Electrode for EEG Recording," Sensors and Actuators, 2013, Vol. 199, 310-317, reports on the development of a novel polymer-based electrode prototype for electroencephalography (EEG) between classic "wet" and "dry" electrodes. (Olesen, 2020), "Development and Assessment of Electrodes and Instrumentation for Plantar Skin Impedance Measurements," Thesis, Master in Electronics, Informatics and Technology, University of Oslo, Autumn, 2020, describes the development and testing of electrodes for plantar bioimpedance measurements. (Ouyang, 2021), "Application of Intrinsically Conducting Polymers in Flexible Electronics," SmartMat, Aug. 18, 2021, 2, discusses the use of intrinsically conducting polymers (ICPs), such as polyacetylene, polyaniline, polypyrrole, polythiophene, and poly(3,4-ethylenedioxythiophene) (PEDOT) for dry electrodes.

(Ruffini, 2008), "First Human Trials of a Dry Electrophysiology Sensor Using a Carbon Nanotube Array Interface," Sensors and Actuators, Jun. 15, 2008, 144, reports the results from the first human trials of a new dry electrode sensor for surface biopotential applications, wherein the contact surface of the electrode is covered with carbon nanotubes. (Shad, 2020), "Impedance and Noise of Passive and Active Dry EEG Electrodes: A Review," IEEE Sensors Journal, 7/27/2020, reviews the impedance and noise of passive and active dry EEG electrodes. (Sunwoo, 2020), "Advances in Soft Bioelectronics for Brain Research and Clinical Neuroengineering," Matter, 2020, 3(6) 1923-1947, reviews recent technological advances using unconventional soft materials, such as silicon/metal nanowires, functionalized hydrogels, and stretchable conductive nanocomposites. (Zhang, 2020), "Fully Organic Compliant Dry Electrodes Self-Adhesive to Skin for Long-Term Motion-Robust Epidermal Biopotential Monitoring," Nature Communications, 2020, 11, 4683, reports an intrinsically conductive polymer dry electrode with excellent self-adhesiveness, stretchability, and conductivity.

SUMMARY OF THE INVENTION

Disclosed herein is a head-worn device (e.g. headband, halo, or headset) with sensors (e.g. electrodes) which record brain activity. In an example, the device can be undulating with concave undulations which rest on the tops of a person's ears. In an example, the device can further comprise right side and left side ear prongs (e.g. arms, segments, or portions) which curve around the posterior and upper surfaces of a person's right and left ears.

BRIEF INTRODUCTION TO THE FIGURES

FIG. 23 shows a head-worn EEG device, wherein the device has upper and lower bands which encircle between 40% and 70% of the circumference of a person's head, including looping around the rear of the person's head.

DETAILED DESCRIPTION OF THE FIGURES

Figure 1:
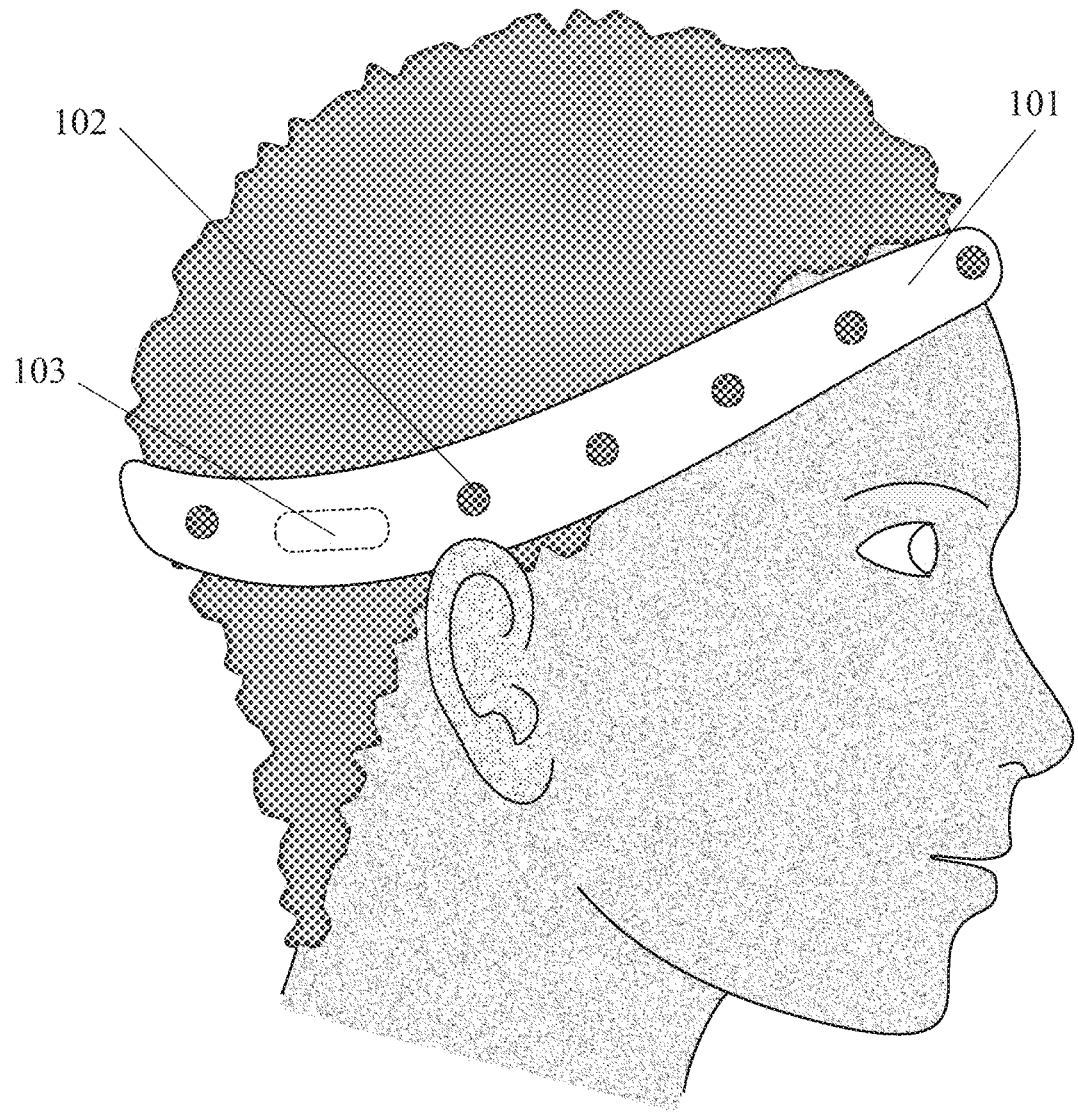
FIG. 1 shows an EEG headband whose rear half is wider than its front half.

Before discussing the specific embodiments of this invention which are shown in FIGS. 1 through 35, this disclosure provides an introductory section which covers some of the general concepts, components, and methods which comprise this invention. Where relevant, these concepts, components, and methods can be applied as variations to the examples shown in FIGS. 1 through 35 which are discussed afterwards.

In an example, a head-worn device for recording brain signals can comprise: an arcuate electrode holder, wherein the electrode holder is a headband, halo, or headset which is configured to be worn around at least 40% of the circumference of a person's head; a plurality of electrodes, wherein the electrodes are held in place by the electrode holder, and wherein the electrodes are configured to receive electrical and/or electromagnetic signals from the person's brain; and an electronics unit, wherein the electronics unit further comprises a data processor, a data transmitter and/or data receiver, and a power source.

In an example, a front portion of the device can span across the person's forehead. In an example, a rear portion of the device can span around the rear of the person's head. In an example, the electrode holder can have undulations. In an example, the undulations can be sinusoidal undulations. In an example, the undulations can be substantially vertical when the person's head is upright. In an example, there can be at least two undulations on each side of the person's head. In an example, an undulation on a side of the person's head can rest on top of the person's ear. In an example, the undulation which rests on top of the person's ear can have a downward-opening concavity.

In an example, a head-worn device for recording brain signals can comprise: an arcuate electrode holder, wherein the electrode holder is a headband, halo, or headset which is configured to be worn around at least 40% of the circumference of a person's head; a plurality of electrodes, wherein the electrodes are held in place by the electrode holder, and wherein the electrodes are configured to receive electrical and/or electromagnetic signals from the person's brain; and an electronics unit, wherein the electronics unit further comprises a data processor, a data transmitter and/or data receiver, and a power source.

In an example, the electrode holder can further comprise: a front arm, band, segment, portion, or loop which is configured to span across a person's forehead; right and left ear prongs, arms, segments, or portions which are configured to curve closely around both the posterior and upper surfaces of the person's right and left ears; and right and left posterior arms, segments, or portions which are configured to extend in posterior and downward directions from the person's right and left ears. In an example, the electrode holder can span a portion of the person's occipital lobe.

In an example, the electrode holder can further comprise: an arcuate element which is configured to loop, from one ear to the other ear, around a front-central portion of the person's head; two upward-protruding arcuate elements which are configured to rise up from an area behind the person's ears and terminate on the right and left sides of the person's head, respectively; and two downward-protruding arcuate elements which are configured to drop down from an area behind the person's ears and terminate in areas below the person's ears, respectively. In an example, the electrode holder can span a portion of the person's occipital lobe.

In an example, a head-worn device for recording brain signals can comprise: an arcuate electrode holder, wherein the electrode holder is a headband, halo, or headset which is configured to be worn around at least 40% of the circumference of a person's head; a plurality of electrodes, wherein the electrodes are held in place by the electrode holder, and wherein the electrodes are configured to receive electrical and/or electromagnetic signals from the person's brain; and an electronics unit, wherein the electronics unit further comprises a data processor, a data transmitter and/or data receiver, and a power source.

In an example, the electrode holder can span between 40% and 80% of the circumference of the person's head. In an example, the electrode holder can loop around the rear of the person's head. In an example, the electrode holder can loop around the rear of the person's head at a height which is greater than the tops of the person's ears when the person's head is upright. In an example, the electrode holder can loop around the rear of the person's head at a height which is less than the height of the person's ears when the person's head is upright.

In an example, the electrode holder can have two posterior-facing concave undulations, one on each side of the person's head, wherein the peaks of these undulations are on the sides of the person's forehead. In an example, the electrode holder can have two posterior-facing concave undulations, one on each side of the person's head, wherein the most-anterior portions of these undulations are on the sides of the person's forehead.

In an example, the electrode holder can: start at a location behind an ear; curve upward around the back of the ear; then curve forward to a location on a side of the person's forehead; then curve upward and backward to form an undulation with a posterior-facing concavity; then curve backward to loop around the rear of the person's head; and then continue in a symmetric manner on an opposite side of the person's head, ending at an ear on the opposite side.

In an example, a device can be used for medical applications. In an example, a device can be used for detection and/or prediction of neurological seizures. In an embodiment, a device can function as a BCI (Brain-to-Computer Interface) for control of body prostheses. In an example, a device can be used for evaluation of a person's alertness and/or level of fatigue. In an example, a device can be used for computer gaming. In an example, a device can be used for telepresence applications. In an embodiment, a device can be used to control the operation of a medical device such as pacemaker or drug pump. In an example, a device can be used to evaluate a person's response to a product or commercial for a product. In an embodiment, a device can be used to monitor brain activity for medical purposes. In an example, a device can function as a BCI (Brain-to-Computer Interface). In an example, a device can function as a BCI (Brain-to-Computer Interface) for remote control of robots. In an example, a device can function as a BCI (Brain-to-Computer Interface) for telerobotics.

In an embodiment, a portion (e.g. portion, arm, segment, or loop) of an electrode-holding ring, headband, halo, or headset spanning the front half of a person's head can have a rear-facing concavity. In an example, a portion (e.g. portion, arm, segment, or loop) of an electrode-holding ring, headband, halo, or headset spanning the rear half of a person's head can have an downward-facing concavity. In an embodiment, a portion (e.g. portion, arm, segment, or loop) of an electrode-holding ring, headband, halo, or headset which loops over the upper half (e.g. the top) of a person's head can have an front-facing concavity. In an example, a posterior half of an electrode-holding ring, headband, halo, or headset can loop over the posterior half of the top of the person's head and the anterior half of an electrode-holding ring, headband, halo, or headset can loop around the person's forehead, forming an overall saddle or hyperboloidal shape on the person's head.

In an embodiment, a section (e.g. section, segment, arm or portion) of an electrode-holding ring, headband, halo, or headset can have a bell-shaped curve shape. In an example, a section (e.g. section, segment, arm or portion) of an electrode-holding ring, headband, halo, or headset can have a half-sinusoidal curve shape. In an example, a section (e.g. section, segment, arm or portion) of an electrode-holding ring, headband, halo, or headset can have a portion of a spiral or helical shape. In an example, a section (e.g. section, segment, arm or portion) of an electrode-holding ring, headband, halo, or headset can have a sinusoidal curve shape. In an example, a section of an electrode-holding ring, headband, halo, or headset can be shaped like the perimeter of a hyperbolic paraboloid.

In an example, a side of an electrode-holding ring, headband, halo, or headset can have a shape like that of a parabolic curve which has been rotated 90 degrees so that its peak faces toward the front of a person's head and its opening faces toward the rear of the person's head. In an embodiment, a side of an electrode-holding ring, headband, halo, or headset can have a shape like that of a parabolic curve which has been rotated 90 degrees so that its peak faces toward the front of a person's head and its opening faces toward the rear of the person's head, wherein one tail of the curve reaches the person's ear and the other tail of the curve reaches the top of the person's head. In an example, an arcuate anterior portion (e.g. portion, arm, segment, or loop) of an electrode-holding ring, headband, halo, or headset can have an front-facing concavity.

In an embodiment, an arcuate posterior portion (e.g. portion, arm, segment, or loop) of an electrode-holding ring, headband, halo, or headset can have an upward-facing concavity. In an example, an arcuate posterior portion (e.g. portion, arm, segment, or loop) of an electrode-holding ring, headband, halo, or headset can have a rear-facing concavity. In an embodiment, an electrode-holding ring, headband, halo, or headset can have a spiral, helical, and/or coil shape. In an example, an electrode-holding ring, headband, halo, or headset can include a main ring or halo with an undulating, serpentine, and/or sinusoidal shape. In an example, an electrode-holding ring, headband, halo, or headset can have a generally circular, elliptical, oval, or egg shape except for two undulations comprising an undulation with a downward-opening concavity over each ear.

In an example, an electrode-holding ring, headband, halo, or headset can have a generally circular, elliptical, or oval shape except for a vertical undulation over a person's outer ear (e.g. auricle). In an example, an electrode-holding ring, headband, halo, or headset can have sinusoidal waves and/or undulations. In an example, an electrode-holding ring, headband, halo, or headset can have sinusoidal waves and/or undulations with an amplitude of at least two inches. In an embodiment, an electrode-holding ring, headband, halo, or headset can have at least two upward-opening concavities on a right side of a person's head and at least two upward-opening concavities on the left side of the person's head. In an example, an electrode-holding ring, headband, halo, or headset can have a saddle and/or hyperboloidal shape. In an embodiment, an electrode-holding ring, headband, halo, or headset can be shaped like the perimeter of a hyperbolic paraboloid.

In an example, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the partial ring has a rear-facing concavity. In an example, a head-worn electrode-holding device can comprise a coil or spiral on each side of a person's head. In an example, a perimeter of an electrode-holding ring, headband, halo, or headset can have saddle or hyperboloidal shape as if, perhaps inspired by Salvatore Dali, a circular or oval ring had been placed on top of a person's head and then melted so that its sides drooped downward. In an example, a portion (e.g. portion, arm, segment, or loop) of an electrode-holding ring, headband, halo, or headset spanning the front half of a person's head can have an upward-facing concavity.

In an example, an electrode-holding ring, headband, halo, or headset can include a spiral and/or helical segment. In an embodiment, an undulating electrode-holding ring, headband, halo, or headset comprises: a posterior loop (e.g. loop, portion, section, or segment) which is worn on the posterior-upper quartile of a person's head, wherein the posterior loop has a forward-facing concavity; a right-side loop (e.g. loop, portion, section, or segment) which is worn on the right side of the person's head, wherein the right-side loop has a spiral or coil shape; and a left-side loop (e.g. loop, portion, section, or segment) which is worn on the left side of the person's head, wherein the left-side loop has a spiral or coil shape. In an example, each side (e.g. right and left) of an electrode-holding ring, headband, halo, or headset can have an undulating, serpentine, and/or sinusoidal shape. In an example, one side (e.g. right or left) of an electrode-holding ring, headband, halo, or headset can have a U shape.

In an example, an electrode-holding ring, headband, halo, or headset can encircle the entire lateral (e.g. horizontal) circumference a person's head. In an example, an electrode-holding ring, headband, halo, or headset can encircle between 40% and 80% of a person's head. In an example, an electrode-holding ring, headband, halo, or headset can span (e.g. partially encircle) the anterior half of a person's head.

In an embodiment, a headband, halo, or headset for recording brain activity can comprise: a front portion (e.g. portion, segment, or loop) which spans across a person's forehead from one ear to the other ear; a right-side rear portion (e.g. portion, arm, or segment) which extends rearward and downward from the person's right ear; a left-side rear portion (e.g. portion, arm, or segment) which extends rearward and downward from the person's left ear; a right-side flexible posterior-ear prong (e.g. prong, arm, or segment) which curves around the posterior and upper surfaces of the person's right ear (e.g. where the auricle connected to the rest of the person's head); a left-side flexible posterior-ear prong (e.g. prong, arm, or segment) which curves around the posterior and upper surfaces of the person's left ear (e.g. where the auricle connected to the rest of the person's head); a plurality of sensors (e.g. electrodes) for recording brain activity; and an electronics unit which includes a data processor, a data transmitter, and a power source.

In an example, a headband, halo, or headset for recording brain activity can comprise: a front portion (e.g. portion, segment, or loop) which spans across a person's forehead; a right side (e.g. temple) portion (e.g. portion, arm, or segment) which spans from the person's right ear to the front portion; a left side (e.g. temple) portion (e.g. portion, arm, or segment) which spans from the person's left ear to the front portion; a right-side rear portion (e.g. portion, arm, or segment) which extends rearward and downward from the person's right ear; a left-side rear portion (e.g. portion, arm, or segment) which extends rearward and downward from the person's left ear; a right-side flexible ear prong (e.g. prong, arm, or segment) which curves around the posterior and upper surfaces of the person's right ear (e.g. where the auricle connected to the rest of the person's head); a left-side flexible ear prong (e.g. prong, arm, or segment) which curves around the posterior and upper surfaces of the person's left ear (e.g. where the auricle connected to the rest of the person's head); a plurality of sensors (e.g. electrodes) for recording brain activity; and an electronics unit which includes a data processor, a data transmitter, and a power source.

In an embodiment, an electrode-holding ring, headband, halo, or headset can undulate with a wave amplitude of at least two inches as it encircles a person's head. In an example, each side (e.g. right and left) of an electrode-holding ring, headband, halo, or headset can have multiple (sinusoidal) undulations. In an example, a device can have horizontal and/or radial undulations or waves around a central circumferential axis, wherein the central circumferential axis is circular, elliptical, or oval. In an example, a posterior arm (e.g. arm, band, segment, or portion) of a device which loops around the back of a person's head can have an undulating (e.g. sinusoidal) shape.

In an example, an anterior portion (e.g. rear half) of an electrode-holding ring, headband, halo, or headset can be wider than a posterior portion (e.g. front half) of the ring, headband, halo, or headset. In an example, an electrode-holding ring, headband, halo, or headset can have an undulating width around its circumference. In an example, an electrode-holding ring, headband, halo, or headset can have a uniform width as it encircles a person's head. In an embodiment, an undulating rear-tilted headband can have a variable width, wherein front and rear portions of the device are wider than side portions of the device. In an example, side portions (e.g. rear half) of an electrode-holding ring, headband, halo, or headset can be wider than posterior and anterior portions (e.g. front half) of the ring, headband, halo, or headset. In an embodiment, the posterior half of an electrode-holding ring, headband, halo, or headset can be wider than the anterior half of the electrode-holding ring, headband, halo, or headset.

In an example, a (right or left) side of an electrode-holding ring, headband, halo, or headset worn on a person's head can comprise: a posterior (one-third) section, a middle (one-third) section, and an anterior (one-third) section, wherein the posterior section has a substantially constant height (e.g. is level) when the person's head is upright, wherein the anterior section has a substantially constant height (e.g. is level) when the person's head is upright, and wherein the middle section is between the posterior and anterior sections, and wherein serpentine with a variable height.

In an embodiment, a middle third of a side (e.g. right or left) of an electrode-holding ring, headband, halo, or headset can have a serpentine shape, wherein the posterior end of this shape meets a substantially-level posterior third section of an electrode-holding ring, headband, halo, or headset and the anterior end of this shape meets a substantially-level anterior third section of an electrode-holding ring, headband, halo, or headset. In an example, an electrode-holding ring, headband, halo, or headset can have a forward-upward slope at an angle between 30 and 60 degrees relative to a horizontal plane when a person's head is upright.

In an example, when a person's head is upright, an electrode-holding ring, headband, halo, or headset can be virtually divided (in a posterior-to-anterior manner) into three sections; wherein these three portions comprise a posterior section, a middle section, and an anterior section; wherein the posterior section has a substantially-constant first height (e.g. is substantially level at this first height), wherein the anterior section has a substantially-constant second height (e.g. is substantially level at this second height), wherein the second height is at least one inch greater than the first height, and wherein the middle section comprises an arcuate transition from the first height to the second height.

In an example, a device with sensors (e.g. electrodes) for monitoring brain activity can comprise a partial ring (e.g. arc) portion (e.g. arm, segment, or section) on each side (e.g. right and left) of a person's head. In an example, a device with sensors (e.g. electrodes) for monitoring brain activity can comprise a partial ring (e.g. arc) portion (e.g. arm, segment, or section) with an anterior-facing concavity on each side (e.g. right and left) of a person's head. In an example, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the partial ring has a forward-facing convexity.

In an example, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the partial ring loops over the upper-anterior quadrant of the person's head. In an embodiment, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the ring and the partial ring are connected to each other, and wherein the connection of the ring and the partial ring forms an acute forward-facing angle, and wherein this angle is between 40 and 50 degrees.

In an example, a partial ring (e.g. arc) portion of a device intersects a ring portion of this device, forming a forward-facing acute angle at this intersection. In an embodiment, a partial ring portion of a device with sensors (e.g. electrodes) for monitoring brain activity can have a parabolic shape. In an example, a ring portion of a device and a partial ring portion of the device can form a forward-facing angle between 5 and 65 degrees where they intersect. In an embodiment, an electrode-holding ring, headband, halo, or headset can comprise: a ring or halo portion which encircles a person's head; and two partial ring (e.g. arc) portions which are connected to the ring or halo portion, wherein partial ring portions of the device connects to the ring or halo portion at locations which are within two inches of the front-to-back midpoint of the side of the person's head.

In an example, an electrode-holding device can comprise: an upper ring, headband, or halo which encircles a person's head; and a lower ring, headband, or halo which encircles the person's head, wherein the lower ring is at a lower height than the upper ring when the person's head is upright. In an example, an electrode-holding device can comprise: an upper ring, headband, or halo which encircles a person's head; and a lower ring, headband, or halo which encircles the person's head, wherein the upper ring and the lower ring are connected to each other directly above (e.g. vertically above) the person's ears.

In an example, an anterior portion of an electrode-holding device can comprise an upper band (e.g. segment, section, portion, arm, or band) and a lower band (e.g. segment, section, portion, arm, or band), wherein the upper band the lower band are substantially parallel as they span the rear of the person's head. In an example, an electrode-holding device can comprise an upper band (e.g. segment, section, portion, arm, or band) and a lower band (e.g. segment, section, portion, arm, or band), wherein the upper band the lower band are substantially parallel as they span the sides of the person's head.

In an example, a device with sensors (e.g. electrodes) for measuring brain activity can comprise a posterior-to-anterior series of side-to-side (e.g. right to left) loops (e.g. arms, loops, segments, arcs, or branches). In an example, a device with sensors (e.g. electrodes) for measuring brain activity can comprise a posterior-to-anterior series of side-to-side (e.g. right to left) loops (e.g. arms, loops, segments, arcs, or branches), wherein a posterior loop spans the back of a person's head, a middle loop spans the top of the person's head, and an anterior loop spans the person's forehead. In an example, a device with sensors (e.g. electrodes) for measuring brain activity can comprise a posterior-to-anterior series of three side-to-side (e.g. right to left) loops (e.g. arms, loops, segments, arcs, or branches), wherein these loops are connected to each other on the sides (e.g. right and left) of a person's head.

In an example, a device with sensors (e.g. electrodes) for measuring brain activity can comprise a posterior-to-anterior series of side-to-side (e.g. right to left) loops (e.g. arms, loops, segments, arcs, or branches), wherein a posterior loop has a forward-facing concavity, a middle loop spans the top of the person's head, and an anterior loop has a posterior-facing concavity. In an embodiment, a device with sensors (e.g. electrodes) for measuring brain activity can comprise a posterior-to-anterior series of undulating (e.g. sinusoidal) side-to-side (e.g. right to left) loops (e.g. arms, loops, segments, arcs, or branches). In an example, an electrode-holding ring, headband, halo, or headset comprises: a ring (e.g. ring, band, or halo) which encircles a person's head around the posterior half of the person's head and also across the person's forehead; and an upper-anterior arm (e.g. arm, loop, segment, arc, or branch) which spans from a location on a middle portion of the ring over the upper surface of the upper-anterior quadrant of the person's head.

In an embodiment, an electrode-holding ring, headband, halo, or headset can comprise a posterior-to-anterior series of three side-to-side loops which are connected to each other on the sides of a person's head, directly above the person's ears. In an example, an electrode-holding ring, headband, halo, or headset can include and a posterior portion (e.g. arm, loop, segment, arc, or branch) which loops around the rear of a person's head and an anterior portion (e.g. arm, loop, segment, arc, or branch) which loops across the person's forehead, wherein the posterior portion has an upward-facing concavity and the anterior portion has a downward-facing concavity.

In an embodiment, a device can include an anterior loop (e.g. loop, portion, band, arm, section) which spans completely across a person's forehead. In an example, an electrode-holding ring, headband, halo, or headset can comprise: a posterior-ear segment (e.g. prong, arm, protrusion, loop, or segment) which is worn around at least a portion of the rear-facing surface of the person's ear; a side segment which spans from the posterior-ear segment (e.g. prong, arm, protrusion, loop, or segment) to the person's temple, a side portion of the person's face, and/or a side portion of the person's forehead; a top segment which spans from the side segment to the top of the person's head; at least one sensor (e.g. electrode); and an electronics unit which includes a data processor, a data transmitter, and a power source.

In an example, a forehead loop of an electrode-holding ring, headband, halo, or headset can have a shape selected from the group consisting of: arc, wave, undulation, semi-circle, semi-oval, half-sinusoidal curve, bell-shaped curve, and conic section. In an example, an anterior segment of a device can span, protrude, extend, or curve from a person's ear to a position which is between one quarter and three-quarters of the way between the ear and the person's temple, eye, and/or forehead. In an example, an electrode-holding ring, headband, halo, or headset can include a loop (e.g. loop, curve, bulge, or undulation) with a rear-facing concavity which is anterior to a person's ear, wherein this loop spans the person's temple and/or part of the person's forehead.

In an example, an electrode-holding ring, headband, halo, or headset can include a forehead loop (e.g. forehead loop, portion, segment, arm, or branch) which spans across a person's forehead. In an example, an electrode-holding ring, headband, halo, or headset can include a forehead loop (e.g. forehead loop, portion, segment, arm, or branch) which spans across a person's forehead, wherein this forehead loop has a posterior-facing concavity. In an example, an electrode-holding ring, headband, halo, or headset comprises: a ring (e.g. ring, band, or halo) which encircles the person's head around the posterior half of the person's head and also across the person's forehead; and an upper-posterior arm (e.g. arm, branch, or loop) which spans from a location on a middle portion of the ring over the upper surface of the upper-posterior quartile of the person's head.

In an example, a posterior portion of an electrode-holding device can comprise an upper band (e.g. segment, section, portion, arm, or band) and a lower band (e.g. segment, section, portion, arm, or band), wherein the upper band the lower band are substantially parallel as they span the rear of the person's head. In an example, a posterior segment (e.g. segment, arm, loop, or portion) of an electrode-holding ring, headband, halo, or headset extends backward and downward from the top of a person's outer ear (e.g. auricle) to span across the rear of the person's head. In an embodiment, a posterior portion (e.g. arm, segment, or loop) of an electrode-holding ring, headband, halo, or headset can loops around the back of a person's head at substantially the same height as the person's ears and an anterior portion (e.g. arm, segment, or loops) can loop around the person's forehead at a height which is greater than the height of the person's ears.

In an example, an electrode-holding ring, headband, halo, or headset can comprise a posterior arm (e.g. arm, segment, or portion) which loops around the back of a person's head and a upper arm (e.g. arm, segment, or portion) which loops over the top of the person's head, wherein the posterior arm and the upper arm are portions of the same continuous member, wherein the posterior arm has a downward-facing concavity, and wherein the upper arm has a forward-facing concavity. In an embodiment, an electrode-holding ring, headband, halo, or headset can loop over the top of a person's head, from the right side to the left side of the person's head. In an example, an electrode-holding ring, headband, halo, or headset can loop over the top of a person's head from one ear to the other ear, starting along the posterior surface of an outer ear (e.g. auricle), then curving forward and upward from the ear toward a side of the person's forehead (and/or temple) to form an undulation with a rear-facing concavity, and then curving backward and upward from the side of the person's forehead (and/or temple), and then curving upward over the top of the person's head.

In an embodiment, a device can comprise a bifurcating ring around a person's head, wherein the ring bifurcates as it spans the rear of the person's head. In an example, a device can comprise a bifurcating ring around a person's head, wherein the ring bifurcates and then reconverges as it spans the front of the person's head. In an example, a device can comprise a bifurcating ring which encircles a person's head. In an example, an electrode-holding device can be a bifurcating ring, halo, or headset which encircles a person's head, wherein the ring, halo, or headset bifurcates and then reconverges as it spans across the front of the person's head.

In an example, an electrode-holding device can be a bifurcating ring, halo, or headset which bifurcates as it loops around the back of the person's head. In an example, an electrode-holding device can be a bifurcating ring, halo, or headset which bifurcates as it spans around a person's ears. In an example, an electrode-holding ring, headband, halo, or headset can bifurcate and then reconverge as it spans the sides (e.g. right and left) of a person's head. In an example, an electrode-holding ring, headband, halo, or headset can bifurcate and then reconverge, wherein between 50% and 80% of the circumference of the ring, headband, halo, or headset is bifurcated.

In an embodiment, an electrode-holding ring, headband, halo, or headset can have a bifurcation which is posterior to a person's ears; wherein an anterior portion (e.g. portion, arm, or segment) of the ring, headband, halo, or headset comprises a single arm, band, or segment which spans across a person's forehead; and wherein the posterior portion of the ring, headband, halo, or headset includes an upper arm, band, or segment which loops around the back of the posterior-upper quadrant of the person's head and a lower arm, band, or segment which loops around the back of the posterior-lower quadrant of the person's head.

In an example, a side portion of an electrode-holding ring, headband, halo, or headset can have a concave undulation which is posterior to a person's ear. In an embodiment, a side portion of an electrode-holding ring, headband, halo, or headset can have a downward-opening concave undulation which is posterior to a person's ear. In an example, a device (e.g. ring portion of a device) can be generally circular, oval, elliptical, or egg-shaped except for two upward undulations (e.g. upward waves) above a person's ears, wherein the peaks of the undulations are at least one inch above the tops of person's ears and the troughs of the undulations are at least one inch below the tops of the person's ears.

In an embodiment, a device (e.g. headband) can be generally circular except for right-side and left-side undulating (e.g. sinusoidal or partially sinusoidal) sections which rest on top of the person's right and left ears, respectively. In an example, a device (e.g. headband) can be generally circular except for right-side and left-side concave sections which rest on top of the person's right and left ears, respectively. In an example, an electrode-holding ring, headband, halo, or headset can include an undulation with an upward-opening concavity which is anterior to a person's ear. In an example, an electrode-holding ring, headband, halo, or headset can include a downward undulation (e.g. a downward dip, curve, or loop) which is directly in front of the upper portion of a person's ear.

In an example, a device can include one or more ear prongs which curve around (e.g. span) 30%-60% of the circumference of the connection between a person's outer ear (e.g. auricle) and the rest of the person's head. In an example, a device with sensors (e.g. electrodes) for monitoring brain activity can comprise a front portion which spans a frontal area of a person's head. In an example, a device with sensors (e.g. electrodes) for monitoring brain activity can comprise: a front portion which spans across a person's forehead; a rear portion which spans part of the occipital area of a person's head; and a side portion between the front portion and the posterior portion.

In an example, a device with sensors (e.g. electrodes) for monitoring brain activity can comprise: a front portion which spans across a person's forehead; a rear portion which spans part of the occipital area of a person's head; a side portion between the front portion and the posterior portion; and a flexible electroconductive posterior-ear prong (e.g. prong, arm, segment) which curves around the posterior and upper surfaces of a person's ear (where the ear is connected to the rest of the person's head). In an example, an electrode-holding ring, headband, halo, or headset can include a posterior-ear segment (e.g. prong, arm, protrusion, loop, or segment) which curves, bends, loops, and/or hooks around the back of a person's ear.

In an example, an electrode-holding ring, headband, halo, or headset includes an anterior ear-engaging member (e.g. prong, arm, protrusion, loop, or segment) which curves, bends, loops, and/or hooks around the upper half of the anterior surface of a person's outer ear (e.g. auricle) and/or the connecting tissue between the auricle and the rest of the person's head. In an example, an electrode-holding ring, headband, halo, or headset includes a posterior ear-engaging member (e.g. prong, arm, protrusion, loop, or segment) which curves, bends, loops, and/or hooks around the upper half of the posterior surface of a person's outer ear (e.g. auricle) and/or the connecting tissue between the auricle and the rest of the person's head.

In an embodiment, an electrode-holding ring, headband, halo, or headset can comprise: a posterior-ear segment (e.g. prong, arm, protrusion, loop, or segment), wherein this posterior-ear segment (e.g. prong, arm, protrusion, loop, or segment) is configured to be worn on the rear-facing surface of a person's ear; an anterior-ear segment (e.g. prong, arm, protrusion, loop, or segment), wherein this anterior-ear segment (e.g. prong, arm, protrusion, loop, or segment) is configured to be worn on the front-facing surface of the person's ear; a forehead segment, wherein this forehead segment is configured to span from the person's ear to the person's temple, side portion of the person's face, and/or side portion of the person's forehead; a rear segment, wherein this rear segment is configured to span from the posterior-ear segment (e.g. prong, arm, protrusion, loop, or segment) or the forehead segment to the rear of the person's head; at least one sensor (e.g. electrode); and an electronics unit including a data processor, a data transmitter, and a power source.

In an example, an electrode-holding ring, headband, halo, or headset can include an arm (e.g. prong, arm, protrusion, loop, or segment) which extends downward from a main circumferential body of an electrode-holding ring, headband, halo, or headset, wherein the arm curves, bends, loops, and/or hooks around part of the anterior of the person's ear (e.g. the connecting portion of the auricle).

In an embodiment, an electrode-holding device (e.g. ring, headband, halo, or headset) can comprise one or more hub-and-spoke (e.g. radial) arrays of arms (e.g. arms, spokes, segments, and/or legs) which hold sensors (e.g. electrodes) on a person's head, wherein there is one hub-and-spoke array on each side (e.g. right and left) of the person's head. In an example, an electrode-holding device (e.g. ring, headband, halo, or headset) can comprise a hub-and-spoke (e.g. radial) arrays of arms (e.g. arms, spokes, segments, and/or legs) which hold sensors (e.g. electrodes) on a person's head, wherein the hub is located between a person's ear and the top of the person's head. In an embodiment, an electrode-holding device (e.g. ring, headband, halo, or headset) can comprise one or more hub-and-spoke (e.g. radial) arrays of arms (e.g. arms, spokes, segments, and/or legs), wherein there are six arms extending out radially from a hub, and wherein each arm holds a sensor (e.g. electrode) on a person's head.

In an example, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein angles between adjacent arms where they connect to the hub are all the same. In an embodiment, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein arms which extend in posterior or anterior directions are longer than arms which extend upwards or downwards from the hub.

In an example, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein the arms span 360 degrees of the perimeter of the hub. In an example, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein some of the arms are concave and some of the arms are convex. In an example, an electrode-holding device (e.g. ring, headband, halo, or headset) can comprise a hub-and-spoke array of electrode-holding arms (e.g. arms, spokes, segments, and/or legs) on each side (e.g. right and left) of a person's head.

In an example, an electrode-holding device (e.g. ring, headband, halo, or headset) can comprise a plurality of hub-and-spoke arrays of electrode-holding arms (e.g. arms, spokes, segments, and/or legs). In an example, an electrode-holding device (e.g. ring, headband, halo, or headset) can comprise a radial array of electrode-holding arms (e.g. arms, spokes, segments, and/or legs) on each side (e.g. right and left) of a person's head. In an example, an electrode-holding device (e.g. ring, headband, halo, or headset) can comprise a plurality of radial arrays of electrode-holding arms (e.g. arms, spokes, segments, and/or legs).

In an example, an electrode-holding ring, headband, halo, or headset can comprise a hexagonal (e.g. honeycomb) structure (e.g. mesh) which encircles a person's head. In an example, an electrode-holding ring, headband, halo, or headset can have openings (e.g. holes) in order to be permeable to gas and/or liquid. In an example, there can be at least one opening (e.g. hole) on each side (e.g. right and left) of an electrode-holding ring, headband, halo, or headset. In an example, there can be one or more openings (e.g. holes) in an electrode-holding ring, headband, halo, or headset. In an example, there can be one or more openings (e.g. holes) in a portion of an electrode-holding ring, headband, halo, or headset which spans the rear of a person's head.

In an embodiment, an electrode-holding ring, headband, halo, or headset can comprise an circumferential series (e.g. chain) of slidably-connected segments and/or components. In an example, an electrode-holding ring, headband, halo, or headset can comprise an circumferential series (e.g. chain) of detachable modular segments and/or components. In an embodiment, an electrode-holding ring, headband, halo, or headset can comprise multiple components which are movably-connected so that the circumference of the ring, headband, halo, or headset can be changed (e.g. customized to the shape of a specific person's head). In an example, an electrode-holding ring, headband, halo, or headset can comprise multiple components which are movably-connected so that the concavity of the ring, headband, halo, or headset can be changed (e.g. customized to the shape of a specific person's head).

In an embodiment, a device can be a ring, headband, halo, or headset which is made from an elastic textile and/or fabric. In an example, a device can comprise: an inner ring (e.g. ring or band) which is worn around a person's head, wherein the inner ring has a first level of elasticity, stretchability, or deformability; an outer ring (e.g. ring or band) which is worn around the person's head, wherein the outer ring has a second level of elasticity, stretchability, or deformability, wherein the inner ring is closer to the surface of the person's head than the outer ring, and wherein the second level is less than the first level. In an example, between 20% and 40% of the circumference of a ring, headband, halo, or headset can be made from an elastic textile and/or fabric. In an example, a device can comprise an elastic (e.g. stretchable textile or fabric) band which is worn around a person's head.

In an example, a device can have alternating elastic and stiff sections around its circumference. In an example, a perimeter of a headband (or halo) can further comprise a spring or other tensile member which causes the headband to exert pressure against the surface of the person's head to better hold the headband on the person's head and/or to better hold the sensors (e.g. electrodes) in proximity to the surface of the person's head. In an example, an anterior loop (e.g. forehead loop) of a device can be elastic or stretchable. In an example, a section (e.g. section or portion) of electrode-holding ring, headband, halo, or headset which spans the side of a person's above the person's ear can be more elastic and/or stretchable than other sections of the ring, headband, halo, or headset.

In an example, a sections (e.g. section or portion) of electrode-holding ring, headband, halo, or headset which span the sides of a person's above the person's ears can be more elastic and/or stretchable than other sections of the ring, headband, halo, or headset. In an example, an electrode-holding ring, headband, halo, or headset can have one or more relatively-inelastic sections (e.g. with a first level of elasticity and/or stretchability) and one or more relatively-elastic sections (e.g. with a second level of elasticity and/or stretchability), wherein the second level is greater than the first level. In an embodiment, an electrode-holding ring, headband, halo, or headset can have a relatively-inelastic section (e.g. with a first level of elasticity and/or stretchability) and a relatively-elastic section (e.g. with a second level of elasticity and/or stretchability), wherein the second level is greater than the first level, and wherein the relatively-elastic section is located on a posterior portion (e.g. posterior half) of the ring, headband, halo, or headset.

In an example, an electrode-holding ring, headband, halo, or headset can have relatively-inelastic sections and relatively-elastic sections, wherein these different sections comprise different segments of the lateral circumference of the electrode-holding ring, headband, halo, or headset. In an embodiment, an electrode-holding ring, headband, halo, or headset can comprise a circumferential series of alternating textile (e.g. textile or fabric) and hard polymer components which encircles a person's head. In an example, anterior and posterior sections of the circumference of an electrode-holding ring, headband, halo, or headset which encircles a person's head can be made from a hard polymer or metal and left and right side sections of this circumference can be made from a flexible fabric or textile.

In an embodiment, between 40% and 60% of the circumferential perimeter of an electrode-holding ring, headband, halo, or headset can be elastic, stretchable, and/or expandable. In an example, one or more sections of the circumferential perimeter of an electrode-holding ring, headband, halo, or headset can be elastic, stretchable, and/or expandable. In an example, right and left side sections of the circumference of an electrode-holding ring, headband, halo, or headset which encircles a person's head can be made from a hard polymer or metal and posterior and anterior sections of this circumference can be made from a flexible fabric or textile.

In an example, the perimeter of an electrode-holding ring, headband, halo, or headset can comprise one or more sections with a first degree of stretchability, elasticity, and/or expandability and one or more sections with a second degree of stretchability, elasticity, and/or expandability, wherein the second degree is greater than the first degree. In an example, the rear section of the circumferential perimeter of an electrode-holding ring, headband, halo, or headset can be elastic, stretchable, and/or expandable.

In an example, a device can be transparent. In an example, portions of an electrode-holding ring, headband, halo, or headset can be transparent. In an example, an anterior arm (e.g. arm, band, portion, section, or loop) of a device which spans a person's forehead can be adjustably-connected to a side portion of the device by a movable joint. In an example, the angle between an upper arm (e.g. arm, band, portion, section, or loop) of a device which loops over the top of a person's head and a side portion of the device can be adjusted by adjusting a movable joint between them.

In an example, a first section of the perimeter of an electrode-holding ring, headband, halo, or headset can be made from one or more metals and/or polymers and a second section of the perimeter of an electrode-holding ring, headband, halo, or headset can be made from one or more fabrics and/or textiles. In an example, a first section of the perimeter of an electrode-holding ring, headband, halo, or headset can be made from one or more metals and/or polymers and a second section of the perimeter of an electrode-holding ring, headband, halo, or headset can be made from one or more fabrics and/or textiles, wherein the first section is between 60% and 80% of the perimeter of an electrode-holding ring, headband, halo, or headset.

In an embodiment, a device can be made with a low-durometer material. In an example, a device can be made with an elastomeric polymer. In an embodiment, a device can be made with steel. In an example, a device can be made with carbon nanotubes. In an embodiment, a device can be made with gold. In an example, a device can be made with hydrogel. In an example, a device can be made with platinum. In an example, a device can be made with polyurethane. In an example, a device can be made with silver-chloride.

In an example, a device can be made with a polymer (e.g. polydimethylsiloxane, polybutylene terephthalate, or polyurethane) which has been impregnated, doped, filled, coated, or embedded with electro-conductive material (e.g. silver, carbon nanotubes or other forms of carbon, copper, aluminum, nickel, platinum, or gold). In an example, a device can be made with a silicone material (such as PDMS) which has been impregnated, doped, filled, coated, or embedded with conductive material (such as metal and/or carbon) in order to provide consistent but comfortable contact with the person's head.

In an example, a device can be made with a silicone-based polymer which has been impregnated, doped, filled, coated, or embedded with a metal powder (e.g. silver, copper, gold, steel, or aluminum), graphite, or carbon nanotubes. In an example, a device can be made with an elastomeric polymer which has been impregnated, doped, filled, coated, or embedded with a metal powder (e.g. silver, copper, gold, steel, or aluminum), graphite, or carbon nanotubes. In an example, a device can be made with polydimethylsiloxane (PDMS) which has been impregnated, doped, filled, coated, or embedded with silver, steel, copper, gold, aluminum, and/or carbon. In an embodiment, a device can be made with polydimethylsiloxane, polybutylene terephthalate, or polyurethane which has been impregnated, doped, filled, coated, or embedded with silver, carbon nanotubes or other forms of carbon, copper, aluminum, nickel, platinum, or gold. In an example, a device can be made by braiding, weaving, and/or twisting together non-conductive yarns, threads, or fibers and conductive yarns, threads, fibers, wires, or strands.

In an embodiment, a sensor (e.g. electrode) can be a dry sensor (e.g. electrode). In an example, a sensor (e.g. electrode) can comprise an electrical energy emitter and an electrical energy receiver. In an embodiment, a sensor (e.g. electrode) can comprise an electromagnetic energy receiver. In an example, a sensor (e.g. electrode) can receive electrical energy which is emitted from a person's brain. In an embodiment, a sensor (e.g. electrode) can be a bipole electrode. In an example, a sensor (e.g. electrode) can be a dry sensor. In an example, a sensor (e.g. electrode) can be an electroconductive electrode. In an example, a sensor (e.g. electrode) can measure electromagnetic conductivity. In an example, a sensor (e.g. electrode) can measure electromagnetic resistance between two locations on a person's head.

In an example, a device can include a sensor (e.g. electrode) with a rounded square, rectangular, trapezoidal, or keystone shape. In an example, a device can include a sensor (e.g. electrode) with a cardioid, paint-palette, or lily-pad shape. In an embodiment, an oblong soft pad can have an elliptical or oval shape. In an example, a sensor (e.g. electrode) can have a dumbbell shape. In an embodiment, a sensor (e.g. electrode) can have a linear shape. In an example, a sensor (e.g. electrode) can have a rectangular shape. In an embodiment, a sensor (e.g. electrode) can have a sinusoidal shape whose peaks protrude into a person's hair. In an example, a sensor (e.g. electrode) can have an annular and/or ring shape. In an example, a sensor (e.g. electrode) can have an hour-glass shape.

In an example, a device can hold electromagnetic energy (EEG) sensors at one or more locations selected from the group of EEG placement sites consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, at least one sensor (e.g. electrode) of a device can be attached (e.g. fastened) to a person's ear lobe.

In an example, a sensor (e.g. electrode) can be made with a non-conductive elastic (e.g. elastomeric) material which has been coated and/or impregnated with electroconductive material. In an example, a sensor (e.g. electrode) can be made with an elastomeric polymer (e.g. PDMS) which has been impregnated, embedded, or coated with carbonaceous material. In an example, a sensor (e.g. electrode) can be made with an elastomeric polymer (e.g. PDMS) which has been impregnated, embedded, or coated with aluminum. In an example, a sensor (e.g. electrode) can be made with cellulose. In an example, a sensor (e.g. electrode) can be made with metallic nanostructures. In an embodiment, a sensor (e.g. electrode) can be made with polyethylene glycol.

In an example, a sensor (e.g. electrode) can be made with silver chloride. In an embodiment, a sensor (e.g. electrode) can be made by 3D printing, wherein conductive ink is printed onto an article of clothing. In an example, a sensor (e.g. electrode) can be made by bonding together alternating layers of conductive and non-conductive elastomeric material. In an embodiment, a sensor (e.g. electrode) can be made by printing conductive graphene-containing ink onto fabric. In an example, a sensor (e.g. electrode) can be made by sewing conductive threads or yarns onto fabric in an orthogonal mesh. In an embodiment, a sensor (e.g. electrode) can be made by stitching conductive threads or yarns onto fabric in an orthogonal mesh.

In an example, a sensor (e.g. electrode) can be made by extruding and curing alternating layers of conductive and non-conductive material. In an example, a sensor (e.g. electrode) can be made by printing conductive ink onto a layer of non-conductive material in a sinusoidal or zigzag pattern. In an example, a sensor (e.g. electrode) can comprise a capacitor which is made by bonding together alternating layers of conductive and non-conductive elastomeric material. In an example, a sensor (e.g. electrode) can comprise a dielectric structure which is made by bonding together alternating layers of conductive and non-conductive polymers. In an example, a sensor (e.g. electrode) can comprise a flexible dielectric elastomer between conductive layers.

In an example, a sensor (e.g. electrode) can comprise two conductive layers separated by an insulating layer. In an example, a sensor (e.g. electrode) can include a capacitive layer. In an example, electroconductive yarns, threads, fibers, or strands can have concentric layers comprising: an inner concentric layer (e.g. a core) with a first conductivity level; a middle concentric layer with a second conductivity level which is around the core; and an outer concentric non-layer with a third conductivity level which is around the middle concentric layer, wherein the second conductivity level is greater than the first conductivity level, and wherein the second conductivity level is greater than the third conductivity level. In an example, sensors (e.g. electrodes) can be more densely distributed (e.g. be closer together) on side portions of an electrode-holding ring, headband, halo, or headset than on posterior and anterior portions of the ring, headband, halo, or headset.

In an example, a device and/or sensor (e.g. electrode) on the device can be made with acrylic. In an example, a device and/or sensor (e.g. electrode) on the device can be made with carbon. In an embodiment, a device and/or sensor (e.g. electrode) on the device can be made with carbon particles. In an example, a device and/or sensor (e.g. electrode) on the device can be made with copper. In an embodiment, a device and/or sensor (e.g. electrode) on the device can be made with elastane. In an example, a device and/or sensor (e.g. electrode) on the device can be made with graphene nanoplatelets.

In an embodiment, a device and/or sensor (e.g. electrode) on the device can be made with latex. In an example, a device and/or sensor (e.g. electrode) on the device can be made with metal particles. In an embodiment, a device and/or sensor (e.g. electrode) on the device can be made with neoprene. In an example, a device and/or sensor (e.g. electrode) on the device can be made with PDMS (polydimethylsiloxane). In an example, a device and/or sensor (e.g. electrode) on the device can be made with PEG [poly (oxyethylene)]. In an example, a device and/or sensor (e.g. electrode) on the device can be made with polyester.

In an example, a device and/or sensor (e.g. electrode) on the device can be made with polypropylene glycol. In an example, a device and/or sensor (e.g. electrode) on the device can be made with PVA (polyvinyl alcohol). In an example, a device and/or sensor (e.g. electrode) on the device can be made with silicone. In an example, a device and/or sensor (e.g. electrode) on the device can be made with silver. In an example, a device and/or sensor (e.g. electrode) on the device can be made with silver ink. In an embodiment, a device and/or sensor (e.g. electrode) on the device can be made with steel. In an example, a sensor (e.g. electrode) can be made with a cellulose derivative. In an embodiment, a sensor (e.g. electrode) can be made with a thermoplastic elastomer (TPE).

In an example, a sensor (e.g. electrode) can be made with cellulose. In an embodiment, a sensor (e.g. electrode) can be made with dimethicone. In an example, a sensor (e.g. electrode) can be made with hydroxypropyl methylcellulose (HPMC). In an embodiment, a sensor (e.g. electrode) can be made with material with a Shore A value between 40 and 80. In an example, a sensor (e.g. electrode) can be made with nylon. In an example, a sensor (e.g. electrode) can be made with small filaments of PEDOT:PSS. In an example, a sensor (e.g. electrode) can be made with a conductive material. In an example, a sensor (e.g. electrode) can be made with a silicone-based polymer.

In an example, a sensor (e.g. electrode) can be made with an electroconductive polymer. In an example, a sensor (e.g. electrode) can be made with aluminum. In an example, a sensor (e.g. electrode) can be made with carbon particles. In an example, a sensor (e.g. electrode) can be made with graphene. In an example, a sensor (e.g. electrode) can be made with nickel. In an example, a sensor (e.g. electrode) can be made with polybutylene terephthalate. In an example, a sensor (e.g. electrode) can be made with silicone. In an embodiment, a sensor (e.g. electrode) can be made with thermoplastic polyurethane (TPU).

In an example, a sensor (e.g. electrode) can be made with a cellulose material (such as HPMC) which is doped, impregnated, coated, sprayed, printed, or embedded with carbon nanotubes. In an embodiment, a sensor (e.g. electrode) can be made with a cellulose material (such as HPMC) which is doped, impregnated, coated, sprayed, printed, or embedded with copper. In an example, a sensor (e.g. electrode) can be made with a cellulose material (such as HPMC) which is doped, impregnated, coated, sprayed, printed, or embedded with metal particles.

In an embodiment, a sensor (e.g. electrode) can be made with a cellulose material (such as HPMC) which is doped, impregnated, coated, sprayed, printed, or embedded with silver chloride. In an example, a sensor (e.g. electrode) can be made with a hydrogel material which is doped, impregnated, coated, sprayed, printed, or embedded with aluminum. In an embodiment, a sensor (e.g. electrode) can be made with a hydrogel material which is doped, impregnated, coated, sprayed, printed, or embedded with carbon particles. In an example, a sensor (e.g. electrode) can be made with a hydrogel material which is doped, impregnated, coated, sprayed, printed, or embedded with graphene nanoplatelets.

In an example, a sensor (e.g. electrode) can be made with a hydrogel material which is doped, impregnated, coated, sprayed, printed, or embedded with metal particles. In an example, a sensor (e.g. electrode) can be made with a hydrogel material which is doped, impregnated, coated, sprayed, printed, or embedded with silver chloride. In an example, a sensor (e.g. electrode) can be made with a hydrogel which is doped, impregnated, coated, sprayed, printed, or embedded with conductive material. In an example, a sensor (e.g. electrode) can be made with a silicone-based material (such as PDMS) which is doped, impregnated, coated, sprayed, printed, or embedded with aluminum. In an example, a sensor (e.g. electrode) can be made with a silicone-based material (such as PDMS) which is doped, impregnated, coated, sprayed, printed, or embedded with carbon particles.

In an example, a sensor (e.g. electrode) can be made with a silicone-based material (such as PDMS) which is doped, impregnated, coated, sprayed, printed, or embedded with graphene nanoplatelets. In an example, a sensor (e.g. electrode) can be made with a silicone-based material (such as PDMS) which is doped, impregnated, coated, sprayed, printed, or embedded with metal powder. In an example, a sensor (e.g. electrode) can be made with a silicone-based material (such as PDMS) which is doped, impregnated, coated, sprayed, printed, or embedded with conductive ink. In an example, a sensor (e.g. electrode) can be made with PEDOT and/or PEDOT:PSS which is doped, impregnated, coated, sprayed, printed, or embedded with aluminum.

In an example, a sensor (e.g. electrode) can be made with PEDOT and/or PEDOT:PSS which is doped, impregnated, coated, sprayed, printed, or embedded with carbon particles. In an example, a sensor (e.g. electrode) can be made with PEDOT and/or PEDOT:PSS which is doped, impregnated, coated, sprayed, printed, or embedded with graphene nanoplatelets. In an embodiment, a sensor (e.g. electrode) can be made with PEDOT and/or PEDOT:PSS which is doped, impregnated, coated, sprayed, printed, or embedded with metal powder. In an example, a sensor (e.g. electrode) can be made with PEDOT and/or PEDOT:PSS which is doped, impregnated, coated, sprayed, printed, or embedded with steel.

In an embodiment, a sensor (e.g. electrode) can be made with polydimethylsiloxane (PDMS) which is doped, impregnated, coated, sprayed, printed, or embedded with silver. In an example, a sensor (e.g. electrode) can be made with thermoplastic polyurethane (TPU) which is doped, impregnated, coated, sprayed, printed, or embedded with carbon. In an embodiment, a sensor (e.g. electrode) can be made with thermoplastic polyurethane (TPU) which is doped, impregnated, coated, sprayed, printed, or embedded with conductive particles. In an example, a sensor (e.g. electrode) can be made with thermoplastic polyurethane (TPU) which is doped, impregnated, coated, sprayed, printed, or embedded with graphite.

In an embodiment, a sensor (e.g. electrode) can be made with thermoplastic polyurethane (TPU) which is doped, impregnated, coated, sprayed, printed, or embedded with silver. In an example, a sensor (e.g. electrode) can be made with thermoplastic polyurethane (TPU) which is doped, impregnated, coated, sprayed, printed, or embedded with steel. In an embodiment, a sensor (e.g. electrode) can be made with a silicone material (such as PDMS) which has been impregnated, doped, filled, coated, or embedded with graphene. In an example, a sensor (e.g. electrode) can be made with a silicone material (such as PDMS) which has been impregnated, doped, filled, coated, or embedded with carbon nanotubes.

In an example, a sensor (e.g. electrode) can be made with an elastomeric polymer which has been impregnated, doped, filled, coated, or embedded with silver, steel, copper, gold, aluminum, and/or carbon. In an example, a sensor (e.g. electrode) can be made with an elastomeric polymer which has been impregnated, doped, filled, coated, or embedded with conductive material (such as silver or carbon particles). In an example, a sensor (e.g. electrode) can be made with polydimethylsiloxane (PDMS) which has been impregnated, doped, filled, coated, or embedded with a metal powder (e.g. silver, copper, gold, steel, or aluminum), graphite, or carbon nanotubes.

In an example, a device can comprise: a first set of sensors (e.g. electrodes) which are worn on a person's forehead, wherein the first set of sensors are made from a soft, deformable, conductive polymer (such as conductive PDMS or TPU) and are configured to generally conform to the curvature of the person's forehead; a second set of sensors (e.g. electrodes) which are worn on the posterior of the person's head, wherein the second set of sensors further comprises a plurality of hair-penetrating protrusions.

In an example, a posterior half of an electrode-holding ring, headband, halo, or headset can have electroconductive prongs, teeth, pins, or other protrusions which penetrates (e.g. slide) between strands of hair. In an example, a posterior half of an electrode-holding ring, headband, halo, or headset can have flexible (e.g. elastomeric) electroconductive prongs, teeth, pins, or other protrusions which penetrate (e.g. slide) between strands of hair. In an example, a sensor (e.g. electrode) can comprise a base and a plurality of protrusions, teeth, prongs, or pins which extend out from the base toward the surface of a person's head.

In an example, a sensor (e.g. electrode) can comprise a base and a plurality of protrusions, teeth, prongs, or pins which extend out from the base toward the surface of a person's head, wherein the protrusions, teeth, prongs, or pins extend out from the base along vectors which are in planes which intersect the plane of the base at acute angles. In an example, a sensor (e.g. electrode) can comprise a base with electroconductive prongs, teeth, pins, or other protrusions made from a polymer which has been coated and/or impregnated with silver. In an example, a sensor (e.g. electrode) can comprise a base with electroconductive prongs, teeth, pins, or other protrusions made from a silicon-based polymer which has been coated and/or impregnated with conductive material.

In an example, a sensor (e.g. electrode) can comprise a base with concave arcuate electroconductive prongs, teeth, pins, or other protrusions wherein their concavities which open away from the center (e.g. the central axis) of the base. In an embodiment, sensors (e.g. electrodes) on a posterior portion of an electrode-holding ring, headband, halo, or headset can have electroconductive prongs, teeth, pins, or other protrusions which penetrate (e.g. slide) between strands of hair. In an example, a sensor (e.g. electrode) for use on a hair-covered area of a person's head can comprise: a sensor base; and a plurality of hair-penetrating prongs (e.g. prongs, protrusions, pins, or legs) which are configured to extend out from the sensor base toward the surface of a person's head.

In an embodiment, hair-penetrating prongs (e.g. prongs, protrusions, pins, or legs) on a sensor can be configured in an orthogonal matrix. In an example, a core of a hair-penetrating prong (e.g. prong, protrusion, pin, or leg) on a sensor can have a lower durometer level than that of an outer layer of the prong. In an embodiment, electroconductive hair-penetrating prongs (e.g. prongs, protrusions, pins, or legs) on a sensor which are closer to the center (or midline) of a sensor base can have a lower durometer level than prongs which are farther from the center (or midline). In an example: a first portion (e.g. half or side) of a cross-section of a hair-penetrating prong (e.g. prong, protrusion, pin, or leg) on a sensor can be made with a first material and a second portion (e.g. half or side) of the cross-section of prong can be made with a second material, wherein the first material is more flexible, more elastic, and/or have a lower durometer than the second material, thereby biasing prong to bend in a selected lateral direction (and slide between strands of hair) when prong is pressed onto the surface of a person's head.

In an embodiment, a core of a hair-penetrating prong (e.g. prong, protrusion, pin, or leg) on a sensor (e.g. electrode) can be made from an elastomeric polymer (e.g. PDMS) which has been doped, impregnated, or filled with conductive material. In an example, a hair-penetrating prong (e.g. prong, protrusion, pin, or leg) on a sensor (e.g. electrode) can have a flexible conductive core which is covered with non-conductive material. In an example, an array of hair-penetrating prongs (e.g. prongs, protrusions, teeth, pins, or legs) on a sensor can be configured in nested (e.g. concentric) rings.

In an example, an outer layer of a hair-penetrating prong (e.g. prong, protrusion, pin, or leg) on a sensor (e.g. electrode) can be more conductive (e.g. have a higher concentration of conductive material) than the core of the hair-penetrating prong. In an example, hair-penetrating prongs (e.g. prongs, protrusions, teeth, pins, or legs) on a sensor (e.g. electrode) can have polygonal (e.g. square, rectangular, or hexagonal) cross-sectional shapes. In an example, hair-penetrating prongs (e.g. prongs, protrusions, teeth, pins, or legs) on a sensor (e.g. electrode) can be made from an elastomeric polymer which has been doped, embedded, impregnated, or coated with conductive material.

In an example, a sensor (e.g. electrode) can comprise a sensor base with a Shore 00 value between 15 and 50 and a plurality of protrusions (e.g. protrusions, prongs, teeth, legs, pins, and/or bumps) with Shore 00 values between 30 and 80. In an example, a radially-outward-facing angle between proximal and distal sections of a hair-penetrating prong (e.g. prong, protrusion, pin, or leg) on a sensor can increase as a sensor (e.g. electrode) is pressed onto the surface of a person's head, thereby causing the tip of the hair-penetrating prong (e.g. prong, protrusion, pin, or leg) on a sensor to slide laterally over the surface of the person's head. In an example, different hair-penetrating prongs (e.g. prongs, protrusions, pins, or legs) on a sensor can extend out from a sensor base at different radially-outward-facing angles.

In an example, a distal section of a hair-penetrating prong (e.g. prong, protrusion, pin, or leg) on a sensor can be more conductive than the proximal section of the prong. In an embodiment, a distal section of a sensor prong can be convex relative to a central longitudinal axis of the prong. In an example, a hair-penetrating prong (e.g. prong, protrusion, pin, or leg) on a sensor can have a proximal section which is closer to the sensor base and a distal section which is farther from the sensor base, wherein the proximal section is concave relative to a central longitudinal axis of the prong, and wherein the distal section is convex relative to a central longitudinal axis of the prong. In an embodiment, a hair-penetrating prong (e.g. prong, protrusion, pin, or leg) on a sensor can have a proximal section which is closer to the sensor base and a distal section which is farther from the sensor base, and wherein the proximal section is bifurcated. In an example, hair-penetrating prongs (e.g. prongs, protrusions, pins, or legs) on a sensor can be tapered in a proximal to distal manner, wherein distal means closer to the person's head.

In an embodiment, a device with sensors (e.g. electrodes) for monitoring brain activity can enable sensors (e.g. electrodes) to be moved in order to adjust (e.g. customize) their positions (e.g. lateral and vertical positions) to the shape of a specific person's head. In an example, a device with sensors (e.g. electrodes) for monitoring brain activity can include a plurality of pneumatic actuators which automatically adjust the positions of sensors (e.g. electrodes). In an embodiment, sensors (e.g. electrodes) can be plugged into different locations on the circumference of an electrode-holding ring, headband, halo, or headset.

In an example, sensors (e.g. electrodes) can be snapped or clipped into different locations an electrode-holding ring, headband, halo, or headset. In an example, the locations of a sensors (e.g. electrodes) on a device with sensors (e.g. electrodes) for monitoring brain activity can be moved laterally with respect to the surface of a person's head. In an example, the locations of a sensors (e.g. electrodes) on a device with sensors (e.g. electrodes) for monitoring brain activity can be moved automatically with respect to the surface of a person's head by actuators. In an example, a sensor (e.g. electrode) can be attached to an eyewear sidepiece (e.g. temple) by a spring inside compressible foam.

In an example, a device can be removably-attached to eyewear via a clip, clasp, magnet, strap, hook, plug, or hook-and-loop fabric. In an example, a sensor (e.g. electrode) can be attached to a wearable device for measuring electromagnetic brain activity using an attachment mechanism selected from the group consisting of: adhesive, band, buckle, button, channel, clasp, clip, electronic connector, flexible channel, hook, hook-and-eye mechanism, magnet, pin, plug, pocket, rivet, sewing, snap, tape, tie, and zipper.

In an example, a device can include one or more pneumatic chambers (e.g. pneumatic pistons) which gently hold one or more sensors (e.g. electrodes) against a person's head. In an example, a sensor (e.g. electrode) or prong extending out of a sensor can be pressed against the surface of a person's head by a helical or spiral spring. In an example, a sensor (e.g. electrode) or prong extending out of a sensor can be pressed against the surface of a person's head by a metal spring. In an embodiment, a sensor (e.g.

electrode) or prong extending out of a sensor can be pressed against the surface of a person's head by a pneumatic mechanism.

In an example, a sensor (e.g. electrode) or prong extending out of a sensor can be pressed against the surface of a person's head by an electromagnetic mechanism. In an embodiment, a sensor (e.g. electrode) can be moved toward the surface of a person's head by an adjustable strap or band. In an example, a sensor (e.g. electrode) can be moved toward the surface of a person's head by a pneumatic mechanism. In an embodiment, a sensor (e.g. electrode) can be moved toward the surface of a person's head by a metal spring. In an example, a sensor (e.g. electrode) can be moved toward the surface of a person's head by a helical or spiral spring.

In an embodiment, a sensor (e.g. electrode) can be configured to rotate when pushed toward the surface of a person's head. In an example, a sensor (e.g. electrode) can be spring-loaded so that it is pushed by a spring toward the surface of a person's head. In an example, pins, prongs, teeth, or other protrusions which extend out from the base of a sensor (e.g. electrode) can be configured to rotate when the base is pushed toward the surface of a person's head.

In an example, a distances between a plurality of sensors (e.g. electrodes) and the surface of a person's head can be individually adjusted. In an example, the distance between a sensor (e.g. electrode) and the surface of a person's head can be adjusted by expanding an inflatable chamber. In an example, the distance between a sensor (e.g. electrode) and the surface of a person's head can be adjusted by a solenoid. In an example, the distance between a sensor (e.g. electrode) and the surface of a person's head can be adjusted by rotating a threaded (e.g. helical) mechanism. In an example, the pressure between a sensor (e.g. electrode) and the surface of a person's head can be adjusted by an electromagnetic actuator. In an example, the pressure between a sensor (e.g. electrode) and the surface of a person's head can be adjusted by a pneumatic mechanism.

In an example, a device can include a sensor (e.g. electrode) vibrator. In an embodiment, a sensor (e.g. electrode) can be vibrated and/or oscillated until it penetrates a layer of a person's hair and achieves a desired level of electromagnetic communication with a person's brain. In an example, a sensor (e.g. electrode) can comprise one or more electromagnetic actuators which vibrate and/or oscillate one or more protrusions (e.g. protrusions, prongs, teeth, legs, pins, and/or bumps) in directions which are substantially parallel to the surface of a person's head and/or to the surface of the sensor base of the electrode, thereby enabling the protrusions to slide between strands of hair on the person's head.

In an embodiment, a flexible sensor base can be changed between being concave, planar (e.g. flat), and convex relative to the surface of a person's head. In an example, a sensor (e.g. electrode) base can be changed from a first configuration which is convex relative to a person's head to a second configuration which is parallel (e.g. flat or planar) relative to the person's head. In an embodiment, a sensor (e.g. electrode) base can be more planar (e.g. closer to fitting within a flat plane) in a second configuration than in a first configuration. In an example, a sensor (e.g. electrode) base can have a first degree of concavity before the sensor (e.g. electrode) has been pressed against the surface of a person's head and a second degree of concavity after the sensor (e.g. electrode) has been pressed onto the surface of a person's head, wherein the second degree is less than the first degree. In an embodiment, a sensor (e.g. electrode) base can comprise a plurality of connected moveable sections.

In an example, a sensor (e.g. electrode) can comprise one or more electromagnetic actuators which move one or more protrusions (e.g. protrusions, prongs, teeth, legs, pins, and/or bumps) closer to, or farther from, the surface of a person's head. In an embodiment, a sensor (e.g. electrode) can comprise one or more electromagnetic actuators which move one or more protrusions (e.g. protrusions, prongs, teeth, legs, pins, and/or bumps) in a direction which is substantially perpendicular to the surface of a person's head and/or to the surface of the sensor base of the electrode.

In an example, a distal section of a hair-penetrating prong (e.g. prong, protrusion, pin, or leg) on a sensor can be wider (e.g. have a larger average cross-sectional size) than a proximal section of the prong. In an example, hair-penetrating prongs (e.g. prongs, protrusions, pins, or legs) on a sensor can have a smaller cross-sectional size in their first configuration for easier insertion between strands of hair and a larger cross-sectional size in their second configuration for greater contact surface with the person's head and/or greater comfort for the person after their insertion between strands of hair.

In an example, a device can include an electronics unit (e.g. control unit) which includes a data processor, a data transceiver, and a power source. In an example, a device can include a wireless data transmitter (e.g., WiFi transceiver, Bluetooth transceiver, or cellular transceiver). In an example, data from sensors (e.g. electrodes) can be partly processed (e.g. amplification) locally within the local device and then further processed after transmission to a remote device. In an example, an electrode-holding ring, headband, halo, or headset can be part of a system, wherein a data processor in the ring, headband, halo, or headset is in wireless communication with a remote data processor. In an embodiment, an electronics unit (e.g. control unit) of an electrode-holding ring, headband, halo, or headset can be in wireless communication with an external (or remote) device and/or with another component of an overall system for monitoring brain activity.

In an example, sensors (e.g. electrodes) on a device can collect data concerning changes in transmission of electrical energy from an energy emitter to an energy receiver due to changes in brain activity. In an embodiment, sensors (e.g. electrodes) on a device can record (e.g. record, measure, monitor) changes in transmission of electrical energy from an energy emitter to an energy receiver due to changes in brain activity. In an example, a power source can transduce, harvest, and/or generate energy from body thermal energy. In an embodiment, an electrode-holding ring, headband, halo, or headset can further comprise a plurality of wires which connect the sensors (e.g. electrodes) to the electronics unit. In an example, an electrode-holding ring, headband, halo, or headset can further comprise elastomeric electroconductive pathways which connect the sensors (e.g. electrodes) to the electronics unit.

In an embodiment, a device can be embodied in an undulating hairband or tiara which spans, from side-to-side, over the upper-anterior quadrant of a person's head. In an example, an electrode-holding device can be embodied in a headset. In an example, an electrode-holding device can be embodied in headphones. In an example, an electrode-holding ring, headband, halo, or headset can be embodied in headphones. In an example, an electrode-holding ring, headband, halo, or headset can be embodied in a hat or cap. In an example, a device can be embodied in a hat or cap. In an example, a device can be embodied in an ear bud or other ear-inserted device. In an example, a device can be embodied in a tiara or crown. In an embodiment, a device can be embodied in eyeglasses.

In an example, an electrode-holding device can be configured to be attached to eyeglasses. In an embodiment, an electrode-holding device can include an attachment (e.g. connection) mechanism which attaches the device to eyeglass temples (e.g. sidepieces). In an example, an electrode-holding device includes an attachment mechanisms which attaches the device to eyeglasses, wherein the attachment mechanism is selected from the group consisting of: button, clamp, clasp, clip, elastic band, hook, hook and loop material, magnet, pin, prong, snap, and tie.

In an embodiment, there can be a bifurcation in an eyewear sidepiece (e.g. temple), wherein a first branch extends forward, upward, and inward to a location on a person's forehead, and wherein a second branch extends in straight forward from the person's auricle (e.g. outer ear) to a front section of the eyewear frame. In an example, the anterior end of an eyewear sidepiece (e.g. temple) can bifurcate. In an example, an eyewear sidepiece (e.g. temple) can bifurcate, wherein there is an opening (e.g. opening, hole, or gap) between the upper branch (e.g. branch, arm, or loop) of the bifurcation and the lower branch of the bifurcation.

In an example, a device can comprise an anterior strap (e.g. strap, band, loop, or arm) which spans across a person's forehead, wherein the strap is connected to eyewear sidepieces (e.g. temples). In an example, a device can comprise a movable (e.g. pivoting) arm which has a first configuration in which it does not span a person's forehead and a second configuration in which it does span the person's forehead, wherein the arm is movably-connected to eyewear sidepieces (e.g. temples). In an example, a device can have a first configuration in which it is aligned with an eyewear sidepiece (e.g. temple) and a second configuration in which is extends out from the sidepiece at an angle. In an embodiment, a device can have a first configuration in which it is parallel to an eyewear sidepiece (e.g. temple) and a second configuration in which is perpendicular to the sidepiece, wherein the device is pivoted and/or rotated from the first configuration to the second configuration.

In an example, an eyewear sidepiece (e.g. temple) can bow, curve, or undulate inward toward the surface of a person's head. In an embodiment, an eyewear sidepiece (e.g. temple) can have a (central) undulation, wave, concavity, and/or bend which curves upward toward a person's forehead. In an example, a device can also include a display screen. In an embodiment, a device can also include a touch screen. In an example, a device can be held on a person's head by frictional engagement with the person's hair.

In an example, a device can comprise: an undulating (rear-tilted) headband which is configured to be worn around the person's head; a plurality of sensors (e.g. electrodes) which are configured to be held in proximity to the person's head by the undulating headband, wherein these sensors (e.g. electrodes) collect data concerning the person's brain activity; and an electronics unit which further comprises a data processor, a wireless data transmitter and/or receiver, and a power source. In an example, a device can function as a BCI (Brain-to-Computer Interface) for people who have lost motor control (e.g. people with ALS). In an example, a device can be used for defense applications. In an example, a device can be used for evaluation of cognitive function.

In an example, a device can be used for navigation applications. In an example, a device can be used for telerobotics. In an example, a device can be used to diagnose a neurological health condition. In an example, a device can be used to interpret words, commands, and/or communication from a person. In an embodiment, a device can be used to monitor sleep quality and/or conditions. In an example, a device can function as a BCI (Brain-to-Computer Interface) for navigating the internet. In an embodiment, a device can function as a BCI (Brain-to-Computer Interface) for people with neuromuscular paralysis. In an example, a device can function as a BCI (Brain-to-Computer Interface) for shopping. In an embodiment, a device can function as a BCI (Brain-to-Computer Interface) in augmented reality (AR) or virtual reality (VR) applications.

In an example, a head-worn electrode-holding device can comprise an array of coils or spirals which span a portion of the upper half of a person's head. In an embodiment, a main circumference-spanning portion of an electrode-holding ring, headband, halo, or headset can have a saddle and/or hyperboloidal shape. In an example, a perimeter of an electrode-holding ring, headband, halo, or headset can have saddle or hyperboloidal shape, wherein the front half of the saddle is anterior to a virtual vertical plane through the person's ears and the rear half of the saddle is posterior to this virtual plane. In an example, a portion (e.g. portion, arm, segment, or loop) of an electrode-holding ring, headband, halo, or headset spanning the front half of a person's head can have an front-facing concavity.

In an example, a portion (e.g. portion, arm, segment, or loop) of an electrode-holding ring, headband, halo, or headset spanning the rear half of a person's head can have an upward-facing concavity. In an example, a portion (e.g. portion, arm, segment, or loop) of an electrode-holding ring, headband, halo, or headset spanning the rear half of a person's head can have a rear-facing concavity. In an example, a portion of an electrode-holding ring, headband, halo, or headset can a semi-elliptical shape. In an example, a section (e.g. section, segment, arm or portion) of an electrode-holding ring, headband, halo, or headset can have a shape which is selected from the group consisting of: arc, bell-shaped curve, conic section, hair-pin curve, carlavian curve, half-sinusoidal curve, hyperbolic, parabolic, portion of a spiral, semi-circle, semi-oval, sinusoidal curve, spiral, and wave.

In an example, a section (e.g. section, segment, arm or portion) of an electrode-holding ring, headband, halo, or headset can have a conic section shape. In an example, a section (e.g. section, segment, arm or portion) of an electrode-holding ring, headband, halo, or headset can have a hyperbolic shape. In an embodiment, a section (e.g. section, segment, arm or portion) of an electrode-holding ring, headband, halo, or headset can have a semi-circle shape. In an example, a section (e.g. section, segment, arm or portion) of an electrode-holding ring, headband, halo, or headset can have a spiral of helical shape. In an embodiment, a side (e.g. left or right) portion of an electrode-holding ring, headband, halo, or headset can have a spiral and/or helical shape.

In an example, a side of an electrode-holding ring, headband, halo, or headset can have a shape like that of one-phase (e.g. one wave) of a sinusoidal which has been rotated 90 degrees so that its peak faces toward the front of a person's head and its opening faces toward the rear of the person's head. In an embodiment, a side of an electrode-holding ring, headband, halo, or headset can have a shape like that of one-phase (e.g. one wave) of a sinusoidal which has been rotated 90 degrees so that its peak faces toward the front of a person's head and its opening faces toward the rear of the person's head, wherein one tail of the curve reaches the person's ear and the other tail of the curve reaches the top of the person's head.

In an example, an arcuate anterior portion (e.g. portion, arm, segment, or loop) of an electrode-holding ring, headband, halo, or headset can have an downward-facing concavity. In an example, an arcuate posterior portion (e.g. portion, arm, segment, or loop) of an electrode-holding ring, headband, halo, or headset can have an front-facing concavity. In an example, an electrode-holding ring, headband, halo, or headset can have a circular, elliptical, oval, or egg shape. In an example, an electrode-holding ring, headband, halo, or headset can have a conic section shape. In an example, an electrode-holding ring, headband, halo, or headset can include a main ring or halo with circular, elliptical, egg, or oval shape.

In an embodiment, an electrode-holding ring, headband, halo, or headset can have an undulating, serpentine, and/or sinusoidal shape, wherein there is a portion with a substantially-vertical, downward-opening concavity over each ear. In an example, an electrode-holding ring, headband, halo, or headset can have a generally circular, elliptical, or oval shape except for one vertical undulation over each of the person's outer ears (e.g. auricles). In an embodiment, an electrode-holding ring, headband, halo, or headset can have sinusoidal waves and/or undulations with an amplitude between one and three inches. In an example, an electrode-holding ring, headband, halo, or headset can have sinusoidal waves and/or undulations with a frequency between one and three inches In an embodiment, an electrode-holding ring, headband, halo, or headset can have four sinusoidal waves and/or undulations.

In an example, an electrode-holding ring, headband, halo, or headset can have at least two downward-opening concavities on a right side of a person's head and at least two downward-opening concavities on the left side of the person's head. In an embodiment, an electrode-holding ring, headband, halo, or headset can comprise a saddle-shaped section on the top of a person's head, figuratively appearing as if a central oval or elliptical loop has been melted on the top of the person's head and droops down the sides of the person's head. In an example, an electrode-holding ring, headband, halo, or headset can be shaped like the perimeter of a saddle, hyperbolic paraboloid, and/or Pringles™ brand chip. In an embodiment, an electrode-holding ring, headband, halo, or headset can include two spiral and/or helical segments.

In an example, an undulating electrode-holding ring, headband, halo, or headset comprises: a posterior loop (e.g. loop, portion, section, or segment) which is worn on the posterior half of a person's head, wherein the posterior loop has a forward-facing concavity; a right-side loop (e.g. loop, portion, section, or segment) which is worn on the right side of the person's head, wherein the right-side loop has a rearward-facing concavity; and a left-side loop (e.g. loop, portion, section, or segment) which is worn on the left side of the person's head, wherein the left-side loop has a rearward-facing concavity. In an embodiment, each side (e.g. right and left) of an electrode-holding ring, headband, halo, or headset can have a spiral, helical, and/or coil shape. In an example, one side (e.g. right or left) of an electrode-holding ring, headband, halo, or headset can have an S shape.

In an embodiment, an electrode-holding ring, headband, halo, or headset can partially-encircle a person's head. In an example, an electrode-holding ring, headband, halo, or headset can encircle between 60% and 80% of a person's head.

In an example, an electrode-holding ring, headband, halo, or headset can encircle a person's head at a 5 to 25 degree angle relative to a horizontal plane (when a person's head is upright).

In an example, a headband, halo, or headset for recording brain activity can comprise: a front portion (e.g. portion, segment, or loop) which spans across a person's forehead from one ear to the other ear; a right-side rear portion (e.g. portion, arm, or segment) which extends rearward and downward between one and three inches from the person's right ear; a left-side rear portion (e.g. portion, arm, or segment) which extends rearward and downward between one and three inches from the person's left ear; a right-side flexible posterior-ear prong (e.g. prong, arm, or segment) which curves around the posterior and upper surfaces of the person's right ear (e.g. where the auricle connected to the rest of the person's head); a left-side flexible posterior-ear prong (e.g. prong, arm, or segment) which curves around the posterior and upper surfaces of the person's left ear (e.g. where the auricle connected to the rest of the person's head); a plurality of sensors (e.g. electrodes) for recording brain activity; and an electronics unit which includes a data processor, a data transmitter, and a power source.

In an example, an electrode-holding ring, headband, halo, or headset can have multiple undulations as it encircles a person's head. In an example, an undulating electrode-holding ring, headband, halo, or headset can have a concave portion over a person's ear, wherein the upper portion of the ear (e.g. auricle) fits into this concavity. In an example, each side (e.g. right and left) of an electrode-holding ring, headband, halo, or headset can have two (sinusoidal) undulations. In an example, a device can have vertical undulations or waves around a central circumferential axis, wherein the central circumferential axis is circular, elliptical, or oval. In an embodiment, an anterior arm (e.g. arm, band, segment, or portion) of a device which loops around a person's forehead can have an undulating (e.g. sinusoidal) shape.

In an embodiment, an electrode-holding ring, headband, halo, or headset can have a uniform width around its circumference. In an embodiment, an electrode-holding ring, headband, halo, or headset can have a width which is between a quarter of an inch and an inch. In an example, an undulating rear-tilted headband can have a variable width, wherein the side portions are wider than the front and rear portions. In an example, an undulating rear-tilted headband can have a variable width, wherein front and rear portions of the device are wider than side portions. In an embodiment, side portions of an electrode-holding ring, headband, halo, or headset can be wider than front and rear portions of the electrode-holding ring, headband, halo, or headset.

In an example, an electrode-holding ring, headband, halo, or headset can encircle a person's head at a substantially constant height when the person's head is upright. In an embodiment, a (right or left) side of an electrode-holding ring, headband, halo, or headset worn on a person's head can comprise: a posterior section, a middle section, and an anterior section, wherein the posterior section has a substantially constant height (e.g. is level) when the person's head is upright, wherein the anterior section has a substantially constant height (e.g. is level) when the person's head is upright, and wherein the middle section is between the posterior and anterior sections, and wherein serpentine with a variable height.

In an example, an electrode-holding ring, headband, halo, or headset can have a forward-upward slope at an angle between 5 and 25 degrees relative to a horizontal plane when a person's head is upright. In an embodiment, when a person's head is upright, an electrode-holding ring, headband, halo, or headset can be virtually divided (in a posterior-to-anterior manner) into three sections; wherein these three portions comprise a posterior section, a middle section, and an anterior section; wherein the posterior section has a substantially-constant first height (e.g. is substantially level at this first height), wherein the anterior section has a substantially-constant second height (e.g. is substantially level at this second height), wherein the second height is greater than the first height, and wherein the middle section comprises an arcuate transition from the first height to the second height.

In an example, when a person's head is upright, an electrode-holding ring, headband, halo, or headset can be virtually divided (in a posterior-to-anterior manner) into three thirds; wherein these three thirds comprise a posterior section, a middle section, and an anterior section; wherein the posterior section has a substantially-constant first height (e.g. is substantially level at this first height), wherein the anterior section has a substantially-constant second height (e.g. is substantially level at this second height), wherein the second height is greater than the first height, and wherein the middle section comprises an arcuate transition from the first height to the second height.

In an example, a device with sensors (e.g. electrodes) for monitoring brain activity can comprise a partial ring (e.g. arc) portion (e.g. arm, segment, or section) with a downward-facing concavity on each side (e.g. right and left) of a person's head. In an embodiment, a device with sensors (e.g. electrodes) for monitoring brain activity can comprise a partial ring (e.g. arc) portion (e.g. arm, segment, or section) with a posterior-facing concavity on each side (e.g. right and left) of a person's head. In an example, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the partial ring has a rear-facing convexity.

In an embodiment, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the partial ring loops across the person's forehead. In another example, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the ring and the partial ring are connected to each other, and wherein the ring and the partial ring are perpendicular to each other.

In an example, a partial ring portion of a device with sensors (e.g. electrodes) for monitoring brain activity can have a conic section shape. In an embodiment, a partial ring portion of a device with sensors (e.g. electrodes) for monitoring brain activity can have a semicircular shape, a semi-oval shape, or a semi-elliptical shape. In an example, an electrode-holding ring, headband, halo, or headset can comprise: a ring or halo portion which encircles a person's head; and two partial ring (e.g. arc) portions which are connected to the ring or halo portion, wherein there is one partial ring portion on each side (e.g. right and left) of the person's head.

In an example, an electrode-holding device can comprise two coaxial electrode-holding rings, headbands, or halos. In an example, an electrode-holding device can comprise: an upper ring, headband, or halo which encircles a person's head; and a lower ring, headband, or halo which encircles the person's head, wherein the lower ring rests on the person's ears (e.g. auricles), but the upper ring does not. In another example, an electrode-holding device can comprise: an upper ring, headband, or halo which encircles a person's head; and a lower ring, headband, or halo which encircles the person's head, wherein the upper ring is smaller than the lower ring.

In an example, an anterior portion of an electrode-holding device can comprise an upper band (e.g. segment, section, portion, arm, or band) and a lower band (e.g. segment, section, portion, arm, or band), wherein the upper band the lower band are substantially parallel as they span the sides of the person's head. In an example, an electrode-holding device can comprise an upper band (e.g. segment, section, portion, arm, or band) and a lower band (e.g. segment, section, portion, arm, or band), wherein between 20% and 40% of the circumferences of the upper and lower bands are substantially parallel.

In an example, a device with sensors (e.g. electrodes) for measuring brain activity can comprise a posterior-to-anterior series of side-to-side (e.g. right to left) loops (e.g. arms, loops, segments, arcs, or branches), wherein these loops are connected to each other on the sides (e.g. right and left) of a person's head. In an example, a device with sensors (e.g. electrodes) for measuring brain activity can comprise a posterior-to-anterior series of side-to-side (e.g. right to left) loops (e.g. arms, loops, segments, arcs, or branches), wherein a posterior loop spans the upper-posterior quadrant of a person's head, a middle loop spans the top of the person's head, and an anterior loop spans the upper-anterior quadrant of the person's head.

In an example, a device with sensors (e.g. electrodes) for measuring brain activity can comprise a posterior-to-anterior series of three side-to-side (e.g. right to left) loops (e.g. arms, loops, segments, arcs, or branches), wherein these loops are connected to each other on the sides (e.g. right and left) of a person's head above the person's ears. In an example, a device with sensors (e.g. electrodes) for measuring brain activity can comprise a posterior-to-anterior series of side-to-side (e.g. right to left) loops (e.g. arms, loops, segments, arcs, or branches), wherein these loops are connected to each other on the sides (e.g. right and left) of a person's head, and wherein these connections form acute angles.

In an embodiment, a device with sensors (e.g. electrodes) for measuring brain activity can comprise: an undulating band which is configured to span from a person's ear on a first side of the person's head to the person's ear on the second side of the person's head, wherein the portion of this undulating band on the first side of the person's head further comprises: a first segment which is configured to span from the rear of the person's head to the person's ear; a second segment which is configured to span from the person's ear to a side of the person's face and/or forehead, wherein this second segment has a concavity which opens upward; and a third segment which configured to span across the person's forehead; sensors (e.g. electrodes); and an electronics unit further comprising a data processor, a data transmitter, and a power source. In an example, an electrode-holding ring, headband, halo, or headset comprises: a ring (e.g. ring, band, or halo) which encircles a person's head around the posterior half of the person's head and also across the person's forehead; and an upper-anterior arm (e.g. arm, loop, segment, arc, or branch) which spans from a location on a middle portion of the ring over the upper surface of the upper-posterior quadrant of the person's head.

In an embodiment, an electrode-holding ring, headband, halo, or headset can comprise: a first arm (e.g. arm, loop, segment, are, or branch) which spans from an area above a person's ear to the person's forehead; a second arm (e.g. arm, loop, segment, arc, or branch) which spans from the area above the person's ear to the rear of the person's head; and a third arm (e.g. arm, loop, segment, arc, or branch) which spans from the area above the person's ear to the rear of the person's head, wherein the first, second, and third arms are connected. In another example, an electrode-holding ring, headband, halo, or headset can comprise: a posterior portion (e.g. arm, loop, segment, arc, or branch) which loops around the rear of a person's head; an anterior portion (e.g. arm, loop, segment, arc, or branch) which loops across the person's forehead; and an adjustable connector, wherein the connector connects the posterior and anterior portions, and wherein the connector enables adjustment of the angle between the posterior and anterior portions.

In an example, a device can include an anterior loop (e.g. loop, portion, band, arm, section) which spans a central portion of a person's forehead. In an embodiment, an electrode-holding ring, headband, halo, or headset can comprise: a rear-ear segment (e.g. prong, arm, protrusion, loop, or segment) which is worn on the rear-facing surface of a person's ear; a side segment which spans from the person's ear to the person's temple, a side portion of the person's face, and/or a side portion of the person's forehead; a top segment which spans from the side segment to the top of the person's head; at least one sensor (e.g. electrode); and an electronics unit comprising a data processor, a data transmitter, and a power source. In another example, a forehead loop of an electrode-holding ring, headband, halo, or headset can be arcuate, wavy, and/or undulating.

In an example, an electrode-holding ring, headband, halo, or headset can include a loop (e.g. loop, curve, bulge, or undulation) with a rear-facing concavity which is anterior to a person's ear. In an embodiment, an electrode-holding ring, headband, halo, or headset can include a loop (e.g. loop, curve, bulge, or undulation) with a rear-facing concavity which is anterior to and higher than a person's ear, wherein this loop spans the person's temple and/or part of the person's forehead. In an example, an electrode-holding ring, headband, halo, or headset can include a forehead loop (e.g. forehead loop, portion, segment, arm, or branch) which spans across a person's forehead, wherein this forehead loop is substantially transparent. In an embodiment, an electrode-holding ring, headband, halo, or headset can include a forehead loop (e.g. forehead loop, portion, segment, arm, or branch) which spans across a person's forehead, wherein this forehead loop bifurcates.

In an example, a device which is worn on a person's head to measure electromagnetic brain activity can comprise: a front (semicircular) loop which spans a person's forehead; wherein the front loop has a first level of elasticity, stretchability, or deformability; and a rear (semicircular) loop which spans the rear of the person's head; wherein the rear loop has a second level of elasticity, stretchability, or deformability; and wherein the second level is less than the first level. In an embodiment, a posterior portion of an electrode-holding device can comprise an upper band (e.g. segment, section, portion, arm, or band) and a lower band (e.g. segment, section, portion, arm, or band), wherein the upper band the lower band are substantially parallel as they span the sides of the person's head.

In an example, an posterior-upper segment (e.g. segment, arm, loop, or portion) of an electrode-holding ring, headband, halo, or headset extends backward and upward from the top of a person's outer ear (e.g. auricle) to span across the rear of the person's head and an posterior-lower segment (e.g. segment, arm, loop, or portion) of an electrode-holding ring, headband, halo, or headset extends backward and downward from the top of a person's outer ear (e.g. auricle) to span across the rear of the person's head. In another example, an electrode-holding ring, headband, halo, or headset comprises an upper loop and a lower loop, both of which span the posterior half of the person's head.

In an example, an electrode-holding ring, headband, halo, or headset can comprise a posterior arm (e.g. arm, segment, or portion) which loops around the back of a person's head and a upper arm (e.g. arm, segment, or portion) which loops over the top of the person's head, wherein the posterior arm and the upper arm are portions of the same continuous member, wherein the posterior arm has a downward-facing concavity, and wherein the upper arm has a rear-facing concavity. In an example, an electrode-holding ring, headband, halo, or headset can loop over the top of a person's head from one ear to the other ear, starting along the posterior surface of an outer ear (e.g. auricle), then curving forward and upward from the ear toward a side of the person's forehead (and/or temple), then curving backward and upward from the side of the person's forehead (and/or temple), and then curving upward over the top of the person's head in a vertical plane which intersects the ear.

In an example, a device can be a (generally circular) band which bifurcates into two branches above a person's ears and re-converges as it spans the sides of a person's head. In another example, a device can comprise a bifurcating ring around a person's head, wherein the ring bifurcates as it spans the front of the person's head. In an example, a device can comprise a bifurcating ring around a person's head, wherein the ring bifurcates as it spans the right and left sides of the person's head. In an example, an electrode-holding device can be a bifurcating ring, halo, or headset which encircles a person's head.

In an example, an electrode-holding device can be a bifurcating ring, halo, or headset which bifurcates as it loops over the top of the person's head. In an example, an electrode-holding device can be a bifurcating ring, halo, or headset which bifurcates as it loops and then reconverges as it loops around the back of the person's head. In an embodiment, an electrode-holding ring, headband, halo, or headset can comprise: a single anterior arm (e.g. arm, segment, band, or loop) which spans across a person's forehead; and two posterior arms (e.g. arms, segments, bands, or loops) which loop around the back of the person's head, wherein an upper posterior arm loops around the back of the person's head at a height above the height of the person's ears and a lower posterior arm loops around the back of the person's head at a height below the height of the person's ears. In another example, an electrode-holding ring, headband, halo, or headset can bifurcate and then reconverge, wherein between 20% and 40% of the circumference of the ring, headband, halo, or headset is bifurcated. In an example, an electrode-holding ring, headband, halo, or headset can bifurcate above a person's ears on each side (e.g. right and left) of their head.

In an embodiment, a side portion of an electrode-holding ring, headband, halo, or headset can have a concave undulation above a person's ear. In another example, a side portion of an electrode-holding ring, headband, halo, or headset can have a downward-opening concave undulation which is above a person's ear. In an example, a device (e.g. ring portion of a device) can be generally circular, oval, elliptical, or egg-shaped except for two upward undulations (e.g. upward waves) above a person's ears. In another example, a device (e.g. headband) can be generally circular except for right-side and left-side undulating (e.g. sinusoidal or partially sinusoidal) sections which curve around upper portions of a person's right ear and left ear, respectively.

In an embodiment, a device (e.g. headband) can be generally circular except for right-side and left-side concave sections which curve around upper portions of the person's right and left ears, respectively. In an example, a ring or band portion can have an ascending-and-descending wave over (and around) a person's ear. In an embodiment, an electrode-holding ring, headband, halo, or headset can include an undulation with a rearward-opening concavity which is anterior to a person's ear. In an example, an electrode-holding ring, headband, halo, or headset can include a downward undulation (e.g. a downward dip, curve, or loop) which is anterior to the upper portion of a person's ear.

In an embodiment, a device can include a posterior-ear prong and an anterior-ear prong which collectively curve around (e.g. span) 50%-75% of the circumference of the connection between a person's outer ear (e.g. auricle) and the rest of the person's head. In an example, a device with sensors (e.g. electrodes) for monitoring brain activity can comprise a front portion which spans across a person's forehead. In another example, a device with sensors (e.g. electrodes) for monitoring brain activity can comprise a side portion which spans part of the posterior auricular area of a person's head.

In an example, an electrode-holding ring, headband, halo, or headset can include an ear prong (e.g. prong, arm, protrusion, loop, or segment) which curves, bends, loops, and/or hooks around at least part of a person's ear (i.e. around at least part of the tissue connection between the person's outer ear, their auricle, and the rest of the person's head). In an example, an electrode-holding ring, headband, halo, or headset includes an anterior ear-engaging member (e.g. prong, arm, protrusion, loop, or segment) which curves, bends, loops, and/or hooks around a portion of the anterior surface of a person's outer ear (e.g. auricle) and/or the connecting tissue between the auricle and the rest of the person's head.

In an example, an electrode-holding ring, headband, halo, or headset includes a posterior ear-engaging member (e.g. prong, arm, protrusion, loop, or segment) which curves, bends, loops, and/or hooks around a portion of the posterior surface of a person's outer ear (e.g. auricle) and/or the connecting tissue between the auricle and the rest of the person's head. In another example, an electrode-holding ring, headband, halo, or headset can include an anterior-ear segment (e.g. prong, arm, protrusion, loop, or segment) with a shape which is selected from the group consisting of: portion of a circle; portion of a spiral; portion of a parabolic curve; portion of a sinusoidal curve; and conic section.

In an example, an electrode-holding ring, headband, halo, or headset can comprise: a posterior-ear segment (e.g. prong, arm, protrusion, loop, or segment) (worn on the rear-facing surface of a person's ear); an anterior-ear segment (e.g. prong, arm, protrusion, loop, or segment) (worn on the front-facing surface of the person's ear); a forehead segment (spanning from the person's ear to a side portion of the person's forehead); a rear segment (spanning from the posterior-ear segment (e.g. prong, arm, protrusion, loop, or segment) or the forehead segment to the rear of the person's head); sensors (e.g. electrodes); and an electronics unit including a data processor, data transmitter, and power source.

In an example, an electrode-holding device (e.g. ring, headband, halo, or headset) can comprise one or more hub-and-spoke (e.g. radial) arrays of arms (e.g. arms, spokes, segments, and/or legs) which hold sensors (e.g. electrodes) on a person's head. In an example, an electrode-holding device (e.g. ring, headband, halo, or headset) can comprise one or more hub-and-spoke (e.g. radial) arrays of arms (e.g. arms, spokes, segments, and/or legs) which hold sensors (e.g. electrodes) on a person's head, wherein there is a hub-and-spoke array on top of the person's head. In an example, an electrode-holding device (e.g. ring, headband, halo, or headset) can comprise a hub-and-spoke (e.g. radial) arrays of arms (e.g. arms, spokes, segments, and/or legs) which hold sensors (e.g. electrodes) on a person's head, wherein the hub is located approximately midway (e.g. within one inch of midway) between a person's ear and the top of the person's head.

In an embodiment, an electrode-holding device (e.g. ring, headband, halo, or headset) can comprise one or more hub-and-spoke (e.g. radial) arrays of arms (e.g. arms, spokes, segments, and/or legs), wherein there are four arms extending out radially from a hub, and wherein each arm holds a sensor (e.g. electrode) on a person's head. In an example, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein the arms are distributed (radially) equally around the hub.

In an embodiment, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein the arms have different lengths. In an example, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein the arms span 270 degrees of the perimeter of the hub. In an embodiment, an electrode-holding device (e.g. ring, headband, halo, or headset) can comprise one or more hub-and-spoke (e.g. radial) arrays of arms (e.g. arms, spokes, segments, and/or legs), wherein the hubs are held in place by a device segment which loops over the top of a person's head.

In an example, an electrode-holding device (e.g. ring, headband, halo, or headset) can comprise a hub-and-spoke array of electrode-holding arms (e.g. arms, spokes, segments, and/or legs) on top of a person's head. In another example, an electrode-holding device (e.g. ring, headband, halo, or headset) can comprise two hub-and-spoke arrays of electrode-holding arms (e.g. arms, spokes, segments, and/or legs), wherein there is one hub on each side (e.g. right and left) of a person's head. In an embodiment, an electrode-holding device (e.g. ring, headband, halo, or headset) can comprise a radial array of electrode-holding arms (e.g. arms, spokes, segments, and/or legs) on top of a person's head.

In an example, an electrode-holding ring, headband, halo, or headset can comprise a hexagonal (e.g. honeycomb) structure (e.g. mesh). In an embodiment, an electrode-holding ring, headband, halo, or headset can comprise an elastic and/or flexible hexagonal (e.g. honeycomb) structure (e.g. mesh). In an example, there can be a plurality of openings (e.g. holes) in an electrode-holding ring, headband, halo, or headset. In another example, there can be one or more longitudinal openings (e.g. holes) in an electrode-holding ring, headband, halo, or headset, wherein the longitudinal axis of an opening is parallel to (e.g. aligned with)

a circumferential axis of the ring, headband, halo, or headset. In an embodiment, there can be one or more openings (e.g. holes) in portions of an electrode-holding ring, headband, halo, or headset which span the sides of a person's head.

In an example, an electrode-holding ring, headband, halo, or headset can comprise an circumferential series (e.g. chain) of interdigitated segments. In an embodiment, an electrode-holding ring, headband, halo, or headset can comprise an circumferential series (e.g. chain) of connected segments and/or components. In an example, an electrode-holding ring, headband, halo, or headset can comprise an arcuate series (e.g. chain) of interconnected segments which can be moved (e.g. tilted, rotated, slid, and/or flexed) relative to each other. In another example, an electrode-holding ring, headband, halo, or headset can comprise multiple components which are connected by sliding connections so that the circumference of the ring, headband, halo, or headset can be changed (e.g. customized to the shape of a specific person's head). In an example, an electrode-holding ring, headband, halo, or headset can comprise multiple components which are connected by sliding connections that the concavity of the ring, headband, halo, or headset can be changed (e.g. customized to the shape of a specific person's head).

In an example, a device can comprise: a generally-circular ring (e.g. ring, headband, halo, or headset) which is worn around a person's head, wherein the circumference of the ring further comprises a first set of partially-circumferential sections with a first level of elasticity, stretchability, or deformability and a second set of partially-circumferential sections with a second level of elasticity, stretchability, or deformability, and wherein the second level is greater than the first level. In an example, a posterior portion (e.g. portion, segment, or band) of a device can more elastic (e.g. made with an elastic textile) than an anterior portion of the device (e.g. made with a hard plastic or metal).

In an example, between 35% and 55% of the circumference of a ring, headband, halo, or headset can be made from an elastic textile and/or fabric. In an example, a device can be made by braiding, weaving, or knitting elastic and/or stretchable yarns or threads. In another example, a headband can be elastic or stretchable. In an example, a perimeter of a headband (or halo) can further comprise a spring or other tensile member which holds the headband (or halo) against the surface of the person's head. In another example, an upper loop (e.g. over the top of the head loop) of a device can be elastic or stretchable. In an embodiment, a section (e.g. section or portion) of electrode-holding ring, headband, halo, or headset which spans the back of a person's head can be more elastic and/or stretchable than other sections of the ring, headband, halo, or headset.

In an example, an anterior section of the circumference of an electrode-holding ring, headband, halo, or headset which encircles a person's head can be made from a hard polymer or metal and a posterior section of this circumference can be made from a flexible fabric or textile. In an embodiment, an electrode-holding ring, headband, halo, or headset can have one or more relatively-inelastic sections (e.g. with a first level of elasticity and/or stretchability) and one or more relatively-elastic sections (e.g. with a second level of elasticity and/or stretchability), wherein the second level is greater than the first level, and wherein the relatively-elastic sections are located on the left and right sides of the ring, headband, halo, or headset.

In an example, an electrode-holding ring, headband, halo, or headset can have a relatively-inelastic section (e.g. with a first level of elasticity and/or stretchability) and a relatively-elastic section (e.g. with a second level of elasticity and/or stretchability), wherein the second level is greater than the first level, and wherein the relatively-elastic section is located on an anterior portion (e.g. the front half) of the ring, headband, halo, or headset. In an embodiment, an electrode-holding ring, headband, halo, or headset can comprise a sequence of alternating relatively-elastic and relatively-inelastic components. In an example, an electrode-holding ring, headband, halo, or headset can comprise an series (e.g. series, sequence, and/or chain) of alternating first segments and second segments, wherein first segments have a first level of elasticity and/or stretchability, wherein second components have a second level of elasticity and/or stretchability, and wherein the second level is greater than the first level.

In an embodiment, between 10% and 30% of the circumferential perimeter of an electrode-holding ring, headband, halo, or headset can be elastic, stretchable, and/or expandable. In another example, between 50% and 80% of the circumferential perimeter of an electrode-holding ring, headband, halo, or headset can be elastic, stretchable, and/or expandable. In an example, portions of the circumference of an electrode-holding ring, headband, halo, or headset which encircles a person's head can be made from a hard polymer or metal and portions of this circumference can be made from a flexible fabric or textile. In another example, side sections of the circumferential perimeter of an electrode-holding ring, headband, halo, or headset can be elastic, stretchable, and/or expandable.

In an embodiment, the rear portion of the perimeter of an electrode-holding ring, headband, halo, or headset (which spans the rear of a person's head) can have a first degree of stretchability, elasticity, and/or expandability and the front portion of the perimeter of the electrode-holding ring, headband, halo, or headset (which spans the person's forehead) can have a second degree of stretchability, elasticity, and/or expandability, wherein the second degree is less than the first degree. In an example, there can be a relatively-elastic section on each side (e.g. right and left) of an electrode-holding ring, headband, halo, or headset. In another example, a forehead loop can be (at least partially) transparent. In an example, a portion of an electrode-holding ring, headband, halo, or headset which spans across a person's forehead can be transparent.

In an example, the angle between an anterior arm (e.g. arm, band, portion, section, or loop) of a device which spans a person's forehead and a side portion of the device can be adjusted by adjusting a movable joint between them. In an example, a posterior arm (e.g. arm, band, portion, section, or loop) of a device which loops around the back of a person's head can be adjustably-connected to a side portion of the device by a movable joint. In an example, a first section of the perimeter of an electrode-holding ring, headband, halo, or headset can be made from one or more metals and/or polymers and a second section of the perimeter of an electrode-holding ring, headband, halo, or headset can be made from one or more fabrics and/or textiles, wherein the first section is between 20% and 40% of the perimeter of an electrode-holding ring, headband, halo, or headset.

In an example, a device can be made with a conductive material. In an example, a device can be made with a silicone-based polymer. In another example, a device can be made with an electroconductive polymer. In an example, a device can be made with aluminum. In another example, a device can be made with carbon particles. In an embodiment, a device can be made with graphene. In another example, a device can be made with nickel. In an example, a device can be made with polybutylene terephthalate. In an embodiment, a device can be made with silicone. In an example, a device can be made with thermoplastic polyurethane (TPU).

In an embodiment, a device can be made with a silicone material (such as PDMS) which has been impregnated, doped, filled, coated, or embedded with graphene. In an example, a device can be made with a silicone material (such as PDMS) which has been impregnated, doped, filled, coated, or embedded with carbon nanotubes. In an embodiment, a device can be made with an elastomeric polymer which has been impregnated, doped, filled, coated, or embedded with silver, steel, copper, gold, aluminum, and/or carbon. In another example, a device can be made with an elastomeric polymer which has been impregnated, doped, filled, coated, or embedded with conductive material (such as silver or carbon particles). In an example, a device can be made with polydimethylsiloxane (PDMS) which has been impregnated, doped, filled, coated, or embedded with a metal powder (e.g. silver, copper, gold, steel, or aluminum), graphite, or carbon nanotubes.

In an example, a device can be made with conductive yarn or thread, wherein the yarn or thread comprises: an inner core of twisted or braided conductive and non-conductive threads, fibers, or strands; and an outer layer non-conductive material around the inner core. In another example, a pair of EEG-monitoring headphones can include sensors (e.g. electrodes) which are knitted or woven from soft, elastic, and/or stretchable yarns and/or threads, wherein some of these yarns or threads are electroconductive. In an example, a sensor (e.g. electrode) can be an EEG sensor. In an example, a sensor (e.g. electrode) can comprise an electrical and/or electromagnetic energy receiver which collects data concerning (changes in) the conductivity, resistance, and/or impedance of energy transmitted through body tissue from an electrical and/or electromagnetic energy emitter to the receiver.

In an example, a sensor (e.g. electrode) can further comprise an energy-emitting electrode and an energy-receiving electrode. In an example, a sensor (e.g. electrode) can receive electromagnetic energy which is emitted from a person's brain. In an example, a sensor (e.g. electrode) can be a dielectric structure which is formed by bonding together alternating layers of conductive and non-conductive elastomeric material. In another example, a sensor (e.g. electrode) can be a monopole electrode. In an example, a sensor (e.g. electrode) can be based on capacitance. In another example, a sensor (e.g. electrode) can measure electromagnetic impedance. In an embodiment, a sensor (e.g. electrode) can measure electromagnetic capacitance.

In an example, a device can include a sensor (e.g. electrode) with a kidney-bean, crescent, or banana shape. In another example, an oblong soft pad can have a crescent or boomerang shape. In an embodiment, a sensor (e.g. electrode) can have a conic-section shape. In an example, a sensor (e.g. electrode) can have a helical shape. In an embodiment, a sensor (e.g. electrode) can have a parabolic shape whose peak penetrates into a person's hair. In an example, a sensor (e.g. electrode) can have a rounded rectangular shape. In an embodiment, a sensor (e.g. electrode) can have a square shape. In another example, a sensor (e.g. electrode) can have an arcuate or round shape. In an example, a sensor (e.g. electrode) can have an oval or elliptical shape. In another example, a device can be attached to a person's ear lobe.

In an embodiment, a sensor (e.g. electrode) can be a dry electrode. In an example, a sensor (e.g. electrode) can be made with a non-conductive elastic (e.g. elastomeric) polymer which has been coated and/or impregnated with electroconductive metal. In another example, a sensor (e.g. electrode) can be made with an elastomeric polymer (e.g. PDMS) which has been impregnated, embedded, or coated with silver. In an example, a sensor (e.g. electrode) can be made with an elastomeric polymer (e.g. PDMS) which has been impregnated, embedded, or coated with copper. In an example, a sensor (e.g. electrode) can be made with conductive ink. In an example, a sensor (e.g. electrode) can be made with nanoparticles, nanotubes, nanofoam, or nanofibers. In another example, a sensor (e.g. electrode) can be made with polypropylene glycol. In an example, a sensor (e.g. electrode) can be made by 3D printing, wherein conductive ink is printed onto fabric.

In an example, a sensor (e.g. electrode) can be made by adhering (or otherwise bonding) a first flexible conductive layer, a flexible non-conductive layer, and a second flexible conductive layer together; wherein the flexible non-conductive layer is between the first flexible conductive layer and the second flexible conductive layer. In another example, a sensor (e.g. electrode) can be made by embroidering or stitching a sinusoidal or zigzag pattern with conductive threads or yarns onto an article of clothing. In an example, a sensor (e.g. electrode) can be made by printing high-conductivity ink onto a low-conductivity textile or fabric. In an example, a sensor (e.g. electrode) can be made by stitching sensors (e.g. electrodes) with conductive threads or yarns.

In an example, a sensor (e.g. electrode) can be made by bonding together alternating layers of conductive and non-conductive polymers. In an example, a sensor (e.g. electrode) can be made by printing (or otherwise adhering) alternating layers of conductive and non-conductive polymers. In an embodiment, a sensor (e.g. electrode) can be made by printing, spraying, or adhering a layer of elastomeric conductive polymer material onto the inner (e.g. body-facing) surface of a headband. In an example, a sensor (e.g. electrode) can comprise a capacitor which is made by bonding together alternating layers of conductive and non-conductive polymers.

In an embodiment, a sensor (e.g. electrode) can comprise a dielectric layer of low-conductivity material between two layers of high-conductivity material. In another example, a sensor (e.g. electrode) can comprise high-conductivity and low-conductivity layers with different thicknesses. In an example, a sensor (e.g. electrode) can comprise two conductive layers separated by a dielectric elastomer. In another example, a sensor (e.g. electrode) can include a high-conductivity layer which is worn closer to the surface of a person's head and a low-conductivity layer which is worn farther from the surface of the person's head.

In an embodiment, sensors (e.g. electrodes) can be more densely distributed (e.g. be closer together) on a posterior portion of an electrode-holding ring, headband, halo, or headset than on an anterior portion of the ring, headband, halo, or headset. In an example, sensors (e.g. electrodes) can be more densely distributed (e.g. be closer together) on posterior and anterior portions of an electrode-holding ring, headband, halo, or headset than on side portions of the ring, headband, halo, or headset.

In an example, a device and/or sensor (e.g. electrode) on the device can be made with activated carbon particles. In an example, a device and/or sensor (e.g. electrode) on the device can be made with carbon black. In an example, a device and/or sensor (e.g. electrode) on the device can be made with conductive particles. In an example, a device and/or sensor (e.g. electrode) on the device can be made with cotton. In an example, a device and/or sensor (e.g. electrode) on the device can be made with gold. In an example, a device and/or sensor (e.g. electrode) on the device can be made with graphite.

In an example, a device and/or sensor (e.g. electrode) on the device can be made with linen. In an example, a device and/or sensor (e.g. electrode) on the device can be made with metal powder. In another example, a device and/or sensor (e.g. electrode) on the device can be made with nickel. In an example, a device and/or sensor (e.g. electrode) on the device can be made with PEDOT [poly(3,4-ethylenedioxythiophene]. In another example, a device and/or sensor (e.g. electrode) on the device can be made with PI (polyimide). In an embodiment, a device and/or sensor (e.g. electrode) on the device can be made with polyethylene glycol. In an example, a device and/or sensor (e.g. electrode) on the device can be made with polypropylene oxide.

In an embodiment, a device and/or sensor (e.g. electrode) on the device can be made with rayon. In an example, a device and/or sensor (e.g. electrode) on the device can be made with silicone-based material. In an embodiment, a device and/or sensor (e.g. electrode) on the device can be made with silver chloride. In another example, a device and/or sensor (e.g. electrode) on the device can be made with single wall carbon nanotubes. In an example, a device and/or sensor (e.g. electrode) on the device can be made with TPU (thermoplastic polyurethane). In another example, a sensor (e.g. electrode) can be made with a conductive rubber. In an embodiment, a sensor (e.g. electrode) can be made with amorphous material. In an example, a sensor (e.g. electrode) can be made with conductive thread.

In an example, a sensor (e.g. electrode) can be made with elastomeric material. In an example, a sensor (e.g. electrode) can be made with ion-permeable material. In an example, a sensor (e.g. electrode) can be made with material with a Shore A value between 5 and 50. In another example, a sensor (e.g. electrode) can be made with rubber. In an embodiment, a sensor (e.g. electrode) can be made with styrene ethylene butylene stryene (SEBS). In another example, a sensor (e.g. electrode) can be made with a deformable polymer. In an example, a sensor (e.g. electrode) can be made with a soft (e.g. elastomeric) conductive polymer-based material. In an embodiment, a sensor (e.g. electrode) can be made with a silicone-based material. In an example, a sensor (e.g. electrode) can be made with carbon. In an embodiment, a sensor (e.g. electrode) can be made with copper. In an example, a sensor (e.g. electrode) can be made with graphite. In an example, a sensor (e.g. electrode) can be made with PEDOT:PSS. In another example, a sensor (e.g. electrode) can be made with polydimethylsiloxane (PDMS). In an example, a sensor (e.g. electrode) can be made with silver.

In an example, a sensor (e.g. electrode) can be made with a cellulose material (such as HPMC) which is doped, impregnated, coated, sprayed, printed, or embedded with aluminum. In another example, a sensor (e.g. electrode) can be made with a cellulose material (such as HPMC) which is doped, impregnated, coated, sprayed, printed, or embedded with carbon particles. In an example, a sensor (e.g. electrode) can be made with a cellulose material (such as HPMC) which is doped, impregnated, coated, sprayed, printed, or embedded with graphene nanoplatelets. In another example, a sensor (e.g. electrode) can be made with a cellulose material (such as HPMC) which is doped, impregnated, coated, sprayed, printed, or embedded with metal powder.

In an example, a sensor (e.g. electrode) can be made with a cellulose material (such as HPMC) which is doped, impregnated, coated, sprayed, printed, or embedded with conductive ink. In an example, a sensor (e.g. electrode) can be made with a hydrogel material which is doped, impregnated, coated, sprayed, printed, or embedded with carbon. In an example, a sensor (e.g. electrode) can be made with a hydrogel material which is doped, impregnated, coated, sprayed, printed, or embedded with conductive particles. In an example, a sensor (e.g. electrode) can be made with a hydrogel material which is doped, impregnated, coated, sprayed, printed, or embedded with graphite. In an embodiment, a sensor (e.g. electrode) can be made with a hydrogel material which is doped, impregnated, coated, sprayed, printed, or embedded with metal powder.

In an example, a sensor (e.g. electrode) can be made with a hydrogel material which is doped, impregnated, coated, sprayed, printed, or embedded with conductive ink. In an embodiment, a sensor (e.g. electrode) can be made with a low-conductivity material which is doped, impregnated, coated, sprayed, printed, or embedded with high-conductivity material. In another example, a sensor (e.g. electrode) can be made with a silicone-based material (such as PDMS) which is doped, impregnated, coated, sprayed, printed, or embedded with carbon. In an example, a sensor (e.g. electrode) can be made with a silicone-based material (such as PDMS) which is doped, impregnated, coated, sprayed, printed, or embedded with conductive particles.

In an embodiment, a sensor (e.g. electrode) can be made with a silicone-based material (such as PDMS) which is doped, impregnated, coated, sprayed, printed, or embedded with graphite. In another example, a sensor (e.g. electrode) can be made with a silicone-based material (such as PDMS) which is doped, impregnated, coated, sprayed, printed, or embedded with silver. In an example, a sensor (e.g. electrode) can be made with a silicone-based material (such as PDMS) which is doped, impregnated, coated, sprayed, printed, or embedded with steel. In another example, a sensor (e.g. electrode) can be made with PEDOT and/or PEDOT:PSS which is doped, impregnated, coated, sprayed, printed, or embedded with carbon.

In an embodiment, a sensor (e.g. electrode) can be made with PEDOT and/or PEDOT:PSS which is doped, impregnated, coated, sprayed, printed, or embedded with conductive particles. In an example, a sensor (e.g. electrode) can be made with PEDOT and/or PEDOT:PSS which is doped, impregnated, coated, sprayed, printed, or embedded with graphite. In another example, a sensor (e.g. electrode) can be made with PEDOT and/or PEDOT:PSS which is doped, impregnated, coated, sprayed, printed, or embedded with silver. In an embodiment, a sensor (e.g. electrode) can be made with polydimethylsiloxane (PDMS) which is doped, impregnated, coated, sprayed, printed, or embedded with aluminum. In an example, a sensor (e.g. electrode) can be made with polydimethylsiloxane, polybutylene terephthalate, or polyurethane which is doped, impregnated, coated, sprayed, printed, or embedded with silver, carbon nanotubes or other forms of carbon, copper, aluminum, nickel, platinum, or gold.

In an example, a sensor (e.g. electrode) can be made with thermoplastic polyurethane (TPU) which is doped, impregnated, coated, sprayed, printed, or embedded with carbon nanotubes. In an example, a sensor (e.g. electrode) can be made with thermoplastic polyurethane (TPU) which is doped, impregnated, coated, sprayed, printed, or embedded with copper. In an example, a sensor (e.g. electrode) can be made with thermoplastic polyurethane (TPU) which is doped, impregnated, coated, sprayed, printed, or embedded with metal particles. In an example, a sensor (e.g. electrode) can be made with thermoplastic polyurethane (TPU) which is doped, impregnated, coated, sprayed, printed, or embedded with silver chloride.

In an example, a sensor (e.g. electrode) can be made with a compressible, malleable, and/or low-durometer non-conductive material (e.g. a non-conductive elastomeric polymer) which has been impregnated, doped, filled, coated, or embedded with a conductive material (e.g. carbon or metal particles). In an example, a sensor (e.g. electrode) can be made with a silicone material (such as PDMS) which has been impregnated, doped, filled, coated, or embedded with silver. In another example, a sensor (e.g. electrode) can be made with a silicone-based polymer which has been impregnated, doped, filled, coated, or embedded with silver, steel, copper, gold, aluminum, and/or carbon.

In an example, a sensor (e.g. electrode) can be made with an elastomeric polymer which has been impregnated, doped, filled, coated, or embedded with electroconductive material (e.g. silver, silver-chloride, steel, aluminum, or carbon). In another example, a sensor (e.g. electrode) can be made with non-conductive yarns (or threads) which has been impregnated, doped, filled, coated, or embedded with conductive material. In another example, a sensor (e.g. electrode) can be made with polydimethylsiloxane (PDMS) which has been impregnated, doped, filled, coated, or embedded with carbon or sliver.

In an embodiment, a device can comprise: a first set of sensors (e.g. electrodes) which are worn on a person's forehead, wherein sensors in this first set are made from a conductive polymer with a first Shore value and are configured to generally conform to the curvature of the person's forehead; a second set of sensors (e.g. electrodes) which are worn on the posterior of the person's head, wherein sensors in this second set further comprise a plurality of hair-penetrating protrusions made from a conductive polymer with a second Shore value, wherein the second Shore value is greater than the first Shore value.

In an example, a posterior half of an electrode-holding ring, headband, halo, or headset can have tapered electroconductive prongs, teeth, pins, or other protrusions which penetrates (e.g. slide) between strands of hair. In an embodiment, a posterior portion of an electrode-holding ring, headband, halo, or headset can have electroconductive prongs, teeth, pins, or other protrusions which penetrate (e.g. slide) between strands of hair. In an example, a sensor (e.g. electrode) can comprise a base and a plurality of protrusions, teeth, prongs, or pins which extend out from the base toward the surface of a person's head, wherein the base is configured to rotate when it is pushed toward the person's head. In an embodiment, a sensor (e.g. electrode) can comprise a base with electroconductive prongs, teeth, pins, or other protrusions.

In an example, a sensor (e.g. electrode) can comprise a base with electroconductive prongs, teeth, pins, or other protrusions made from a polymer which has been coated and/or impregnated with carbon nanotubes. In an embodiment, a sensor (e.g. electrode) can comprise a base with electroconductive prongs, teeth, pins, or other protrusions made from PDMS which has been coated and/or impregnated with conductive material. In another example, sensors (e.g. electrodes) on a posterior half of an electrode-holding ring, headband, halo, or headset can have electroconductive prongs, teeth, pins, or other protrusions which penetrate (e.g. slide) between strands of hair. In another example, sensors (e.g. electrodes) on a posterior portion of an electrode-holding ring, headband, halo, or headset can have electroconductive prongs, teeth, pins, or other protrusions to penetrate between strands of hair and sensors (e.g. electrodes) on an anterior portion of the ring, headband, halo, or headset do not.

In an example, hair-penetrating prongs (e.g. prongs, protrusions, pins, or legs) on a sensor can be configured in nested rings. In another example, hair-penetrating prongs (e.g. prongs, protrusions, pins, or legs) on a sensor can be configured in a single circle. In an embodiment, a distal section of a hair-penetrating prong (e.g. prong, protrusion, pin, or leg) on a sensor can be more have a lower durometer level than the proximal section of the prong. In an example, electroconductive hair-penetrating prongs (e.g. prongs, protrusions, pins, or legs) on a sensor which are closer to the center (or midline) of a sensor base can have a higher durometer level than prongs which are farther from the center (or midline).

In an example, a core of a hair-penetrating prong (e.g. prong, protrusion, pin, or leg) on a sensor (e.g. electrode) can be more conductive (e.g. have a higher concentration of conductive material) than the outer layer of the hair-penetrating prong. In another example, a core of a hair-penetrating prong (e.g. prong, protrusion, pin, or leg) on a sensor (e.g. electrode) can be made from a hydrogel. In an example, a hair-penetrating prong (e.g. prong, protrusion, pin, or leg) on a sensor (e.g. electrode) can be made with a low-conductivity flexible material which has been doped, impregnated, coated, dipped, sprayed, or printed with a high-conductivity material.

In an example, an array of hair-penetrating prongs (e.g. prongs, protrusions, teeth, pins, or legs) on a sensor can be configured in nested (e.g. concentric) polygons. In another example, hair-penetrating prongs (e.g. prongs, protrusions, teeth, pins, or legs) on a sensor can be configured in nested polygons. In an example, hair-penetrating prongs (e.g. prongs, protrusions, teeth, pins, or legs) on a sensor (e.g. electrode) can be made from polydimethylsiloxane, polybutylene terephthalate, or polyurethane which has been impregnated, doped, filled, and/or coated with silver, carbon nanotubes or other forms of carbon, copper, aluminum, nickel, platinum, or gold. In another example, a sensor (e.g. electrode) can include a plurality of electroconductive protrusions (e.g. protrusions, prongs, teeth, legs, pins, and/or bumps) with spherical, ball-shaped, or hemispherical ends, wherein the protrusions extend out from the sensor (e.g. electrode) base and have spherical ends.

In an example, a hair-penetrating prong (e.g. prong, protrusion, pin, or leg) on a sensor can have a proximal section which is closer to the sensor base and a distal section which is farther from the sensor base, wherein the proximal section has a central longitudinal axis which intersects the plane of the sensor base at a first radially-outward-facing angle, wherein the distal section has a central longitudinal axis whose virtual extension intersects the plane of the sensor base at a second radially-outward-facing angle, wherein the second angle is greater than the first angle. In an example, central longitudinal axes of proximal and distal sections of a hair-penetrating prong (e.g. prong, protrusion, pin, or leg) on a sensor can intersect each other at an obtuse angle. In an example, hair-penetrating prongs (e.g. prongs, protrusions, pins, or legs) on a sensor can be angled toward the periphery of the array in a windmill, whorl, or whorl-windmill pattern.

In an example, a distal section of a hair-penetrating prong (e.g. prong, protrusion, pin, or leg) on a sensor can have a shape selected from the group consisting of: articulated, bifurcated, chevron, column, concave, cone, conic-section, convex, ellipsoid, frustum, funnel-shaped, helical, hourglass, loop, paraboloid, semicircle, serpentine, shaped like the letter U, shaped like the letter V, sinusoidal, spheroid, spiral, and tapered.

In an example, a hair-penetrating prong (e.g. prong, protrusion, pin, or leg) on a sensor can comprise: a proximal section with a first shape which is selected from the group consisting of: articulated, bifurcated, chevron, column, concave, cone, conic-section, convex, ellipsoid, frustum, funnel-shaped, helical, hourglass, loop, paraboloid, semicircle, serpentine, shaped like the letter U, shaped like the letter V, sinusoidal, spheroid, spiral, and tapered; and a distal section with a second shape selected from the group consisting of: articulated, bifurcated, chevron, column, concave, cone, conic-section, convex, ellipsoid, frustum, funnel-shaped, helical, hourglass, loop, paraboloid, semicircle, serpentine, shaped like the letter U, shaped like the letter V, sinusoidal, spheroid, spiral, and tapered.

In an example, a hair-penetrating prong (e.g. prong, protrusion, pin, or leg) on a sensor can have a proximal section which is closer to the sensor base and a distal section which is farther from the sensor base, wherein the proximal section is convex relative to a central longitudinal axis of the prong, and wherein the distal section is concave relative to a central longitudinal axis of the prong. In an embodiment, a hair-penetrating prong (e.g. prong, protrusion, pin, or leg) on a sensor can comprise two of more sections which are attached to each other at their mid-sections (e.g. between proximal and distal portions) by movable joints or hinges.

In an example, a device can comprise a channel (e.g. channel, track, slot, or groove) along which one or more sensors (e.g. electrodes) can be slid. In an embodiment, a device with sensors (e.g. electrodes) for monitoring brain activity can include a plurality of electromagnetic actuators which automatically adjust the positions of sensors (e.g. electrodes). In another example, sensors (e.g. electrodes) can be moved (e.g. slid) along the circumference of an electrode-holding ring, headband, halo, or headset. In an example, sensors (e.g. electrodes) can be plugged into different locations an electrode-holding ring, headband, halo, or headset.

In an embodiment, sensors (e.g. electrodes) on a device for monitoring brain activity can be modular and/or removably-attachable. In another example, the locations of a sensors (e.g. electrodes) on a device with sensors (e.g. electrodes) for monitoring brain activity can be moved manually with respect to the surface of a person's head. In an example, a sensor (e.g. electrode) can be attached to an eyewear sidepiece (e.g. temple) by two or more springs. In an embodiment, a device can be removably-attached to eyewear. In an example, a device can be removably-attached to the posterior third of the length of an eyewear sidepiece (e.g. temple). In another example, a sensor (e.g. electrode) can be inserted into a slot (e.g. receptacle, slot, port, opening, or hole) on an eyewear sidepiece (e.g. temple).

In an example, a sensor (e.g. electrode) can be pushed toward the surface of a person's head by a mechanism selected from the group consisting of: compressible foam or gel; a spring; a flexible prong; an inflatable chamber; a hydraulic piston; a rotatable threaded member; an electromagnetic solenoid; and a magnet. In an example, a sensor (e.g. electrode) or prong extending out of a sensor can be pressed against the surface of a person's head by a hydraulic mechanism. In another example, a sensor (e.g. electrode) or prong extending out of a sensor can be pressed against the surface of a person's head by a piston mechanism.

In an example, a sensor (e.g. electrode) or prong extending out of a sensor can be pressed against the surface of a person's head by a solenoid mechanism. In another example, a sensor (e.g. electrode) can be moved toward the surface of a person's head by compressible foam. In an example, a sensor (e.g. electrode) can be moved toward the surface of a person's head by a telescoping mechanism. In an example, a sensor (e.g. electrode) can be moved toward the surface of a person's head by a plastic spring. In an example, a sensor (e.g. electrode) can be moved toward the surface of a person's head by a leaf spring.

In an example, a sensor (e.g. electrode) can be moved toward the surface of a person's head by a compressible material. In an example, a sensor (e.g. electrode) can be configured to rotate an array of pins, prongs, teeth, or other protrusions when the sensor is pushed toward the surface of a person's head. In an embodiment, a sensor (e.g. electrode) can have a telescoping configuration so that it extends out toward the surface of a person's head. In an example, pins, prongs, teeth, or other protrusions which extend out from the base of a sensor (e.g. electrode) can be configured to bend and/or flex laterally with respect to the surface of a person's head when the base is pushed toward the surface of a person's head.

In an embodiment, a force with which a sensor (e.g. electrode) is pressed against the surface of a person's head can be (manually or automatically) adjusted. In another example, the distance between a sensor (e.g. electrode) and the surface of a person's head can be adjusted by an electromagnetic actuator. In an example, the distance between a sensor (e.g. electrode) and the surface of a person's head can be adjusted by a pneumatic mechanism. In another example, the pressure between a sensor (e.g. electrode) and the surface of a person's head can be adjusted by changing the tension on a spring. In an embodiment, the pressure between a sensor (e.g. electrode) and the surface of a person's head can be adjusted by a hydraulic mechanism. In another example, the pressure between a sensor (e.g. electrode) and the surface of a person's head can be adjusted by changing the tension of an elastic strap and/or band.

In an example, a device can include an electromagnetic mechanism which oscillates and/or vibrates a sensor (e.g. electrode) to secure better electroconductive contact with the surface of the person's head. In an embodiment, a sensor (e.g. electrode) can be rotated, in an oscillating manner, around an axis which is substantially orthogonal to the surface of a person's head so as to penetrate a layer of a person's hair and achieve better electromagnetic communication with the person's brain. In an example, a sensor (e.g. electrode) can be rotated around an axis which is substantially orthogonal to the surface of a person's head so as to penetrate a layer of a person's hair and achieve better electromagnetic communication with the person's brain.

In an example, a sensor (e.g. electrode) base can be a flexible structure which deforms (e.g. from curved to flat or vice versa) in response to pressure. In an example, a sensor (e.g. electrode) base can be changed from a first configuration which is concave relative to a person's head to a second configuration which is parallel (e.g. flat or planar) relative to the person's head. In an example, a sensor (e.g. electrode) base can have a concave shape when not subjected to external force and can have a substantially-flat shape when subjected to external force.

In an example, a sensor can comprise: a sensor base, wherein the sensor base has a first configuration with a first amount of curvature, wherein the sensor base has a second configuration with a second amount of curvature, wherein the second amount is less than the first amount, and wherein the sensor base is changed from the first configuration to the second configuration when the sensor base is pressed onto a person's head; and hair-penetrating prongs (e.g. prongs, protrusions, pins, or legs) on a sensor which extend out from the sensor base, wherein there is a first average distance between tips of the prongs in the first configuration, wherein there is a second average distance between tips of the prongs in the second configuration, and wherein the second average distance is greater than the first average distance. In another example, a sensor (e.g. electrode) base can comprise a plurality of moveable sections, wherein these sections collectively form a convex structure in a first configuration and a substantially-flat structure in a second configuration.

In an example, a sensor (e.g. electrode) can comprise one or more electromagnetic actuators which move one or more protrusions (e.g. protrusions, prongs, teeth, legs, pins, and/or bumps). In an example, a sensor (e.g. electrode) can comprise one or more electromagnetic actuators which move one or more protrusions (e.g. protrusions, prongs, teeth, legs, pins, and/or bumps) in a direction which is oblique to the surface of a person's head and/or to the surface of the sensor base of the electrode, thereby enabling the protrusions to slide between strands of hair on the person's head. In another example, a distal section of a hair-penetrating prong (e.g. prong, protrusion, pin, or leg) on a sensor can be narrower (e.g. have a smaller average cross-sectional size) than a proximal section of the prong.

In an example, a device can include an electronics unit (e.g. control unit). In an example, a device can include a data processor (e.g., CPU, GPU, and/or memory). In another example, analog data from sensors (e.g. electrodes) can be converted to digital data by (local, within device) analog-to-digital convertors. In an example, a first data processor and/or data transmitter which is physically part of a wearable device can be in electronic communication with a second data processor and/or data receiver which is not physically part of the wearable device. In an embodiment, an electrode-holding ring, headband, halo, or headset can be part of a system, wherein a data processor which is physically part of the in the ring, headband, halo, or headset is in wireless communication with a remote data processor.

In an example, sensors (e.g. electrodes) on a device can collect data concerning the emission of electrical energy by a person's brain. In an embodiment, sensors (e.g. electrodes) on a device can record (e.g. record, measure, monitor) the emission of electrical energy by a person's brain. In an example, a power source can be a battery. In an embodiment, a power source can transduce, harvest, and/or generate energy from body motion or kinetic energy. In another example, an electrode-holding ring, headband, halo, or headset can further comprise flexible and/or elastic electroconductive pathways which connect the sensors (e.g. electrodes) to the electronics unit.

In an example, a device can be embodied in a hairband or tiara which spans, from side-to-side, over the top of a person's head. In an example, an electrode-holding device can be embodied in a cap or hat. In another example, an electrode-holding device can be embodied in a headband. In an example, an electrode-holding ring, headband, halo, or headset can be embodied in a hair comb or tiara. In another example, an electrode-holding ring, headband, halo, or headset can be embodied in a headband. In an example, a device can be embodied in a headband or halo. In an example, a device can be embodied in a headset. In an example, a device can be embodied in a helmet. In an example, a device can be embodied in an ear ring.

In an example, a device for monitoring brain activity can include a clip or other attachment mechanism to which a side-piece of the frame of a pair of eyeglasses can be attached so that this device can be worn in combination with eyeglasses. In another example, an electrode-holding device can include an attachment (e.g. connection) mechanism which enables it to be attached to eyeglasses. In another example, an electrode-holding device can include an opening into which eyeglasses can be inserted. In another example, an electrode-holding ring, headband, halo, or headset can include an opening which is configured to receive the temples (e.g. side-pieces) of the frame of a pair of eyeglasses so that this device can be attached to (and worn in combination with) eyeglasses.

In an example, the posterior end of an eyewear sidepiece (e.g. temple) can bifurcate. In an embodiment, an eyewear sidepiece (e.g. temple) can have a bifurcated section, wherein an upper branch of the bifurcated section has an upwardly-convex wave (or curve) and a lower branch of the bifurcated section has a downwardly-convex wave (or curve). In an example, an eyewear sidepiece (e.g. temple) can bifurcate, wherein there is a kidney-bean, crescent, or banana shaped opening (e.g. opening, hole, or gap) between an upper branch (e.g. branch, arm, or loop) of the bifurcation and a lower branch of the bifurcation.

In an embodiment, a device can comprise a posterior strap (e.g. strap, band, loop, or arm) which spans around the rear of a person's head, wherein the strap is connected to eyewear sidepieces (e.g. temples). In an example, a device can comprise a movable (e.g. pivoting) arm which has a first configuration in which it does not span the rear of a person's head and a second configuration in which it does span the rear of the person's head, wherein the arm is movably-connected to eyewear sidepieces (e.g. temples). In another example, a device can have a first configuration in which it is aligned with an eyewear sidepiece (e.g. temple) and a second configuration in which is extends out from the sidepiece at an acute angle.

In an embodiment, an eyewear sidepiece (e.g. temple) can span forward from the rear of a person's auricle (e.g. outer ear) in the following manner: start with a posterior (rear) end which is worn posterior to (behind) the person's auricle; then curve upward and forward around the tissue connection between the person's outer auricle and the rest of the person's head, to the top of this tissue connection; then curve downward and forward; then curve upward, forward, and inward to a location on the person's temple and/or forehead; and then curve downward, forward, and outward to an anterior (front) end which connects to (or becomes part of) an eyewear front piece. In another example, the middle (e.g. middle third) of the longitudinal axis of an eyewear sidepiece (e.g. temple) can bow, curve, or undulate inward toward the surface of a person's head. In another example, a device can also include one or more inertial motion units (e.g. accelerometers, gyroscopes, and/or inclinometers) as well as sensors (e.g. electrodes). In an example, a device can also include a signal amplifier. In an embodiment, a device can also include an analog-to-digital converter. In an example, a device can be held on a person's head by clamping, clipping, and/or latching onto the person's hair.

In an embodiment, a device can be used for cognitive training. In another example, a device can be used for detection and/or prediction of adverse health events. In another example, a device can be used for health and wellness applications. In another example, a device can be used for sports applications. In an example, a device can be used to collect data concerning brain activity. In an example, a device can be used to evaluate a person's emotional state. In another example, a device can be used to monitor a person's stress level. In an example, a device can be used to provide biofeedback. In another example, a device can function as a BCI (Brain-to-Computer Interface) for communication for people who are unable to communicate vocally. In an example, a device can function as a BCI (Brain-to-Computer Interface) for remote control of computers or other devices. In an example, a device can function as a BCI (Brain-to-Computer Interface) for situations when other forms of human-to-computer interaction (such as a touch-based interface or a speech-based interface) are undesirable, difficult, or impossible.

In an example, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the partial ring has a forward-facing concavity. In an example, a head-worn electrode-holding device can comprise an array of coils or spirals which span the upper third of a person's head. In an example, a main portion of an electrode-holding ring, headband, halo, or headset can be shaped like the perimeter of a saddle, hyperbolic paraboloid, and/or Pringles™ brand chip. In another example, a portion (e.g. part, arm, or segment) of an electrode-holding ring, headband, halo, or headset can have a shape which is a portion (e.g. a section) of a spiral or helix.

In an embodiment, a portion (e.g. portion, arm, segment, or loop) of an electrode-holding ring, headband, halo, or headset spanning the front half of a person's head can have an downward-facing concavity. In an example, a portion (e.g. portion, arm, segment, or loop) of an electrode-holding ring, headband, halo, or headset spanning the rear half of a person's head can have an front-facing concavity. In another example, a portion (e.g. portion, arm, segment, or loop) of an electrode-holding ring, headband, halo, or headset which loops over the upper half (e.g. the top) of a person's head can have a rear-facing concavity. In an embodiment, a portion of an electrode-holding ring, headband, halo, or headset can have a spiral and/or helical shape.

In an example, a section (e.g. section, segment, arm or portion) of an electrode-holding ring, headband, halo, or headset can have an arc shape. In another example, a section (e.g. section, segment, arm or portion) of an electrode-holding ring, headband, halo, or headset can have a hair-pin curve shape. In an embodiment, a section (e.g. section, segment, arm or portion) of an electrode-holding ring, headband, halo, or headset can have a parabolic shape. In an example, a section (e.g. section, segment, arm or portion) of an electrode-holding ring, headband, halo, or headset can have a semi-oval shape. In an embodiment, a section (e.g. section, segment, arm or portion) of an electrode-holding ring, headband, halo, or headset can have a wave shape.

In an example, a side of an electrode-holding ring, headband, halo, or headset can have a shape like that of a normal curve which has been rotated 90 degrees so that its peak faces toward the front of a person's head and its opening faces toward the rear of the person's head. In an embodiment, a side of an electrode-holding ring, headband, halo, or headset can have a shape like that of a normal curve which has been rotated 90 degrees so that its peak faces toward the front of a person's head and its opening faces toward the rear of the person's head, wherein one tail of the curve reaches the person's ear and the other tail of the curve reaches the top of the person's head. In an example, an arcuate anterior portion (e.g. portion, arm, segment, or loop) of an electrode-holding ring, headband, halo, or headset can have an upward-facing concavity.

In an example, an arcuate anterior portion (e.g. portion, arm, segment, or loop) of an electrode-holding ring, headband, halo, or headset can have a rear-facing concavity. In another example, an arcuate posterior portion (e.g. portion, arm, segment, or loop) of an electrode-holding ring, headband, halo, or headset can have an downward-facing concavity. In an example, an electrode-holding ring, headband, halo, or headset can have an undulating, serpentine, and/or sinusoidal shape. In another example, an electrode-holding ring, headband, halo, or headset can have an undulating, serpentine, and/or sinusoidal shape. In an example, an electrode-holding ring, headband, halo, or headset can have a circular, elliptical, egg, or oval shape.

In an example, an electrode-holding ring, headband, halo, or headset can have a generally circular, elliptical, oval, or egg shape except for an upward bump over each ear. In another example, an electrode-holding ring, headband, halo, or headset can have a generally circular, elliptical, or oval shape except for an undulation with a downward-facing concavity over each of the person's outer ears (e.g. auricles). In an example, an electrode-holding ring, headband, halo, or headset can have sinusoidal waves and/or undulations with an amplitude of at least one inch. In an embodiment, an electrode-holding ring, headband, halo, or headset can have six sinusoidal waves and/or undulations. In an example, an electrode-holding ring, headband, halo, or headset can have an elliptical, oblong, or egg shape.

In an embodiment, an electrode-holding ring, headband, halo, or headset can comprise: a saddle-shaped section which loops over the top of a person's head (figuratively appearing as if a central oval or elliptical loop has been melted on the top of the person's head and droops down the sides of the person's head); and two arcs which extend from the bottom portions of the saddle-shaped section to curve down around the rear portions of the person's ears. In an example, an electrode-holding ring, headband, halo, or headset can include a segment which is portion of a spiral and/or helix.

In an embodiment, an undulating electrode-holding ring, headband, halo, or headset comprises: a posterior loop (e.g. loop, portion, section, or segment) which is worn on the posterior-upper quartile of a person's head, wherein the posterior loop has a forward-facing concavity; a right-side loop (e.g. loop, portion, section, or segment) which is worn on the right side of the person's head, wherein the right-side loop has a shape which is a spiral or a portion of a spiral; and a left-side loop (e.g. loop, portion, section, or segment) which is worn on the left side of the person's head, wherein the left-side loop has a shape which is a spiral or a portion of a spiral. In an example, each side (e.g. right and left) of an electrode-holding ring, headband, halo, or headset can have a circular, elliptical, oval, or egg shape. In another example, each side (e.g. right and left) of an electrode-holding ring, headband, halo, or headset can have a conic section shape.

In an example, an electrode-holding ring, headband, halo, or headset can encircle a person's head. In an example, an electrode-holding ring, headband, halo, or headset can encircle between 40% and 60% of a person's head. In another example, an electrode-holding ring, headband, halo, or headset can span (e.g. partially encircle) the posterior half of a person's head. In an example, an electrode-holding ring, headband, halo, or headset can encircle a person's head at a 15 to 35 degree angle relative to a horizontal plane (when a person's head is upright).

In an example, a headband, halo, or headset for recording brain activity can comprise: a front portion (e.g. portion, segment, or loop) which spans across a person's forehead; a right side (e.g. temple) portion (e.g. portion, arm, or segment) which spans from the person's right ear to the front portion; a left side (e.g. temple) portion (e.g. portion, arm, or segment) which spans from the person's left ear to the front portion; a right-side rear portion (e.g. portion, arm, or segment) which extends rearward and downward from the person's right ear; a left-side rear portion (e.g. portion, arm, or segment) which extends rearward and downward from the person's left ear; a right-side flexible posterior-ear prong (e.g. prong, arm, or segment) which curves around the posterior and upper surfaces of the person's right ear (e.g. where the auricle connected to the rest of the person's head); a left-side flexible posterior-ear prong (e.g. prong, arm, or segment) which curves around the posterior and upper surfaces of the person's left ear (e.g. where the auricle connected to the rest of the person's head); a plurality of sensors (e.g. electrodes) for recording brain activity; and an electronics unit which includes a data processor, a data transmitter, and a power source.

In an embodiment, an electrode-holding ring, headband, halo, or headset can undulate in a sinusoidal manner as it encircles a person's head. In another example, an undulating electrode-holding ring, headband, halo, or headset can have a concave portion over a person's ear, wherein the concavity rests on the upper portion of the ear (e.g. auricle). In an example, each side (e.g. right and left) of an electrode-holding ring, headband, halo, or headset can have three or more (sinusoidal) undulations. In an embodiment, an upper arm (e.g. arm, band, segment, or portion) of a device which loops over the top of a person's head can have an undulating (e.g. sinusoidal) shape.

In an example, a posterior portion (e.g. rear half) of an electrode-holding ring, headband, halo, or headset can be wider than an anterior portion (e.g. front half) of the ring, headband, halo, or headset. In an embodiment, an electrode-holding ring, headband, halo, or headset can have a variable width around its circumference. In an example, an electrode-holding ring, headband, halo, or headset can have a width which is between a half of an inch and two inches. In another example, an undulating rear-tilted headband can have a variable width, wherein side portions are wider than front and rear portions. In an embodiment, posterior and anterior portions (e.g. rear half) of an electrode-holding ring, headband, halo, or headset can be wider than side portions (e.g. front half) of the ring, headband, halo, or headset. In another example, the anterior half of an electrode-holding ring, headband, halo, or headset can be wider than the posterior half of the electrode-holding ring, headband, halo, or headset.

In an example, an electrode-holding ring, headband, halo, or headset can have a forward-upward slope. In another example, a front portion of a undulating rear-tilted headband can span the front portion of the person's head at an average first distance from the top of the person's head; a side portion of the undulating rear-tilted headband can span the side of the person's head at an average second distance from the top of the person's head; and a rear portion of the undulating rear-tilted headband can span the rear of the person's head at an average third distance from the top of the person's head; wherein the second average distance is greater than the first average distance; and wherein the third average distance is greater than the second average distance.

In an embodiment, an electrode-holding ring, headband, halo, or headset can have a forward-upward slope at an angle between 15 and 35 degrees relative to a horizontal plane when a person's head is upright. In an example, when a person's head is upright, an electrode-holding ring, headband, halo, or headset can be virtually divided (in a posterior-to-anterior manner) into three sections; wherein these three portions comprise a posterior section, a middle section, and an anterior section; wherein the posterior section has a substantially-constant first height (e.g. is substantially level at this first height), wherein the anterior section has a substantially-constant second height (e.g. is substantially level at this second height), wherein the second height is greater than the first height, and wherein the middle section comprises an S-shaped transition from the first height to the second height.

In an embodiment, when a person's head is upright, the most-posterior third of an electrode-holding ring, headband, halo, or headset has a first substantially-level height and the most-anterior third of the electrode-holding ring, headband, halo, or headset has a second substantially-level height, wherein the second height is greater than the first average height, and wherein the height of an electrode-holding ring, headband, halo, or headset transitions from the first height to the second height in an arcuate middle-third section of an electrode-holding ring, headband, halo, or headset.

In an example, a device with sensors (e.g. electrodes) for monitoring brain activity can comprise a partial ring (e.g. arc) portion (e.g. arm, segment, or section) with an upward-facing concavity on each side (e.g. right and left) of a person's head. In another example, a device with sensors (e.g. electrodes) for monitoring brain activity can comprise a ring or headband portion which encircles the top of the person's head like the rim of a cap and a partial ring (e.g. arc) portion which loops over the top of the person's head like the upper portion of a pair of headphones. In an embodiment, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the partial ring loops over the upper-posterior quadrant of the person's head.

In an example, a device with sensors (e.g. electrodes) for monitoring brain activity can comprise a ring which encircles the entire circumference of a person's head and a partial ring (e.g. arc) which loops over the upper half of the person's head (both of which hold sensors in place), wherein the ring and the partial ring are connected to each other, and wherein the connection of the ring and the partial ring forms an acute forward-facing angle, and wherein this angle is between 30 and 60 degrees. In another example, a device with sensors (e.g. electrodes) for monitoring brain activity can comprise: a circular, elliptical, or oval electrode-holding ring, headband, or halo portion which encircles a person's head; and a partial ring (e.g. semi-circular) portion above the ring, headband, or halo above (e.g. higher than) the ring, headband, or halo portion, wherein a concavity of the partial ring opens downward, and wherein the ends of the partial ring connect with the circular, elliptical, or oval electrode-holding ring, headband, or halo portion.

In an example, a partial ring portion of a device with sensors (e.g. electrodes) for monitoring brain activity can have a normal (e.g. bell-shaped) curve shape. In an example, a partial ring portion of a device with sensors (e.g. electrodes) for monitoring brain activity can have a sinusoidal phase shape. In an example, an electrode-holding ring, headband, halo, or headset can comprise: a ring or halo portion which encircles a person's head; and two partial ring (e.g. arc) portions which are connected to the ring or halo portion, wherein there is one partial ring portion on each side (e.g. right and left) of the person's head, and wherein concavities of the partial ring portions open downwards.

In an example, an electrode-holding device can comprise two nested (e.g. concentric) electrode-holding rings, headbands, or halos. In an example, an electrode-holding device can comprise: an upper ring, headband, or halo which encircles a person's head; and a lower ring, headband, or halo which encircles the person's head, wherein the upper ring and the lower ring are centrally connected to each other. In an embodiment, an electrode-holding device can comprise: an upper ring, headband, or halo which encircles a person's head; and a lower ring, headband, or halo which encircles the person's head, wherein the upper ring has a smaller circumference than the lower ring.

In an example, an electrode-holding device can comprise an upper band (e.g. segment, section, portion, arm, or band) and a lower band (e.g. segment, section, portion, arm, or band), wherein the upper band the lower band are substantially parallel as they span the rear of the person's head. In an embodiment, an electrode-holding device can comprise an upper band (e.g. segment, section, portion, arm, or band) and a lower band (e.g. segment, section, portion, arm, or band), wherein between 40% and 60% of the circumferences of the upper and lower bands are substantially parallel.

In an example, a device with sensors (e.g. electrodes) for measuring brain activity can comprise a posterior-to-anterior series of side-to-side (e.g. right to left) loops (e.g. arms, loops, segments, arcs, or branches), wherein these loops are connected to each other on the sides (e.g. right and left) of a person's head above the person's ears. In another example, a device with sensors (e.g. electrodes) for measuring brain activity can comprise a posterior-to-anterior series of side-to-side (e.g. right to left) loops (e.g. arms, loops, segments, arcs, or branches), wherein a posterior loop spans the back of a person's head, a middle loop spans the top of the person's head, and an anterior loop spans the person's forehead, wherein the anterior loop is higher than the posterior loop.

In an embodiment, a device with sensors (e.g. electrodes) for measuring brain activity can comprise a posterior-to-anterior series of side-to-side (e.g. right to left) loops (e.g. arms, loops, segments, arcs, or branches), wherein a posterior loop has a rear-facing concavity, a middle loop spans the top of the person's head, and an anterior loop has a forward-facing concavity. In an example, a device with sensors (e.g. electrodes) for measuring brain activity can comprise a posterior-to-anterior series of side-to-side (e.g. right to left) loops (e.g. arms, loops, segments, arcs, or branches), wherein these loops are connected to each other on the sides (e.g. right and left) of a person's head, and wherein these connections form right angles.

In an example, a device with sensors (e.g. electrodes) for measuring brain activity can comprise: an undulating band which is configured to encircle a person's head, wherein a portion of this undulating band on a side of the person's head further comprises: a first segment which is configured to span from the rear of the person's head to the person's ear; a second segment which is configured to span from the person's ear to a side of the person's face and/or forehead, wherein this second segment has a concavity which opens upward; and a third segment which configured to span across the person's forehead; at least one sensor (e.g. electrode) which is held in proximity to the person's head by the undulating band, wherein the at least one sensor (e.g. electrode) collects data concerning brain activity; an electronics unit which further comprises a data processor, a data transmitter, and a power source.

In an example, an electrode-holding ring, headband, halo, or headset comprises: a ring (e.g. ring, band, or halo) which encircles the person's head around the posterior half of the person's head and also across the person's forehead; and an upper arm (e.g. arm, loop, segment, arc, or branch) which spans from a location on a middle portion of the ring over the top of the person's head. In another example, an electrode-holding ring, headband, halo, or headset can include and a posterior portion (e.g. arm, loop, segment, arc, or branch) which loops around the rear of a person's head and an anterior portion (e.g. arm, loop, segment, arc, or branch) which loops across the person's forehead.

In an example, a device can include an anterior loop (e.g. loop, portion, band, arm, section) which spans across a person's forehead. In an example, a device can include a transparent anterior loop (e.g. loop, portion, band, arm, section) which spans across a person's forehead. In another example, a device can curve upwards around the rear of a person's ear, curve forward and upward to the person's temple, and then curve upward and rearward to span the top of the person's head. In an example, a left side of an electrode-holding ring, headband, halo, or headset can curve upward around the posterior of a person's ear (e.g. the connecting portion of the auricle), then curve further upward to form an undulation with a posterior-facing concavity; and then curve further upward to loop over the top of the person's head and meet the right side of an electrode-holding ring, headband, halo, or headset.

In an example, an electrode-holding ring, headband, halo, or headset can include a loop (e.g. loop, curve, bulge, or undulation) with a rear-facing concavity which is anterior to and higher than a person's ear. In an embodiment, an electrode-holding ring, headband, halo, or headset can: start behind an ear; curve upward around the back of the ear; then curve forward to a location on a side of the person's forehead; then curve upward and backward to form an undulation with a posterior-facing concavity; then curve backward to loop around the posterior half of the person's head; and then continue in a symmetric manner on the opposite side of the person's head, ending at the ear on the opposite side. In an example, an electrode-holding ring, headband, halo, or headset can include a forehead loop (e.g. forehead loop, portion, segment, arm, or branch) which spans across a person's forehead, wherein this forehead loop has a downward-facing concavity. In another example, an electrode-holding ring, headband, halo, or headset can include a forehead loop (e.g. forehead loop, portion, segment, arm, or branch) which spans across a person's forehead, wherein this forehead loop has multiple openings (e.g. holes).

In an embodiment, a device which is worn on a person's head to measure electromagnetic brain activity can comprise: a front (semicircular) loop which spans a person's forehead, wherein the front loop has a first Shore A value; and a rear (semicircular) loop which spans the rear of the person's head, wherein the rear loop has a second Shore A value; wherein the second level is greater than the first level. In an example, a posterior segment (e.g. segment, arm, loop, or portion) of an electrode-holding ring, headband, halo, or headset extends backward and downward from the top of a person's outer ear (e.g. auricle) to the rear of the person's head. In another example, a first arm (e.g. arm, prong, branch, loop, and/or protrusion) of a posterior portion of an electrode-holding ring, headband, halo, or headset can curve upward to end on a location on the upper-posterior quadrant of the person's head and a second arm (e.g. arm, prong, branch, loop, and/or protrusion) of the posterior portion curves downward around the back of the person's ear.

In an embodiment, an electrode-holding ring, headband, halo, or headset can comprise a posterior arm (e.g. arm, segment, or portion) which loops around the back of a person's head and a upper arm (e.g. arm, segment, or portion) which loops over the top of the person's head, wherein the posterior arm and the upper arm are portions of the same continuous member, wherein the a first plane best fits the posterior arm, wherein a second plane best fits the upper arm, and wherein the first plane and the second plane are substantially orthogonal to each other. In an example, an electrode-holding ring, headband, halo, or headset can loop over the top of a person's head, from one ear to the other ear. In an embodiment, an electrode-holding ring, headband, halo, or headset can loop over the top of a person's head from one ear to the other ear, starting along the posterior surface of an outer ear (e.g. auricle), then curving forward and upward from the ear toward a side of the person's forehead (and/or temple), then curving backward and upward from the side of the person's forehead (and/or temple), and then curving upward over the top of the person's head.

In an example, a device can be generally circular except that it locally bifurcates into two branches, one over an ear and one under an ear, and then reconverges as it spans the side of a person's head. In an embodiment, a device can comprise a bifurcating ring around a person's head, wherein the ring bifurcates and then reconverges as it spans the rear of the person's head. In an example, a device can comprise a bifurcating ring around a person's head, wherein the ring bifurcates and then reconverges as it spans the right and left sides of the person's head. In another example, an electrode-holding device can be a bifurcating ring, halo, or headset which encircles a person's head, wherein the ring, halo, or headset bifurcates as it spans across the front of the person's head (e.g. the person's forehead).

In an embodiment, an electrode-holding device can be a bifurcating ring, halo, or headset which bifurcates and then reconverges as it loops over the top of the person's head. In an example, an electrode-holding device can be a bifurcating ring, halo, or headset which bifurcates as it spans over a person's ears. In another example, an electrode-holding ring, headband, halo, or headset can bifurcate on each side (e.g. right and left) of a person's head. In an example, an electrode-holding ring, headband, halo, or headset can bifurcate and then reconverge, wherein between 30% and 60% of the circumference of the ring, headband, halo, or headset is bifurcated. In another example, an electrode-holding ring, headband, halo, or headset can bifurcate and then reconverge as it spans across a person's forehead.

In an example, a side portion of an electrode-holding ring, headband, halo, or headset can have a concave undulation which is anterior to a person's ear. In an example, a side portion of an electrode-holding ring, headband, halo, or headset can have a downward-opening concave undulation which is anterior to a person's ear. In an example, a device (e.g. ring portion of a device) can be generally circular, oval, elliptical, or egg-shaped except for two upward undulations (e.g. upward waves) above a person's ears, wherein the peaks of the undulations are above the tops of person's ears and the troughs of the undulations are below the tops of the person's ears.

In an example, a device (e.g. headband) can be generally circular except for right-side and left-side undulating (e.g. sinusoidal or partially sinusoidal) sections which loop over upper portions of a person's right ear and left ear, respectively. In an example, a device (e.g. headband) can be generally circular except for right-side and left-side concave sections which loop over upper portions of the person's right and left ears, respectively. In an example, an electrode-holding ring, headband, halo, or headset can include a downward undulation (e.g. a downward dip, curve, or loop) which is anterior to a person's ear. In another example, an electrode-holding ring, headband, halo, or headset can include right and left side undulations with an upward-opening concavities which are anterior to a person's right and left ears, respectively.

In an example, a device can include one or more ear prongs which curve around (e.g. span) 50%-75% of the circumference of the connection between a person's outer ear (e.g. auricle) and the rest of the person's head. In an embodiment, a device with sensors (e.g. electrodes) for monitoring brain activity can comprise a flexible band which is generally shaped to fit a person's head. In another example, a device with sensors (e.g. electrodes) for monitoring brain activity can comprise a rear portion which spans part of the occipital area of a person's head. In an example, a device with sensors (e.g. electrodes) for monitoring brain activity can comprise a flexible electroconductive posterior-ear prong (e.g. prong, arm, segment) which curves around the posterior and upper surfaces of a person's ear (where the ear is connected to the rest of the person's head).

In an embodiment, an electrode-holding ring, headband, halo, or headset can include an anterior-ear segment (e.g. prong, arm, protrusion, loop, or segment) which curves, bends, loops, and/or hooks around the front of a person's ear. In another example, an electrode-holding ring, headband, halo, or headset includes an anterior ear-engaging member (e.g. prong, arm, protrusion, loop, or segment) which curves, bends, loops, and/or hooks around at least half of the anterior surface of a person's outer ear (e.g. auricle) and/or the connecting tissue between the auricle and the rest of the person's head. In an example, an electrode-holding ring, headband, halo, or headset includes a posterior ear-engaging member (e.g. prong, arm, protrusion, loop, or segment) which curves, bends, loops, and/or hooks around at least half of the posterior surface of a person's outer ear (e.g. auricle) and/or the connecting tissue between the auricle and the rest of the person's head.

In an embodiment, an electrode-holding ring, headband, halo, or headset can include an posterior-ear segment (e.g. prong, arm, protrusion, loop, or segment) with a shape which is selected from the group consisting of: portion of a circle; portion of a spiral; portion of a parabolic curve; portion of a sinusoidal curve; and conic section. In an example, an electrode-holding ring, headband, halo, or headset can include an arm (e.g. prong, arm, protrusion, loop, or segment) which extends downward from a main circumferential body of an electrode-holding ring, headband, halo, or headset, wherein the arm curves, bends, loops, and/or hooks around the posterior of the person's ear (e.g. the connecting portion of the auricle).

In an embodiment, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head. In an example, an electrode-holding device (e.g. ring, headband, halo, or headset) can comprise one or more hub-and-spoke (e.g. radial) arrays of arms (e.g. arms, spokes, segments, and/or legs) which hold sensors (e.g. electrodes) on a person's head, wherein there is a hub-and-spoke array on the upper half of the person's head. In an example, an electrode-holding device (e.g. ring, headband, halo, or headset) can comprise two hub-and-spoke (e.g. radial) arrays of arms (e.g. arms, spokes, segments, and/or legs) which hold sensors (e.g. electrodes) on a person's head, wherein there is one hub on each side (e.g. right and left) of the person's head, and wherein a hub is located approximately midway (e.g. within one inch of midway) between a person's ear and the top of the person's head.

In an example, an electrode-holding device (e.g. ring, headband, halo, or headset) can comprise one or more hub-and-spoke (e.g. radial) arrays of arms (e.g. arms, spokes, segments, and/or legs), wherein there are three arms extending out radially from a hub, and wherein each arm holds a sensor (e.g. electrode) on a person's head. In another example, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein the arms are all the same length. In an example, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein the arms span 180 degrees of the perimeter of the hub.

In an example, an electrode-holding device (e.g. ring, headband, halo, or headset) can comprise one or more hub-and-spoke (e.g. radial) arrays of arms (e.g. arms, spokes, segments, and/or legs), wherein each arm holds a sensor (e.g. electrode) on a person's head, and wherein the arms are all concave. In another example, an electrode-holding device (e.g. ring, headband, halo, or headset) can comprise one or more hub-and-spoke (e.g. radial) arrays of arms (e.g. arms, spokes, segments, and/or legs), wherein the hubs are held in place by a device segment which loops around the back of a person's head.

In an example, an electrode-holding device (e.g. ring, headband, halo, or headset) can comprise a hub-and-spoke array of electrode-holding arms (e.g. arms, spokes, segments, and/or legs). In another example, an electrode-holding device (e.g. ring, headband, halo, or headset) can comprise a radial array of electrode-holding arms (e.g. arms, spokes, segments, and/or legs). In an example, an electrode-holding device (e.g. ring, headband, halo, or headset) can comprise two radial arrays of electrode-holding arms (e.g. arms, spokes, segments, and/or legs). In an example, an electrode-holding ring, headband, halo, or headset can comprise a hexagonal (e.g. honeycomb) structure (e.g. mesh) which is worn on the upper half of a person's head.

In an embodiment, a person's head can be visible through openings (e.g. holes) in electrode-holding ring, headband, halo, or headset. In an example, there can be at least four openings (e.g. holes) on each side (e.g. right and left) of an electrode-holding ring, headband, halo, or headset. In an embodiment, there can be one or more longitudinal openings (e.g. holes) in an electrode-holding ring, headband, halo, or headset, wherein the length of the opening is at least twice the width of the opening. In an example, there can be one or more openings (e.g. holes) in a portion of an electrode-holding ring, headband, halo, or headset which spans a person's forehead.

In an embodiment, an electrode-holding ring, headband, halo, or headset can comprise an circumferential series (e.g. chain) of movably-connected segments and/or components. In another example, an electrode-holding ring, headband, halo, or headset can comprise an circumferential series (e.g. chain) of modular segments and/or components. In an example, an electrode-holding ring, headband, halo, or headset can comprise: an arcuate series (e.g. chain) of interconnected and/or interdigitated segments which can move (e.g. tilt, rotate, slide, and/or flex) relative to each other; and flexible wires which connect the segments (e.g. provide electrical connection among the segments).

In an embodiment, an electrode-holding ring, headband, halo, or headset can comprise multiple components which are connected by movable joints so that the circumference of the ring, headband, halo, or headset can be changed (e.g. customized to the shape of a specific person's head). In another example, an electrode-holding ring, headband, halo, or headset can comprise multiple components which are connected by movable joints so that the concavity of the ring, headband, halo, or headset can be changed (e.g. customized to the shape of a specific person's head).

In an example, a device can comprise: an inner partial ring (e.g. ring or band) which is worn around a person's head, wherein the inner partial ring has a first level of elasticity, stretchability, or deformability; an outer partial ring (e.g. ring or band) which is worn around the person's head, wherein the outer partial ring has a second level of elasticity, stretchability, or deformability, wherein the partial rings have a semicircular or semielliptical shape, wherein the inner partial ring is closer to the surface of the person's head than the outer partial ring, and wherein the second level is less than the first level. In an example, an anterior portion (e.g. portion, segment, or band) of a device can more elastic (e.g. made with an elastic textile) than a posterior portion of the device (e.g. made with a hard plastic or metal).

In an example, between 50% and 75% of the circumference of a ring, headband, halo, or headset can be made from an elastic textile and/or fabric. In another example, a device can comprise a sequence of alternating elastic (e.g. stretchable) and stiff (e.g. rigid) sections around its circumference. In an example, a perimeter of a headband (or halo) can comprise one or more sections with a first degree of stretchability, elasticity, and/or expandability and one or more sections with a second degree of stretchability, elasticity, and/or expandability, wherein the second degree is greater than the first degree. In another example, a posterior loop (e.g. rear loop) of a device can be elastic or stretchable. In an example, a posterior section of the circumference of an electrode-holding ring, headband, halo, or headset which encircles a person's head can be made from a hard polymer or metal and an anterior section of this circumference can be made from a flexible fabric or textile.

In an example, a section (e.g. section or portion) of electrode-holding ring, headband, halo, or headset which spans a person's forehead can be more elastic and/or stretchable than other sections of the ring, headband, halo, or headset. In an example, an electrode-holding ring, headband, halo, or headset can be made with an elastic and/or stretchable fabric and/or textile. In an example, an electrode-holding ring, headband, halo, or headset can have one or more relatively-inelastic sections (e.g. with a first level of elasticity and/or stretchability) and one or more relatively-elastic sections (e.g. with a second level of elasticity and/or stretchability), wherein the second level is greater than the first level, and wherein a relatively-elastic section is located on a posterior portion (e.g. posterior half) of the ring, headband, halo, or headset.

In an embodiment, an electrode-holding ring, headband, halo, or headset can have two relatively-inelastic sections and two relatively-elastic sections. In an example, an electrode-holding ring, headband, halo, or headset can comprise a circumferential series of alternating relatively-elastic and relatively-inelastic components which encircles a person's head. In another example, an electrode-holding ring, headband, halo, or headset can comprise an series (e.g. series, sequence, and/or chain) of alternating first segments and second segments, wherein first segments are made from a flexible fabric and/or textiles, and wherein second segments are made from a hard (e.g. rigid) polymer or metal. In an embodiment, between 25% and 45% of the circumferential perimeter of an electrode-holding ring, headband, halo, or headset can be elastic, stretchable, and/or expandable. In another example, one or more sections of an electrode-holding ring, headband, halo, or headset can be made with an elastic and/or stretchable fabric and/or textile.

In an example, relatively-inelastic sections (e.g. segments, portions, or sections) of an electrode-holding ring, headband, halo, or headset can be made primarily from one or more metals or hard polymers and relatively-elastic sections (e.g. segments, portions, or sections) of the electrode-holding ring, headband, halo, or headset can be made (primarily) from one or more fabrics or textiles. In an embodiment, the front section of the circumferential perimeter of an electrode-holding ring, headband, halo, or headset can be elastic, stretchable, and/or expandable.

In an example, the rear portion of the perimeter of an electrode-holding ring, headband, halo, or headset (which spans the rear of a person's head) can have a first degree of stretchability, elasticity, and/or expandability and the front portion of the perimeter of the electrode-holding ring, headband, halo, or headset (which spans the person's forehead) can have a second degree of stretchability, elasticity, and/or expandability, wherein the second degree is greater than the first degree. In an example, two sections of the circumference of an electrode-holding ring, headband, halo, or headset which encircles a person's head can be made from a hard polymer or metal and two other sections of this circumference can be made from a flexible fabric or textile. In another example, an electrode-holding ring, headband, halo, or headset can be made from a transparent material. In an example, a portion of an electrode-holding ring, headband, halo, or headset which spans over the top of a person's head can be transparent.

In an example, an upper arm (e.g. arm, band, portion, section, or loop) of a device which loops over the top of a person's head can be adjustably-connected to a side portion of the device by a movable joint. In another example, the angle between a posterior arm (e.g. arm, band, portion, section, or loop) of a device which loops around the back of a person's head and a side portion of the device can be adjusted by adjusting a movable joint between them. In an example, a first section of the perimeter of an electrode-holding ring, headband, halo, or headset can be made from one or more metals and/or polymers and a second section of the perimeter of an electrode-holding ring, headband, halo, or headset can be made from one or more fabrics and/or textiles, wherein the first section is between 45% and 55% of the perimeter of an electrode-holding ring, headband, halo, or headset.

In an example, a device can be made with a deformable polymer. In another example, a device can be made with a soft (e.g. elastomeric) conductive polymer-based material. In another example, a device can be made with a silicone-based material. In an example, a device can be made with carbon. In an example, a device can be made with copper. In an embodiment, a device can be made with graphite. In another example, a device can be made with PEDOT:PSS. In another example, a device can be made with polydimethylsiloxane (PDMS). In another example, a device can be made with silver.

In an example, a device can be made with a compressible, malleable, and/or low-durometer non-conductive material (e.g. a non-conductive elastomeric polymer) which has been impregnated, doped, filled, coated, or embedded with a conductive material (e.g. carbon or metal particles). In an embodiment, a device can be made with a silicone material (such as PDMS) which has been impregnated, doped, filled, coated, or embedded with silver. In an example, a device can be made with a silicone-based polymer which has been impregnated, doped, filled, coated, or embedded with silver, steel, copper, gold, aluminum, and/or carbon.

In an embodiment, a device can be made with an elastomeric polymer which has been impregnated, doped, filled, coated, or embedded with electroconductive material (e.g. silver, silver-chloride, steel, aluminum, or carbon). In an example, a device can be made with non-conductive yarns (or threads) which has been impregnated, doped, filled, coated, or embedded with conductive material. In another example, a device can be made with polydimethylsiloxane (PDMS) which has been impregnated, doped, filled, coated, or embedded with carbon or sliver. In another example, a device can be made with conductive yarn or thread, wherein the yarn or thread comprises: an inner core of twisted or braided conductive threads, fibers, or strands; and an outer layer of non-conductive material around the inner core.

In an embodiment, a sensor (e.g. electrode) can be a capacitive sensor (e.g. electrode). In another example, a sensor (e.g. electrode) can comprise an electrical energy emitter at a first location and an electrical energy receiver at a second location, wherein the energy receiver receives energy which has been transmitted from the emitter through body tissue. In an example, a sensor (e.g. electrode) can comprise an electroconductive pathway, wherein changes in the transmission of electrical energy through the pathway caused by brain activity are recorded. In an example, a sensor (e.g. electrode) can further comprise an energy-emitting component which emits electrical energy and an energy-receiving component which receives electrical energy.

In an example, the sensor (e.g. electrode) can be an inductive sensor. In another example, a sensor (e.g. electrode) can be a dipole electrode. In an embodiment, a sensor (e.g. electrode) can be a single-pole electrode. In another example, a sensor (e.g. electrode) can be based on impedance. In an example, a sensor (e.g. electrode) can measure electromagnetic energy conductivity, resistance, impedance, or capacitance. In another example, a sensor (e.g. electrode) can measure voltage differences between two locations on a person's head.

In an embodiment, a device can include a sensor (e.g. electrode) with a circular, elliptical, or oval shape. In an example, an oblong soft pad can have a rounded rectangular shape. In another example, a sensor (e.g. electrode) can have a crescent or boomerang shape. In an embodiment, a sensor (e.g. electrode) can have a hexagonal shape. In another example, a sensor (e.g. electrode) can have a peanut shape.

In an example, a sensor (e.g. electrode) can have a sawtooth shape whose peaks protrude into a person's hair. In an example, a sensor (e.g. electrode) can have a zigzag shape whose peaks protrude into a person's hair. In an example, a sensor (e.g. electrode) can have an elliptical or oval shape. In an example, a sensor (e.g. electrode) can have an undulating and/or sinusoidal shape. In another example, an earring can function as an electrode.

In an example, a sensor (e.g. electrode) can be coated with silver or gold. In an example, a sensor (e.g. electrode) can be made with an elastomeric polymer (e.g. PDMS) which has been impregnated, embedded, or coated with an electroconductive metal. In another example, a sensor (e.g. electrode) can be made with an elastomeric polymer (e.g. PDMS) which has been impregnated, embedded, or coated with carbon nanotubes. In an example, a sensor (e.g. electrode) can be made with an elastomeric polymer (e.g. PDMS) which has been impregnated, embedded, or coated with graphene. In another example, a sensor (e.g. electrode) can be made with graphene nanoplatelets. In an example, a sensor (e.g. electrode) can be made with polydimethylsiloxane (PDMS).

In an example, a sensor (e.g. electrode) can be made with polyvinyl alcohol. In another example, a sensor (e.g. electrode) can be made by 3D printing, wherein conductive ink is printed onto a headband. In an example, a sensor (e.g. electrode) can be made by adhering (or otherwise bonding) together a first flexible non-conductive layer, a flexible conductive layer, and a second flexible non-conductive layer together; wherein the flexible conductive layer is between the first flexible non-conductive layer and the second flexible non-conductive layer. In an example, a sensor (e.g. electrode) can be made by embroidering or stitching an orthogonal mesh with conductive threads or yarns onto an article of clothing. In an embodiment, a sensor (e.g. electrode) can be made by sewing conductive threads or yarns onto fabric in a sinusoidal and/or zigzag pattern.

In an example, a sensor (e.g. electrode) can be made by stitching conductive threads or yarns onto fabric in a sinusoidal and/or zigzag pattern. In another example, a sensor (e.g. electrode) can be made by coating open-cell foam with a conductive layer. In an embodiment, a sensor (e.g. electrode) can be made by printing sensors (e.g. electrodes) onto a layer of non-conductive material with conductive ink. In another example, a sensor (e.g. electrode) can be made by weaving, knitting, sewing, embroidering, layering, laminating, adhering, melting, fusing, printing, spraying, painting, or pressing electroconductive material into (or onto) a fabric or textile. In another example, a sensor (e.g. electrode) can comprise a conductive layer and a non-conductive layer.

In an example, a sensor (e.g. electrode) can comprise a dielectric layer between conductive layers. In an embodiment, a sensor (e.g. electrode) can comprise high-conductivity and low-conductivity layers with different orientations. In an example, a sensor (e.g. electrode) can have a dielectric layer. In another example, an electronically-functional fabric or textile with sensors (e.g. electrodes) can be created by weaving, knitting, sewing, embroidering, layering, laminating, adhering, melting, fusing, printing, spraying, painting, or pressing together electroconductive threads, fibers, yarns, strands, filaments, traces, and/or layers. In an example, sensors (e.g. electrodes) can be more densely distributed (e.g. be closer together) on an anterior portion of an electrode-holding ring, headband, halo, or headset than on a posterior portion of the ring, headband, halo, or headset.

In an example, a device and/or sensor (e.g. electrode) on the device can be made with acetate. In another example, a device and/or sensor (e.g. electrode) on the device can be made with aluminum. In an example, a device and/or sensor (e.g. electrode) on the device can be made with carbon nanotubes. In another example, a device and/or sensor (e.g. electrode) on the device can be made with conductive polymer. In an example, a device and/or sensor (e.g. electrode) on the device can be made with denim. In an example, a device and/or sensor (e.g. electrode) on the device can be made with graphene. In an embodiment, a device and/or sensor (e.g. electrode) on the device can be made with hydrogel. In an example, a device and/or sensor (e.g. electrode) on the device can be made with Lycra™. In an embodiment, a device and/or sensor (e.g. electrode) on the device can be made with multiwall carbon nanotubes.

In an example, a device and/or sensor (e.g. electrode) on the device can be made with nylon. In another example, a device and/or sensor (e.g. electrode) on the device can be made with PEDOT:PSS [poly(3,4-ethylenedioxythiophene): poly(styrene sulfonate)]. In an embodiment, a device and/or sensor (e.g. electrode) on the device can be made with polyacetylene. In another example, a device and/or sensor (e.g. electrode) on the device can be made with polyphenylene vinylene. In an example, a device and/or sensor (e.g. electrode) on the device can be made with PU (polyurethane). In another example, a device and/or sensor (e.g. electrode) on the device can be made with rubber. In an example, a device and/or sensor (e.g. electrode) on the device can be made with silk.

In an example, a device and/or sensor (e.g. electrode) on the device can be made with silver fibers. In another example, a device and/or sensor (e.g. electrode) on the device can be made with spandex. In an example, a sensor (e.g. electrode) can be made with wool. In another example, a sensor (e.g. electrode) can be made with a hydroxypropyl cellulose. In an example, a sensor (e.g. electrode) can be made with an aqueous suspension of PEDOT:PSS. In an example, a sensor (e.g. electrode) can be made with deformable material. In an embodiment, a sensor (e.g. electrode) can be made with flexible material. In an example, a sensor (e.g. electrode) can be made with material which has a low Shore A value. In another example, a sensor (e.g. electrode) can be made with natural or synthetic sponge material.

In an embodiment, a sensor (e.g. electrode) can be made with silk. In an example, a sensor (e.g. electrode) can be made with thermoplastic vulcanizate (TPV). In another example, a sensor (e.g. electrode) can be made with a low-durometer material. In another example, a sensor (e.g. electrode) can be made with an elastomeric polymer. In an embodiment, a sensor (e.g. electrode) can be made with steel. In an example, a sensor (e.g. electrode) can be made with carbon nanotubes. In another example, a sensor (e.g. electrode) can be made with gold. In an example, a sensor (e.g. electrode) can be made with hydrogel. In another example, a sensor (e.g. electrode) can be made with platinum. In an example, a sensor (e.g. electrode) can be made with polyurethane. In another example, a sensor (e.g. electrode) can be made with silver-chloride.

In an example, a sensor (e.g. electrode) can be made with a cellulose material (such as HPMC) which is doped, impregnated, coated, sprayed, printed, or embedded with carbon. In an example, a sensor (e.g. electrode) can be made with a cellulose material (such as HPMC) which is doped, impregnated, coated, sprayed, printed, or embedded with conductive particles. In an example, a sensor (e.g. electrode) can be made with a cellulose material (such as HPMC) which is doped, impregnated, coated, sprayed, printed, or embedded with graphite. In an example, a sensor (e.g.

electrode) can be made with a cellulose material (such as HPMC) which is doped, impregnated, coated, sprayed, printed, or embedded with silver.

In an example, a sensor (e.g. electrode) can be made with a cellulose material (such as HPMC) which is doped, impregnated, coated, sprayed, printed, or embedded with steel. In an example, a sensor (e.g. electrode) can be made with a hydrogel material which is doped, impregnated, coated, sprayed, printed, or embedded with carbon nanotubes. In an embodiment, a sensor (e.g. electrode) can be made with a hydrogel material which is doped, impregnated, coated, sprayed, printed, or embedded with copper. In an example, a sensor (e.g. electrode) can be made with a hydrogel material which is doped, impregnated, coated, sprayed, printed, or embedded with jaskonium. In another example, a sensor (e.g. electrode) can be made with a hydrogel material which is doped, impregnated, coated, sprayed, printed, or embedded with silver. In another example, a sensor (e.g. electrode) can be made with a hydrogel material which is doped, impregnated, coated, sprayed, printed, or embedded with steel.

In an embodiment, a sensor (e.g. electrode) can be made with a polymer which is doped, impregnated, coated, sprayed, printed, or embedded with metal powder. In another example, a sensor (e.g. electrode) can be made with a silicone-based material (such as PDMS) which is doped, impregnated, coated, sprayed, printed, or embedded with carbon nanotubes. In an example, a sensor (e.g. electrode) can be made with a silicone-based material (such as PDMS) which is doped, impregnated, coated, sprayed, printed, or embedded with copper. In an embodiment, a sensor (e.g. electrode) can be made with a silicone-based material (such as PDMS) which is doped, impregnated, coated, sprayed, printed, or embedded with metal particles.

In an example, a sensor (e.g. electrode) can be made with a silicone-based material (such as PDMS) which is doped, impregnated, coated, sprayed, printed, or embedded with silver chloride. In another example, a sensor (e.g. electrode) can be made with cellulose material (such as HPMC) which is doped, impregnated, coated, sprayed, printed, or embedded with carbon particles. In an embodiment, a sensor (e.g. electrode) can be made with PEDOT and/or PEDOT:PSS which is doped, impregnated, coated, sprayed, printed, or embedded with carbon nanotubes. In another example, a sensor (e.g. electrode) can be made with PEDOT and/or PEDOT:PSS which is doped, impregnated, coated, sprayed, printed, or embedded with copper.

In an example, a sensor (e.g. electrode) can be made with PEDOT and/or PEDOT:PSS which is doped, impregnated, coated, sprayed, printed, or embedded with metal particles. In an example, a sensor (e.g. electrode) can be made with PEDOT and/or PEDOT:PSS which is doped, impregnated, coated, sprayed, printed, or embedded with silver chloride. In an example, a sensor (e.g. electrode) can be made with polydimethylsiloxane (PDMS) which is doped, impregnated, coated, sprayed, printed, or embedded with carbon. In an example, a sensor (e.g. electrode) can be made with thermoplastic polyurethane (TPU) which is doped, impregnated, coated, sprayed, printed, or embedded with aluminum. In an example, a sensor (e.g. electrode) can be made with thermoplastic polyurethane (TPU) which is doped, impregnated, coated, sprayed, printed, or embedded with carbon particles.

In an example, a sensor (e.g. electrode) can be made with thermoplastic polyurethane (TPU) which is doped, impregnated, coated, sprayed, printed, or embedded with graphene nanoplatelets. In another example, a sensor (e.g. electrode) can be made with thermoplastic polyurethane (TPU) which is doped, impregnated, coated, sprayed, printed, or embedded with metal powder. In an example, a sensor (e.g. electrode) can be made with thermoplastic polyurethane (TPU) which is doped, impregnated, coated, sprayed, printed, or embedded with conductive ink. In another example, a sensor (e.g. electrode) can be made with a polymer (e.g. polydimethylsiloxane, polybutylene terephthalate, or polyurethane) which has been impregnated, doped, filled, coated, or embedded with electro-conductive material (e.g. silver, carbon nanotubes or other forms of carbon, copper, aluminum, nickel, platinum, or gold).

In an example, a sensor (e.g. electrode) can be made with a silicone material (such as PDMS) which has been impregnated, doped, filled, coated, or embedded with conductive material (such as metal and/or carbon) in order to provide consistent but comfortable contact with the person's head. In another example, a sensor (e.g. electrode) can be made with a silicone-based polymer which has been impregnated, doped, filled, coated, or embedded with a metal powder (e.g. silver, copper, gold, steel, or aluminum), graphite, or carbon nanotubes.

In an embodiment, a sensor (e.g. electrode) can be made with an elastomeric polymer which has been impregnated, doped, filled, coated, or embedded with a metal powder (e.g. silver, copper, gold, steel, or aluminum), graphite, or carbon nanotubes. In an example, a sensor (e.g. electrode) can be made with polydimethylsiloxane (PDMS) which has been impregnated, doped, filled, coated, or embedded with silver, steel, copper, gold, aluminum, and/or carbon. In another example, a sensor (e.g. electrode) can be made with polydimethylsiloxane, polybutylene terephthalate, or polyurethane which has been impregnated, doped, filled, coated, or embedded with silver, carbon nanotubes or other forms of carbon, copper, aluminum, nickel, platinum, or gold.

In an embodiment, a device can comprise: a first set of sensors (e.g. electrodes) which are worn on a person's forehead, wherein sensors in this first set are made from a conductive polymer with a first durometer level and are configured to generally conform to the curvature of the person's forehead; a second set of sensors (e.g. electrodes) which are worn on the posterior of the person's head, wherein sensors in this second set further comprise a plurality of hair-penetrating protrusions made from a conductive polymer with a second durometer level, wherein the second durometer level is greater than the first durometer level.

In an example, a posterior half of an electrode-holding ring, headband, halo, or headset can have articulated (e.g. jointed) electroconductive prongs, teeth, pins, or other protrusions which penetrates (e.g. slide) between strands of hair. In an embodiment, a posterior portion of an electrode-holding ring, headband, halo, or headset can have electroconductive prongs, teeth, pins, or other protrusions which penetrate (e.g. slide) between strands of hair and an anterior portion of the ring, headband, halo, or headset does not. In another example, a sensor (e.g. electrode) can comprise a base and a plurality of protrusions, teeth, prongs, or pins which extend out from the base toward the surface of a person's head, wherein the protrusions, teeth, prongs, or pins extend out from the base along vectors which are in not a planes which are perpendicular to the plane of the base.

In an example, a sensor (e.g. electrode) can comprise a base with electroconductive prongs, teeth, pins, or other protrusions made from a polymer which has been coated and/or impregnated with conductive material. In an embodiment, a sensor (e.g. electrode) can comprise a base with electroconductive prongs, teeth, pins, or other protrusions made from an elastomeric polymer which has been coated and/or impregnated with conductive material. In another example, a sensor (e.g. electrode) can comprise a base with concave arcuate electroconductive prongs, teeth, pins, or other protrusions wherein their concavities which open toward the center (e.g. the central axis) of the base.

In an example, sensors (e.g. electrodes) on a posterior half of an electrode-holding ring, headband, halo, or headset can have flexible (e.g. elastomeric) electroconductive prongs, teeth, pins, or other protrusions which penetrate (e.g. slide) between strands of hair. In an embodiment, sensors (e.g. electrodes) on a posterior portion of an electrode-holding ring, headband, halo, or headset can have electroconductive prongs, teeth, pins, or other protrusions to penetrate between strands of hair, but sensors (e.g. electrodes) on an anterior portion of the ring, headband, halo, or headset are flat. In another example, hair-penetrating prongs (e.g. prongs, protrusions, pins, or legs) on a sensor can be configured in nested circles.

In an example, a core of a hair-penetrating prong (e.g. prong, protrusion, pin, or leg) on a sensor can have a higher durometer level than that of an outer layer of the prong. In another example, a flexibility, elasticity, and/or durometer of a hair-penetrating prong (e.g. prong, protrusion, pin, or leg) on a sensor can be changed by application of electrical energy, wherein the prong is made with material whose flexibility, elasticity, and/or durometer is changed by application of electrical energy. In an example, hair-penetrating prongs (e.g. prongs, protrusions, pins, or legs) on a sensor can have a higher durometer in their first configuration for easier insertion between strands of hair and a lower durometer in their second configuration for greater contact surface with the person's head and/or greater comfort for the person.

In an example, a core of a hair-penetrating prong (e.g. prong, protrusion, pin, or leg) on a sensor (e.g. electrode) can be made from an electroconductive polymer. In another example, a distal portion of a hair-penetrating prong (e.g. prong, protrusion, pin, or leg) on a sensor (e.g. electrode) can be more conductive (e.g. have a higher concentration of conductive material) than a proximal portion of the hair-penetrating prong. In an example, a proximal portion of a hair-penetrating prong (e.g. prong, protrusion, pin, or leg) on a sensor (e.g. electrode) can be more conductive (e.g. have a higher concentration of conductive material) than a distal portion of the hair-penetrating prong. In an example, an array of hair-penetrating prongs (e.g. prongs, protrusions, teeth, pins, or legs) on a sensor (e.g. electrode) can be configured in a single polygon.

In an example, hair-penetrating prongs (e.g. prongs, protrusions, teeth, pins, or legs) on a sensor (e.g. electrode) can have arcuate (e.g. circular, elliptical, oval, or rounded polygonal) cross-sectional shapes. In an example, hair-penetrating prongs (e.g. prongs, protrusions, teeth, pins, or legs) on a sensor (e.g. electrode) can be made with a soft (e.g. elastomeric) conductive polymer-based material. In an example, a sensor (e.g. electrode) can comprise a sensor base with a Shore 00 value between 30 and 80 and a plurality of protrusions (e.g. protrusions, prongs, teeth, legs, pins, and/or bumps) with Shore 00 values between 15 and 50.

In an embodiment, a hair-penetrating prong (e.g. prong, protrusion, pin, or leg) on a sensor can have a proximal section which is closer to the sensor base and a distal section which is farther from the sensor base, wherein the proximal section has a central longitudinal axis which intersects the plane of the sensor base at a first radially-outward-facing angle, wherein the distal section has a central longitudinal axis whose virtual extension intersects the plane of the sensor base at a second radially-outward-facing angle, wherein the second angle is less than the first angle. In an example, central longitudinal axes of proximal and distal sections of a hair-penetrating prong (e.g. prong, protrusion, pin, or leg) on a sensor can intersect each other at an acute angle.

In an embodiment, a distal section of a hair-penetrating prong (e.g. prong, protrusion, pin, or leg) on a sensor can be more flexible and/or elastic than the proximal section of the prong. In another example, a distal section of a sensor prong can be concave relative to a central longitudinal axis of the prong. In an example, a hair-penetrating prong (e.g. prong, protrusion, pin, or leg) on a sensor can have a proximal section which is closer to the sensor base, a distal section which is farther from the sensor base, and a middle section between the proximal section and the distal section; and wherein the middle section is bifurcated.

In an example, a hair-penetrating prong (e.g. prong, protrusion, pin, or leg) on a sensor can have a proximal section which is closer to the sensor base and a distal section which is farther from the sensor base, and wherein the distal section is bifurcated. In another example, a proximal section of a hair-penetrating prong (e.g. prong, protrusion, pin, or leg) on a sensor can have a shape selected from the group consisting of: articulated, bifurcated, chevron, column, concave, cone, conic-section, convex, ellipsoid, frustum, funnel-shaped, helical, hourglass, loop, paraboloid, semicircle, serpentine, shaped like the letter U, shaped like the letter V, sinusoidal, spheroid, spiral, and tapered.

In an example, a device can have a plurality of receptacles (e.g. receptacles, ports, slots, openings, holes) into which one or more sensors (e.g. electrodes) can be selectively connected. In another example, a device with sensors (e.g. electrodes) for monitoring brain activity can include a plurality of hydraulic actuators which automatically adjust the positions of sensors (e.g. electrodes). In an example, sensors (e.g. electrodes) can be moved (e.g. slid) along a track, channel, or groove on the circumference of an electrode-holding ring, headband, halo, or headset. In an example, sensors (e.g. electrodes) can be removably-attached to different locations on an electrode-holding ring, headband, halo, or headset.

In an example, sensors (e.g. electrodes) on an electrode-holding ring, headband, halo, or headset which collect data concerning brain activity can be held at one or more standard EEG placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, DJC, TP8, T5/P7, P5, P3, P1, Pz, P2, P4, P6, T6/P8, PO7, PO5, PO3, POz, PO4, PO6, PO8, O1, Oz, and O2. In an embodiment, the locations of a sensors (e.g. electrodes) on a device with sensors (e.g. electrodes) for monitoring brain activity can be moved automatically with respect to the surface of a person's head. In an example, a sensor (e.g. electrode) can be attached to an eyewear sidepiece (e.g. temple) by both a spring and compressible foam. In another example, a device can be removably-attached to an eyewear sidepiece (e.g. temple). In an embodiment, a device can be removably-attached to the middle third of the length of an eyewear sidepiece (e.g. temple).

In an example, a device can include one or more inflatable chambers (e.g. balloons or other type of inflatable chambers) which gently hold one or more sensors (e.g. electrodes) against a person's head. In another example, a sensor (e.g.

electrode) or prong extending out of a sensor can be pressed against the surface of a person's head by foam or other compressible material. In an embodiment, a sensor (e.g. electrode) or prong extending out of a sensor can be pressed against the surface of a person's head by a leaf spring. In another example, a sensor (e.g. electrode) or prong extending out of a sensor can be pressed against the surface of a person's head by a plastic spring.

In an example, a sensor (e.g. electrode) or prong extending out of a sensor can be pressed against the surface of a person's head by a telescoping mechanism. In another example, a sensor (e.g. electrode) can be moved toward the surface of a person's head by an electromagnetic mechanism. In an example, a sensor (e.g. electrode) can be moved toward the surface of a person's head by a solenoid mechanism. In another example, a sensor (e.g. electrode) can be moved toward the surface of a person's head by a piston mechanism. In an example, a sensor (e.g. electrode) can be moved toward the surface of a person's head by a hydraulic mechanism.

In an example, a sensor (e.g. electrode) can be configured to move laterally when pushed toward the surface of a person's head. In an example, a sensor (e.g. electrode) can be configured to translate a force which pushes the sensor based toward the surface of a person's head into rotation of an array of pins, prongs, teeth, or other protrusions extending out from the base relative to the surface of the person's head. In an example, pins, prongs, teeth, or other protrusions which extend out from the base of a sensor (e.g. electrode) can be configured to move laterally when the base is pushed toward the surface of a person's head.

In an example, a distance between a sensor (e.g. electrode) and the surface of a person's head can be (manually or automatically) adjusted. In an embodiment, the distance between a sensor (e.g. electrode) and the surface of a person's head can be adjusted by changing the tension on a spring. In an example, the distance between a sensor (e.g. electrode) and the surface of a person's head can be adjusted by a hydraulic mechanism. In another example, the distance between a sensor (e.g. electrode) and the surface of a person's head can be adjusted by changing the tension of an elastic strap and/or band. In an embodiment, the pressure between a sensor (e.g. electrode) and the surface of a person's head can be adjusted by expanding an inflatable chamber. In another example, the pressure between a sensor (e.g. electrode) and the surface of a person's head can be adjusted by a solenoid. In an example, the pressure between a sensor (e.g. electrode) and the surface of a person's head can be adjusted by rotating a threaded (e.g. helical) mechanism.

In an embodiment, a sensor (e.g. electrode) can be vibrated and/or oscillated in order to penetrate a layer of a person's hair and achieve better electromagnetic communication with a person's brain. In another example, a sensor (e.g. electrode) can comprise one or more electromagnetic actuators which vibrate and/or oscillate one or more protrusions (e.g. protrusions, prongs, teeth, legs, pins, and/or bumps) in directions which are oblique to the surface of a person's head and/or to the surface of the sensor base of the electrode, thereby enabling the protrusions to slide between strands of hair on the person's head.

In an example, a curvature of a sensor base in a plane which is substantially perpendicular to the surface of a person's head can be changed from a first configuration to a second configuration when the sensor base is pressed toward the surface of the person's head, wherein the sensor base is less-curved (and more planar) in its second configuration than in its first configuration. In an example, a sensor (e.g. electrode) base can be changed from a first configuration to a second configuration as the sensor is pressed toward the surface of the person's head. In another example, a sensor (e.g. electrode) base can be flatter in a second configuration than in a first configuration.

In an example, a sensor (e.g. electrode) base can have a concave shape before being pressed onto a person's head and can have a substantially-flat shape after being pressed onto the person's head. In an example, a sensor (e.g. electrode) base can have a first configuration and a second configuration, wherein moveable sections are more co-planar in the second configuration than in the first configuration. In another example, a sensor (e.g. electrode) base can comprise a plurality of moveable sections, wherein the sections become more co-planar as the sensor is pressed toward the surface of a person's head.

In an example, a sensor (e.g. electrode) can comprise one or more electromagnetic actuators which move one or more protrusions (e.g. protrusions, prongs, teeth, legs, pins, and/or bumps) in a direction which is substantially parallel to the surface of a person's head and/or to the surface of the sensor base of the electrode.

In an example, the cross-sectional size of a hair-penetrating prong (e.g. prong, protrusion, pin, or leg) on a sensor can be changed by a mechanism selected from the group consisting of: applying electrical energy to the prong which is made with material which expands upon application of electrical energy; inserting a longitudinal member (e.g. a rod or screw) into the center of the prong; pumping a fluid or gas into the prong; and uncoiling the prong using an electromagnetic actuator. In an example, electroconductive hair-penetrating prongs (e.g. prongs, protrusions, pins, or legs) on a sensor can extend out from a sensor base, wherein the prongs can have a first configuration with a first average cross-sectional size, wherein the prongs can have a second configuration with a second cross-sectional size, wherein the second cross-sectional size is greater than the first cross-sectional size, and wherein the prongs are changed from the first configuration to the second configuration after the prongs have been inserted between strands of hair on the surface of a person's head.

In an example, a device can include an electronics unit (e.g. control unit) which includes a data processor, a data transmitter, and a power source. In an embodiment, a device can include a data transmitter which transmits sensor data to a remote data processor in a separate wearable device or mobile device. In an example, data from sensors (e.g. electrodes) can be amplified by (local, within-device) amplifiers. In another example, an electrode-holding ring, headband, halo, or headset can be part of a system, wherein a data processor in the ring, headband, halo, or headset is in electronic communication with a remote data processor. In an embodiment, an electrode-holding ring, headband, halo, or headset can be part of a system, wherein a data processor in the ring, headband, halo, or headset is in electronic communication with one or more remote devices selected from the group consisting of: cellphone, communication network tower, electronic pad, electronic tablet, home control system, implanted medical device, internet-connected remote computer, mobile computer, mobile phone, modem, router, satellite, smart clothing, and smart watch.

In an example, sensors (e.g. electrodes) on a device can collect data concerning the emission of electromagnetic energy by a person's brain. In another example, sensors (e.g. electrodes) on a device can record (e.g. record, measure, monitor) the emission of electromagnetic energy by a person's brain. In an embodiment, a power source can transduce, harvest, and/or generate energy from ambient light energy. In another example, a power source can transduce, harvest, and/or generate energy from ambient electrical and/or electromagnetic energy. In an example, an electrode-holding ring, headband, halo, or headset can further comprise sinusoidal wires or other electroconductive pathways which connect the sensors (e.g. electrodes) to the electronics unit.

In an example, a device can be embodied in an undulating hairband or tiara which spans, from side-to-side, over the top of a person's head. In an example, an electrode-holding device can be embodied in a hair comb. In an example, an electrode-holding device can be embodied in a tiara or crown. In another example, an electrode-holding ring, headband, halo, or headset can be embodied in a headset. In an example, an electrode-holding ring, headband, halo, or headset can be embodied in a crown. In an example, a device can be embodied in a hair comb, hair band, or hair clip. In an embodiment, a device can be embodied in a hearable device, such as an ear bud, ear insert, or hearing aid. In an example, a device can be embodied in a respiratory mask. In an embodiment, a device can be embodied in augmented reality (AR) eyewear.

In an example, a device for monitoring brain activity can include an indentation, groove, or track into (or against) which a side-piece of the frame of a pair of eyeglasses can be placed so that this device can be worn in combination with eyeglasses. In another example, an electrode-holding device can include an attachment (e.g. connection) mechanism which attaches the device to eyeglass frames. In another example, an electrode-holding device can include an opening into which eyeglass temples (e.g. sidepieces) can be inserted. In an embodiment, a sensor (e.g. electrode) can be part of (or removably-attached to) an eyewear sidepiece (e.g. temple) worn by a person, wherein the sensor (e.g. electrode) monitors and/or records electromagnetic signals from the person's brain (e.g. brainwaves).

In an example, the posterior end of an eyewear sidepiece (e.g. temple) can bifurcate into upper and lower branches. In an example, an eyewear sidepiece (e.g. temple) can bifurcate in a horizontal plane, wherein an inner branch (e.g. branch, arm, or loop) of the temple is closer to the person's head and wherein an outer branch of the temple is farther from the person's head. In an example, an eyewear sidepiece (e.g. temple) can bifurcate, wherein there is a circular, elliptical, or oval opening (e.g. opening, hole, or gap) between an upper branch (e.g. branch, arm, or loop) of the bifurcation and a lower branch of the bifurcation.

In an example, a device can comprise an upper strap (e.g. strap, band, loop, or arm) which spans over the top of a person's head, wherein the strap is connected to eyewear sidepieces (e.g. temples). In an example, a device can comprise a movable (e.g. pivoting) arm which has a first configuration in which it does not span over the top of a person's head and a second configuration in which it does span over the top of the person's head, wherein the arm is movably-connected to eyewear sidepieces (e.g. temples). In another example, a device can have a first configuration in which it is aligned with an eyewear sidepiece (e.g. temple) and a second configuration in which is extends out from the sidepiece, wherein the device is pivoted and/or rotated from the first configuration to the second configuration.

In an example, an eyewear sidepiece (e.g. temple) can span forward from the rear of a person's auricle (e.g. outer ear) in the following manner: start with a posterior (rear) end which is worn posterior to (behind) the person's auricle; then curve upward and forward around the tissue connection between the person's outer auricle and the rest of the person's head, to the top of this tissue connection; then curve downward and forward 1 to 3 inches; then curve upward, forward, and inward 1 to 3 inches to a location on the person's temple and/or forehead; and then curve downward, forward, and outward to an anterior (front) end which connects to (or becomes part of) an eyewear front piece.

In an embodiment, an eyewear sidepiece (e.g. temple) can have a (central) undulation, wave, concavity, and/or bend which curves inward toward the surface of a person's head. In an example, a device can also include a camera. In another example, a device can also include a speaker and a microphone. In an example, a device can also include an augmented reality (AR) display. In an example, a device can comprise: an arcuate electrode-holding ring, headband, halo, or headset, wherein the ring, headband, halo, or headset spans at least 40% of the lateral circumference of a person's head; a plurality of electrodes which are held in place by the ring, headband, halo, or headset, wherein the electrodes are configured to receive electrical and/or electromagnetic signals from the person's brain; and an electronics unit which includes a data processor, a data transmitter and/or data receiver, and a power source.

FIG. 1 shows the right side of a head-worn device for recording brain signals comprising: an arcuate electrode holder 101, wherein the electrode holder is a headband, halo, or headset which is configured to be worn around at least 40% of the lateral circumference of a person's head; a plurality of electrodes including electrode 102, wherein the electrodes are held in place by the electrode holder, and wherein the electrodes are configured to receive electrical and/or electromagnetic signals from the person's brain; and an electronics unit 103, wherein the electronics unit further comprises a data processor, a data transmitter and/or data receiver, and a power source. It is assumed that the left side of the device is symmetric to the right side, with the possible exception of the electronics unit, unless stated otherwise.

In this example, the posterior half of the electrode holder is wider than the anterior half of the electrode holder. In this example, the electrode holder rests on top of the auricle-connecting portion of the person's ear. In this example, the electrode holder is tilted at a forward-facing angle between 10 and 50 degrees relative to a horizontal plane when the person's head is upright. In this example, the electrode holder is embodied in a headband or other head ring (e.g. halo or crown). In this example, the electrode holder spans the entire lateral circumference of the person's head. In this example, the electrode holder spans (e.g. curves around or loops over) the posterior of the person's head and the person's forehead.

In this example, side portions of a device are wider than front and rear portions of the device. In this example, a headband or halo has a variable width. In this example, an undulating rear-tilted headband has a variable width, wherein side portions are wider than front and rear portions. In another example, an undulating rear-tilted headband can have a variable width, wherein front and rear portions of the device are wider than side portions. In another example, front and rear portions of a headband or halo can be wider than side portions of the halo and/or headband. Example variations discussed elsewhere in this disclosure or in priority-linked disclosures can also be applied to this example where relevant.

Figure 2:
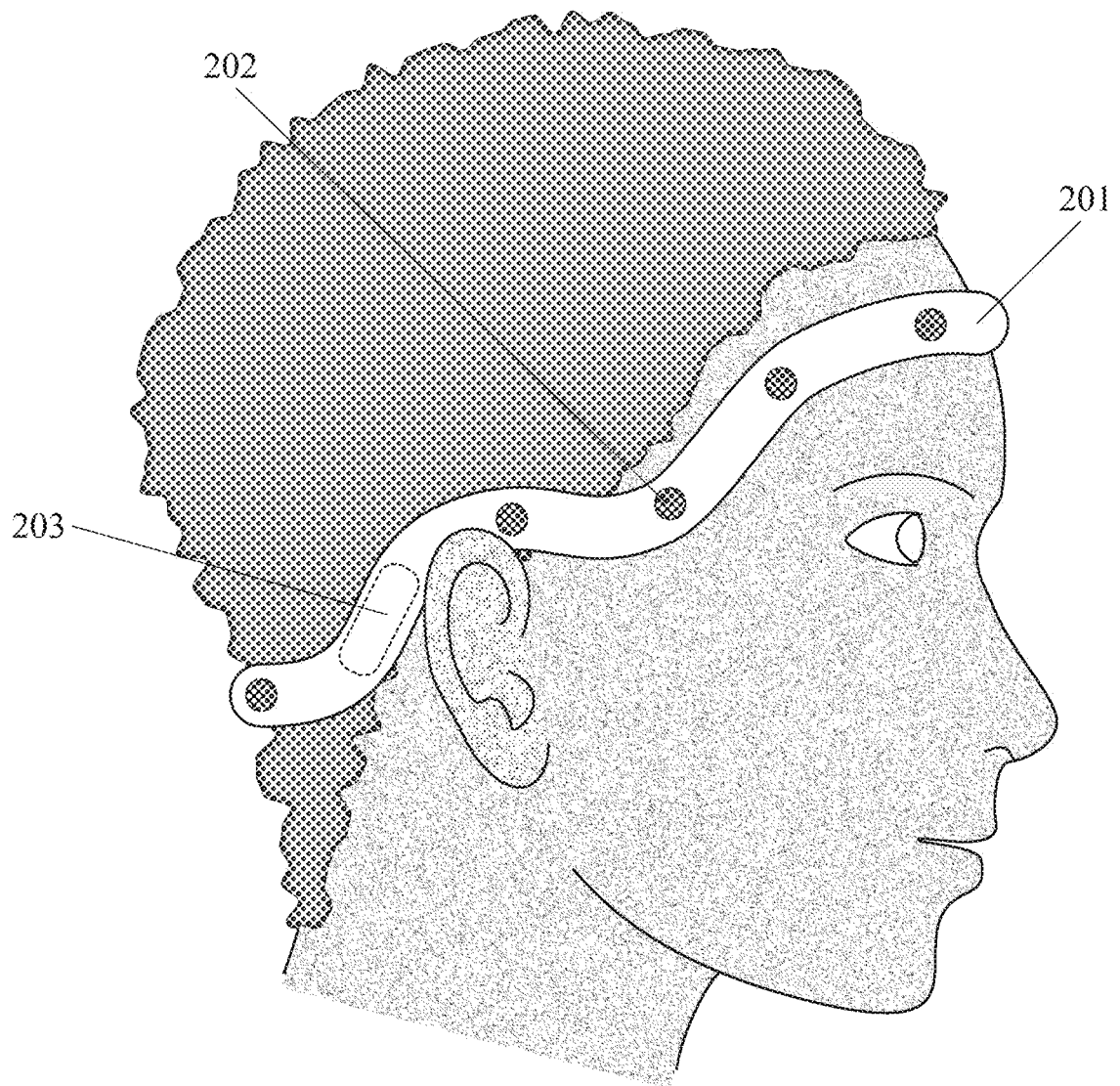
FIG. 2 shows an undulating EEG headband.

FIG. 2 shows the right side of a head-worn device for recording brain signals comprising: an arcuate electrode holder 201, wherein the electrode holder is a headband, halo, or headset which is configured to be worn around at least 40% of the lateral circumference of a person's head; a plurality of electrodes including electrode 202, wherein the electrodes are held in place by the electrode holder, and wherein the electrodes are configured to receive electrical and/or electromagnetic signals from the person's brain; and an electronics unit 203, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder has an undulating, serpentine, and/or sinusoidal shape. In this example, the electrode holder has at least two up-and-down undulations on each side of the person's head. In this example, the electrode holder has a concave undulation which rests on top of the auricle-connecting portion of the person's ear. In this example, the electrode holder is embodied in a headband or other head ring (e.g. halo or crown). In this example, the electrode holder spans the entire lateral circumference of the person's head. In this example, the electrode holder spans (e.g. curves around or loops over) the posterior of the person's head and the person's forehead.

In this example, a device is an undulating rear-tilted headband which holds a plurality of sensors (e.g. electrodes) in proximity to the person's head. In this example, a device comprises: an undulating (rear-tilted) headband which is configured to be worn around the person's head; a plurality of sensors (e.g. electrodes) which are configured to be held in proximity to the person's head by the undulating headband, wherein these sensors (e.g. electrodes) collect data concerning the person's brain activity; and an electronics unit which further comprises a data processor, a wireless data transmitter and/or receiver, and a power source.

In this example, a front portion of an undulating rear-tilted headband is configured to span the front of the person's head within two inches of the person's hairline and/or the top of the person's forehead. In this example, a side portion of an undulating rear-tilted headband is configured to span the side of the person's head within a distance of one inch from the top of the person's ear on that side. In this example, an undulating headband spans the front of the person's head over the center of the person's forehead. In this example, a device is an undulating headband or ring which is configured to span the front of the person's head over the center of the person's forehead. In this example, an undulating rear-tilted headband has at least two undulations as it spans a side of the person's head. In this example, an undulating rear-tilted headband has four wavelike undulations.

In this example, a device encircles the person's head in a tilted and sinusoidal manner. In this example, a device encircles the person's head in a sinusoidal manner and rests on the tops of the person's ears. In this example, a device comprises an undulating ring which encircles the person's head, spanning their forehead and the rear of their head, with sinusoidal waves over the tops of the person's ears. In this example, an undulating rear-tilted headband has a wave shape which is sinusoidal or the composite of multiple sinusoidal waves. In this example, a device has between 2 and 8 sinusoidal oscillations as it encircles the person's head. In an example, an undulating rear-tilted headband or ring can have four sinusoidal undulations. In this example, a forward loop of a device and a rear loop of the device together comprise an undulating (e.g. sinusoidal) ring which encircles the person's head. In this example, a device comprises a ring with sinusoidal waves. In this example, a device comprises a crown-like sinusoidal headband (which encircles the person's head) with a plurality of electrodes.

In this example, an undulating rear-tilted headband has at least two upward-opening concavities on the right side of the person's head and at least two upward-opening concavities on the left side of the person's head. In this example, a device has a front loop with a downward-facing concavity. In this example, an undulating rear-tilted headband has at least two downward-opening concavities on the right side of the person's head and at least two downward-opening concavities on the left side of the person's head. In this example, a device has a rear loop with an upward-facing concavity. In this example, an undulating rear-tilted headband has four upward-opening concavities and four downward-opening concavities. In this example, a side of an undulating rear-tilted headband includes a downward-opening concavity which spans at least a portion of the perimeter of the ear on that side. In this example, an undulating rear-tilted headband has a first upward-opening concavity as it spans between the rear of the person's head and the person's ear and a second upward-opening concavity as it spans between the person's ear and the frontal center of the person's head.

In this example, a device comprises a ring which rests on the person's ears. In this example, a device comprises a ring which rests on top of the person's ears. In this example, right and left sides of an undulating rear-tilted headband rest on top of the person's right and left ears, respectively. In this example, a device comprises a ring or headband around the person's head with downward-facing concave portions over the person's ears. In this example, a device comprises an undulating ring which encircles the person's head, spanning their forehead and the rear of their head, with upward undulations over the tops of the person's ears. In this example, an undulating rear-tilted headband has a downward-opening concavity above the person's ear. In this example, a forward loop of a device and a rear loop of the device together comprise an undulating ring which encircles the person's head with a downward-facing concavity over the person's ear. In this example, an undulating rear-tilted headband includes a wave and/or curve which is configured to peak above the person's ear. In this example, an undulating rear-tilted headband rests on the top of the person's ear (and/or the portion of the person's ear which connects it to the head). In this example, right and left sides of an undulating rear-tilted headband curve around the upper-rear portions of the person's right and left ears, respectively.

In this example, a front loop of a device is higher than a rear loop of the device. In this example, the centroid of a front arm/portion of a device is higher than the centroid of the rear arm/portion of the device. In this example, an undulating rear-tilted headband circles the person's head from the lower-rear portion of the person's head to the upper-front portion of the person's head (including the person's forehead). In other words, the front portion of the rear-tilted headband is higher and the rear portion of this headband is lower. In this example, a device encircles an upper portion of the person's head at an angle with respect to a horizontal plane when the head is upright which is within the range of 30 to 60 degrees. In this example, this angle is approximately 45 degrees. In this example, an undulating rear-tilted headband is tilted at an angle (relative to a horizontal plane when the head is upright) between 10 degree and 70 degrees.

In this example, the front portion of a undulating rear-tilted headband spans the front portion of the person's head at an average first distance from the top of the person's head; a side portion of the undulating rear-tilted headband spans the side of the person's head at an average second distance from the top of the person's head; the rear portion of the undulating rear-tilted headband spans the rear of the person's head at an average third distance from the top of the person's head; the second average distance is greater than the first average distance; and the third average distance is greater than the second average distance.

In this example, a device includes a front portion/loop which loops around the person's forehead and a rear portion/loop which loops around the rear of the person's head. In this example, a front arm/portion of a device and a rear arm/portion of a device together comprise a ring which encircles the person's head. In this example, a front arm/portion of a device extends forward and upward from the top of the person's ear to their forehead. In this example, a rear arm/portion of a device extends backward from the top or middle of the person's ear to the rear of their head. In this example, a rear arm/portion of a device extends backward and downward from the top or middle of the person's ear to the rear of their head.

In an example, a device can comprise: a forward loop which loops (from the person's ears) around the person's forehead and holds at least one sensor (e.g. electrode) substantially located at an electrode position selected from the group consisting of FPz, AF3, F5, FT7, FC5, T9, and T7; and a rear loop which loops (from the person's ears) around the rear of the person's head and holds at least one sensor (e.g. electrode) substantially located at an electrode position selected from the group consisting of Iz, P9, TP9, TP7, and T7. In an example, a device can comprise: a front arm/portion which spans from the person's ear to their forehead and holds at least one first sensor (e.g. electrode) substantially located at an electrode position selected from the group consisting of FP1, FPz, AF7, F7, TP7, FF7, and T7; and a rear arm/portion which spans from the person's ear to the rear of their head and holds at least one second sensor (e.g. electrode) substantially located at an electrode position selected from the group consisting of Iz, P9, TP9, TP7, and T7.

In an example, a device can comprise: a front portion which spans from the person's ear to their forehead and holds at least one first sensor (e.g. electrode) substantially located at an electrode position selected from the group consisting of FPz, AF3, F5, and FT7, wherein the front portion has a downward-facing concavity; a middle portion which is connected to the front portion, curves over the top of the person's outer ear, and holds at least one second sensor (e.g. electrode) substantially located at an electrode position selected from the group consisting of TP7, T9, and T7; and a rear portion which is connected to the middle portion, spans the rear of the person's head, and holds at least one third sensor (e.g. electrode) substantially located at an electrode position selected from the group consisting of P9 and TP9.

In an example, a device can comprise: a front portion which spans from the person's ear to their forehead and holds at least one first sensor (e.g. electrode) substantially located at an electrode position selected from the group consisting of FPz, AF3, F5, and FT7, wherein the front portion has a downward-facing concavity; a middle portion which is connected to the front portion and curves over the top of the person's outer ear; and a rear portion which is connected to the middle portion and spans the rear of the person's head. In an example, a device can comprise: a front portion which spans from the person's ear to their forehead and has a downward-facing concavity; a middle portion which is connected to the front portion and curves over the top of the person's outer ear; a rear portion which is connected to the middle portion, spans the rear of the person's head, and holds at least one third sensor (e.g. electrode) substantially located at an electrode position selected from the group consisting of P9 and TP9.

In an example, a device can comprise: a front portion/loop, which spans from the person's ear to their forehead and holds at least one sensor (e.g. electrode) substantially located at an electrode position selected from the group consisting of FP1, FPz, AF7, F9, F7, FT9, T9, and T7; and a rear portion/loop which spans from the person's ear to the rear of the person's head and holds at least one sensor (e.g. electrode) substantially located at an electrode position selected from the group consisting of Iz, P9, TP9, and T7. In an example, a device can comprises a front portion which spans from the person's ear to their forehead and has a downward-facing concavity; a middle portion which is connected to the front portion, curves over the top of the person's outer ear, and holds at least one second sensor (e.g. electrode) substantially located at an electrode position selected from the group consisting of TP7, T9, and T7; a rear portion which is connected to the middle portion and spans the rear of the person's head.

In this example, a device is embodied in a headband. In this example, a device comprises: a headband which is configured to be worn around the person's head; one or more electrodes or other brain activity sensors which are configured by the headband to be less than one inch from the surface of the person's head; and an electronics unit which further comprises a data processor, a data transmitter, and a power source.

In an example, a head-worn device for recording brain signals can comprise: an arcuate electrode holder, wherein the electrode holder is a headband, halo, or headset which is configured to be worn around at least 40% of the circumference of a person's head; a plurality of electrodes, wherein the electrodes are held in place by the electrode holder, and wherein the electrodes are configured to receive electrical and/or electromagnetic signals from the person's brain; and an electronics unit, wherein the electronics unit further comprises a data processor, a data transmitter and/or data receiver, and a power source.

In an example, a front portion of the device can span across the person's forehead. In an example, a rear portion of the device can span around the rear of the person's head. In an example, the electrode holder can have undulations. In an example, the undulations can be sinusoidal undulations. In an example, the undulations can be substantially vertical when the person's head is upright. In an example, there can be at least two undulations on each side of the person's head. In an example, an undulation on a side of the person's head can rest on top of the person's ear. In an example, the undulation which rests on top of the person's ear can have a downward-opening concavity. Example variations discussed elsewhere in this disclosure or in priority-linked disclosures can also be applied to this example where relevant.

Figure 3:
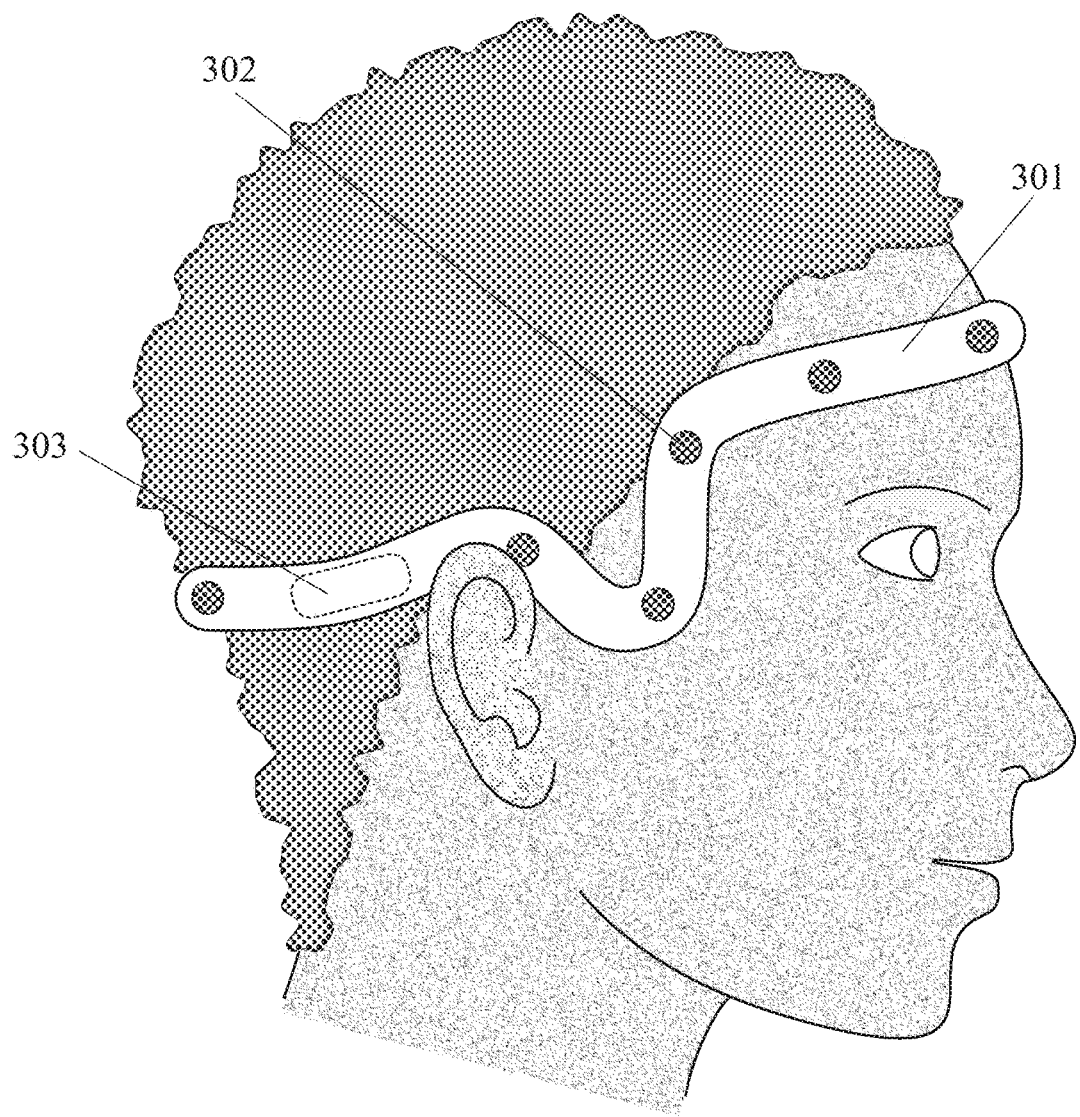
FIG. 3 shows an EEG headband with a downward undulation in front of an ear.

FIG. 3 shows the right side of a head-worn device for recording brain signals comprising: an arcuate electrode holder 301, wherein the electrode holder is a headband, halo, or headset which is configured to be worn around at least 40% of the lateral circumference of a person's head; a plurality of electrodes including electrode 302, wherein the electrodes are held in place by the electrode holder, and wherein the electrodes are configured to receive electrical and/or electromagnetic signals from the person's brain; and an electronics unit 303, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder has an undulating or serpentine shape. In this example, the electrode holder has a downward undulation which is laterally-anterior to the person's ear. In this example, the electrode holder rests on top of the auricle-connecting portion of the person's ear. In this example, the electrode holder spans the entire lateral circumference of the person's head. In this example, the electrode holder spans (e.g. curves around or loops over) the posterior of the person's head and the person's forehead.

In this example, a device comprises: (a) an undulating band which is configured to encircle a person's head, wherein a portion of this undulating band on a side of the person's head further comprises: a first segment which is configured to span from the rear of the person's head to the person's ear; a second segment which is configured to span from the person's ear to a side of the person's face and/or forehead, wherein this second segment has a concavity which opens upward; and a third segment which configured to span across the person's forehead; (b) at least one sensor (e.g. electrode) which is held in proximity to the person's head by the undulating band, wherein the at least one sensor (e.g. electrode) collects data concerning brain activity; (c) an electronics unit which further comprises a data processor, a data transmitter, and a power source.

In this example, a device comprises: (a) an undulating band which is configured to span from a person's ear on a first side of the person's head to the person's ear on the second side of the person's head, wherein the portion of this undulating band on the first side of the person's head further comprises: a first segment which is configured to span from the rear of the person's head to the person's ear; a second segment which is configured to span from the person's ear to a side of the person's face and/or forehead, wherein this second segment has a concavity which opens upward; and a third segment which configured to span across the person's forehead; (b) at least one sensor (e.g. electrode) which is held in proximity to the person's head by the undulating band, wherein the at least one sensor (e.g. electrode) collects data concerning brain activity; (c) an electronics unit which further comprises a data processor, a data transmitter, and a power source.

In this example, a device comprises: an undulating band which is configured to span from a person's ear on a first side of the person's head to the person's ear on the second side of the person's head, wherein the portion of this undulating band on the first side of the person's head further comprises a first segment which is configured to span from the rear of the person's head to the person's ear, a second segment which is configured to span from the person's ear to a side of the person's face and/or forehead, wherein this second segment has a concavity which opens upward, a third segment which configured to span across the person's forehead; sensors (e.g. electrodes); and an electronics unit further comprising a data processor, a data transmitter, and a power source.

In this example, a first segment of a device spans forward from the rear of a person's head within two inches of a horizontal line rearward from the top of the ear. In this example, a first segment of a device spans from the rear of the person's head to a second segment. In this example, a first segment of a device spans from the rear of the person's head to a person's ear. In this example, a first segment of a device spans the rear of a person's head within four inches of a horizontal line rearward from the top of the ear. In this example, a second segment of a device extends, protrudes, curves, or loops from the person's ear toward the person's temple and/or forehead. In this example, a second segment of a device extends, protrudes, curves, or loops from the person's ear to a side portion of the person's face.

In this example, a second segment of a device has a concavity whose opening faces upward. In this example, a second segment of a device has a shape which is selected from the group consisting of: arc, wave, undulation, semi-circle, semi-oval, loop, half-sinusoidal curve, bell-shaped curve, and conic section. In this example, the most-forward point of a second segment of a device is located on a person's temple and/or forehead. In this example, this device includes a second segment which spans from a person's ear to a side portion of their face and/or forehead. In this example, a third segment of a device extends across a person's forehead. Example variations discussed elsewhere in this disclosure or in priority-linked disclosures can also be applied to this example where relevant.

Figure 4:
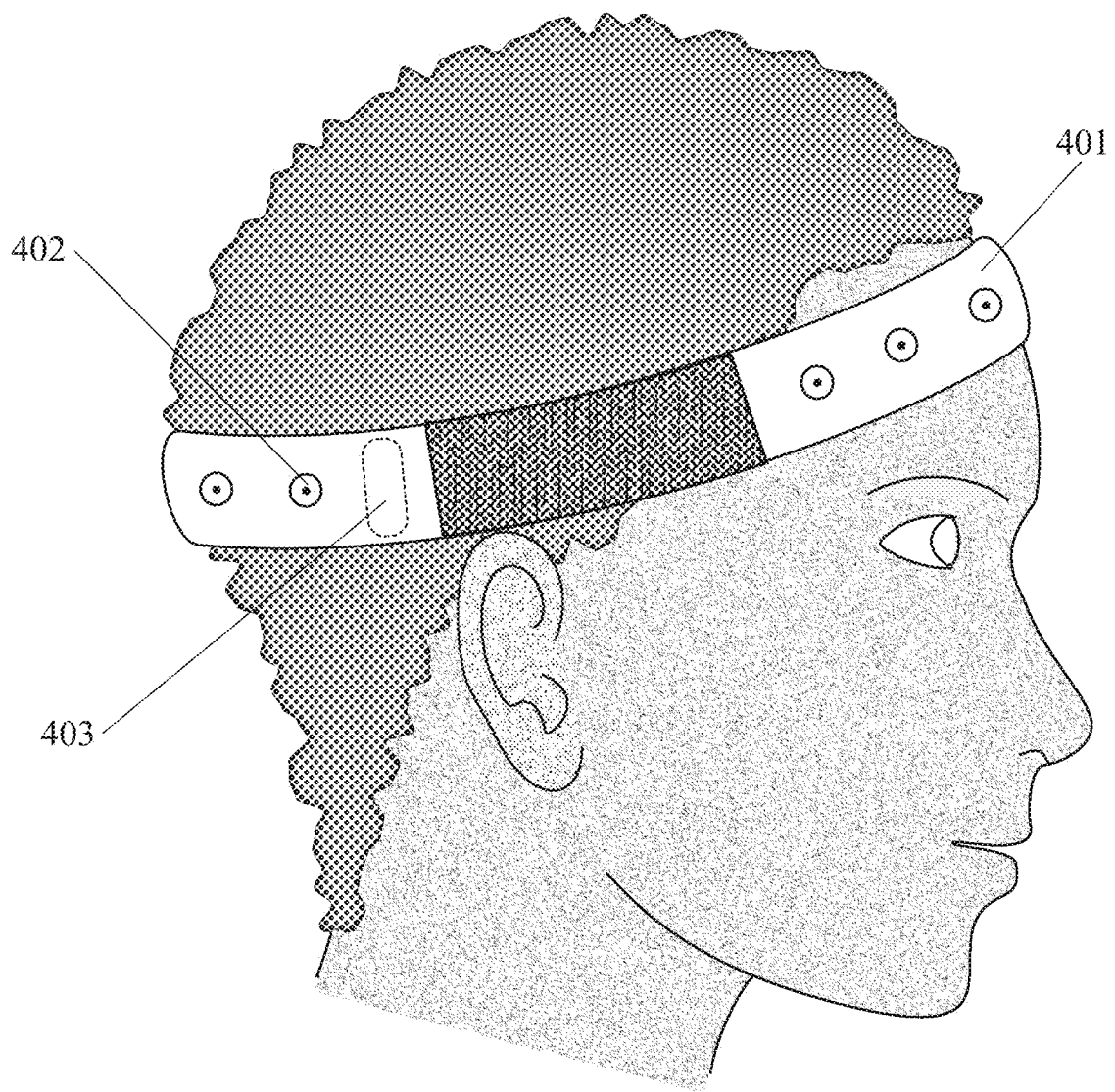
FIG. 4 shows an EEG headband with inelastic and elastic sections.

FIG. 4 shows the right side of a head-worn device for recording brain signals comprising: an arcuate electrode holder 401, wherein the electrode holder is a headband, halo, or headset which is configured to be worn around at least 40% of the lateral circumference of a person's head; a plurality of electrodes including electrode 402, wherein the electrodes are held in place by the electrode holder, and wherein the electrodes are configured to receive electrical and/or electromagnetic signals from the person's brain; and an electronics unit 403, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder has one or more relatively-inelastic sections (e.g. with a first level of elasticity or stretchability) and one or more relatively-elastic sections (e.g. with a second level of elasticity or stretchability), wherein the second level is greater than the first level. In this figure, the relatively-elastic sections are shown with a darker weave pattern. In this example, the relatively-inelastic sections are made (primarily) from one or more metals or hard polymers and the relatively-inelastic sections are made (primarily) from one or more fabrics or textiles. In this example, the relatively-inelastic sections and the relatively-elastic sections span different portions of the lateral circumference of the electrode holder. In this example, the electrode holder has two relatively-inelastic sections and two relatively-elastic sections. In this example, there is a relatively-elastic section on each side (e.g. right and left) of the person's head. In this example, a relatively-elastic section is directly above an ear.

In this example, one or more sections of the perimeter of a headband or halo are stretchable, elastic, and/or expandable. In this example, the perimeter of a headband or halo comprises one or more sections with a first degree of stretchability, elasticity, and/or expandability and one or more sections with a second degree of stretchability, elasticity, and/or expandability, wherein the second degree is greater than the first degree. In an example, the rear portion of the perimeter of a headband (spanning the rear of the person's head) can have a first degree of stretchability, elasticity, and/or expandability and the front portion of the perimeter of the headband (spanning the person's forehead) can have a second degree of stretchability, elasticity, and/or expandability, wherein the second degree is less than the first degree. In an example, the rear portion of the perimeter of a headband (spanning the rear of the person's head) can have a first degree of stretchability, elasticity, and/or expandability and the front portion of the perimeter of the headband (spanning the person's forehead) can have a second degree of stretchability, elasticity, and/or expandability, wherein the second degree is greater than the first degree. Example variations discussed elsewhere in this disclosure or in priority-linked disclosures can also be applied to this example where relevant.

Figure 5:
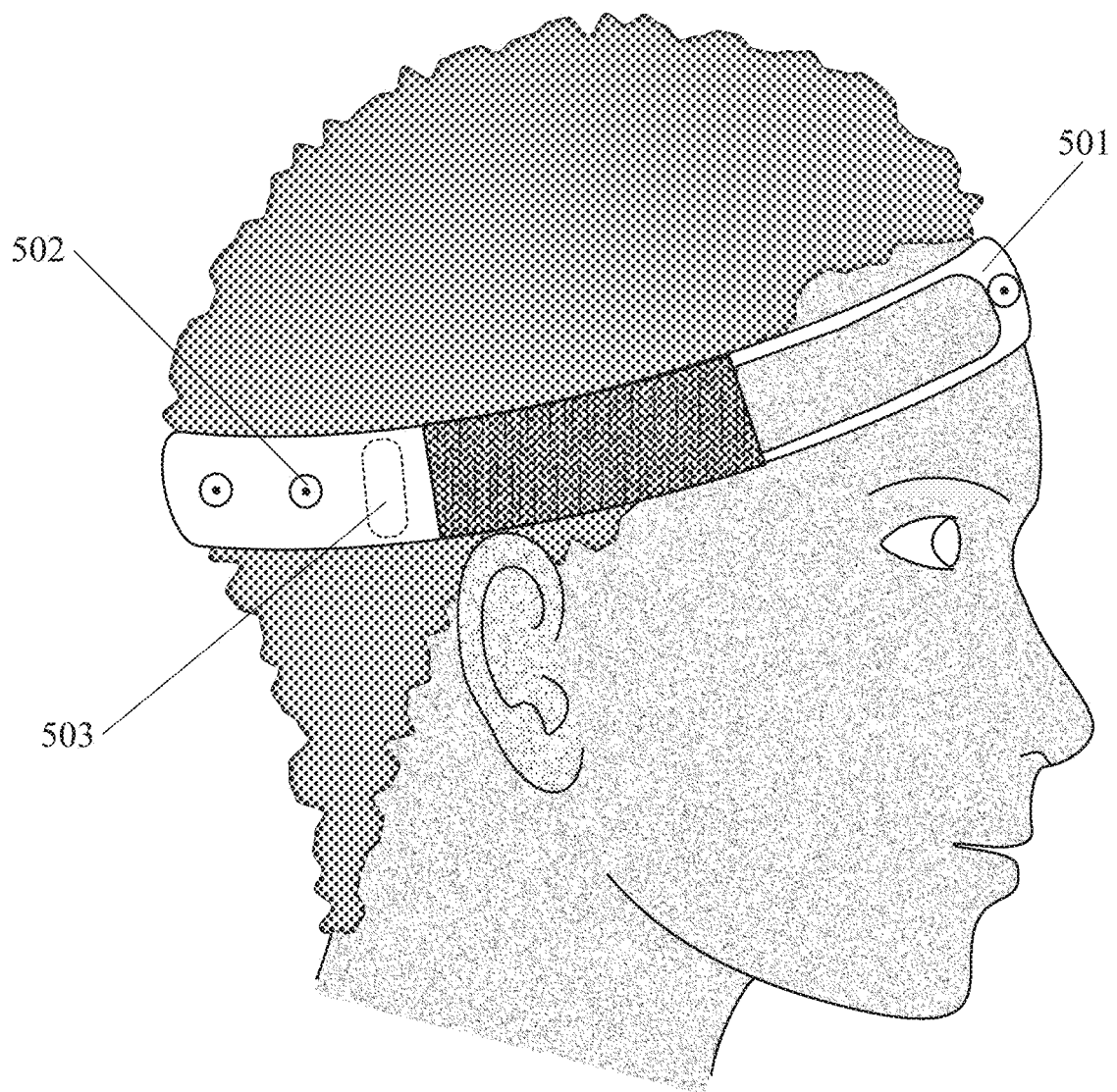
FIG. 5 shows an EEG headband with elastic sections and openings.

FIG. 5 shows the right side of a head-worn device for recording brain signals comprising: an arcuate electrode holder 501, wherein the electrode holder is a headband, halo, or headset which is configured to be worn around at least 40% of the lateral circumference of a person's head; a plurality of electrodes including electrode 502, wherein the electrodes are held in place by the electrode holder, and wherein the electrodes are configured to receive electrical and/or electromagnetic signals from the person's brain; and an electronics unit 503, wherein the electronics unit further comprises a data processor, a data transmitter and/or data receiver, and a power source. It is assumed that the left side of the device is symmetric to the right side, with the possible exception of the electronics unit, unless stated otherwise.

In this example, there are a plurality of openings (e.g. holes) in the electrode holder. In this example, the openings (e.g. holes) are on a section of the electrode holder which spans the person's forehead, wherein the person's forehead is visible through these openings. In this example, there is an opening (e.g. hole) along the central circumferential axis of the electrode holder on each side (e.g. right and left) of the electrode holder. In this example, the electrode holder bifurcates as it spans the person's forehead. In this example, the electrode holder has one or more relatively-inelastic sections (e.g. with a first level of elasticity or stretchability) and one or more relatively-elastic sections (e.g. with a second level of elasticity or stretchability), wherein the second level is greater than the first level. In this figure, the relatively-elastic sections are shown with a darker weave pattern.

In this example, a device comprises a bifurcating ring which encircles a person's head. In this example, a device can comprise a ring which bifurcates into an upper front loop and a lower front loop. In this example, a device is a bifurcating ring around a person's head which bifurcates as it spans the front of the person's head. In this example, segments of a device have holes so as to be permeable to gas and/or liquid.

In this example, one or more sections of the perimeter of a headband or halo are stretchable, elastic, and/or expandable. In this example, the perimeter of a headband or halo comprises one or more sections with a first degree of stretchability, elasticity, and/or expandability and one or more sections with a second degree of stretchability, elasticity, and/or expandability, wherein the second degree is greater than the first degree. In an example, the rear portion of the perimeter of a headband (spanning the rear of the person's head) can have a first degree of stretchability, elasticity, and/or expandability and the front portion of the perimeter of the headband (spanning the person's forehead) can have a second degree of stretchability, elasticity, and/or expandability, wherein the second degree is less than the first degree. In an example, the rear portion of the perimeter of a headband (spanning the rear of the person's head) can have a first degree of stretchability, elasticity, and/or expandability and the front portion of the perimeter of the headband (spanning the person's forehead) can have a second degree of stretchability, elasticity, and/or expandability, wherein the second degree is greater than the first degree. Example variations discussed elsewhere in this disclosure or in priority-linked disclosures can also be applied to this example where relevant.

Figure 6:
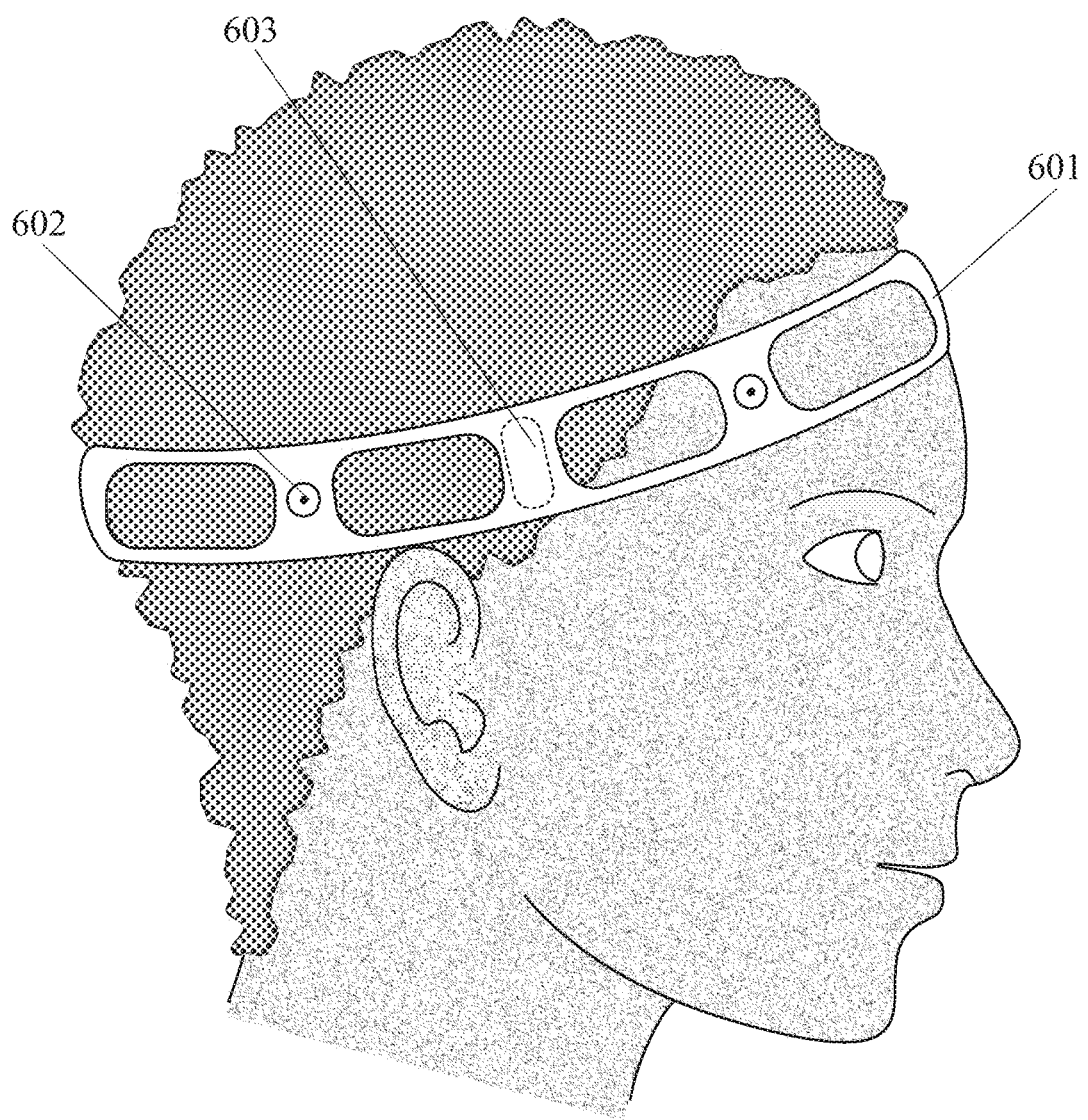
FIG. 6 shows an EEG headband with a plurality of openings along its circumferential axis.

FIG. 6 shows the right side of a head-worn device for recording brain signals comprising: an arcuate electrode holder 601, wherein the electrode holder is a headband, halo, or headset which is configured to be worn around at least 40% of the lateral circumference of a person's head; a plurality of electrodes including electrode 602, wherein the electrodes are held in place by the electrode holder, and wherein the electrodes are configured to receive electrical and/or electromagnetic signals from the person's brain; and an electronics unit 603, wherein the electronics unit further comprises a data processor, a data transmitter and/or data receiver, and a power source. It is assumed that the left side of the device is symmetric to the right side, with the possible exception of the electronics unit, unless stated otherwise.

In this example, there are a plurality of openings (e.g. holes) in the electrode holder. In this example, the person's head is visible through the openings. In this example, the plurality of openings (e.g. holes) are along the central circumferential axis of the electrode holder, including a plurality of openings on each side (e.g. right and left) of the electrode holder. In this example, there are at least four openings (e.g. holes) on each side (e.g. right and left) of the electrode holder. In this example, openings (e.g. holes) are longitudinal openings, wherein lengths of the openings along a central circumferential axis of the electrode holder are greater than widths of the openings in directions which are perpendicular to the circumferential axis.

In this example, there are a plurality of openings (e.g. holes) in the electrode holder. In this example, the openings (e.g. holes) are on a section of the electrode holder which spans the person's forehead, wherein the person's forehead is visible through these openings. In this example, there is an opening (e.g. hole) along the central circumferential axis of the electrode holder on each side (e.g. right and left) of the electrode holder. In this example, the electrode holder bifurcates as it spans the person's forehead. In this example, the electrode holder has one or more relatively-inelastic sections (e.g. with a first level of elasticity or stretchability) and one or more relatively-elastic sections (e.g. with a second level of elasticity or stretchability), wherein the second level is greater than the first level. In this figure, the relatively-elastic sections are shown with a darker weave pattern. Example variations discussed elsewhere in this disclosure or in priority-linked disclosures can also be applied to this example where relevant.

Figure 7:
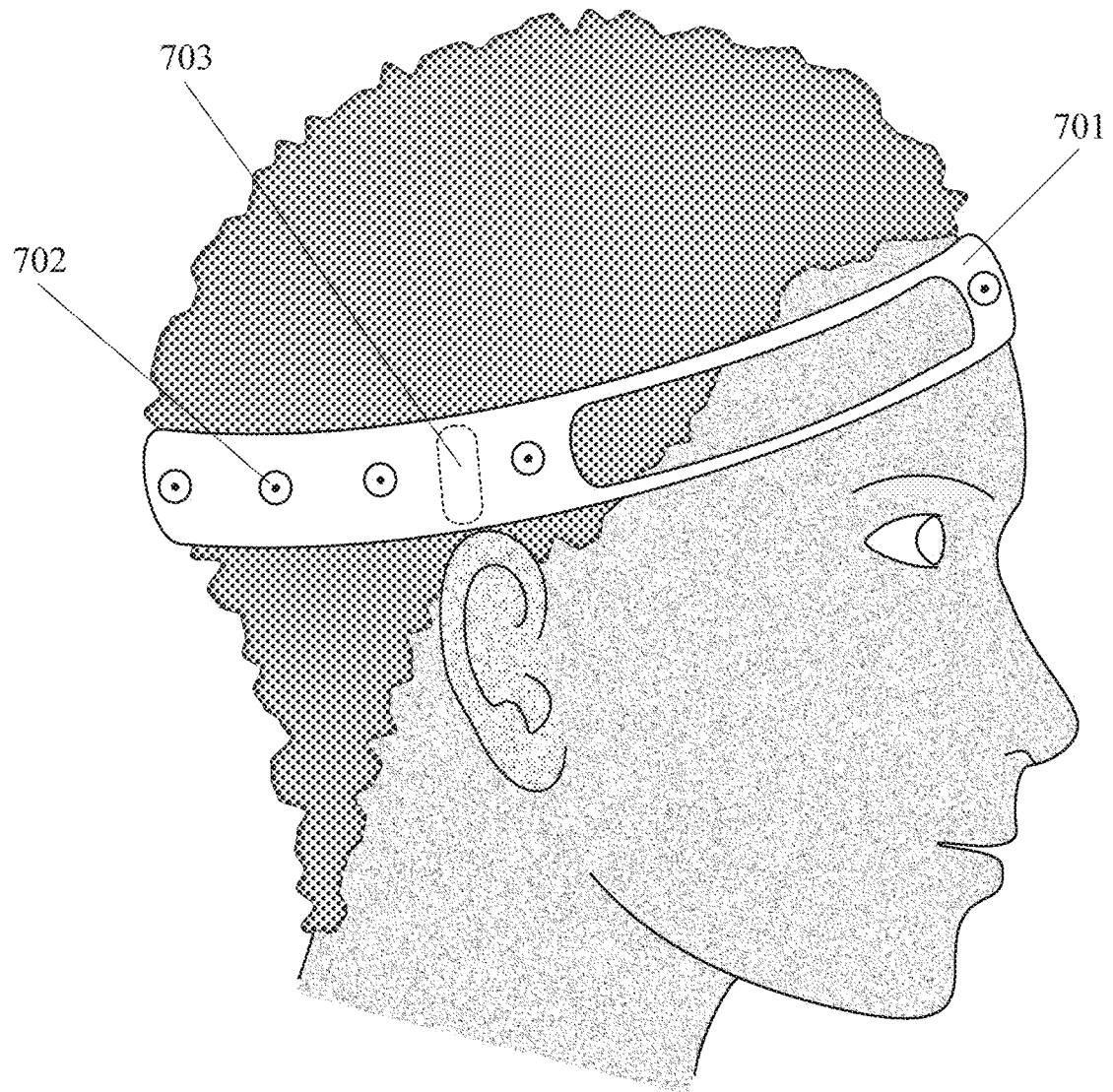
FIG. 7 shows an EEG headband with an opening whose length is at least twice its width.

FIG. 7 shows the right side of a head-worn device for recording brain signals comprising: an arcuate electrode holder 701, wherein the electrode holder is a headband, halo, or headset which is configured to be worn around at least 40% of the lateral circumference of a person's head; a plurality of electrodes including electrode 702, wherein the electrodes are held in place by the electrode holder, and wherein the electrodes are configured to receive electrical and/or electromagnetic signals from the person's brain; and an electronics unit 703, wherein the electronics unit further comprises a data processor, a data transmitter and/or data receiver, and a power source. It is assumed that the left side of the device is symmetric to the right side, with the possible exception of the electronics unit, unless stated otherwise.

In this example, there is at least one opening (e.g. hole) in the electrode holder. In this example, the person's head is visible through the opening. In this example, there is at least one opening (e.g. hole) along the central circumferential axis of the electrode holder on each side (e.g. right and left) of the electrode holder. In this example, an opening (e.g. hole) is a longitudinal opening, wherein the length of the opening along a central circumferential axis of the electrode holder is at least twice the width of the opening in a direction which is perpendicular to the circumferential axis. In this example, the electrode holder bifurcates on each side (e.g. right and left) of the person's head.

In this example, there are a plurality of openings (e.g. holes) in the electrode holder. In this example, the openings (e.g. holes) are on a section of the electrode holder which spans the person's forehead, wherein the person's forehead is visible through these openings. In this example, there is an opening (e.g. hole) along the central circumferential axis of the electrode holder on each side (e.g. right and left) of the electrode holder. In this example, the electrode holder bifurcates as it spans the person's forehead. In this example, the electrode holder has one or more relatively-inelastic sections (e.g. with a first level of elasticity or stretchability) and one or more relatively-elastic sections (e.g. with a second level of elasticity or stretchability), wherein the second level is greater than the first level. In this figure, the relatively-elastic sections are shown with a darker weave pattern. Example variations discussed elsewhere in this disclosure or in priority-linked disclosures can also be applied to this example where relevant.

Figure 8:
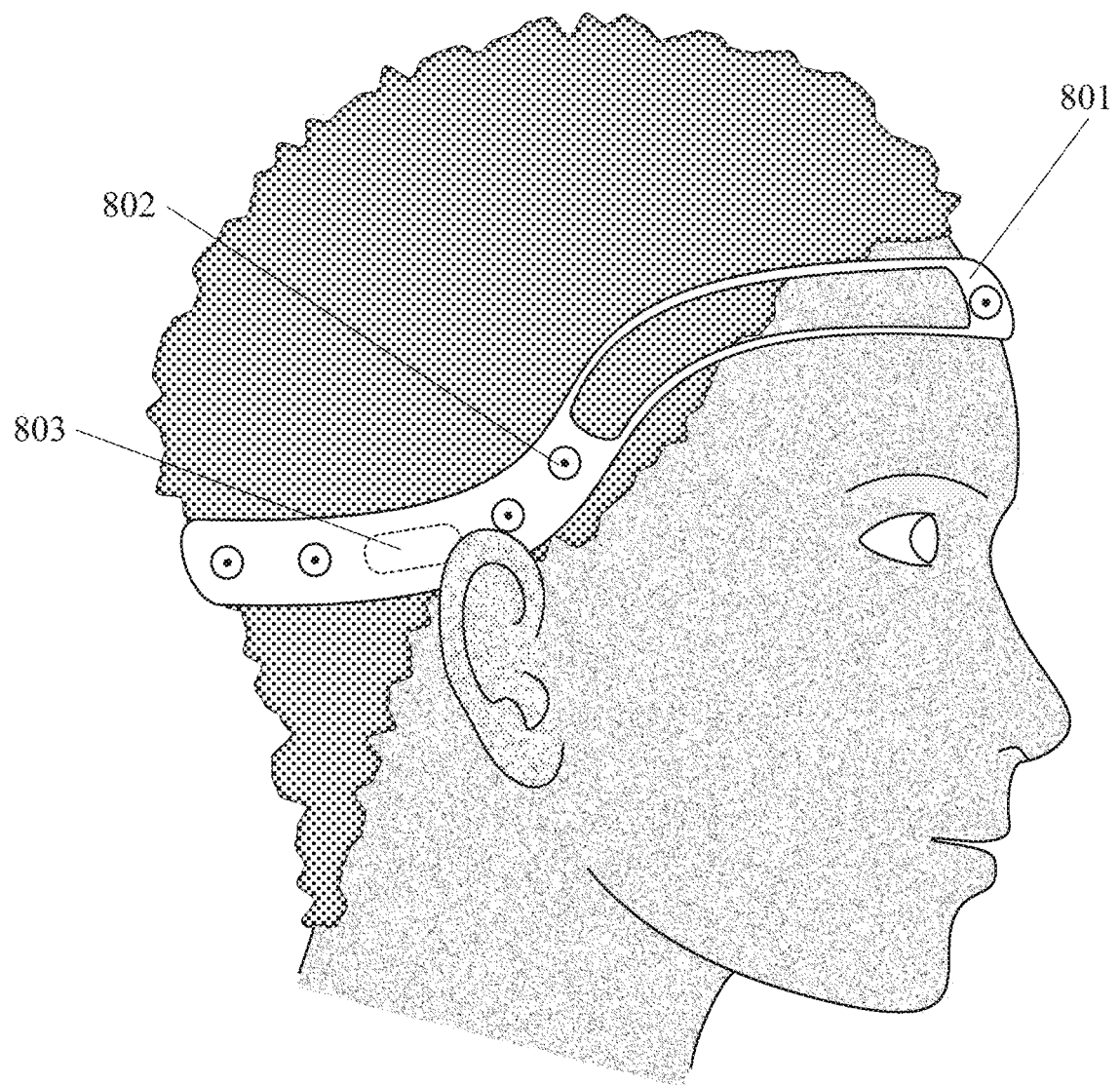
FIG. 8 shows an EEG headband with a rear section at a first level and a front section at a second level, wherein the second level is higher than the first level.

FIG. 8 shows the right side of a head-worn device for recording brain signals comprising: an arcuate electrode holder 801, wherein the electrode holder is a headband, halo, or headset which is configured to be worn around at least 40% of the lateral circumference of a person's head; a plurality of electrodes including electrode 802, wherein the electrodes are held in place by the electrode holder, and wherein the electrodes are configured to receive electrical and/or electromagnetic signals from the person's brain; and an electronics unit 803, wherein the electronics unit further comprises a data processor, a data transmitter and/or data receiver, and a power source. It is assumed that the left side of the device is symmetric to the right side, with the possible exception of the electronics unit, unless stated otherwise.

In this example, there is at least one opening (e.g. hole) on each side (e.g. right and left) of the electrode holder. In this example, the person's head is visible through the openings. In this example, when the person's head is upright, the posterior half of the electrode holder has a first average height and the anterior half of the electrode has a second average height, wherein the second average height is greater than the first average height. In this example, when the person's head is upright, the most-posterior third of the electrode holder has a first substantially-level height and most-anterior third of the electrode has a second substantially-level height, wherein the second height is greater than the first average height, and wherein the height of the electrode holder transitions from the first height to the second height in an arcuate middle-third section of the electrode holder.

In this example, there are a plurality of openings (e.g. holes) in the electrode holder. In this example, the openings (e.g. holes) are on a section of the electrode holder which spans the person's forehead, wherein the person's forehead is visible through these openings. In this example, there is an opening (e.g. hole) along the central circumferential axis of the electrode holder on each side (e.g. right and left) of the electrode holder. In this example, the electrode holder bifurcates as it spans the person's forehead. In this example, the electrode holder has one or more relatively-inelastic sections (e.g. with a first level of elasticity or stretchability) and one or more relatively-elastic sections (e.g. with a second level of elasticity or stretchability), wherein the second level is greater than the first level. In this figure, the relatively-elastic sections are shown with a darker weave pattern. Example variations discussed elsewhere in this disclosure or in priority-linked disclosures can also be applied to this example where relevant.

Figure 9:
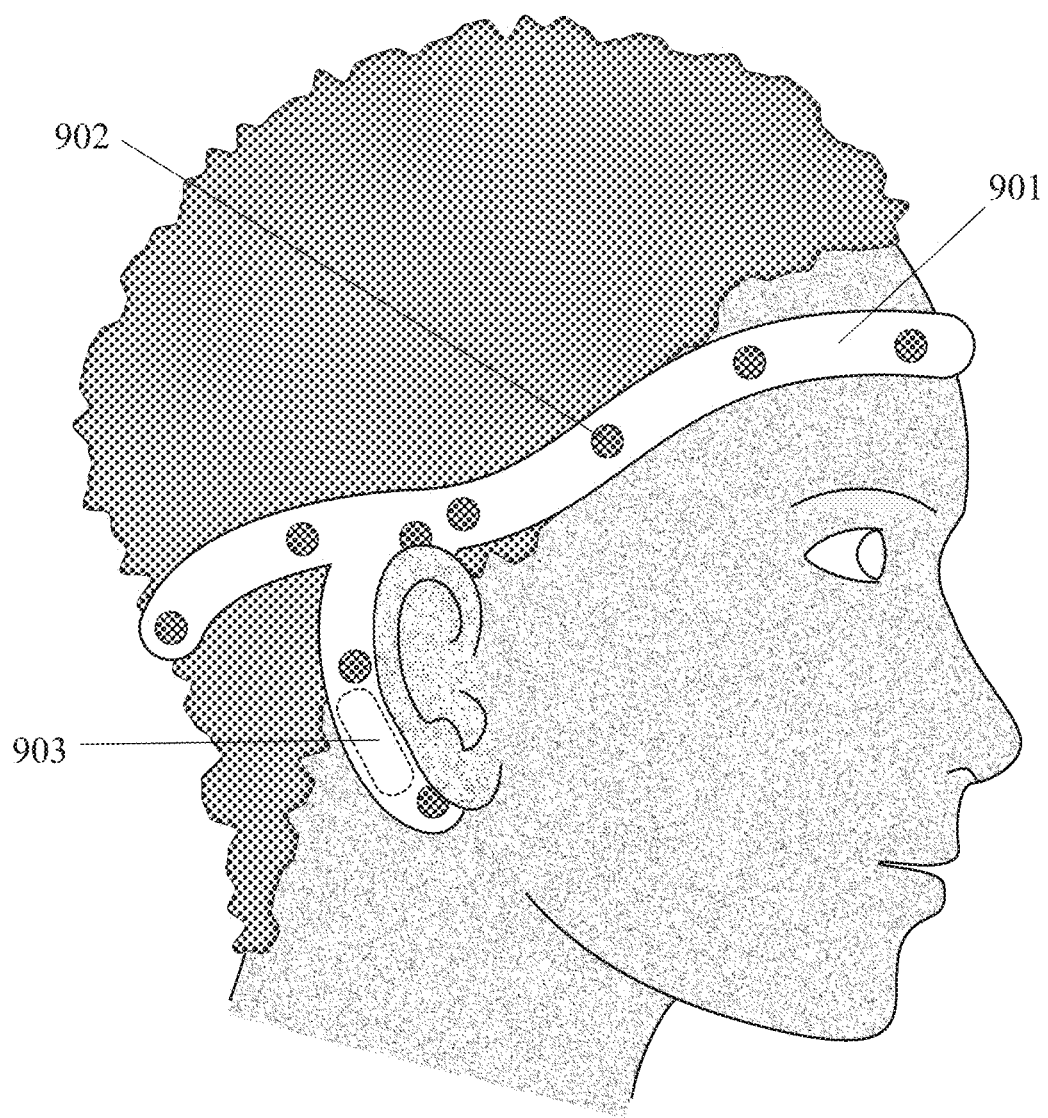
FIG. 9 shows an EEG headband with an arm extending downward around the rear of an ear.

FIG. 9 shows the right side of a head-worn device for recording brain signals comprising: an arcuate electrode holder 901, wherein the electrode holder is a headband, halo, or headset which is configured to be worn around at least 40% of the lateral circumference of a person's head; a plurality of electrodes including electrode 902, wherein the electrodes are held in place by the electrode holder, and wherein the electrodes are configured to receive electrical and/or electromagnetic signals from the person's brain; and an electronics unit 903, wherein the electronics unit further comprises a data processor, a data transmitter and/or data receiver, and a power source. It is assumed that the left side of the device is symmetric to the right side, with the possible exception of the electronics unit, unless stated otherwise.

In this example, an arm (e.g. arm, prong, branch, loop, and/or protrusion) of the electrode holder extends downward and curves around the posterior of the person's ear (e.g. the connecting portion of the auricle). In this example, an arm (e.g. arm, prong, branch, loop, and/or protrusion) of the electrode holder extends downward from a main circumferential body of the electrode holder, wherein the arm curves around the posterior of the person's ear (e.g. the connecting portion of the auricle). In this example, the main circumferential body of the electrode holder rests on top of the person's ear (e.g. the connecting portion of the auricle).

In this example, a device is an undulating headband which encircles a person's head. In this example, right and left side portions of the main circumferential body of an undulating headband dip down to within one inch of the person's right and left ears, respectively. In this example, the main circumferential body of an undulating headband is sinusoidal, with the lowest points of the sinusoidal waves being (directly) above the person's ears. In this example, the front portion of an undulating headband spans across a person's forehead.

In this example, a device includes ear prongs (e.g. arms and/or protrusions) which frictionally-engage the person's outer ears and help to hold the undulating headband in place. In this example, right and left side portions of the undulating headband include right and left ear prongs (e.g. arms and/or protrusions), wherein each ear prong partially encircles the perimeter of the person's outer ear and/or the connection between the main body of the head and the outer ear. In this example, a front portion of this headband spans the person's forehead and the rear portion of this headband spans the rear of the person's head. In this example, a front portion of an undulating headband is higher than the rear portion of the undulating headband.

In this example, a device comprises: a forward-upward sloped headband (including rear portion and front portion) which is configured to be worn around a person's head and also an ear prong (e.g. arm or protrusion) which engages the perimeter of the person's outer ear; a plurality of sensors (e.g. electrodes) which are configured to be held in proximity to the person's head by the undulating headband, wherein these sensors (e.g. electrodes) collect data concerning electromagnetic activity of the person's brain; an electronics unit with a data processor, a data transmitter and/receiver and a power source.

In this example, a device comprises: an undulating headband (including a rear portion and a front portion) which is configured to be worn around a person's head and also an ear prong (e.g. arm or protrusion) which engages a portion of the perimeter of the person's outer ear; a plurality of sensors (e.g. electrodes) which are configured to be held in proximity to the person's head by the undulating headband, wherein these sensors (e.g. electrodes) collect data concerning electromagnetic activity of the person's brain; and an electronics unit comprising a data processor, data transmitter and/or receiver, and a power source. Example variations discussed elsewhere in this disclosure or in priority-linked disclosures can also be applied to this example where relevant.

Figure 10:
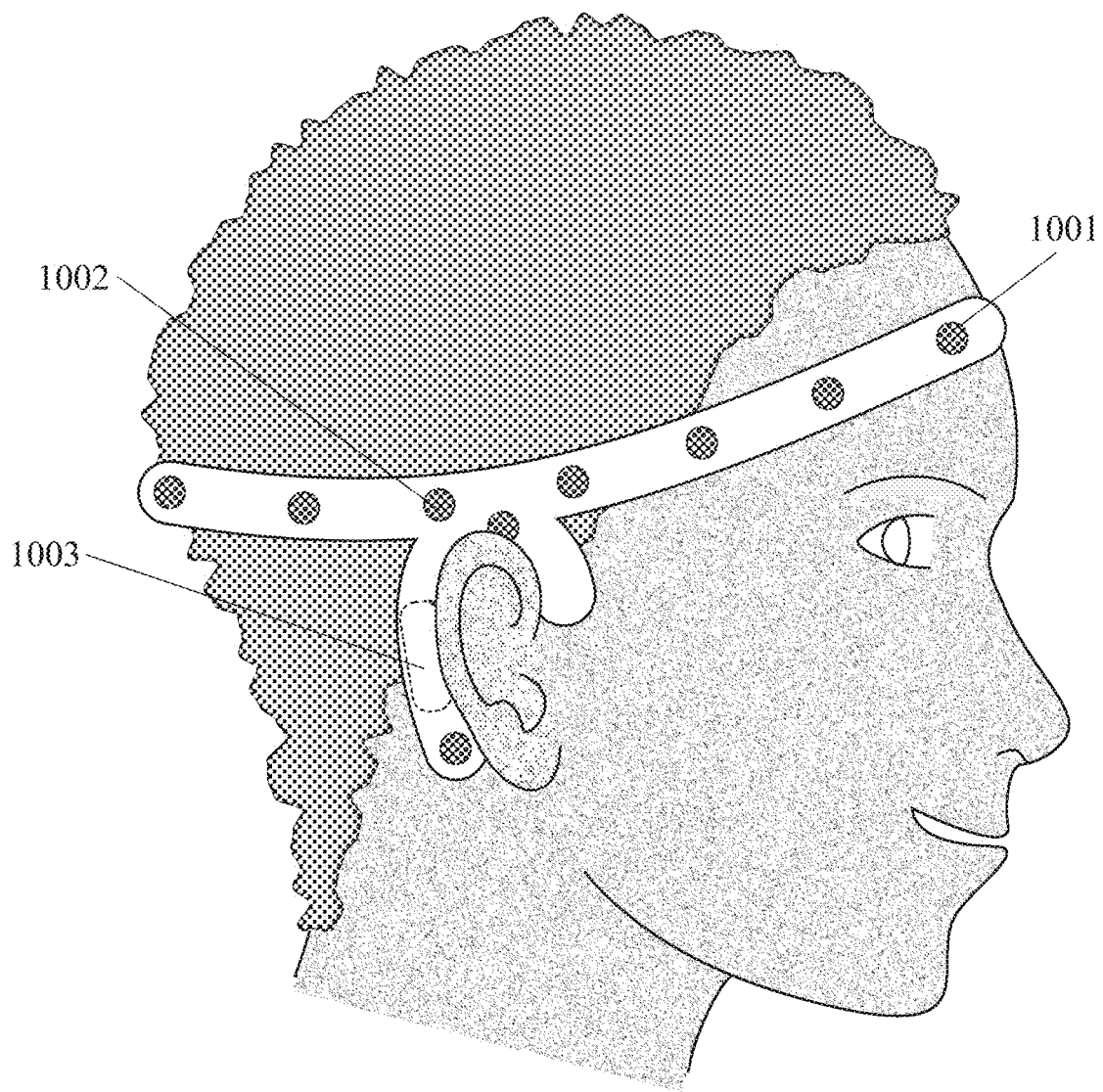
FIG. 10 shows an EEG headband with a first arm extending downward around the rear of an ear and a second arm extending down around the front of the ear.

FIG. 10 shows the right side of a head-worn device for recording brain signals comprising: an arcuate electrode holder 1001, wherein the electrode holder is a headband, halo, or headset which is configured to be worn around at least 40% of the lateral circumference of a person's head; a plurality of electrodes including electrode 1002, wherein the electrodes are held in place by the electrode holder, and wherein the electrodes are configured to receive electrical and/or electromagnetic signals from the person's brain; and an electronics unit 1003, wherein the electronics unit further comprises a data processor, a data transmitter and/or data receiver, and a power source. It is assumed that the left side of the device is symmetric to the right side, with the possible exception of the electronics unit, unless stated otherwise.

In this example, a first arm (e.g. arm, prong, branch, loop, and/or protrusion) of the electrode holder extends downward and curves around the posterior of the person's ear (e.g. the connecting portion of the auricle). In this example, a first arm (e.g. arm, prong, branch, loop, and/or protrusion) of the electrode holder extends downward from a main circumferential body of the electrode holder, wherein the arm curves around the posterior of the person's ear (e.g. the connecting portion of the auricle). In this example, a second arm (e.g. arm, prong, branch, loop, and/or protrusion) of the electrode holder extends downward and curves around part of the anterior of the person's ear (e.g. the connecting portion of the auricle).

In this example, a second arm (e.g. arm, prong, branch, loop, and/or protrusion) of the electrode holder extends downward from a main circumferential body of the electrode holder, wherein the arm curves around part of the anterior of the person's ear (e.g. the connecting portion of the auricle). In this example, a device includes a rear-ear segment (e.g. arm or protrusion) worn on the rear-facing surface of a person's ear and a frontal-ear segment (e.g. arm or protrusion) worn on the front-facing surface of the person's ear. In this example, a device includes ear prongs (e.g. arms or protrusions) which frictionally-engage the person's outer ears and help to hold the undulating headband in place.

In this example, a device comprises: a headband or halo; a rearward ear-engaging member (e.g. arm or protrusion); a frontal ear-engaging member (e.g. arm or protrusion); a plurality of sensors (e.g. electrodes) which are configured to be held in proximity to the person's head by the headband or halo, wherein these sensors collect data concerning the person's brain activity; and an electronics unit comprising a data processor, data transmitter and/or receiver, and a power source. In this example, a device includes frontal-ear and rear segments which are both part of the same continuous member and/or piece of material.

In this example, a device includes a frontal ear-engaging member (e.g. arm or protrusion) which curves around (and frictionally engages) a front portion of the perimeter of a person's outer ear. In this example, a device includes a frontal-ear segment (e.g. arm or protrusion) which curves around (a portion of) the front of the person's outer ear. In this example, a device includes a frontal-ear segment (e.g. arm or protrusion) that is worn on the front-facing surface of the person's ear. In this example, a device includes a frontal-ear segment (e.g. arm or protrusion) curves, loops, protrudes, undulates, and/or hooks around the front of a person's ear.

In this example, a device includes a frontal-ear segment (e.g. arm or protrusion) which curves, loops, protrudes, undulates, and/or hooks around (some or all of) the frontal portion of tissue which connects the outer ear with the rest of the head. In this example, a device includes a frontal-ear segment (e.g. arm or protrusion) which gently presses against or otherwise engage the outer surface of a person's ear in order to help hold the device on the person's head. In this example, a device includes a frontal-ear segment (e.g. arm or protrusion) which helps to hold the device on a person's head by engaging the frontal surface of the outer ear.

In this example, a device includes a frontal-ear segment (e.g. arm or protrusion) with a shape which is selected from the group consisting of: portion of a circle; portion of a spiral; portion of a parabolic curve; portion of a sinusoidal curve; and conic section. In this example, a device includes a frontal-ear segment (e.g. arm or protrusion) helps to hold the device on a person's head by resting on top of the outer ear (or the tissue connection between the outer ear and the rest of the person's head). In this example, a device includes a frontal-ear segment (e.g. arm or protrusion) which curves, loops, protrudes, undulates, and/or hooks around a side portion of the person's face which is within one inch of the person's ear.

In this example, a device includes a frontal-ear segment (e.g. arm or protrusion) is worn entirely within two inches of the person's outer ear. In this example, a device includes a frontal-ear segment (e.g. arm or protrusion) which curves, loops, protrudes, undulates, and/or hooks around (some or all of) the front-facing surface of the person's outer ear. In this example, a device includes a rearward ear-engaging member (e.g. arm or protrusion) which spans between 10% and 30% of the perimeter of a person's ear. In this example, a device includes a rearward ear-engaging member (e.g. arm or protrusion) which curves around (and frictionally engage) a rear portion of the perimeter of a person's outer ear. Example variations discussed elsewhere in this disclosure or in priority-linked disclosures can also be applied to this example where relevant.

Figure 11:
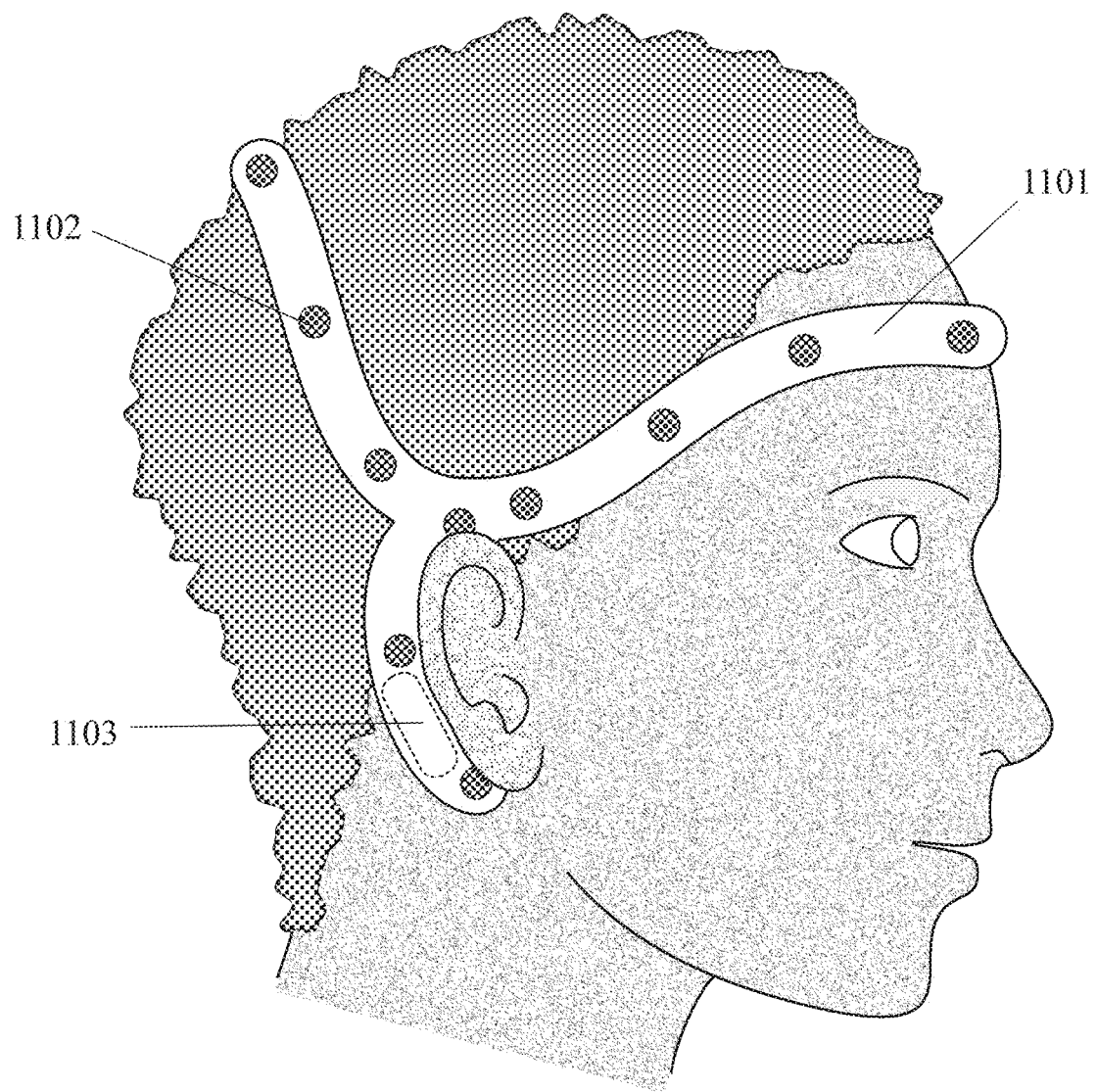
FIG. 11 shows a saddle-shaped EEG headband with an arm extending downward around the rear of an ear.

FIG. 11 shows the right side of a head-worn device for recording brain signals comprising: an arcuate electrode holder 1101, wherein the electrode holder is a headband, halo, or headset which is configured to be worn around at least 40% of the lateral circumference of a person's head; a plurality of electrodes including electrode 1102, wherein the electrodes are held in place by the electrode holder, and wherein the electrodes are configured to receive electrical and/or electromagnetic signals from the person's brain; and an electronics unit 1103, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder spans (e.g. curves around or loops over) an upper-posterior portion (e.g. quadrant) of the person's head and also the person's forehead. In this example, a posterior half of the electrode holder loops over the posterior half of the top of the person's head and the anterior half of the electrode holder loops around the person's forehead, forming an overall saddle or hyperboloidal shape on the person's head. In this example, an arm (e.g. arm, prong, branch, loop, and/or protrusion) of the electrode holder extends downward from the main saddle or hyperboloidal shape and curves around the posterior of the person's ear (e.g. the connecting portion of the auricle).

In this example, a device includes a plurality of sensors (e.g. electrodes) which are held in proximity to a person's head by a saddle-shaped halo. In this example, a saddle-shaped halo holds at least eight sensors (e.g. electrodes), at least two on each side of a person's head, at least two on a person's forehead, and at least two on the rear portion of a person's head. In this example, the perimeter of a saddle-shaped halo can be shaped like a circle or oval which has been placed on top of a person's head and then virtually melted (inspired perhaps by Salvatore Dali?) so that its sides droop downward.

In this example, a device also includes ear prongs (e.g. arms and/or protrusions) which frictionally-engage the person's outer ears and help to hold the undulating headband in place. In this example, a device comprises: a saddle-shaped section which loops over the top of the person's head (figuratively appearing as if a central oval or elliptical loop has been melted on the top of the person's head and droops down the sides of the person's head); and two arcs which extend from the bottom portions of the saddle-shaped section to curve down around the rear portions of the person's ears.

In this example, the front portion of an undulating headband spans across a person's forehead. In this example, a device comprises: an undulating headband (including a rear portion and a front portion) which is configured to be worn around a person's head; an ear prong (e.g. arm or protrusion) which engages a portion of the perimeter of the person's outer ear; a plurality of sensors (e.g. electrodes) which are configured to be held in proximity to the person's head by the undulating headband, wherein these sensors (e.g. electrodes) collect data concerning the person's brain activity; and an electronics unit comprising a data processor, data transmitter and/or receiver, and a power source. In this example, right and left side portions of the undulating headband include right and left ear prongs (e.g. arms and/or protrusions), wherein each ear prong partially encircles the perimeter of the person's outer ear and/or the connection between the main body of the head and the outer ear. Example variations discussed elsewhere in this disclosure or in priority-linked disclosures can also be applied to this example where relevant.

Figure 12:
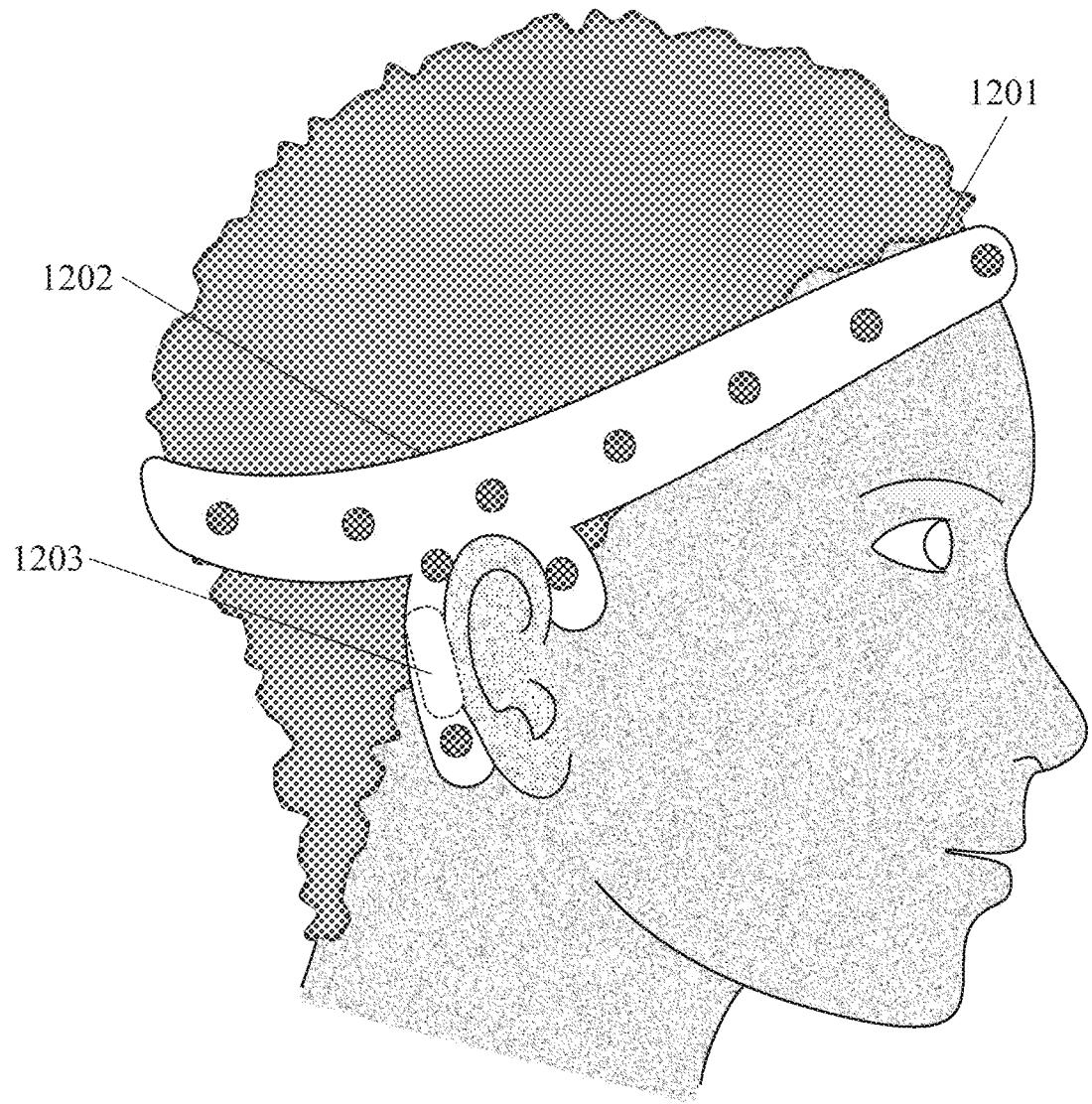
FIG. 12 shows an EEG headband whose rear half is wider than its front half, wherein it has a first arm extending downward around the rear of an ear and a second arm extending downward around the front of the ear.

FIG. 12 shows the right side of a head-worn device for recording brain signals comprising: an arcuate electrode holder 1201, wherein the electrode holder is a headband, halo, or headset which is configured to be worn around at least 40% of the lateral circumference of a person's head; a plurality of electrodes including electrode 1202, wherein the electrodes are held in place by the electrode holder, and wherein the electrodes are configured to receive electrical and/or electromagnetic signals from the person's brain; and an electronics unit 1203, wherein the electronics unit further comprises a data processor, a data transmitter and/or data receiver, and a power source. It is assumed that the left side of the device is symmetric to the right side, with the possible exception of the electronics unit, unless stated otherwise.

In this example, the posterior half of the electrode holder is wider than the anterior half of the electrode holder. In this example, a first arm (e.g. arm, prong, branch, loop, and/or protrusion) of the electrode holder extends downward and curves around the posterior of the person's ear (e.g. the connecting portion of the auricle). In this example, a first arm (e.g. arm, prong, branch, loop, and/or protrusion) of the electrode holder extends downward from a main circumferential body of the electrode holder, wherein the arm curves around the posterior of the person's ear (e.g. the connecting portion of the auricle).

In this example, a second arm (e.g. arm, prong, branch, loop, and/or protrusion) of the electrode holder extends downward and curves around part of the anterior of the person's ear (e.g. the connecting portion of the auricle). In this example, a second arm (e.g. arm, prong, branch, loop, and/or protrusion) of the electrode holder extends downward from a main circumferential body of the electrode holder, wherein the arm curves around part of the anterior of the person's ear (e.g. the connecting portion of the auricle).

In this example, a device which is embodied in a headband or halo has a variable width. In this example, side portions of a device are wider than front and rear portions of the device. In this example, an undulating rear-tilted headband has a variable width, wherein the side portions are wider than the front and rear portions. In another example, an undulating rear-tilted headband can have a variable width, wherein front and rear portions of the device are wider than side portions of the device. In another example, front and rear portions of a headband or halo can be wider than side portions of the halo and/or headband. In this example, the front portion of a headband spans across a person's forehead.

In this example, a device also includes a frontal ear-engaging member (e.g. arm or protrusion) which curves around (and frictionally engages) a front portion of the perimeter of a person's outer ear. In this example, a device includes a frontal-ear segment (e.g. arm or protrusion) which curves around (a portion of) the front of the person's outer ear. In this example, a device includes a frontal-ear segment (e.g. arm or protrusion) that is worn on the front-facing surface of the person's ear. In this example, a device includes a frontal-ear segment (e.g. arm or protrusion) curves, loops, protrudes, undulates, and/or hooks around the front of a person's ear.

In this example, a device includes a frontal-ear segment (e.g. arm or protrusion) which curves, loops, protrudes, undulates, and/or hooks around (some or all of) the frontal portion of tissue which connects the outer ear with the rest of the head. In this example, a device includes a frontal-ear segment (e.g. arm or protrusion) which gently presses against or otherwise engage the outer surface of a person's ear in order to help hold the device on the person's head. In this example, a device includes a frontal-ear segment (e.g. arm or protrusion) which helps to hold the device on a person's head by engaging the frontal surface of the outer ear.

In this example, a device includes a frontal-ear segment (e.g. arm or protrusion) with a shape which is selected from the group consisting of: portion of a circle; portion of a spiral; portion of a parabolic curve; portion of a sinusoidal curve; and conic section. In this example, a device includes a frontal-ear segment (e.g. arm or protrusion) helps to hold the device on a person's head by resting on top of the outer ear (or the tissue connection between the outer ear and the rest of the person's head). In this example, a device includes a frontal-ear segment (e.g. arm or protrusion) which curves, loops, protrudes, undulates, and/or hooks around a side portion of the person's face which is within one inch of the person's ear.

In this example, a device includes a frontal-ear segment (e.g. arm or protrusion) is worn entirely within two inches of the person's outer ear. In this example, a device includes a frontal-ear segment (e.g. arm or protrusion) which curves, loops, protrudes, undulates, and/or hooks around (some or all of) the front-facing surface of the person's outer ear. In this example, a device includes a rearward ear-engaging member (e.g. arm or protrusion) which spans between 10% and 30% of the perimeter of a person's ear. In this example, a device includes a rearward ear-engaging member (e.g. arm or protrusion) which curves around (and frictionally engage) a rear portion of the perimeter of a person's outer ear. Example variations discussed elsewhere in this disclosure or in priority-linked disclosures can also be applied to this example where relevant.

Figure 13:
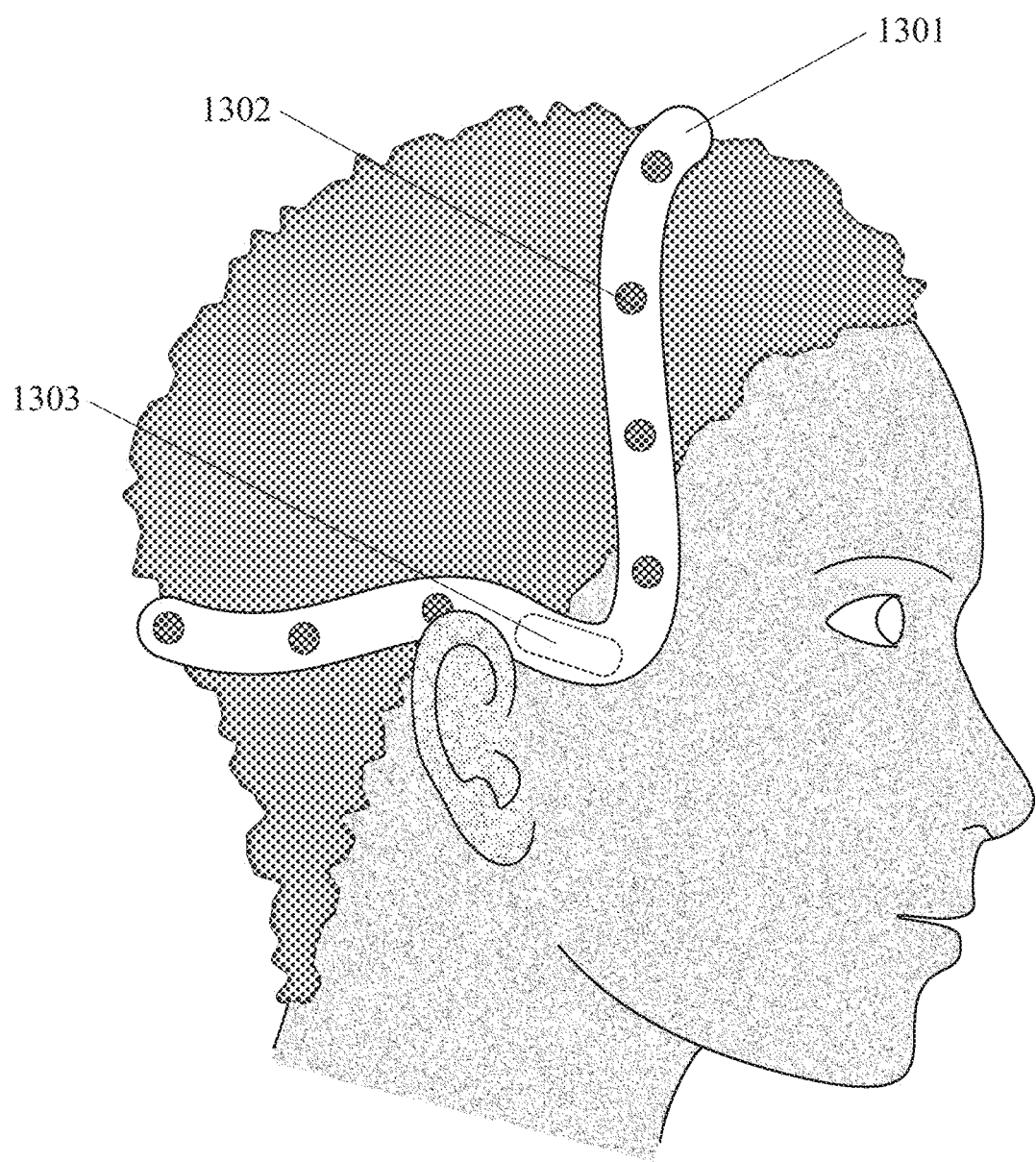
FIG. 13 shows a head-worn EEG device which loops over the top and also around the rear of a person's head.

FIG. 13 shows the right side of a head-worn device for recording brain signals comprising: an arcuate electrode holder 1301, wherein the electrode holder is a headband, halo, or headset which is configured to be worn around at least 40% of the lateral circumference of a person's head; a plurality of electrodes including electrode 1302, wherein the electrodes are held in place by the electrode holder, and wherein the electrodes are configured to receive electrical and/or electromagnetic signals from the person's brain; and an electronics unit 1303, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder spans (e.g. curves around or loops over) an upper-anterior portion (e.g. quadrant) person's head. In this example, the electrode holder spans (e.g. curves around or loops over) the anterior half of the top of the person's head. In this example, the electrode holder spans (e.g. curves around or loops over) the posterior half of the person's head. In this example, the electrode holder spans (e.g. curves around or loops over) the posterior half of the person's head at substantially the same height as the person's ear when the head is upright. In this example, the posterior half of the electrode holder spans (e.g. curves around or loops over) the posterior half of the person's head at substantially the same height as the person's ear when the head is upright and the anterior half of the electrode holder spans (e.g. curves around or loops over) the anterior half of the top of the person's head.

In this example, a device comprises: a first arm/portion which spans from a location within two inches of a person's ear to the top of the person's head and holds at least one first sensor (e.g. electrode) substantially located at an electrode position selected from the group consisting of FT7, FC5, FC3, FC1, FCz, and T7; and a second arm/portion which spans from the location to the rear of the person's head and holds at least one second sensor (e.g. electrode) substantially located at an electrode position selected from the group consisting of Iz, O1, Oz, PO7, P7, TP7, and T7.

In this example, a best fitting virtual plane for the first arm/portion and a best fitting virtual plane for the second arm/portion are substantially perpendicular to each other. In this example, the first arm/portion has a forward-facing concavity. In this example, the first arm/portion loops over the top of the person's head. In this example, the second arm/portion has a downward-facing concavity. In this example, the second arm/portion loops around the rear of the person's head. In this example, the device overall (including all portions) has an upward-and-rear-facing concavity.

In this example, the left side of a device comprises: a first arm/portion which spans from a location within two inches of a person's ear to the top of the person's head and holds at least one first sensor (e.g. electrode) substantially located at an electrode position selected from the group consisting of FT7, FC5, FC3, FC1, FCz, and T7; and a second arm/portion which spans from the location to the rear of the person's head. In this example, the left side of a device comprises: a first arm/portion which spans from a location within two inches of a person's ear to the top of the person's head; and a second arm/portion which spans from the location to the rear of the person's head and holds at least one second sensor (e.g. electrode) substantially located at an electrode position selected from the group consisting of Iz, O1, Oz, PO7, P7, TP7, and T7. Example variations discussed elsewhere in this disclosure or in priority-linked disclosures can also be applied to this example where relevant.

Figure 14:
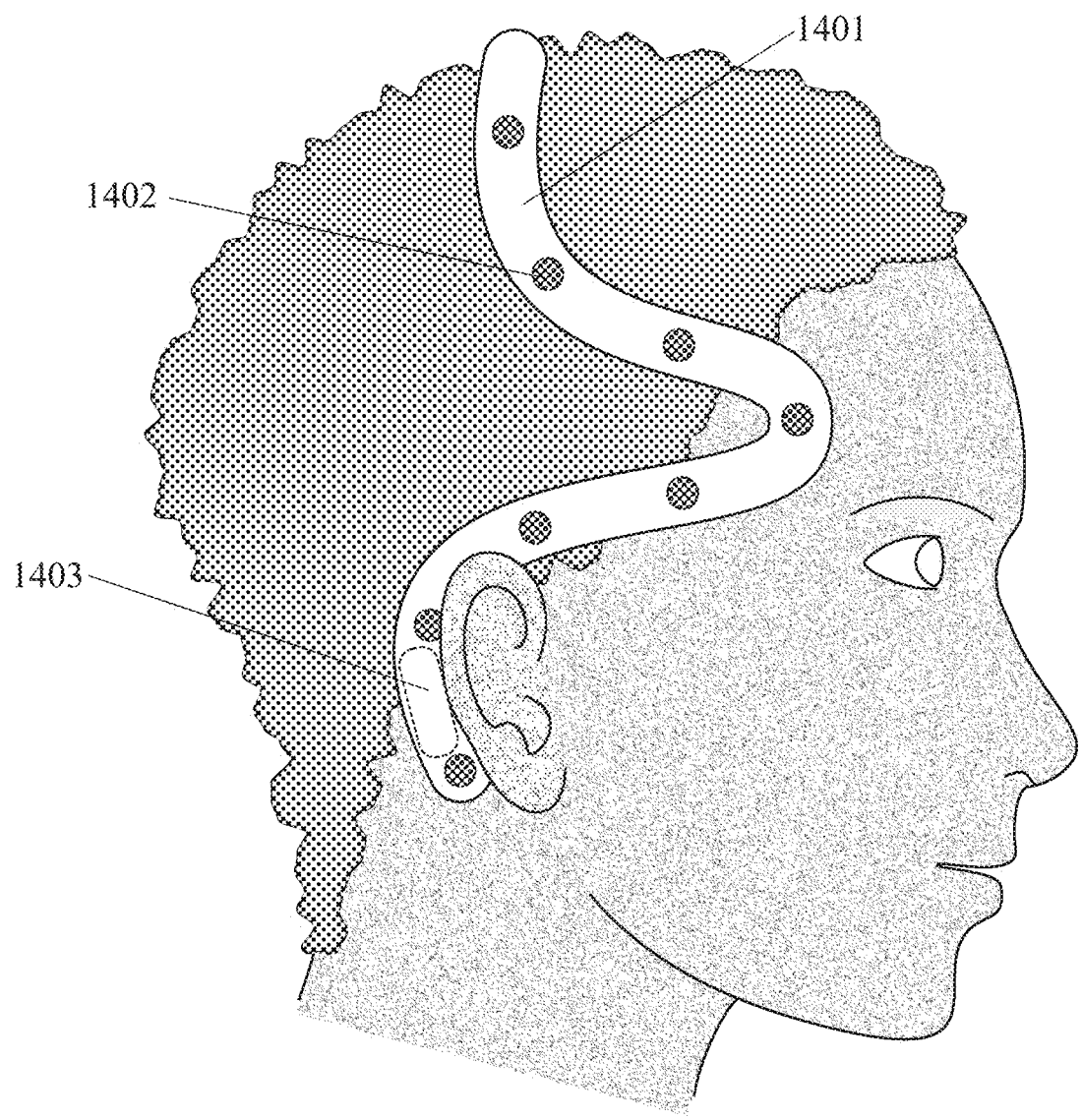
FIG. 14 shows a head-worn EEG device with an undulation having a posterior-facing concavity on a person's forehead.

FIG. 14 shows the right side of a head-worn device for recording brain signals comprising: an arcuate electrode holder 1401, wherein the electrode holder is a headband, halo, or headset which is configured to be worn around at least 40% of the lateral circumference of a person's head; a plurality of electrodes including electrode 1402, wherein the electrodes are held in place by the electrode holder, and wherein the electrodes are configured to receive electrical and/or electromagnetic signals from the person's brain; and an electronics unit 1403, wherein the electronics unit further comprises a data processor, a data transmitter and/or data receiver, and a power source. It is assumed that the left side of the device is symmetric to the right side, with the possible exception of the electronics unit, unless stated otherwise.

In this example, the left side of an electrode holder curves upward around the posterior of the person's ear (e.g. the connecting portion of the auricle), then curves further upward to form an undulation with a posterior-facing concavity; and then curves further upward to loop over the top of the person's head and meet the right side of the electrode holder. In this example, the electrode has posterior-anterior undulations, wherein at least one undulation has a posterior-facing concavity and extends onto the person's forehead. In this example, the electrode holder loops over a person's head, from the person's right ear to the person's left ear. In this example, the electrode holder rests on top of the person's ear (e.g. the connecting portion of the auricle).

In this example, a device comprises: a rear ear-engaging segment which is worn around at least a portion of the rear-facing surface of the person's ear; a side segment which spans from the rear ear-engaging segment to the person's temple, a side portion of the person's face, and/or a side portion of the person's forehead; a top segment which spans from the side segment to the top of the person's head; at least one sensor (e.g. electrode); and an electronics unit which includes a data processor, a data transmitter, and a power source. In this example, a device comprises: a rear segment (worn on the rear-facing surface of a person's ear); a side segment (spanning from the person's ear to a side portion of the person's forehead); a top segment (spanning from the side segment to the top of the person's head); sensors (e.g. electrodes); and an electronics unit including a data processor, data transmitter, and power source.

In this example, a device comprises: a rear segment which is worn on the rear-facing surface of a person's ear; a side segment which spans from the person's ear to the person's temple, a side portion of the person's face, and/or a side portion of the person's forehead; a top segment which spans from the side segment to the top of the person's head; at least one sensor (e.g. electrode); and an electronics unit comprising a data processor, a data transmitter, and a power source. In this example, a device comprises: an undulating hairband-style loop which spans from the right ear to the left ear (or vice versa) over the upper-front portion a person's head; a plurality of sensors (e.g. electrodes); and an electronics unit comprising a data processor, a data transmitter and/or receiver, and a power source. In this example, an undulating hairband-style loop starts behind a person's right ear, loops over the top of the right ear, curves forward toward (but does not reach) the person's right eye, curves upward toward the top of the head, spans the upper-front of the person's head, curves downward (but does not reach) the person's left eye, curves backward toward the left ear, loops over the top of the left ear, and then curves behind the person's left ear.

In this example, a rear ear-engaging segment, a side segment, and a top segment of a device are all parts of an arcuate undulating band. In another example, a device can comprise: a upper portion which extends rearward and upward from a location above and forward of a person's ear, and which loops over the rear half of the top of the person's head; and a lower portion which extends downward and rearward from the location and which curves around the person's ear. In another example, a device can curve upwards around the rear of the person's ear, curve forward and upward to the person's temple, and then curve upward and rearward to span the top of the person's head.

In another example, a device comprises: a rear segment (worn on the rear-facing surface of a person's ear); a frontal-ear segment (worn on the front-facing surface of the person's ear); a side segment (spanning from the person's ear to a side portion of the person's forehead); a top segment (spanning from the side segment to the top of the person's head); sensors (e.g. electrodes); and an electronics unit including a data processor, data transmitter, and power source. In this example, a rear segment of a device curves, loops, and/or hooks behind a person's ear. In this example, a rear segment of a device curves, loops, or hooks around (some or all of) the rear-facing surface of the person's outer ear and/or the tissue connecting the outer ear with the rest of the head.

In this example, a rear segment of a device helps to hold the device on a person's head by resting on top of the outer ear (or the tissue connection between the outer ear and the rest of the person's head). In this example, the left end of an undulating hairband-style device curves around the rear portion of a person's left ear and the right-side end of the undulating hairband-type device curves around the rear portion of the person's right ear. In this example, the most rearward points of a device are on portions which curve around the rear portions of ears. In this example, a device rests on the (tops of the) person's ears.

In this example, a device has a forward curve or bulge above and forward of the person's ear. In this example, a side segment of a device has a concavity with a peak which faces frontward. In this example, a side segment of a device has a concavity whose opening faces rearward. In this example, a side segment of a device has a lower portion which rests on the outer ear and an upper portion which is vertically above the outer ear. In this example, a side segment of a device has a lower portion which is above the outer ear by a first distance and an upper portion which is above the outer ear by a second distance, wherein the second distance is greater than the first distance.

In this example, a side segment of a device has a shape selected from the group consisting of: arc, wave, undulation, semi-circle, semi-oval, loop, half-sinusoidal curve, bell-shaped curve, and conic section. In this example, a side segment of a device has an arc, wave, or undulation with a rear-facing concavity and a forward-facing peak. In this example, a side segment of a device is arcuate, wavy, and/or undulating. In this example, a side segment of a device spans (in an arcuate and/or undulating manner) upward and forward from a person's ear to a location on the side of a person's forehead and then spans (in an arcuate and/or undulating manner) upward and rearward to a location above the ear. In this example, a side segment of a device spans from a person's ear to a side portion of their face and/or forehead.

In this example, a side segment of a device spans, protrudes, curves, and/or loops from a person's ear toward the person's temple. In this example, a side segment of a device spans, protrudes, curves, and/or loops from a person's ear to a side portion of the person's forehead. In this example, a side segment of a device spans, protrudes, curves, and/or loops from a person's ear to a side portion of the person's face. In this example, a side segment of a device spans, protrudes, curves, and/or loops from a person's ear toward the center of person's forehead. In this example, the most-forward point of a side segment of a device is on a side of a person's forehead. In another example, a side segment of a device can span (in an arcuate and/or undulating manner) downward and forward from a person's ear to a location on the side of a person's face and then span (in an arcuate and/or undulating manner) upward and rearward to a location above the ear on the side of the head. In another example, a side segment of a device can span, protrude, curve, and/or loop from the person's ear toward a person's eye.

In this example, a top segment of a device spans from the side segment to the top of the person's head. In this example, a top segment of a device spans from the upper portion of the side segment to the top of the person's head. In this example, a top segment of a device on a first side of the person's head connects with the top segment of a device on a second (opposite) side of the person's head. In this example, a top segment of a device spans the top of a person's head within four inches of the position on the person's head which is the shortest vertically-oriented are connecting the person's right and left ears. In this example, right and left side top segments connect at the top of the person's head. Example variations discussed elsewhere in this disclosure or in priority-linked disclosures can also be applied to this example where relevant.

Figure 15:
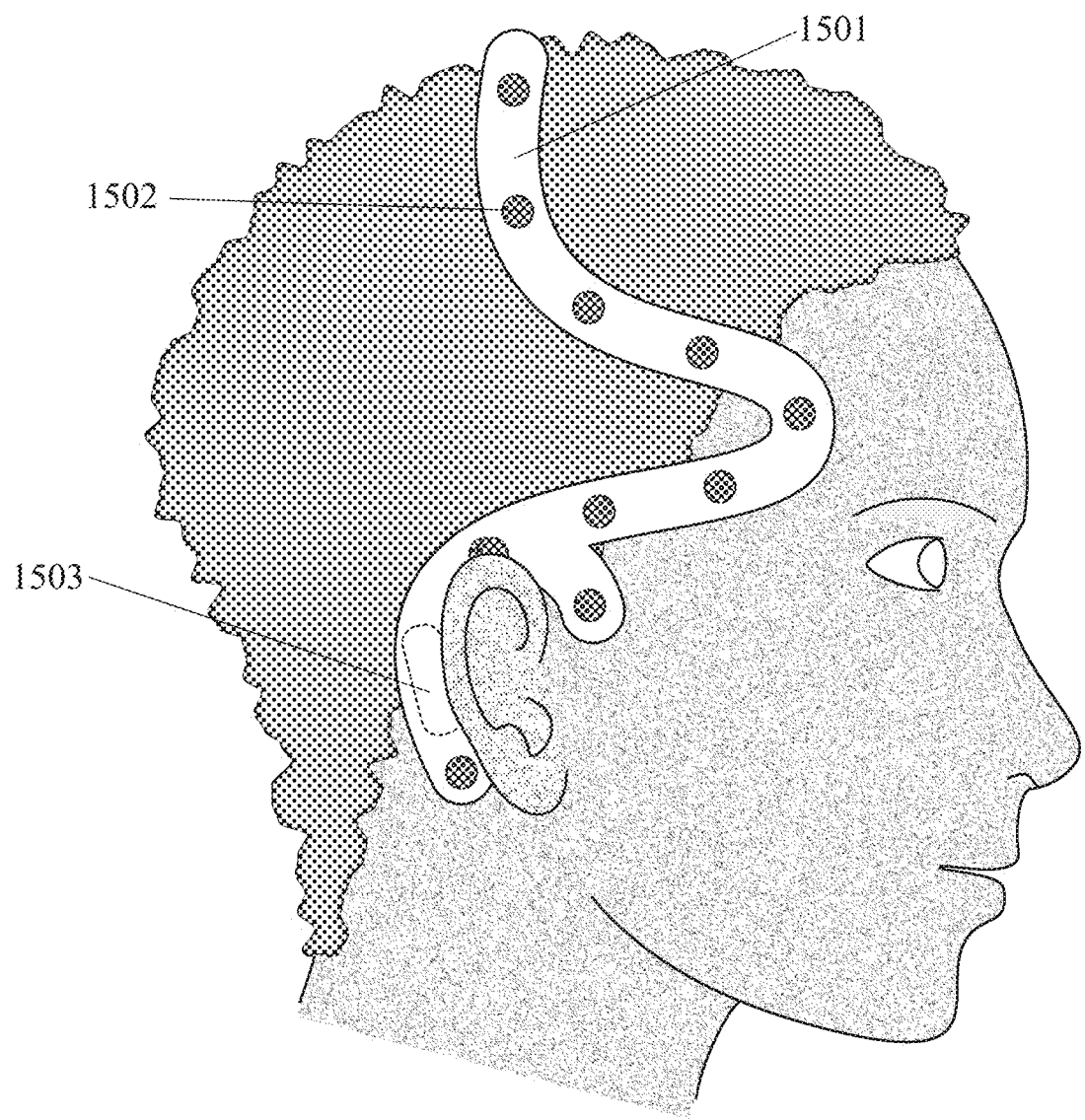
FIG. 15 shows a head-worn EEG device with an undulation with a posterior-facing concavity on a person's forehead, a first arm extending downward around the rear of an ear, and a second arm extending down around the front of the ear.

FIG. 15 shows the right side of a head-worn device for recording brain signals comprising: an arcuate electrode holder 1501, wherein the electrode holder is a headband, halo, or headset which is configured to be worn around at least 40% of the lateral circumference of a person's head; a plurality of electrodes including electrode 1502, wherein the electrodes are held in place by the electrode holder, and wherein the electrodes are configured to receive electrical and/or electromagnetic signals from the person's brain; and an electronics unit 1503, wherein the electronics unit further comprises a data processor, a data transmitter and/or data receiver, and a power source. It is assumed that the left side of the device is symmetric to the right side, with the possible exception of the electronics unit, unless stated otherwise.

In this example, a device comprises: a rear segment (worn on the rear-facing surface of a person's ear); a frontal-ear segment (worn on the front-facing surface of the person's ear); a side segment (spanning from the person's ear to a side portion of the person's forehead); a top segment (spanning from the side segment to the top of the person's head); sensors (e.g. electrodes); and an electronics unit including a data processor, data transmitter, and power source.

In this example, the electrode holder loops over the top of a person's head, from the person's right ear to the person's left ear. In this example, the electrode has at least one posterior-anterior undulation on each side (e.g. right and left) of the person's head, wherein the undulation extends onto the person's forehead. In this example, a first portion (e.g. section, arm, prong, branch, loop, and/or protrusion) of the electrode holder extends downward and curves around the posterior of the person's ear (e.g. the connecting portion of the auricle). In this example, a second portion (e.g. section, arm, prong, branch, loop, and/or protrusion) of the electrode holder extends downward and curves around part of the anterior of the person's ear (e.g. the connecting portion of the auricle).

In this example, a device comprises: a rear ear-engaging segment which is worn around at least a portion of the rear-facing surface of the person's ear; a side segment which spans from the rear ear-engaging segment to the person's temple, a side portion of the person's face, and/or a side portion of the person's forehead; a top segment which spans from the side segment to the top of the person's head; at least one sensor (e.g. electrode); and an electronics unit which includes a data processor, a data transmitter, and a power source. In this example, a device comprises: a rear segment (worn on the rear-facing surface of a person's ear); a side segment (spanning from the person's ear to a side portion of the person's forehead); a top segment (spanning from the side segment to the top of the person's head); sensors (e.g. electrodes); and an electronics unit including a data processor, data transmitter, and power source.

In this example, a device comprises: a rear segment which is worn on the rear-facing surface of a person's ear; a side segment which spans from the person's ear to the person's temple, a side portion of the person's face, and/or a side portion of the person's forehead; a top segment which spans from the side segment to the top of the person's head; at least one sensor (e.g. electrode); and an electronics unit comprising a data processor, a data transmitter, and a power source. In this example, a device comprises: an undulating hairband-style loop which spans from the right ear to the left ear (or vice versa) over the upper-front portion a person's head; a plurality of sensors (e.g. electrodes); and an electronics unit comprising a data processor, a data transmitter and/or receiver, and a power source. In this example, an undulating hairband-style loop starts behind a person's right ear, loops over the top of the right ear, curves forward toward (but does not reach) the person's right eye, curves upward toward the top of the head, spans the upper-front of the person's head, curves downward (but does not reach) the person's left eye, curves backward toward the left ear, loops over the top of the left ear, and then curves behind the person's left ear.

In this example, a rear ear-engaging segment, a side segment, and a top segment of a device are all parts of an arcuate undulating band. In another example, a device can comprise: a upper portion which extends rearward and upward from a location above and forward of a person's ear, and which loops over the rear half of the top of the person's head; and a lower portion which extends downward and rearward from the location and which curves around the person's ear. In another example, a device can curve upwards around the rear of the person's ear, curve forward and upward to the person's temple, and then curve upward and rearward to span the top of the person's head.

In another example, a device comprises: a rear segment (worn on the rear-facing surface of a person's ear); a frontal-ear segment (worn on the front-facing surface of the person's ear); a side segment (spanning from the person's ear to a side portion of the person's forehead); a top segment (spanning from the side segment to the top of the person's head); sensors (e.g. electrodes); and an electronics unit including a data processor, data transmitter, and power source. In this example, a rear segment of a device curves, loops, and/or hooks behind a person's ear. In this example, a rear segment of a device curves, loops, or hooks around (some or all of) the rear-facing surface of the person's outer ear and/or the tissue connecting the outer ear with the rest of the head.

In this example, a rear segment of a device helps to hold the device on a person's head by resting on top of the outer ear (or the tissue connection between the outer ear and the rest of the person's head). In this example, the left end of an undulating hairband-style device curves around the rear portion of a person's left ear and the right-side end of the undulating hairband-type device curves around the rear portion of the person's right ear. In this example, the most rearward points of a device are on portions which curve around the rear portions of ears. In this example, a device rests on the (tops of the) person's ears.

In this example, a device has a forward curve or bulge above and forward of the person's ear. In this example, a side segment of a device has a concavity with a peak which faces frontward. In this example, a side segment of a device has a concavity whose opening faces rearward. In this example, a side segment of a device has a lower portion which rests on the outer ear and an upper portion which is vertically above the outer ear. In this example, a side segment of a device has a lower portion which is above the outer ear by a first distance and an upper portion which is above the outer ear by a second distance, wherein the second distance is greater than the first distance.

In this example, a side segment of a device has a shape selected from the group consisting of: arc, wave, undulation, semi-circle, semi-oval, loop, half-sinusoidal curve, bell-shaped curve, and conic section. In this example, a side segment of a device has an arc, wave, or undulation with a rear-facing concavity and a forward-facing peak. In this example, a side segment of a device is arcuate, wavy, and/or undulating. In this example, a side segment of a device spans (in an arcuate and/or undulating manner) upward and forward from a person's ear to a location on the side of a person's forehead and then spans (in an arcuate and/or undulating manner) upward and rearward to a location above the ear. In this example, a side segment of a device spans from a person's ear to a side portion of their face and/or forehead.

In this example, a side segment of a device spans, protrudes, curves, and/or loops from a person's ear toward the person's temple. In this example, a side segment of a device spans, protrudes, curves, and/or loops from a person's ear to a side portion of the person's forehead. In this example, a side segment of a device spans, protrudes, curves, and/or loops from a person's ear to a side portion of the person's face. In this example, a side segment of a device spans, protrudes, curves, and/or loops from a person's ear toward the center of person's forehead. In this example, the most-forward point of a side segment of a device is on a side of a person's forehead. In another example, a side segment of a device can span (in an arcuate and/or undulating manner) downward and forward from a person's ear to a location on the side of a person's face and then span (in an arcuate and/or undulating manner) upward and rearward to a location above the ear on the side of the head. In another example, a side segment of a device can span, protrude, curve, and/or loop from the person's ear toward a person's eye.

In this example, a top segment of a device spans from the side segment to the top of the person's head. In this example, a top segment of a device spans from the upper portion of the side segment to the top of the person's head. In this example, a top segment of a device on a first side of the person's head connects with the top segment of a device on a second (opposite) side of the person's head. In this example, a top segment of a device spans the top of a person's head within four inches of the position on the person's head which is the shortest vertically-oriented are connecting the person's right and left ears. In this example, right and left side top segments connect at the top of the person's head.

In this example, a device also includes a frontal ear-engaging member (e.g. arm or protrusion) which curves around (and frictionally engages) a front portion of the perimeter of a person's outer ear. In this example, a device includes a frontal-ear segment (e.g. arm or protrusion) which curves around (a portion of) the front of the person's outer ear. In this example, a device includes a frontal-ear segment (e.g. arm or protrusion) that is worn on the front-facing surface of the person's ear. In this example, a device includes a frontal-ear segment (e.g. arm or protrusion) curves, loops, protrudes, undulates, and/or hooks around the front of a person's ear.

In this example, a device includes a frontal-ear segment (e.g. arm or protrusion) which curves, loops, protrudes, undulates, and/or hooks around (some or all of) the frontal portion of tissue which connects the outer ear with the rest of the head. In this example, a device includes a frontal-ear segment (e.g. arm or protrusion) which gently presses against or otherwise engage the outer surface of a person's ear in order to help hold the device on the person's head. In this example, a device includes a frontal-ear segment (e.g. arm or protrusion) which helps to hold the device on a person's head by engaging the frontal surface of the outer ear.

In this example, a device includes a frontal-ear segment (e.g. arm or protrusion) with a shape which is selected from the group consisting of: portion of a circle; portion of a spiral; portion of a parabolic curve; portion of a sinusoidal curve; and conic section. In this example, a device includes a frontal-ear segment (e.g. arm or protrusion) helps to hold the device on a person's head by resting on top of the outer ear (or the tissue connection between the outer ear and the rest of the person's head). In this example, a device includes a frontal-ear segment (e.g. arm or protrusion) which curves, loops, protrudes, undulates, and/or hooks around a side portion of the person's face which is within one inch of the person's ear.

In this example, a device includes a frontal-ear segment (e.g. arm or protrusion) is worn entirely within two inches of the person's outer ear. In this example, a device includes a frontal-ear segment (e.g. arm or protrusion) which curves, loops, protrudes, undulates, and/or hooks around (some or all of) the front-facing surface of the person's outer ear. In this example, a device includes a rearward ear-engaging member (e.g. arm or protrusion) which spans between 10% and 30% of the perimeter of a person's ear. In this example, a device includes a rearward ear-engaging member (e.g. arm or protrusion) which curves around (and frictionally engage) a rear portion of the perimeter of a person's outer ear. Example variations discussed elsewhere in this disclosure or in priority-linked disclosures can also be applied to this example where relevant.

Figure 16:
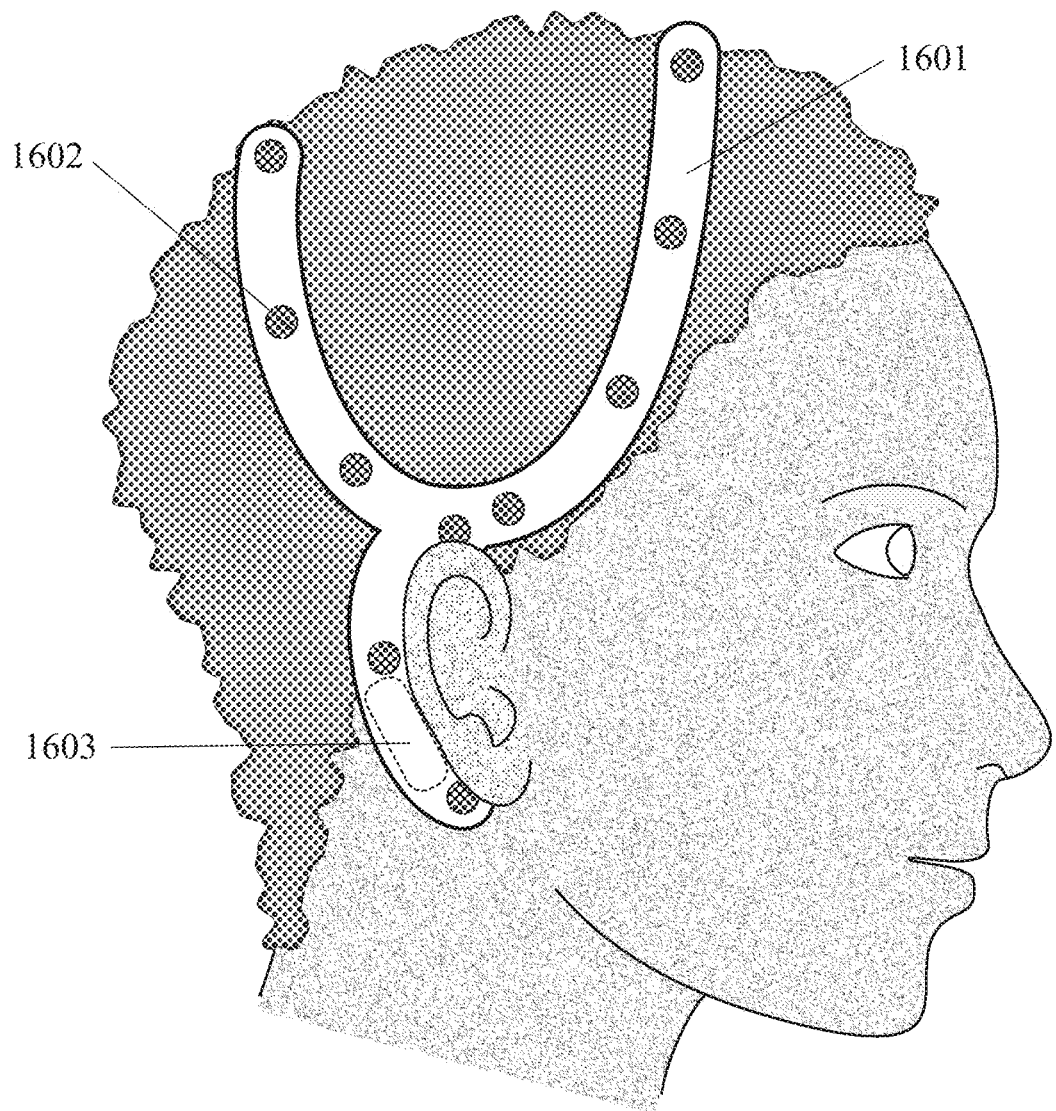
FIG. 16 shows a head-worn EEG device with two loops over the top of a person's head and an arm extending downward around the rear of an ear.

FIG. 16 shows the right side of a head-worn device for recording brain signals comprising: an arcuate electrode holder 1601, wherein the electrode holder is a headband, halo, or headset which is configured to be worn around at least 40% of the lateral circumference of a person's head; a plurality of electrodes including electrode 1602, wherein the electrodes are held in place by the electrode holder, and wherein the electrodes are configured to receive electrical and/or electromagnetic signals from the person's brain; and an electronics unit 1603, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder spans (e.g. curves around or loops over) a posterior-upper portion (e.g. quadrant) of the person's head. In this example, the electrode holder spans (e.g. curves around or loops over) the posterior half of the top of the person's head. In this example, the electrode holder spans (e.g. curves around or loops over) an anterior-upper portion (e.g. quadrant) of the person's head. In this example, the electrode holder spans (e.g. curves around or loops over) the anterior half of the top of the person's head. In this example, the main body of one side (e.g. right or left) of the electrode has a generally "U" shape. In this example, the main body of the electrode holder has a saddle or hyperboloidal shape. In this example, a first arm (e.g. arm, prong, branch, loop, and/or protrusion) of the electrode holder extends downward and curves around the posterior of the person's ear (e.g. the connecting portion of the auricle).

In this example, a device is shaped like a saddle on top of the person's head. In this example, a device includes a saddle-shaped halo which is shaped like the perimeter of a hyperbolic paraboloid. In this example, a device includes a saddle-shaped halo which is shaped like the perimeter of a Pringles™ brand chip. In this example, a perimeter of a saddle-shaped halo of a device is shaped like a circle or oval which has been placed on top of a person's head and then virtually melted so that its sides droop downward, perhaps inspired by Salvatore Dali. In this example, a device comprises: a saddle-shaped section which loops over the top of the person's head (figuratively appearing as if a central oval or elliptical loop has been melted on the top of the person's head and droops down the sides of the person's head); and two arcs which extend from the bottom portions of the saddle-shaped section to curve down around the rear portions of the person's ears.

In this example, a device comprises: an undulating headband which is configured to be worn around a person's head; an ear prong (e.g. arm or protrusion) which engages a portion of the perimeter of the person's outer ear; a plurality of sensors (e.g. electrodes); and an electronics unit comprising a data processor, data transmitter and/or receiver, and a power source. In this example, device comprises: right and left side portions of an undulating headband; and right and left ear prongs (e.g. arms and/or protrusions), wherein each ear prong partially encircles the perimeter of the person's outer ear and/or the connection between the main body of the head and the outer ear. In this example, a device comprises: a saddle-shaped halo which is worn around the upper portion of a person's head; a plurality of sensors (e.g. electrodes); and an electronics unit which includes a data processor, a data transmitter and/or receiver, and a power source.

In this example, a forward arm/portion of a device has a forward-facing concavity. In this example, a forward arm/ portion of a device spans the top of the person's head at a location which is anterior to a virtual vertical plane which connects the person's ears. In this example, a rear arm/ portion of a device spans the top of the person's head at a location which is posterior to a virtual vertical plane which connects the person's ears. In this example, a front arm/ portion and a rear arm/portion of a device connect at an area which is over the person's ear. In this example, a device includes ear prongs (e.g. arms and/or protrusions) which frictionally-engage the person's outer ears and help to hold the undulating headband in place. Example variations discussed elsewhere in this disclosure or in priority-linked disclosures can also be applied to this example where relevant.

Figure 17:
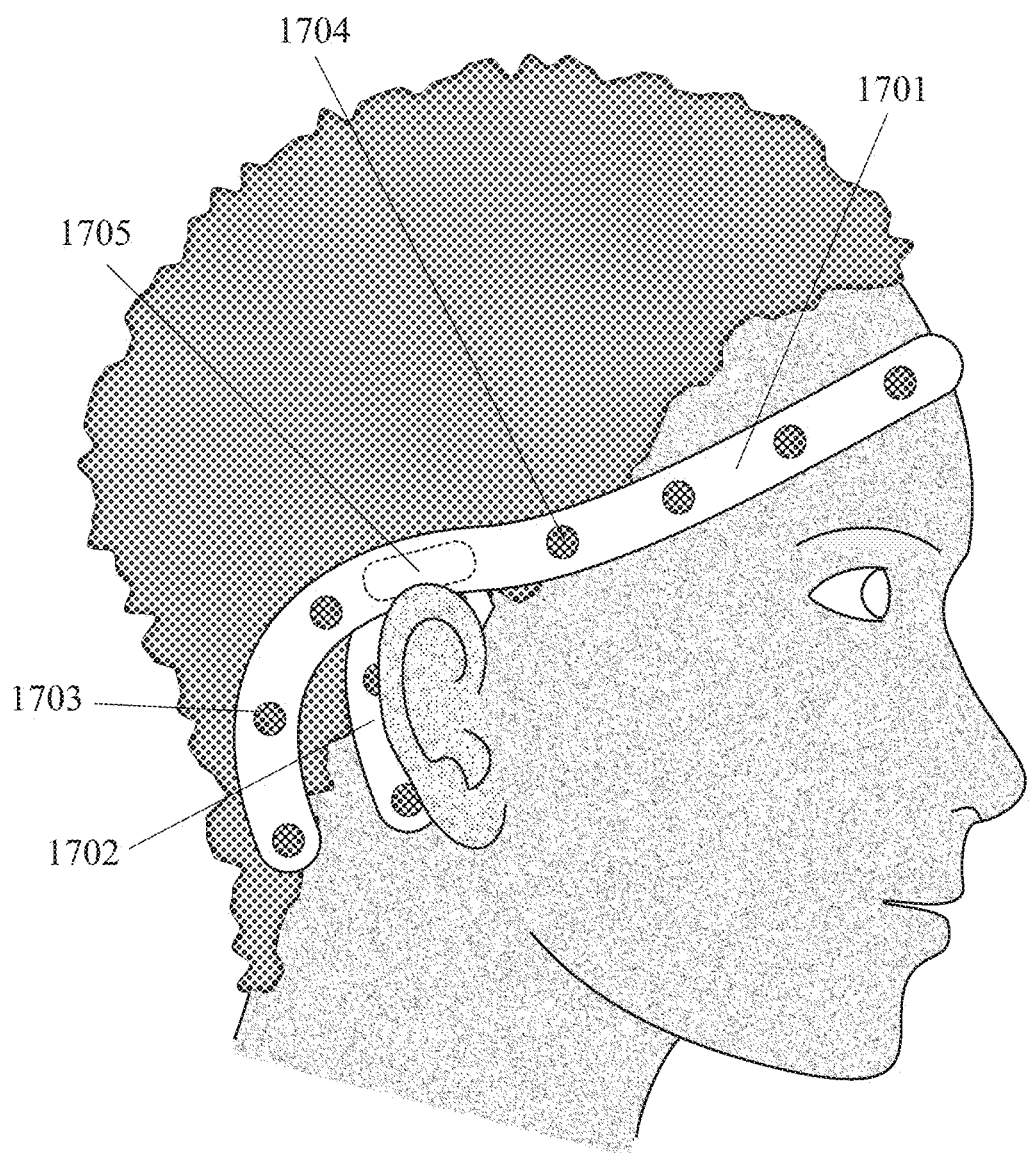
FIG. 17 shows a head-worn EEG device with a front loop across a person's forehead, right and left ear prongs, and right and left posterior arms.

FIG. 17 shows the right side of a head-worn device for recording brain signals comprising: an arcuate electrode holder, wherein the electrode holder is a headband, halo, or headset which is configured to be worn around at least 40% of the lateral circumference of a person's head; a plurality of electrodes, wherein the electrodes are held in place by the electrode holder, and wherein the electrodes are configured to receive electrical and/or electromagnetic signals from the person's brain; and an electronics unit, wherein the electronics unit further comprises a data processor, a data transmitter and/or data receiver, and a power source. It is assumed that the left side of the device is symmetric to the right side, with the possible exception of the electronics unit, unless stated otherwise.

With respect to specific components, FIG. 17 shows a sensor-positioning member (e.g. an electrode-holding ring, halo, or headset) which holds electrodes (including electrode 1704) on a person's head. This device includes a control unit (e.g. electronics unit) 1705 with a data processor, a data transmitter, and a power source. This sensor-positioning (e.g. electrode holding) member comprises: a front loop (e.g. arm, band, segment, portion, or loop) 1701 which loops across a person's forehead; right side and left side ear prongs (e.g. arms, segments, or portions), including 1702 on the right side, which curve closely around the posterior and upper surfaces of the person's right side and left side ears (e.g. where the outer ear connects to the rest of the person's head), respectively; and right side and left side posterior arms (e.g. arms, segments, or portions), including 1703 on the right side, which extend in a posterior and downward direction from the person's right side and left side ears, respectively; wherein sensor-positioning member spans a portion of the person's occipital lobe.

This sensor-positioning member can also be described as comprising: an arcuate element which loops, from the top of one ear to the top of the other ear, around the front-central portion of the wearer's head; two upward-protruding arcuate elements, which rise up from an area behind the wearer's ears and terminate on the right and left sides of their head, respectively, over their occipital lobe; and two downward-protruding arcuate elements, which drop down from an area behind the wearer's ears and terminate in areas below their ears, respectively.

In an example, a head-worn device for recording brain signals can comprise: an arcuate electrode holder, wherein the electrode holder is a headband, halo, or headset which is configured to be worn around at least 40% of the circumference of a person's head; a plurality of electrodes, wherein the electrodes are held in place by the electrode holder, and wherein the electrodes are configured to receive electrical and/or electromagnetic signals from the person's brain; and an electronics unit, wherein the electronics unit further comprises a data processor, a data transmitter and/or data receiver, and a power source.

In an example, the electrode holder can further comprise: a front arm, band, segment, portion, or loop which is configured to span across a person's forehead; right and left ear prongs, arms, segments, or portions which are configured to curve closely around both the posterior and upper surfaces of the person's right and left ears; and right and left posterior arms, segments, or portions which are configured to extend in posterior and downward directions from the person's right and left ears. In an example, the electrode holder can span a portion of the person's occipital lobe.

In an example, the electrode holder can further comprise: an arcuate element which is configured to loop, from one ear to the other ear, around a front-central portion of the person's head; two upward-protruding arcuate elements which are configured to rise up from an area behind the person's ears and terminate on the right and left sides of the person's head, respectively; and two downward-protruding arcuate elements which are configured to drop down from an area behind the person's ears and terminate in areas below the person's ears, respectively. In an example, the electrode holder can span a portion of the person's occipital lobe. Example variations discussed elsewhere in this disclosure or in priority-linked disclosures can also be applied to this example where relevant.

Figure 18:
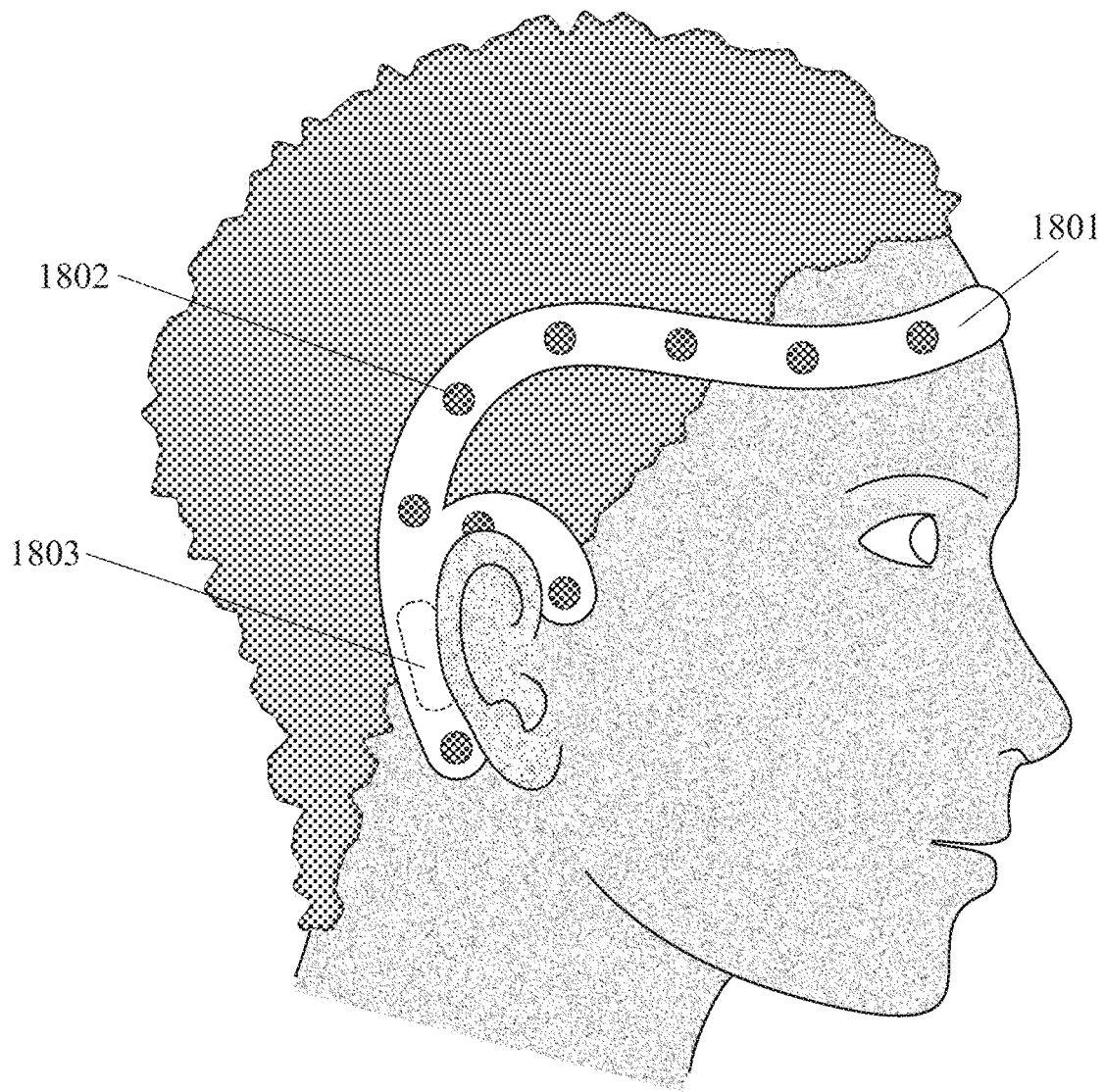
FIG. 18 shows a head-worn EEG device which encircles between 40% and 70% of the circumference of a person's head, including spanning the person's forehead, a first arm extending downward around the rear of an ear, and a second arm extending down around the front of the ear.

FIG. 18 shows the right side of a head-worn device for recording brain signals comprising: an arcuate electrode holder 1801, wherein the electrode holder is a headband, halo, or headset which is configured to be worn around at least 40% of the lateral circumference of a person's head; a plurality of electrodes including electrode 1802, wherein the electrodes are held in place by the electrode holder, and wherein the electrodes are configured to receive electrical and/or electromagnetic signals from the person's brain; and an electronics unit 1803, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder has an upper portion which spans (e.g. encircles) between 40% and 70% of the lateral circumference of the person's head at a height which is at least two inches above the person's ears. In this example, the upper portion spans (loops across) the person's forehead. In this example, the upper portion encircles between 40% and 70% of the person's the head at a substantially-constant height when the head is upright.

In this example, a substantially constant height can be defined as a height which does not vary by more than an inch. In this example, the electrode holder further comprises has a posterior portion, wherein the posterior portion is contiguous with the upper portion. In this example, the posterior portion curves downward from the upper portion to the person's ear, wherein a first arm (e.g. arm, prong, branch, loop, and/or protrusion) of the posterior portion curves around the back of the person's ear and a second arm (e.g. arm, prong, branch, loop, and/or protrusion) curves around part of the front of the person's ear.

In this example, a device comprises: an undulating band which is configured to span from a person's ear on a first side of the person's head to the person's ear on the second side of the person's head, wherein a portion of this undulating band on the first side of the person's head further comprises: a first segment which curves around the rear-facing portion of an ear, a second segment which curves around the front-facing portion of an ear, a third segment which extends upward from the ear along the side of the person's head, and a fourth segment which spans across the person's forehead; sensors (e.g. electrodes); and an electronics unit with a data processor, a data transmitter, and a power source.

In this example, a first segment of a device curves, loops, and/or hooks behind a person's ear. In this example, a first segment of a device curves, loops, or hooks around (some or all of) the rear-facing surface of the person's outer ear and/or the tissue connecting the outer ear with the rest of the head. In this example, a first segment of a device helps to hold the device on a person's head by engaging the rear surface of the outer ear. In this example, a first segment of a device helps to hold the device on a person's head by resting on top of the outer ear (or the tissue connection between the outer ear and the rest of the person's head).

In this example, a second segment of a device curves, loops, protrudes, undulates, and/or hooks around (some or all of) the frontal portion of tissue which connects the outer ear with the rest of the head. In this example, a second segment of a device curves, loops, protrudes, undulates, and/or hooks around (some or all of) the front-facing surface of the person's outer ear. In this example, a second segment of a device curves, loops, protrudes, undulates, and/or hooks around the front of a person's ear. In this example, a second segment of a device has a shape which is selected from the group consisting of: portion of a circle; portion of a spiral; portion of a parabolic curve; portion of a sinusoidal curve; and conic section. In this example, a second segment of a device helps to hold the device on a person's head by resting on top of the outer ear (or the tissue connection between the outer ear and the rest of the person's head). In this example, a second segment of this device is worn on the front-facing surface of a person's ear.

In this example, a third segment of a device extends upward from a person's ear along the side of their head. In this example, a third segment of a device has a shape selected from the group consisting of: arc, wave, undulation, semi-circle, semi-oval, loop, half-sinusoidal curve, bell-shaped curve, and conic section. In this example, a third segment of a device is an arc, wave, or undulation with a rear-facing concavity and a forward-facing peak. In this example, a third segment of a device is arcuate, wavy, and/or undulating. In this example, a third segment of a device spans, curves, and/or loops upward from an ear. In this example, a fourth segment of a device extends across a person's forehead. In this example, a fourth segment of a device on the right side of a person's head connects to a fourth segment of the device on the left side of the person's head. Example variations discussed elsewhere in this disclosure or in priority-linked disclosures can also be applied to this example where relevant.

Figure 19:
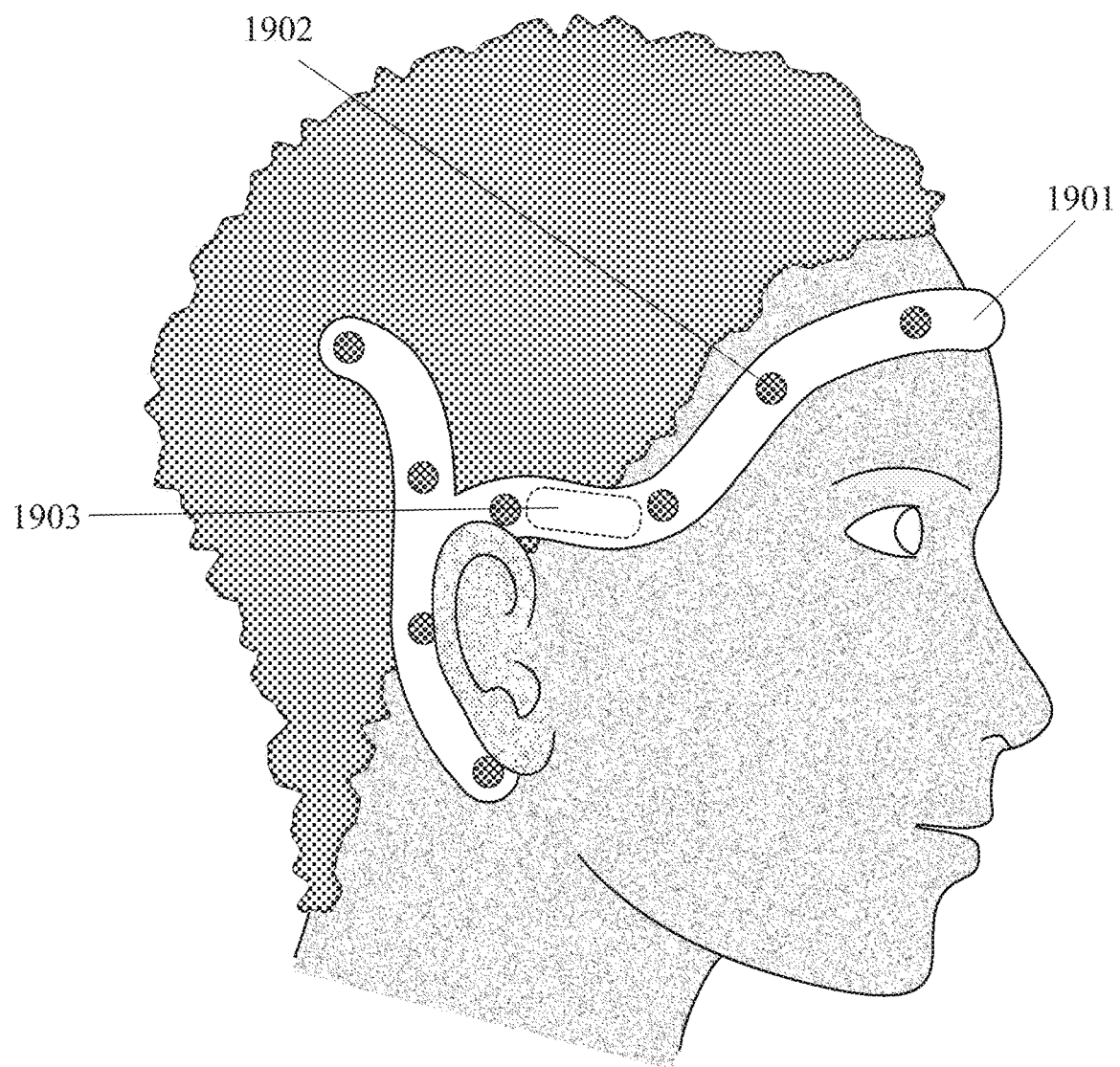
FIG. 19 shows a head-worn EEG device which encircles between 40% and 70% of the circumference of a person's head, including spanning the person's forehead, and an arm extending downward around the rear of the ear.

FIG. 19 shows the right side of a head-worn device for recording brain signals comprising: an arcuate electrode holder 1901, wherein the electrode holder is a headband, halo, or headset which is configured to be worn around at least 40% of the lateral circumference of a person's head; a plurality of electrodes including electrode 1902, wherein the electrodes are held in place by the electrode holder, and wherein the electrodes are configured to receive electrical and/or electromagnetic signals from the person's brain; and an electronics unit 1903, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder has an anterior-upper portion which spans (e.g. encircles) between 40% and 80% of the lateral circumference of the person's head, spanning across the person's forehead from one ear to the other. In this example, the anterior-upper portion is serpentine and/or undulating. In this example, the electrode holder also has a posterior portion which is contiguous with the upper portion. In this example, a first arm (e.g. arm, prong, branch, loop, and/or protrusion) of the posterior portion curves upward to end on a location on the upper-posterior quadrant of the person's head and a second arm (e.g. arm, prong, branch, loop, and/or protrusion) of the posterior portion curves downward around the back of the person's ear. Example variations discussed elsewhere in this disclosure or in priority-linked disclosures can also be applied to this example where relevant.

Figure 20:
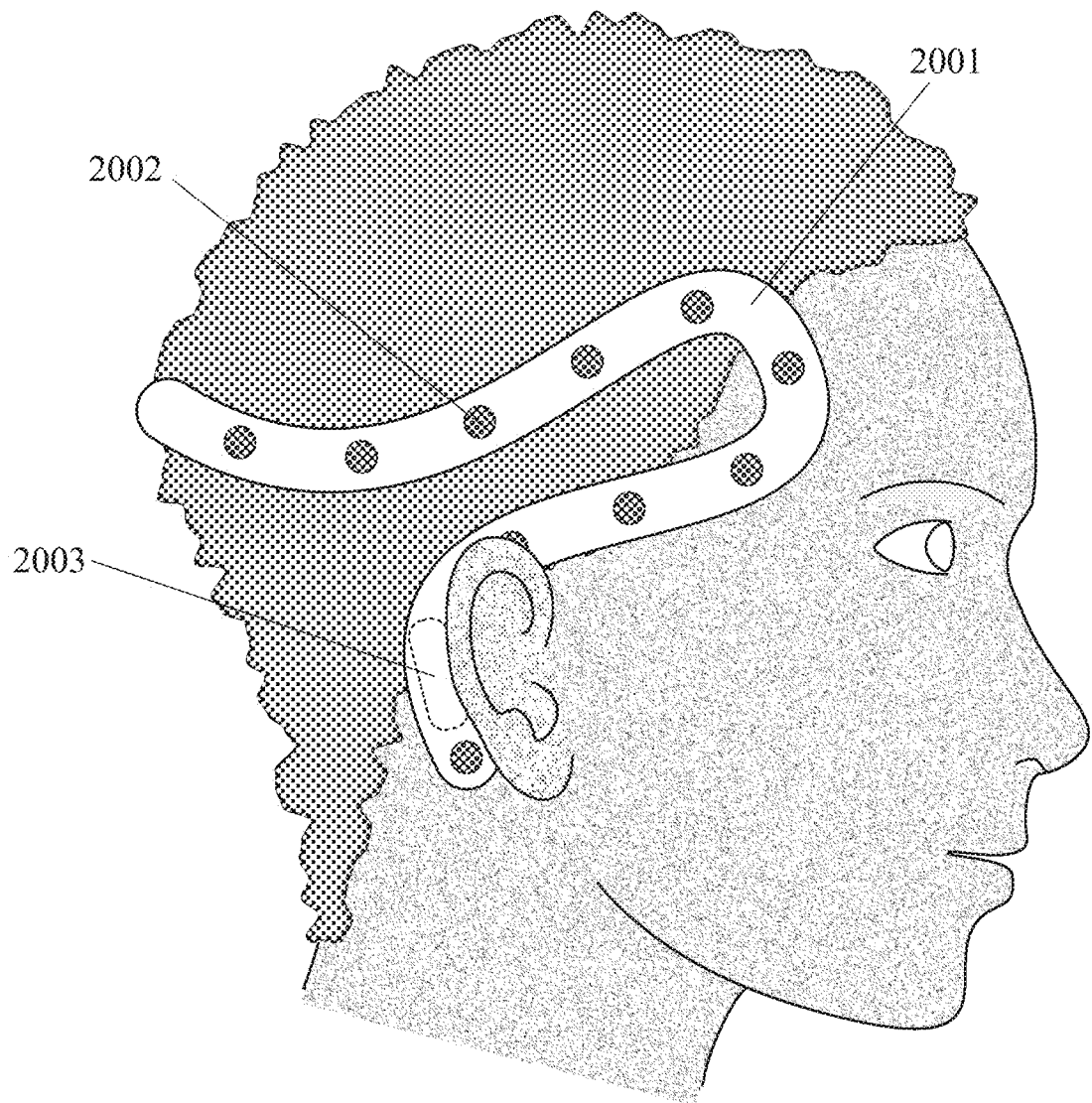
FIG. 20 shows a head-worn EEG device which encircles between 40% and 80% of the circumference of a person's head, including posterior-facing concavities on the person's forehead, and a loop which spans the rear of the person's head.

FIG. 20 shows the right side of a head-worn device for recording brain signals comprising: an arcuate electrode holder 2001, wherein the electrode holder is a headband, halo, or headset which is configured to be worn around at least 40% of the lateral circumference of a person's head; a plurality of electrodes including electrode 2002, wherein the electrodes are held in place by the electrode holder, and wherein the electrodes are configured to receive electrical and/or electromagnetic signals from the person's brain; and an electronics unit 2003, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder spans (e.g. encircles) between 40% and 80% of the lateral circumference of the person's head. In this example, the electrode holder loops around the posterior half of the person's head, from one ear to the other. In this example, between the portion of the electrode holder which loops around the posterior half of the person's head and the portions of the electrode holder which contact the person's ears, there are two posterior-facing concave undulations, one on each side of the person's head, wherein the peaks of these undulations are on the sides of the person's forehead. In this example, the electrode holder: starts behind an ear; curves upward around the back of the ear; then curves forward to a location on a side of the person's forehead; then curves upward and backward to form an undulation with a posterior-facing concavity; then curves backward to loop around the posterior half of the person's head; and then continues in a symmetric manner on the opposite side of the person's head, ending at the ear on the opposite side.

In an example, a head-worn device for recording brain signals can comprise: an arcuate electrode holder, wherein the electrode holder is a headband, halo, or headset which is configured to be worn around at least 40% of the circumference of a person's head; a plurality of electrodes, wherein the electrodes are held in place by the electrode holder, and wherein the electrodes are configured to receive electrical and/or electromagnetic signals from the person's brain; and an electronics unit, wherein the electronics unit further comprises a data processor, a data transmitter and/or data receiver, and a power source.

In an example, the electrode holder can span between 40% and 80% of the circumference of the person's head. In an example, the electrode holder can loop around the rear of the person's head. In an example, the electrode holder can loop around the rear of the person's head at a height which is greater than the tops of the person's ears when the person's head is upright. In an example, the electrode holder can loop around the rear of the person's head at a height which is less than the height of the person's ears when the person's head is upright.

In an example, the electrode holder can have two posterior-facing concave undulations, one on each side of the person's head, wherein the peaks of these undulations are on the sides of the person's forehead. In an example, the electrode holder can have two posterior-facing concave undulations, one on each side of the person's head, wherein the most-anterior portions of these undulations are on the sides of the person's forehead.

In an example, the electrode holder can: start at a location behind an ear; curve upward around the back of the ear; then curve forward to a location on a side of the person's forehead; then curve upward and backward to form an undulation with a posterior-facing concavity; then curve backward to loop around the rear of the person's head; and then continue in a symmetric manner on an opposite side of the person's head, ending at an ear on the opposite side. Example variations discussed elsewhere in this disclosure or in priority-linked disclosures can also be applied to this example where relevant.

Figure 21:
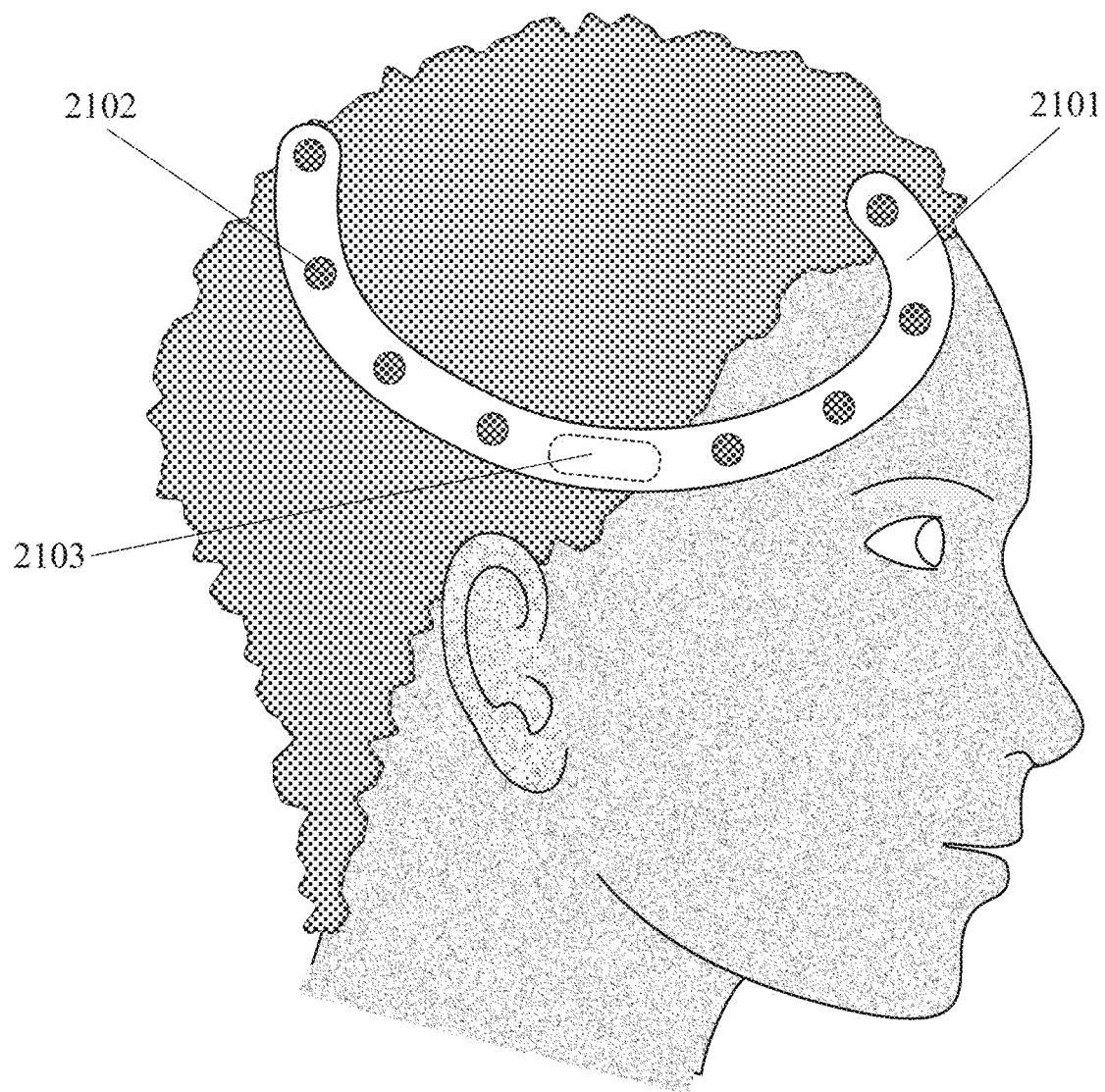
FIG. 21 shows a head-worn EEG device with two partial-spiral arms.

FIG. 21 shows the right side of a head-worn device for recording brain signals comprising: an arcuate electrode holder 2101, wherein the electrode holder is a headband, halo, or headset which is configured to be worn around at least 40% of the lateral circumference of a person's head; a plurality of electrodes including electrode 2102, wherein the electrodes are held in place by the electrode holder, and wherein the electrodes are configured to receive electrical and/or electromagnetic signals from the person's brain; and an electronics unit 2103, wherein the electronics unit further comprises a data processor, a data transmitter and/or data receiver, and a power source. It is assumed that the left side of the device is symmetric to the right side, with the possible exception of the electronics unit, unless stated otherwise.

In this example, a device comprises: a head-worn sensor-positioning member (e.g. electrode holder) which positions a plurality of sensors (e.g. electrodes) at selected locations on the person's head. In this example, a sensor-positioning member (e.g. electrode holder) loops over the top portion of the person's head in a manner similar to the rim of a (skull) cap in which the right and left sides have been elongated. In this example, a portion of a sensor-positioning member (e.g. electrode holder) that is anterior to a person's ears spans portions of the person's temporal lobe, central sulcus, and cerebral cortex. In this example, a portion of a sensor-positioning member (e.g. electrode holder) that is posterior to a person's ears spans portions of the person's temporal lobe and occipital lobe.

In this example, a sensor-holding member (e.g. electrode holder) is shaped like an ellipse, oblong shape, or egg shape which has been curved in three-dimensional space in order to conform to the top portion of the person's head. In this example, the right and left sides of a sensor-positioning member (e.g. electrode holder) come down to locations above a person's ears. In this example, a device can also be described as comprising: a front loop over a front portion of a person's head which holds at least one first sensor (e.g. electrode) at an electrode position selected from the group consisting of FP1, FPz, AF7, F7, FT7, and T7; and an upper loop over the top of the person's head which holds at least one second sensor (e.g. electrode) at an electrode position selected from the group consisting of T7, C5, C3, C1, and Cz. In an example, a portion a device can have shape which is semielliptical. In an example, a segment of a device can have a shape which is a portion of a spiral. Example variations discussed elsewhere in this disclosure or in priority-linked disclosures can also be applied to this example where relevant.

Figure 22:
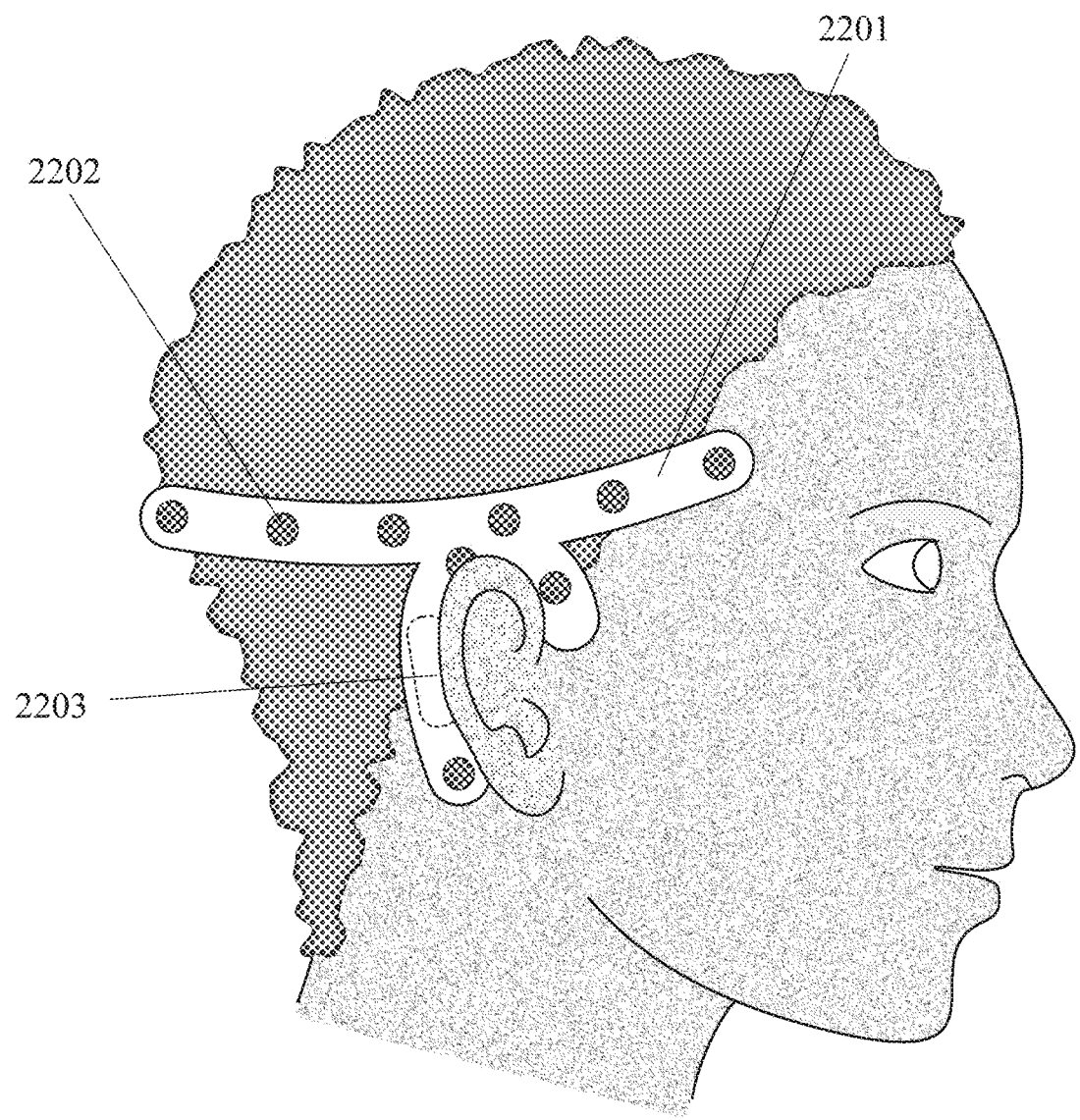
FIG. 22 shows a head-worn EEG device which encircles between 40% and 70% of the circumference of a person's head, including looping around the rear of the person's head, a first arm extending downward around the rear of the ear, and a second arm extending downward around the front of the ear.
Figure 22:
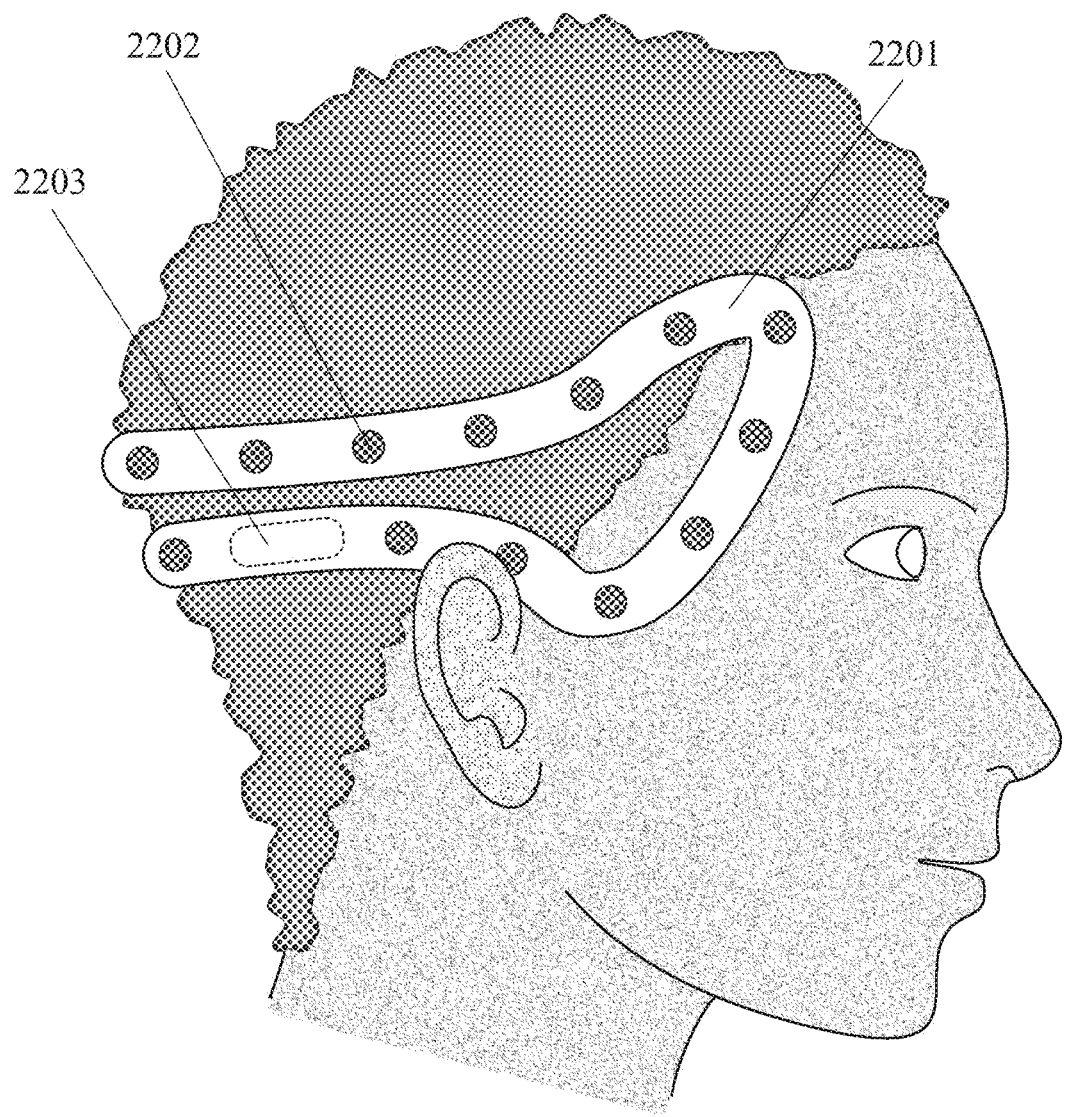

FIG. 22 shows the right side of a head-worn device for recording brain signals comprising: an arcuate electrode holder 2201, wherein the electrode holder is a headband, halo, or headset which is configured to be worn around at least 40% of the lateral circumference of a person's head; a plurality of electrodes including electrode 2202, wherein the electrodes are held in place by the electrode holder, and wherein the electrodes are configured to receive electrical and/or electromagnetic signals from the person's brain; and an electronics unit 2203, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder spans (e.g. encircles) between 40% and 80% of the lateral circumference of the person's head. In this example, the electrode holder loops around the posterior half of the person's head, from one ear to the other. In this example, a side of the electrode holder has three portions: an upper portion which extends forward from the back of the person's head to a location on the side of the person's forehead; a first arm (e.g. arm, prong, branch, loop, and/or protrusion) which curves downward from the upper portion around the posterior of the person's ear; and a second arm (e.g. arm, prong, branch, loop, and/or protrusion) which curves downward from the upper portion around part of the anterior of the person's ear.

In this example, a device comprises: a posterior-ear segment (worn on the rear-facing surface of a person's ear); a frontal-ear segment (worn on the front-facing surface of the person's ear); a forehead segment (spanning from the person's ear to a side portion of the person's forehead); a rear segment (spanning from the posterior-ear segment or the forehead segment to the rear of the person's head); sensors (e.g. electrodes); and an electronics unit including a data processor, data transmitter, and power source.

In this example, a device comprises: a posterior-ear segment, wherein this posterior-ear segment is configured to be worn on the rear-facing surface of a person's ear; a frontal-ear segment, wherein this frontal-ear segment is configured to be worn on the front-facing surface of the person's ear; a forehead segment, wherein this forehead segment is configured to span from the person's ear to the person's temple, side portion of the person's face, and/or side portion of the person's forehead; a rear segment, wherein this rear segment is configured to span from the posterior-ear segment or the forehead segment to the rear of the person's head; at least one sensor (e.g. electrode); and an electronics unit including a data processor, a data transmitter, and a power source.

In this example, a posterior-ear segment of a device curves, loops, and/or hooks behind a person's ear. In this example, a posterior-ear segment of a device curves, loops, or hooks around (some or all of) the rear-facing surface of the person's outer ear and/or the tissue connecting the outer ear with the rest of the head. In this example, a posterior-ear segment of a device helps to hold the device on a person's head by engaging the rear surface of the outer ear.

In this example, a frontal-ear segment of a device curves, loops, protrudes, undulates, and/or hooks around (some or all of) the front-facing surface of the person's outer ear. In this example, a frontal-ear segment of a device curves, loops, protrudes, undulates, and/or hooks around (some or all of) the frontal portion of tissue which connects the outer ear with the rest of the head. In this example, a frontal-ear segment of a device curves, loops, protrudes, undulates, and/or hooks around a side portion of the person's face which is within one inch of the person's ear. In this example, a frontal-ear segment of a device has a shape which is selected from the group consisting of: portion of a circle; portion of a spiral; portion of a parabolic curve; portion of a sinusoidal curve; and conic section. In this example, a frontal-ear segment of a device is directly connected to a rear segment and/or forehead segment.

In this example, a forehead segment of a device spans from a person's ear to a side portion of their face and/or forehead. In this example, a forehead segment of a device spans, protrudes, extends, or curves from a person's ear to a position which is at least two inches from a person's ear toward the person's temple, eye, and/or forehead. In this example, a forehead segment of a device spans, protrudes, extends, or curves from the person's ear to a position which is between one quarter and three-quarters of the way toward the person's temple, eye, and/or forehead. In this example, a rear segment of a device spans from a posterior-ear or forehead segment to the rear of the person's head. In this example, a rear segment of a device on one side of the person's head connects with a rear segment on the second (opposite) side of the person's head. Example variations discussed elsewhere in this disclosure or in priority-linked disclosures can also be applied to this example where relevant.

FIG. 23 shows the right side of a head-worn device for recording brain signals comprising: an arcuate electrode holder 2301, wherein the electrode holder is a headband, halo, or headset which is configured to be worn around at least 40% of the lateral circumference of a person's head; a plurality of electrodes including electrode 2302, wherein the electrodes are held in place by the electrode holder, and wherein the electrodes are configured to receive electrical and/or electromagnetic signals from the person's brain; and an electronics unit 2303, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder spans (e.g. encircles) between 50% and 80% of the lateral circumference of the person's head. In this example, the electrode holder loops around the posterior half of the person's head, from one ear to the other. In this example, the electrode holder comprises an upper loop and a lower loop, both of which span the posterior half of the person's head. In this example, the upper loop and the lower loop are substantially parallel as they span the posterior half of the person's head. In this example, the upper loop and the lower loop are part of the same continuous member. In this example, the upper loop and the lower loop join together over a side of the person's face and/or forehead, forming an undulation with a rear-facing concavity.

In this example, a device comprises: a forehead loop (spanning from a person's ear to a side portion of the person's forehead); a lower-rear segment (spanning from the forehead loop to the rear of the person's head); an upper-rear segment (spanning from the forehead loop to the rear of the person's head, above the lower-rear segment); sensors (e.g. electrodes); and an electronics unit including a data processor, data transmitter, and power source.

In this example, a device comprises: a forehead loop, wherein this forehead loop spans from a person's ear to the person's temple, a side portion of the person's face, and/or a side portion of the person's forehead; a lower-rear segment, wherein this lower-rear segment spans from the forehead loop to the rear of the person's head at a first height; an upper-rear segment, wherein this upper-rear segment spans from the forehead loop to the rear of the person's head at a second height, wherein the second height is greater than the first height; at least one sensor (e.g. electrode); and an electronics unit including a data processor, data transmitter, and power source.

In this example, a forehead loop of a device is arcuate, wavy, and/or undulating. In this example, a forehead loop of a device has a shape selected from the group consisting of: arc, wave, undulation, semi-circle, semi-oval, half-sinusoidal curve, bell-shaped curve, and conic section. In this example, a forehead loop of a device has a concavity whose opening faces rearward. In this example, a forehead loop of a device has a concavity with a peak which faces frontward. In this example, a forehead loop of a device is an arc, wave, or undulation with a rear-facing concavity and a forward-facing peak.

In this example, a forehead loop of a device spans (in an arcuate and/or undulating manner) downward and forward from a person's ear to a location on a side of a person's forehead, then spans (in an arcuate and/or undulating manner) upward, and then spans (in an arcuate and/or undulating manner) to a location above the ear. In this example, a forehead loop of a device spans from a person's ear to a side portion of their face and/or forehead. In this example, a forehead loop of a device spans, protrudes, or curves from the person's ear to a side portion of the person's face. In this example, the most-forward point of a forehead loop of a device is located on the side of a person's forehead. In this example, a forehead loop of a device spans, protrudes, or curves from the person's ear to a side portion of the person's forehead. In this example, a forehead loop of a device spans, protrudes, curves, and/or undulates from the person's ear toward a person's temple, eye, and/or forehead.

In this example, a forehead loop of a device spans, protrudes, curves, and/or undulates from the person's ear to a position which is between one quarter and three-quarters of the way toward the person's temple, eye, and/or forehead. In an example, the most-forward point of a forehead loop of a device can be located on a person's temple. In this example, a device includes a lower-rear segment and an upper-rear segment. In this example, a device includes a lower-rear segment and/or upper-rear segment which are directly attached to a forehead loop. In this example, a portion of the lower-rear segment can rest on top of the person's outer ear (and/or the tissue connecting the outer ear to the rest of the person's head).

In this example, a device includes lower-rear and upper-rear segments which connect to the forehead loop and then span rearward to the rear of the person's head where they connect to (symmetric) rear segments from the other side of the person's head. In this example, a device includes lower-rear and upper-rear segments which are arcs, loops, or semi-circles which partially encircle the person's head in a lateral manner. In this example, a device includes lower-rear and upper-rear segments which are arcs, loops, or semi-circles which partially encircle the person's head. In this example, a device includes lower-rear segment and/or upper-rear segments which are substantially horizontal. In this example, at least a portion of the lower-rear segment and at least a portion of the upper-rear segment can be substantially parallel to each other. Example variations discussed elsewhere in this disclosure or in priority-linked disclosures can also be applied to this example where relevant.

Figure 24:
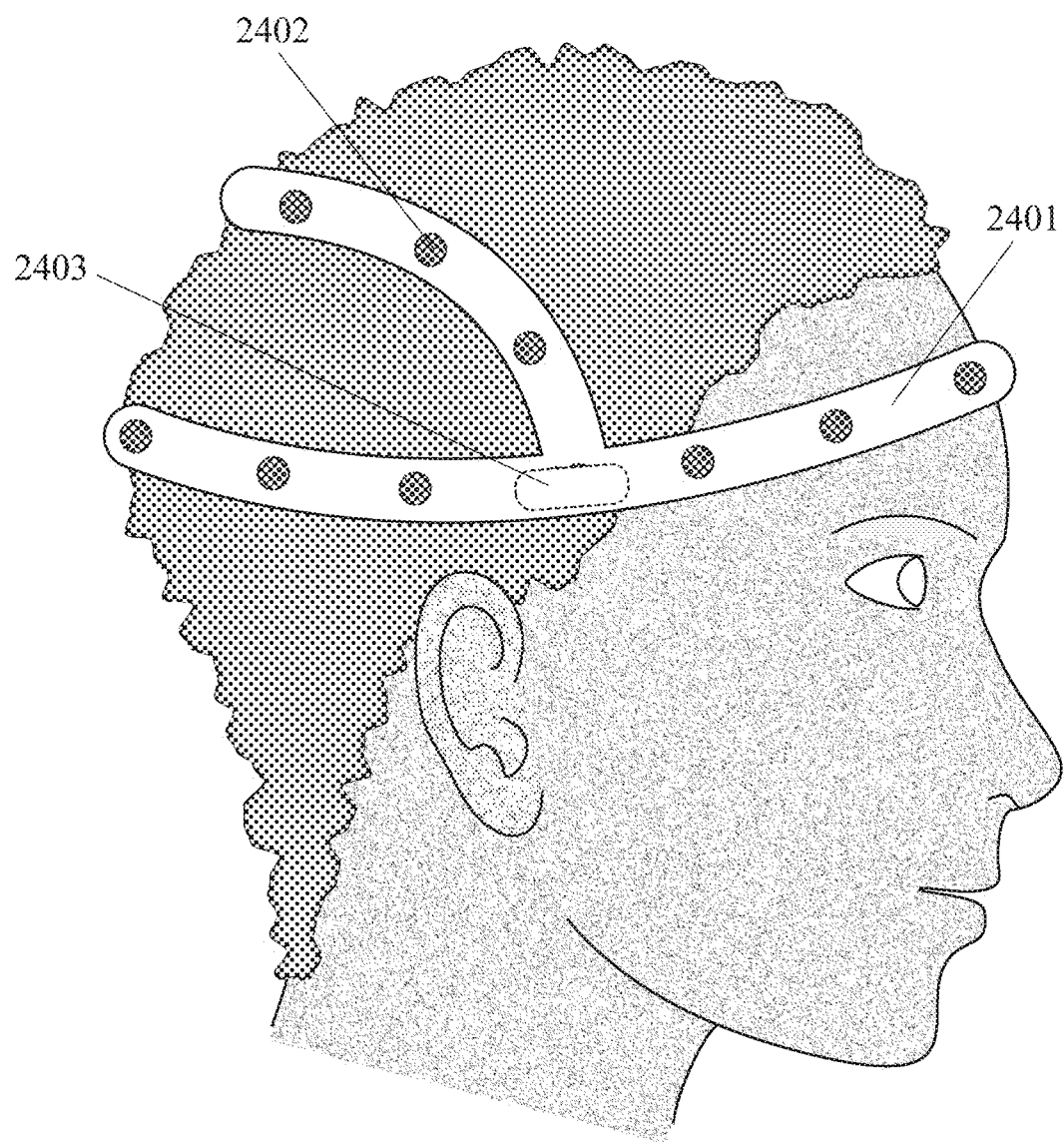
FIG. 24 shows a head-worn EEG device comprising a ring around the person's head and an upper-posterior arm over the top half of the person's head, wherein the arm has a posterior-facing concavity.

FIG. 24 shows the right side of a head-worn device for recording brain signals comprising: an arcuate electrode holder 2401, wherein the electrode holder is a headband, halo, or headset which is configured to be worn around at least 40% of the lateral circumference of a person's head; a plurality of electrodes including electrode 2402, wherein the electrodes are held in place by the electrode holder, and wherein the electrodes are configured to receive electrical and/or electromagnetic signals from the person's brain; and an electronics unit 2403, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder encircles a lateral circumference of the person's head. In this example, the electrode holder comprises: a ring (e.g. ring, band, or halo) which encircles the person's head around the posterior half of the person's head and also across the person's forehead; and an upper-posterior arm (e.g. arm, branch, or loop) which spans from a location on a middle portion of the ring over the upper surface of the upper-posterior quartile of the person's head. In this example, the electrode holder can also be described as comprising: a posterior segment which loops around the posterior half of the person's head; an anterior segment which loops across the person's forehead; and an upper segment which loops over the upper surface of the upper-posterior quadrant of the person's head, wherein these three segments are connected. In this example, the upper-posterior arm (or segment) has a rear-facing and/or downward-facing concavity.

In this example, a device comprises a ring or headband portion which encircles the top of the person's head like the rim of a cap and an arc portion (e.g. branch or arm) which loops over the top of the person's head like the upper portion of a pair of headphones. In this example, a device can also be described as a bifurcating ring around a person's head, wherein the ring bifurcates as it spans the rear of the person's head.

In this example, a device can also be described as comprising: a first arm (e.g. arm or portion) which spans from an area above a person's ear to the person's forehead; a second arm (e.g. arm or portion) which spans from the area above the person's ear to the rear of the person's head; and a third arm (e.g. arm or portion) which spans from the area above the person's ear to the rear of the person's head, wherein the first, second, and third arms (e.g. arms or portions) are connected. In this example, the three arms (e.g. arms or portions) of a device intersect at a location which is above the person's ear and within two inches of the front-to-back midpoint of the side of the person's head. In this example, a first arm (e.g. arm or portion) of a device has an upward-facing concavity. In this example, a second arm (e.g. arm or portion) of a device has an upwardly-facing concavity. Example variations discussed elsewhere in this disclosure or in priority-linked disclosures can also be applied to this example where relevant.

Figure 25:
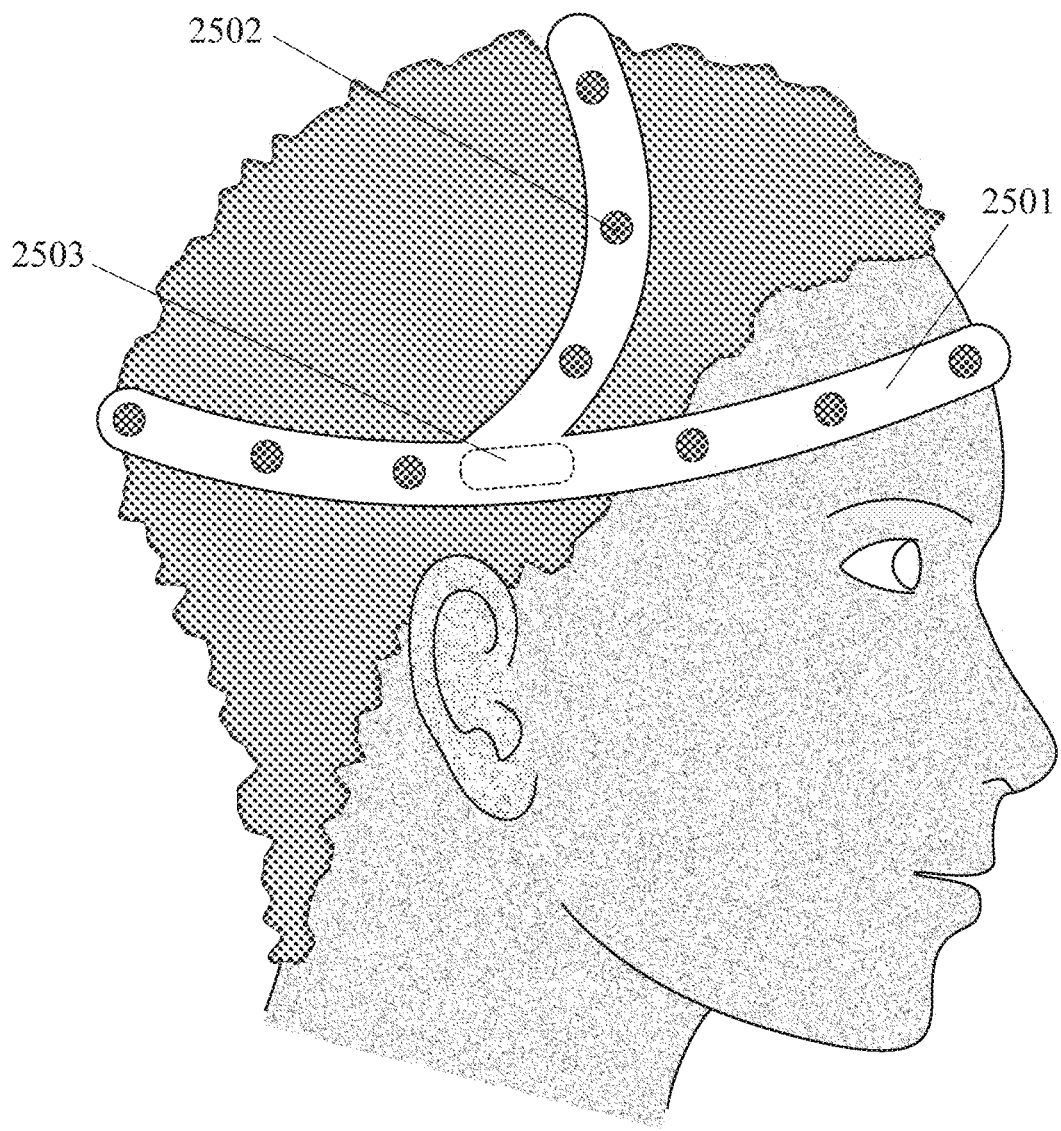
FIG. 25 shows a head-worn EEG device comprising a ring around the person's head and an upper arm over the top of the person's head, wherein the arm has a posterior-facing concavity.

FIG. 25 shows the right side of a head-worn device for recording brain signals comprising: an arcuate electrode holder 2501, wherein the electrode holder is a headband, halo, or headset which is configured to be worn around at least 40% of the lateral circumference of a person's head; a plurality of electrodes including electrode 2502, wherein the electrodes are held in place by the electrode holder, and wherein the electrodes are configured to receive electrical and/or electromagnetic signals from the person's brain; and an electronics unit 2503, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder encircles a lateral circumference of the person's head. In this example, the electrode holder comprises: a ring (e.g. ring, band, or halo) which encircles the person's head around the posterior half of the person's head and also across the person's forehead; and an upper arm (e.g. arm, branch, or loop) which spans from a location on a middle portion of the ring over the top of the person's head. In this example, the electrode holder can also be described as comprising: a posterior segment which loops around the posterior half of the person's head; an anterior segment which loops across the person's forehead; and an upper segment which loops over the top the person's head, wherein these three segments are connected. In this example, the upper arm (or segment) has a rear-facing concavity.

In this example, there are three loops in a posterior-to-anterior series of loops. In this example, a device comprises a posterior-to-anterior series of side-to-side loops comprising three loops (e.g. arms or branches) which originate on the right side of a person's head, diverge as they loop around the head from right to left, and then reconverge on the left side of the person's head. In this example, a device comprises: a lower front loop which loops around a person's forehead; an upper front loop which loops around the front of a person's head, wherein the lower front loop is below the upper front loop; and a rear loop which loops around the rear of the person's head.

In this example, a device comprises: a posterior-to-anterior series of side-to-side loops, wherein a posterior (rear) loop originates on the right side of a person's head, loops around the rear of the head, and then terminates on the left side of the head, wherein a middle (top) loop originates on the right side of a person's head, loops around the top of the head, and then ends on the left side of the head, and wherein an anterior (front) loop originates on the right side of the head, loops around the front of the head, and then ends on the left side of the head. In this example, a device comprises: a posterior-to-anterior series loops (e.g. arms or branches), wherein each loop is configured to span a person's head from side to side.

In this example, loops in a device with a posterior-to-anterior series of loops converge at two loop convergence locations, one on the right side and one on the left side a person's head. In this example, loops on a device converge in a location above an ear. In this example, portions (e.g. branches or arms) are joined on at locations over the person's left ear and right ear, respectively. In this example, the most anterior loop in a posterior-to-anterior series of right-to-left loops spans a person's forehead. In this example, this series of loops originates on the right side of a person's head, diverge as the loops span around the head from right to left, and then reconverge on the left side of the head, or vice versa.

In this example, a device can also be described as a bifurcating ring which encircles a person's head. In this example, a device comprises a ring portion which encircles a person's head in a manner like the rim of a (skull) cap and an arc portion (e.g. branch or arm) which loops over the top of the person's head like the upper portion of a pair of headphones. In this example, an upper front loop of a device and a rear loop of the device together comprise a ring which encircles the person's head. In this example, a lower front loop has an upward-facing convexity. In this example, a ring portion of a device (which goes around a person's head) of a device is circular. In this example, a ring portion of a device has a shape which is selected from the group consisting of: circle, ellipse, and oval. Example variations discussed elsewhere in this disclosure or in priority-linked disclosures can also be applied to this example where relevant.

Figure 26:
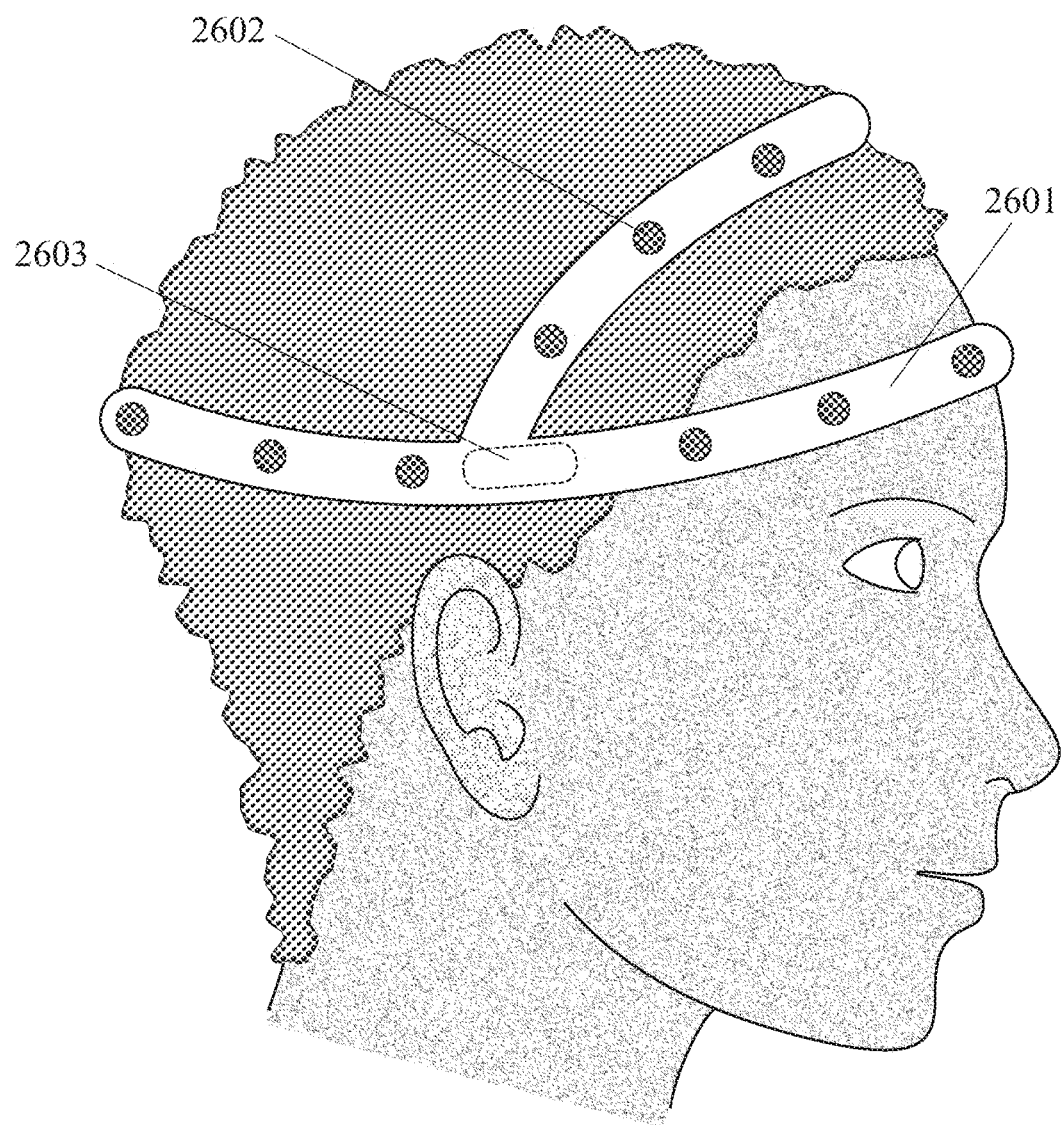
FIG. 26 shows a head-worn EEG device comprising a ring around the person's head and an upper-anterior arm over the top half of the person's head, wherein the arm has an anterior-facing concavity.

FIG. 26 shows the right side of a head-worn device for recording brain signals comprising: an arcuate electrode holder 2601, wherein the electrode holder is a headband, halo, or headset which is configured to be worn around at least 40% of the lateral circumference of a person's head; a plurality of electrodes including electrode 2602, wherein the electrodes are held in place by the electrode holder, and wherein the electrodes are configured to receive electrical and/or electromagnetic signals from the person's brain; and an electronics unit 2603, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder encircles a lateral circumference of the person's head. In this example, the electrode holder comprises: a ring (e.g. ring, band, or halo) which encircles the person's head around the posterior half of the person's head and also across the person's forehead; and an upper-anterior arm (e.g. arm, branch, or loop) which spans from a location on a middle portion of the ring over the upper surface of the upper-anterior quadrant of the person's head. In this example, the electrode holder can also be described as comprising: a posterior segment which loops around the posterior half of the person's head; an anterior segment which loops across the person's forehead; and an upper-anterior segment which loops over the upper surface of the upper-anterior quadrant of the person's head, wherein these three segments are connected. In this example, the upper-anterior arm (or segment) has a forward-facing concavity.

In this example, a device comprises a ring portion which encircles the top of the person's head like the rim of a cap and a partial ring (e.g. arc) portion (e.g. branch or arm) which loops over the top of the person's head. In this example, a device comprises a ring portion which encircles a person's head (spanning the front and the back of the head) and a partial ring portion which partially encircles the person's head (spanning the front of the person's head). In this example, a partial ring (e.g. arc) portion of a device loops over an anterior (anterior relative to the top of the head or relative to the person's ear) portion of a person's head. In this example, a ring portion of this device is circular. In an example, a ring portion of a device can be circular, oval, or elliptical. In this example, a ring portion of this device has a shape selected from the group consisting of circle, ellipse, and oval. In this example, a partial ring portion of a device is a semicircle, a semi-oval, or a semi-ellipse. In this example, an partial ring (e.g. arc) portion of a device has a forward-facing concavity.

In this example, a device can also be described as comprising a posterior-to-anterior series of side-to-side loops (e.g. arms or branches), wherein each loop is configured to span a person's head from one side to the other. In this example, a device comprises a series of loops which originate on the right side of a person's head, diverge as the loops span around the head from right to left, and then reconverge on the left side of the head. In this example, the most anterior loop in a posterior-to-anterior series of right-to-left loops in the frame of a wearable brain activity device spans a person's forehead. In this example, a device comprises a posterior-to-anterior series of three loops.

In this example, a device comprises a posterior-to-anterior series of side-to-side loops, wherein three loops (e.g. arms or branches) originate on the right side of a person's head, diverge as they loop around the head from right to left, and then reconverge on the left side of the person's head. In this example, a device comprises a posterior-to-anterior series of side-to-side loops, wherein a posterior (rear) loop originates on the right side of a person's head, loops around the rear of the head, and then terminates on the left side of the head, wherein a middle (top) loop which originates on the right side of a person's head, loops around the top of the head, and then ends on the left side of the head, and wherein an anterior (front) loop which originates on the right side of the head, loops around the front of the head, and then ends on the left side of the head.

In this example, loops in a posterior-to-anterior series of loops converge at two loop convergence locations, one on the right side and one on the left side a person's head. In this example, loops of a device converge at a location above an ear. In this example, two portions (e.g. branches or arms) of a device are joined on the left side and right side at locations just over the person's left ear and right ear, respectively. In this example, a partial ring portion of a device intersects and/or joins a ring portion of the device at a location within two inches of the front-to-back midpoint of the side of the person's head.

In this example, a partial ring (e.g. arc) portion of a device intersects a ring portion of this device, forming a forward-facing acute angle at this intersection. In this example, this angle can be between 40 and 80 degrees. In this example, anterior and middle loops of a three-loop posterior-to-anterior series of right-to-left loops form a forward-facing angle as they intersect. In this example, this forward-facing angle is between 40 and 90 degrees. In an example, a ring portion of a device and a partial ring portion of the device can form a forward-facing angle between 5 and 65 degrees where they intersect. In this example, a device can be described as a bifurcating ring around a person's head, wherein the ring bifurcates as it spans the front of the person's head. In this example, a device can be described as a headband. Example variations discussed elsewhere in this disclosure or in priority-linked disclosures can also be applied to this example where relevant.

Figure 27:
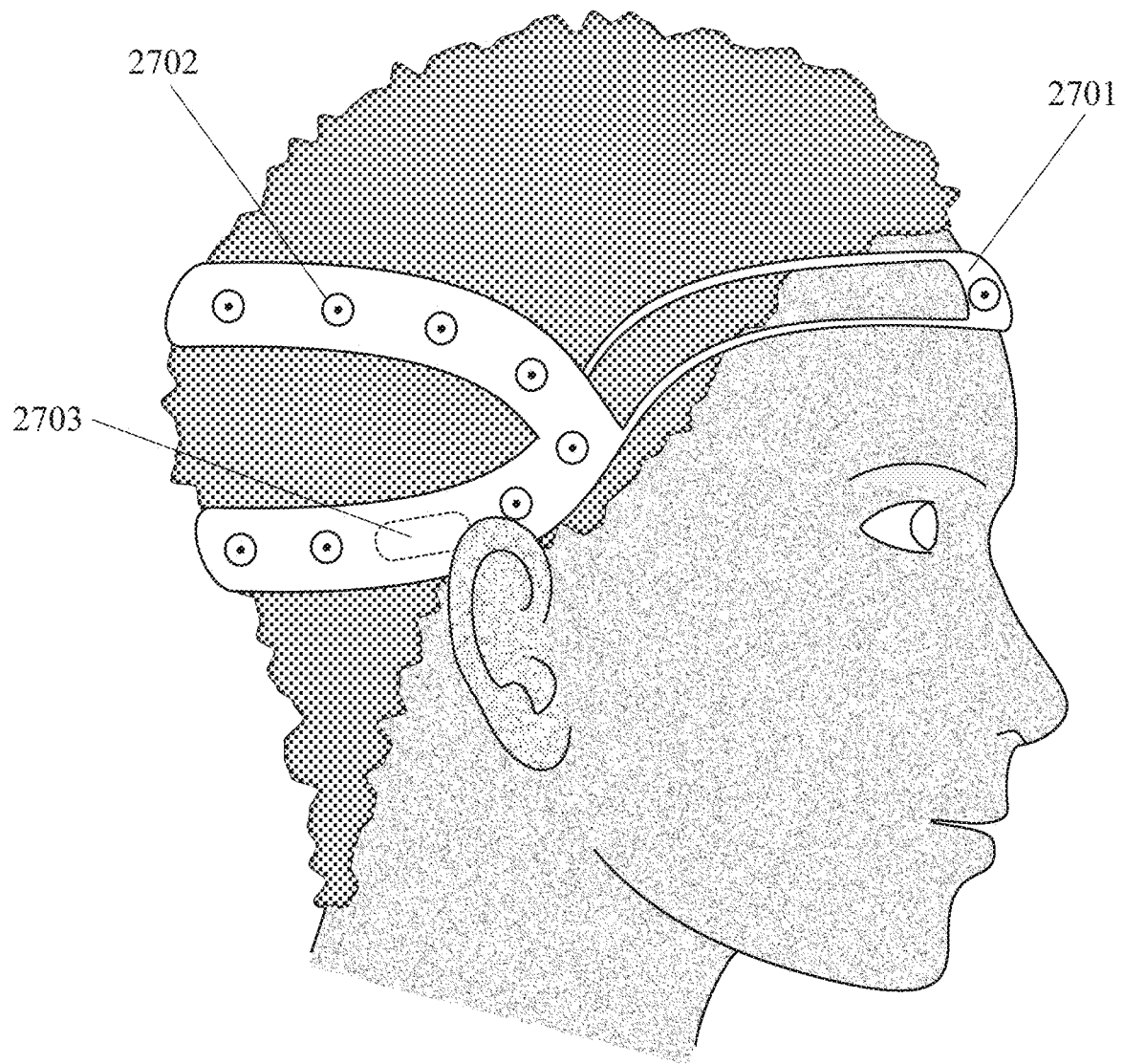
FIG. 27 shows a head-worn EEG device with an upper-posterior loop around the back of a person's head at a first height and a lower-posterior loop around the back of the person's head at a second height.

FIG. 27 shows the right side of a head-worn device for recording brain signals comprising: an arcuate electrode holder 2701, wherein the electrode holder is a headband, halo, or headset which is configured to be worn around at least 40% of the lateral circumference of a person's head; a plurality of electrodes including electrode 2702, wherein the electrodes are held in place by the electrode holder, and wherein the electrodes are configured to receive electrical and/or electromagnetic signals from the person's brain; and an electronics unit 2703, wherein the electronics unit further comprises a data processor, a data transmitter and/or data receiver, and a power source. It is assumed that the left side of the device is symmetric to the right side, with the possible exception of the electronics unit, unless stated otherwise.

In this example, the electrode holder comprises: an upper-posterior segment which loops around the back of a person's head at a first height (when the head is upright); a lower-posterior segment which loops around the back of the person's head at a second height (when the head is upright), wherein the first height is greater than the second height; and an anterior segment which loops across the person's forehead, wherein there are one or more openings (e.g. holes) on the anterior segment; wherein the upper-posterior segment, the lower-posterior segment, and the anterior segment are connected to each other at a location above the person's ear. In this example, the upper-posterior segment has a downward-facing concavity. In this example, the lower-posterior segment has an upward-facing concavity.

In this example, a device comprises a ring or headband portion which encircles the top of the person's head like the rim of a cap and an arc portion (e.g. branch or arm) which loops over the top of the person's head like the upper portion of a pair of headphones. In this example, a device can also be described as a bifurcating ring around a person's head, wherein the ring bifurcates as it spans the rear of the person's head.

In this example, a device can also be described as comprising: a first arm (e.g. arm or portion) which spans from an area above a person's ear to the person's forehead; a second arm (e.g. arm or portion) which spans from the area above the person's ear to the rear of the person's head; and a third arm (e.g. arm or portion) which spans from the area above the person's ear to the rear of the person's head, wherein the first, second, and third arms (e.g. arms or portions) are connected. In this example, the three arms (e.g. arms or portions) of a device intersect at a location which is above the person's ear and within two inches of the front-to-back midpoint of the side of the person's head. In this example, a first arm (e.g. arm or portion) of a device has an upward-facing concavity. In this example, a second arm (e.g. arm or portion) of a device has an upwardly-facing concavity. Example variations discussed elsewhere in this disclosure or in priority-linked disclosures can also be applied to this example where relevant.

Figure 28:
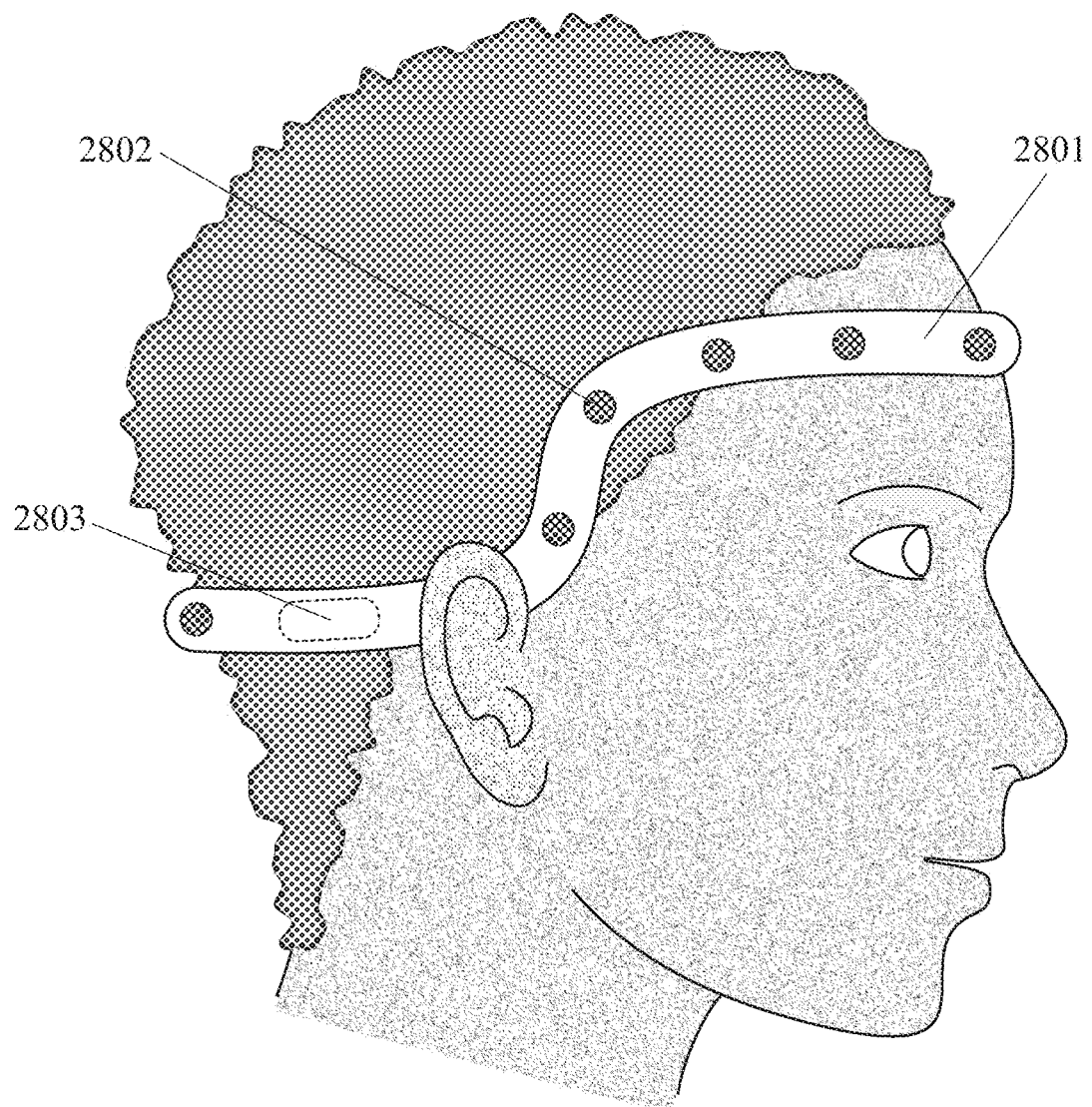
FIG. 28 shows an EEG headband, wherein the most-posterior third of the device has a first substantially-level height, the most-anterior third of the device has a second substantially-level height, and the height of the device transitions from the first height to the second height in an arcuate middle-third section.

FIG. 28 shows the right side of a head-worn device for recording brain signals comprising: an arcuate electrode holder 2801, wherein the electrode holder is a headband, halo, or headset which is configured to be worn around at least 40% of the lateral circumference of a person's head; a plurality of electrodes including electrode 2802, wherein the electrodes are held in place by the electrode holder, and wherein the electrodes are configured to receive electrical and/or electromagnetic signals from the person's brain; and an electronics unit 2803, wherein the electronics unit further comprises a data processor, a data transmitter and/or data receiver, and a power source. It is assumed that the left side of the device is symmetric to the right side, with the possible exception of the electronics unit, unless stated otherwise.

In this example, when the person's head is upright, the most-posterior third of the electrode holder has a first substantially-level height and most-anterior third of the electrode has a second substantially-level height, wherein the second height is greater than the first average height, and wherein the height of the electrode holder transitions from the first height to the second height in an arcuate middle-third section of the electrode holder.

In this example, the middle section of a side (e.g. right or left) of the electrode holder has a serpentine shape, wherein the posterior end of this shape meets a substantially-level posterior third section of the electrode holder and the anterior end of this shape meets a substantially-level anterior third section of the electrode holder. In this example, the middle third of a side (e.g. right or left) of the electrode holder has a serpentine shape, wherein the posterior end of this shape meets a substantially-level posterior third section of the electrode holder and the anterior end of this shape meets a substantially-level anterior third section of the electrode holder.

In this example, a device comprises: a forward-upward sloped headband (including a rear portion and a front portion) which is worn around a person's head; a plurality of sensors (e.g. electrodes); and an electronics unit with a data processor, data transmitter, and power source. In this example, a device has a front portion which spans from a person's ear to their forehead and a rear portion which spans from the person's ear to the rear of their head. In this example, a front portion of a device extends forward and upward from the top of the person's ear to their forehead. In this example, a front portion of a device spans across a person's forehead. In this example, a rear portion of a device extends backward from the top or middle of the person's ear to the rear of their head.

In this example, a front portion of a device is higher than the rear portion of this device. In this example, a front portion of an undulating headband is higher than the rear portion of the undulating headband. In this example, a centroid of a front portion of this device is higher than a centroid of a rear portion of this device. In this example, a front third of an undulating headband is relatively level and a rear third of the undulating headband is relatively level. In this example, a front third of an undulating headband has a uniform first height, a rear third of the undulating headband has a uniform second height, and a middle third of the headband has an arcuate transition from the first height to the second height. In this example, the first height is between one and three inches higher than the second height.

In this example, a rear portion of a device extends backward and downward from the top or middle of the person's ear to the rear of their head. In this example, side portions of an undulating headband dip down to within one inch of a person's ears. In this example, a rear portion of the undulating headband spans the rear of the person's head at the level to which the side portions dip down. In this example, a device comprises an undulating headband which spans across a person's forehead. In this example, a front portion and a rear portion of a device together comprise an undulating ring. In this example, a device comprises a ring which rests on top of a person's ears. Example variations discussed elsewhere in this disclosure or in priority-linked disclosures can also be applied to this example where relevant.

Figure 29:
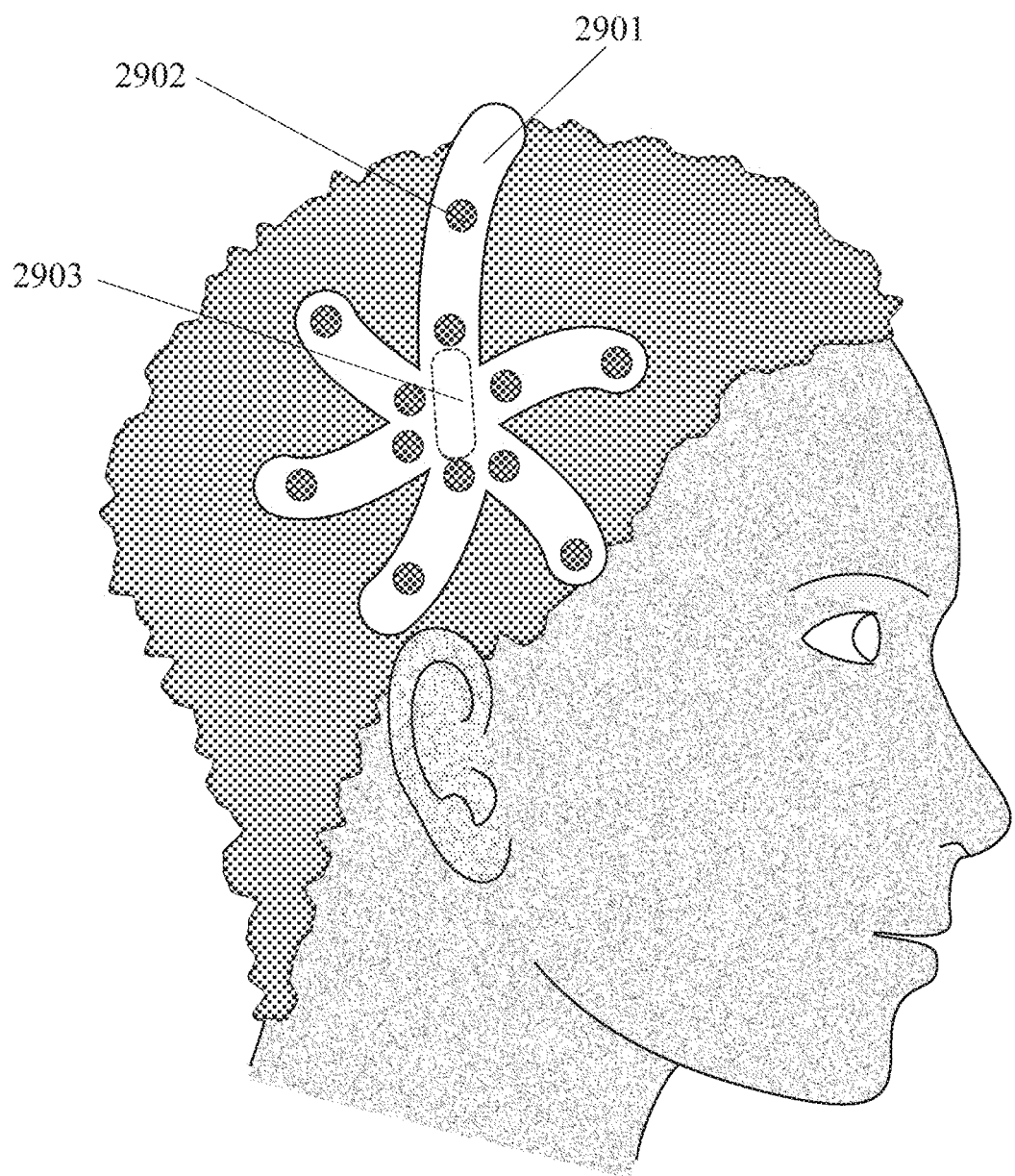
FIG. 29 shows a head-worn EEG device including hub-and-spoke arm arrays on a loop that goes over the top of a person's head.

FIG. 29 shows the right side of a head-worn device for recording brain signals comprising: an arcuate electrode holder 2901, wherein the electrode holder is a headband, halo, or headset which is configured to be worn around at least 40% of the lateral circumference of a person's head; a plurality of electrodes including electrode 2902, wherein the electrodes are held in place by the electrode holder, and wherein the electrodes are configured to receive electrical and/or electromagnetic signals from the person's brain; and an electronics unit 2903, wherein the electronics unit further comprises a data processor, a data transmitter and/or data receiver, and a power source. It is assumed that the left side of the device is symmetric to the right side, with the possible exception of the electronics unit, unless stated otherwise.

In this example, a head-worn device includes two hub-and-spoke (e.g. radial) arrays of arms (e.g. arms, segments, spokes, branches, or legs), one on each side (e.g. right and left) of a person's head, wherein arms in a hub-and-spoke (e.g. radial) array extend out in a radial manner from a hub, and wherein there are one or more electrodes on each arm. In this example, a head-worn device comprises: an upper loop (e.g. loop, arm, segment, or portion) which loops over the top half of a person's head; a right-side hub on the upper loop on the right side of the person's head; a left-side hub on the upper loop on the left side of the person's head; a right-side radial array of arms (e.g. arms, segments, spokes, branches, or legs) which extend out radially from the right-side hub; a left-side radial array of arms (e.g. arms, segments, branches, or legs) which extend out radially from the left-side hub; a plurality of sensors (e.g. electrodes); and an electronics unit which include a data processor, data transmitter, and power source. In this example, the upper loop takes the position of one arm (e.g. arm, segment, spoke, branch, or leg) in each radial array of arms. In this example, in addition to the upper loop extending from a hub, there are five arms (e.g. arms, segments, spokes, branches, or legs) which extend out in a radial manner from a hub. Example variations discussed elsewhere in this disclosure or in priority-linked disclosures can also be applied to this example where relevant.

Figure 30:
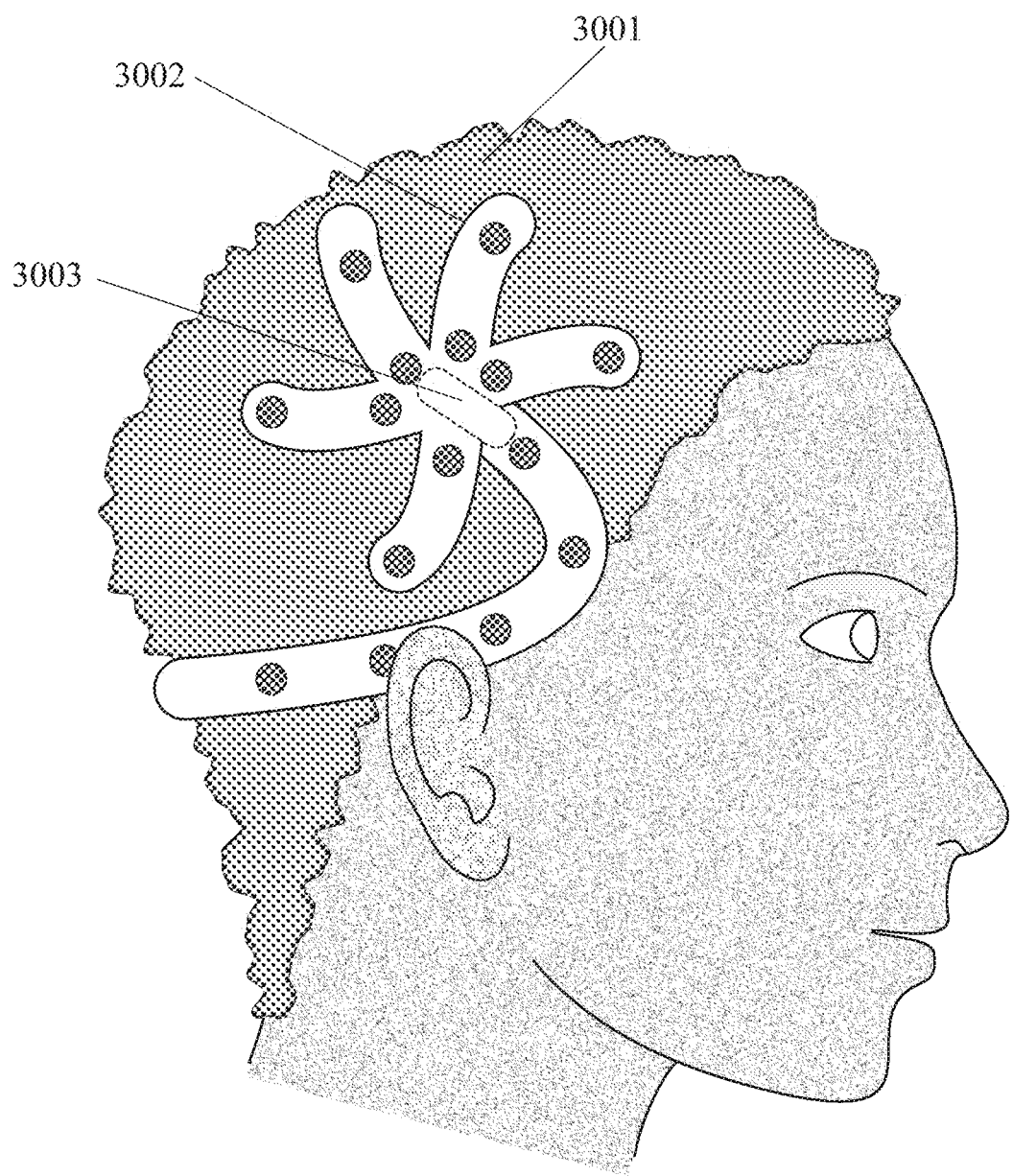
FIG. 30 shows a head-worn EEG device including hub-and-spoke arm arrays on a loop that goes around the back of a person's head.

FIG. 30 shows the right side of a head-worn device for recording brain signals comprising: an arcuate electrode holder 3001, wherein the electrode holder is a headband, halo, or headset which is configured to be worn around at least 40% of the lateral circumference of a person's head; a plurality of electrodes including electrode 3002, wherein the electrodes are held in place by the electrode holder, and wherein the electrodes are configured to receive electrical and/or electromagnetic signals from the person's brain; and an electronics unit 3003, wherein the electronics unit further comprises a data processor, a data transmitter and/or data receiver, and a power source. It is assumed that the left side of the device is symmetric to the right side, with the possible exception of the electronics unit, unless stated otherwise.

In this example, a head-worn device includes two hub-and-spoke (e.g. radial) arrays of arms (e.g. arms, segments, spokes, branches, or legs), one on each side (e.g. right and left) of a person's head, wherein arms in a hub-and-spoke (e.g. radial) array extend out in a radial manner from a hub, and wherein there are one or more electrodes on each arm. In this example, a head-worn device comprises: a posterior loop (e.g. loop, arm, segment, or portion) which loops around the posterior half of a person's head; a right-side hub on the posterior loop on the right side of the person's head; a left-side hub on the posterior loop on the left side of the person's head; a right-side radial array of arms (e.g. arms, segments, spokes, branches, or legs) which extend out radially from the right-side hub; a left-side radial array of arms (e.g. arms, segments, branches, or legs) which extend out radially from the left-side hub; a plurality of sensors (e.g. electrodes); and an electronics unit which include a data processor, data transmitter, and power source. In this example, the posterior loop takes the position of one arm (e.g. arm, segment, spoke, branch, or leg) in each radial array of arms. In this example, in addition to the posterior loop extending from a hub, there are five arms (e.g. arms, segments, spokes, branches, or legs) which extend out in a radial manner from a hub. Example variations discussed elsewhere in this disclosure or in priority-linked disclosures can also be applied to this example where relevant.

Figure 31:
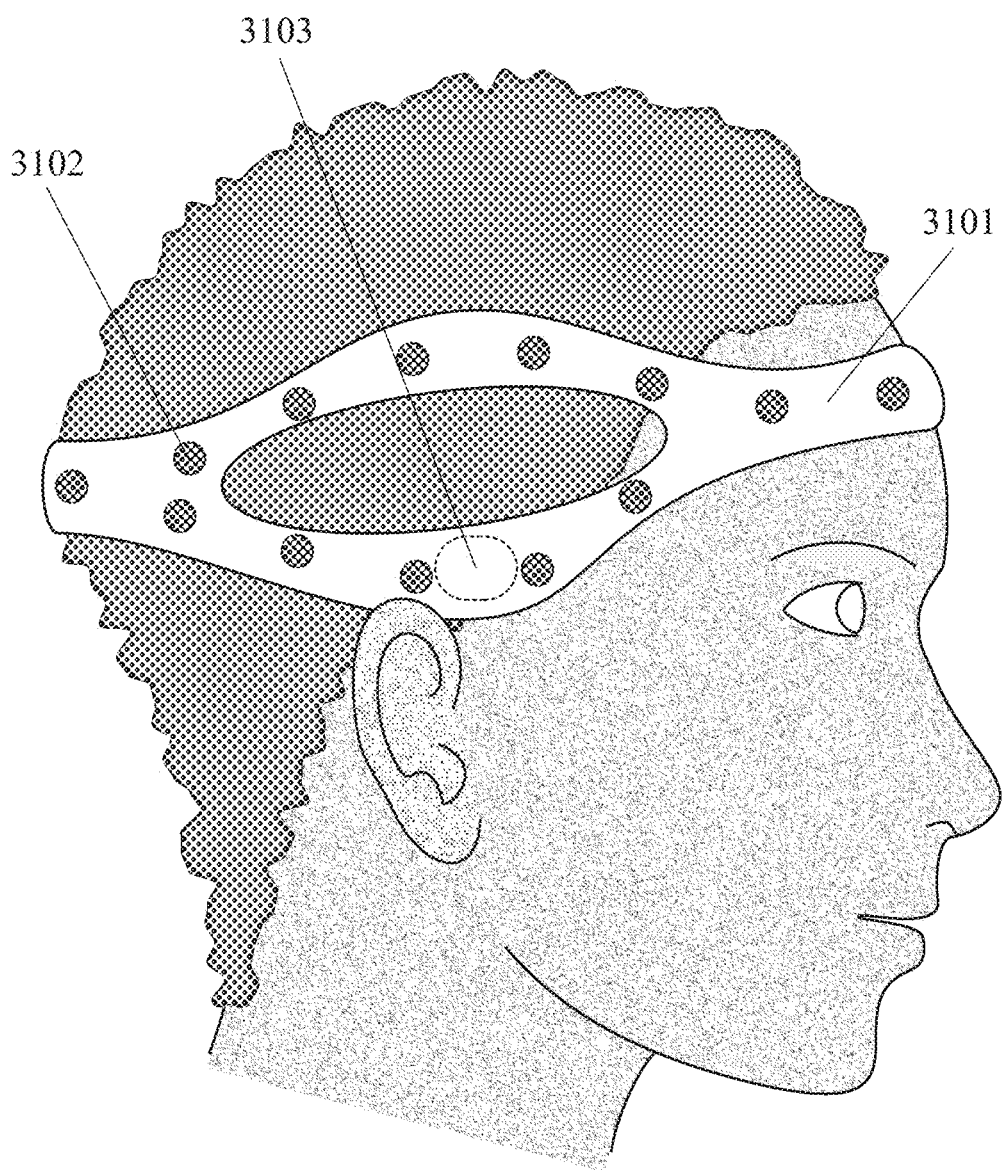
FIG. 31 shows an EEG headband which bifurcates above a person's ears.

FIG. 31 shows the right side of a head-worn device for recording brain signals comprising: an arcuate electrode holder 3101, wherein the electrode holder is a headband, halo, or headset which is configured to be worn around at least 40% of the lateral circumference of a person's head; a plurality of electrodes including electrode 3102, wherein the electrodes are held in place by the electrode holder, and wherein the electrodes are configured to receive electrical and/or electromagnetic signals from the person's brain; and an electronics unit 3103, wherein the electronics unit further comprises a data processor, a data transmitter and/or data receiver, and a power source. It is assumed that the left side of the device is symmetric to the right side, with the possible exception of the electronics unit, unless stated otherwise.

In this example, a head-worn device for recording brain signals comprises an electrode-holding ring, headband, halo, or headset which encircles a person's head, wherein the ring, headband, halo, or headset bifurcates and then reconverges on each side (e.g. right and left) of the person's head above the person's right and left ears, respectively. This electrode-holding ring, headband, halo, or headset loops across the person's forehead as a single band (e.g. band, loop, or segment) and loops over the back of the person's head as a single band (e.g. band, loop, or segment), but bifurcates into two branches (e.g. branches, bands, loops, or segments) and then reconverges as it spans the sides (e.g. right and left) of the person's head. In this example, a lower branch of a bifurcation rests on a person's ear. In an example, bifurcating portions of the ring, headband, halo, or headset can span between 20% and 50% of the circumference of the person's head. In an example, bifurcating portions of the ring, headband, halo, or headset can span between 30% and 70% of the circumference of the person's head. Example variations discussed elsewhere in this disclosure or in priority-linked disclosures can also be applied to this example where relevant.

Figure 32:
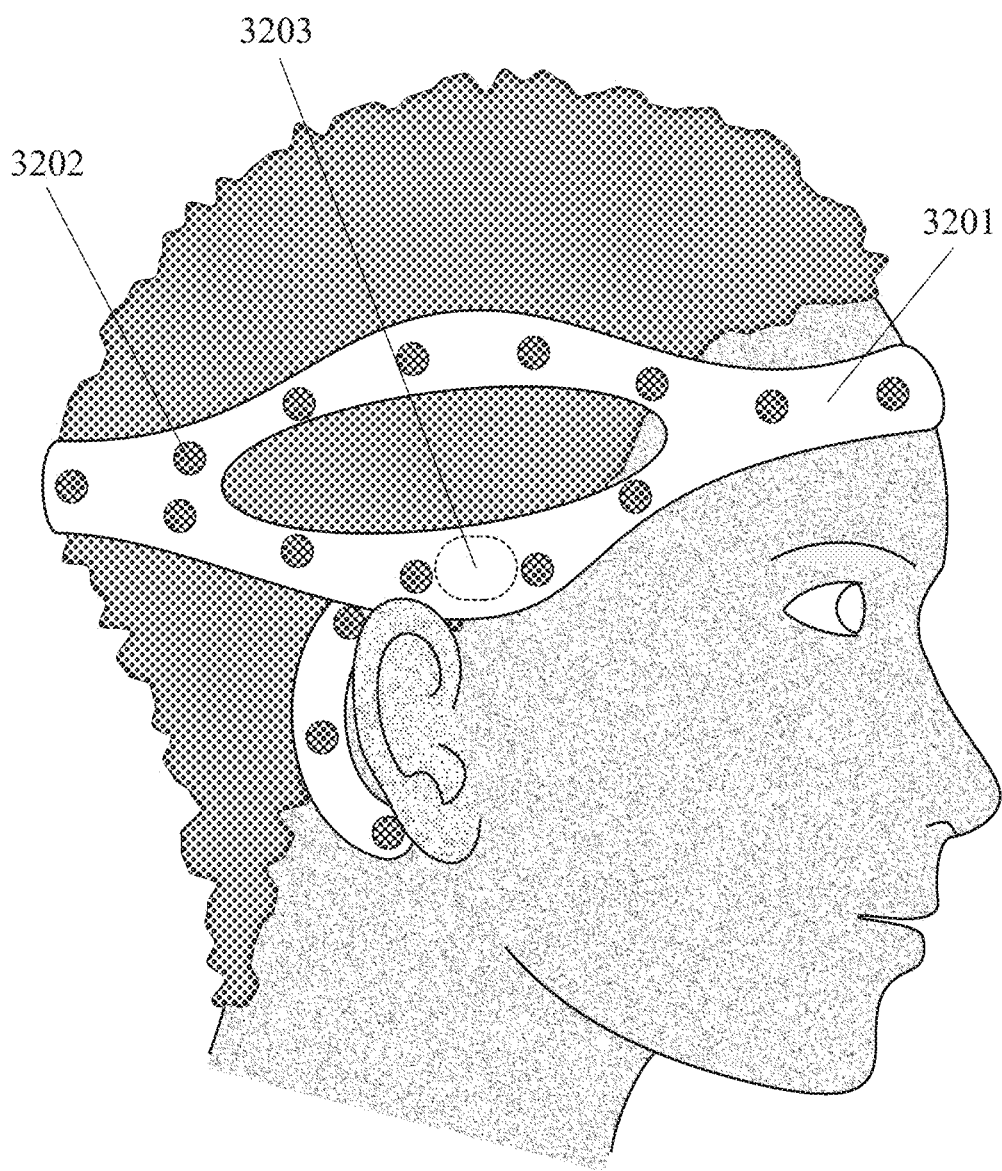
FIG. 32 shows an EEG headband which bifurcates above a person's ears, wherein the headband includes an arm extending downward around the rear of the ear.

FIG. 32 shows the right side of a head-worn device for recording brain signals comprising: an arcuate electrode holder 3201, wherein the electrode holder is a headband, halo, or headset which is configured to be worn around at least 40% of the lateral circumference of a person's head; a plurality of electrodes including electrode 3202, wherein the electrodes are held in place by the electrode holder, and wherein the electrodes are configured to receive electrical and/or electromagnetic signals from the person's brain; and an electronics unit 3203, wherein the electronics unit further comprises a data processor, a data transmitter and/or data receiver, and a power source. It is assumed that the left side of the device is symmetric to the right side, with the possible exception of the electronics unit, unless stated otherwise.

In this example, a head-worn device for recording brain signals comprises: an electrode-holding ring, headband, halo, or headset which encircles a person's head, wherein the ring, headband, halo, or headset bifurcates and then reconverges on each side (e.g. right and left) of the person's head above the person's right and left ears, respectively; and a posterior-ear prong on each side of the person's head, wherein an ear prong curves around the posterior surface of a person's ear. This electrode-holding ring, headband, halo, or headset loops across the person's forehead as a single band (e.g. band, loop, or segment) and loops over the back of the person's head as a single band (e.g. band, loop, or segment), but bifurcates into two branches (e.g. branches, bands, loops, or segments) and then reconverges as it spans the sides (e.g. right and left) of the person's head. In this example, a lower branch of a bifurcation rests on a person's ear. In an example, bifurcating portions of the ring, headband, halo, or headset can span between 20% and 50% of the circumference of the person's head. In an example, bifurcating portions of the ring, headband, halo, or headset can span between 30% and 70% of the circumference of the person's head. Example variations discussed elsewhere in this disclosure or in priority-linked disclosures can also be applied to this example where relevant.

Figure 33:
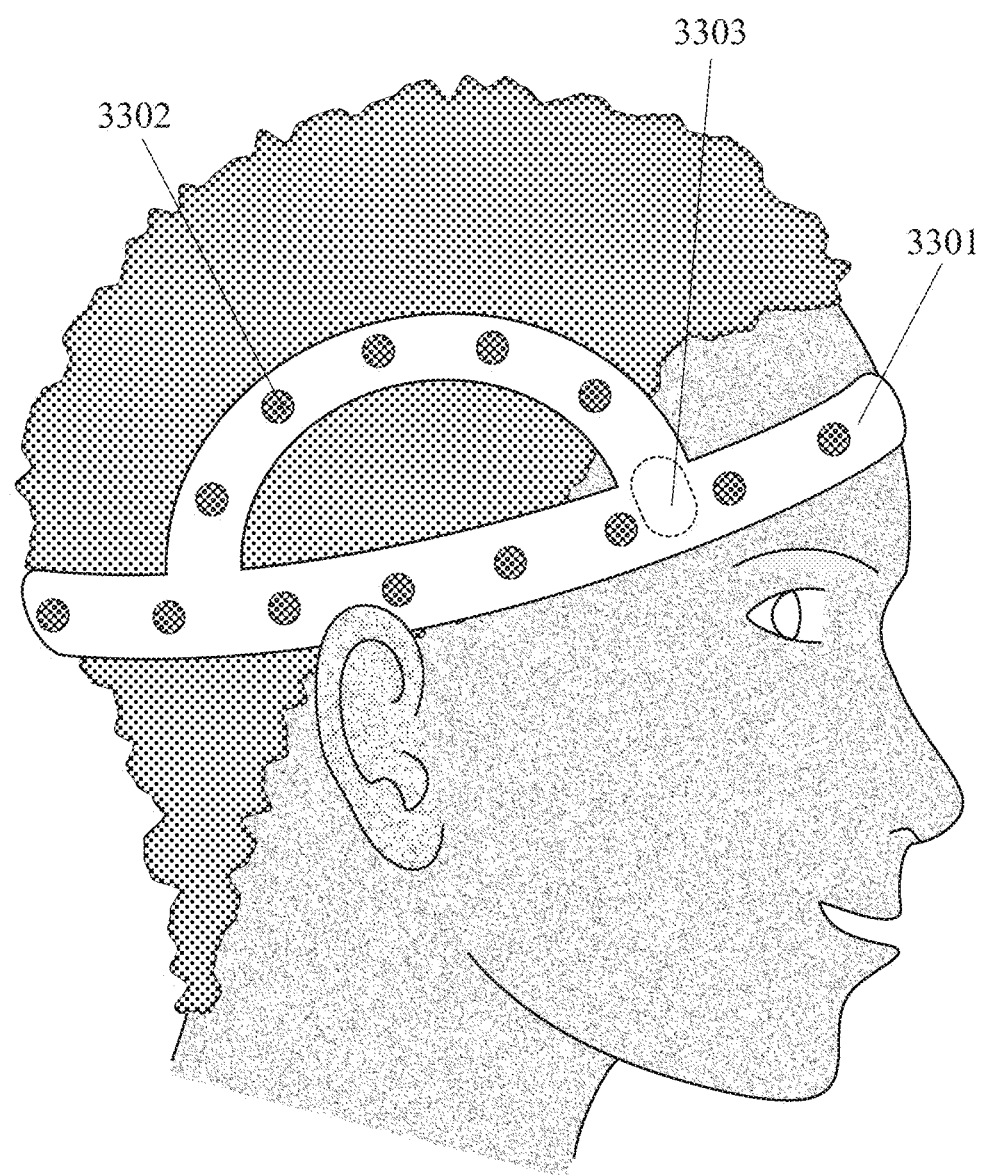
FIG. 33 shows an EEG headband comprising a ring and right and left side concave partial rings which open downward.

FIG. 33 shows the right side of a head-worn device for recording brain signals comprising: an arcuate electrode holder 3301, wherein the electrode holder is a headband, halo, or headset which is configured to be worn around at least 40% of the lateral circumference of a person's head; a plurality of electrodes including electrode 3302, wherein the electrodes are held in place by the electrode holder, and wherein the electrodes are configured to receive electrical and/or electromagnetic signals from the person's brain; and an electronics unit 3303, wherein the electronics unit further comprises a data processor, a data transmitter and/or data receiver, and a power source. It is assumed that the left side of the device is symmetric to the right side, with the possible exception of the electronics unit, unless stated otherwise.

In this example, an electrode-holding ring, headband, halo, or headset completely encircles the lateral circumference of a person's head. In this example, an electrode-holding ring, headband, halo, or headset comprises: a ring which encircles a person's head, wherein an anterior portion of the ring spans across the person's forehead and a posterior portion of the ring portion spans across the back of the person's head; two arcuate concave bands (e.g. bands, arms, branches, loops, or sections), wherein there is an arcuate concave band on each side (e.g. right and left) of the person's head, wherein the concavities of the concave bands open downward, and wherein the concave bands are connected to (e.g. part of or attached to) the ring; a plurality of sensors (e.g. electrodes) which are held on the person's head by the ring and the concave bands; and an electronics unit which includes a data processor, data transmitter, and power source.

In this example, a concave band has a semicircular or semi-elliptical shape. In an example, a concave band can have a different conic section shape. In this example, the concavity of a concave band is above a person's ear. In this example, an anterior portion of a concave band is anterior to a person's ear and a posterior portion of a concave band is posterior to the person's ear. In this example, the peak of a concave band is between 30% and 70% of the way between the top of a person's outer ear (e.g. auricle) and the top of the person's head. In an example, the peak of a concave band can be between 40% and 60% of the way between the top of a person's outer ear (e.g. auricle) and the top of the person's head. In this example, there is one concave band on each side (right and left) of a person's head. In another example, there can be two or more concave bands on each side (right and left) of a person's head. Example variations discussed elsewhere in this disclosure or in priority-linked disclosures can also be applied to this example where relevant.

Figure 34:
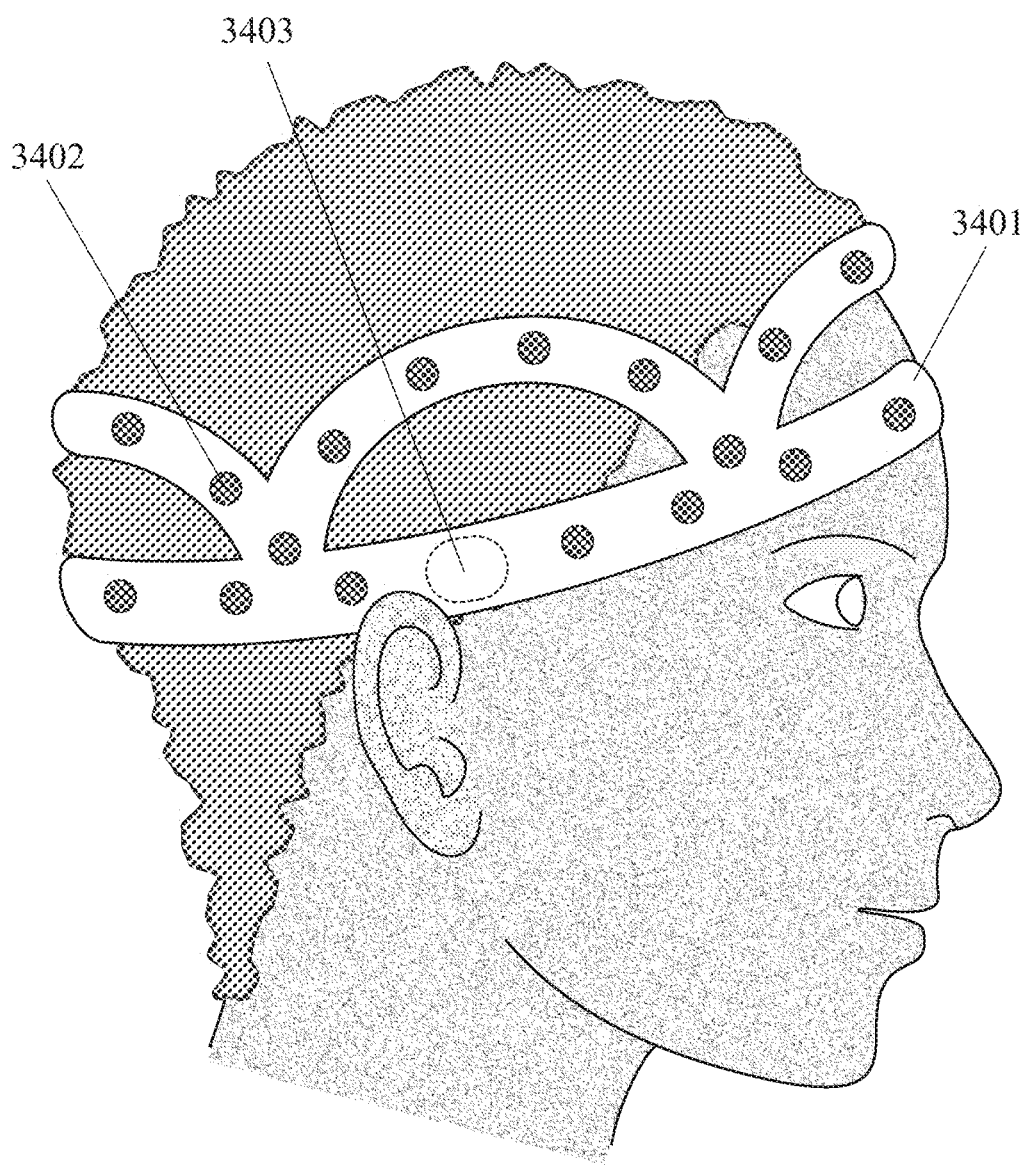
FIG. 34 shows an EEG headband comprising a ring and four concave partial rings which open downward.

FIG. 34 shows the right side of a head-worn device for recording brain signals comprising: an arcuate electrode holder 3401, wherein the electrode holder is a headband, halo, or headset which is configured to be worn around at least 40% of the lateral circumference of a person's head; a plurality of electrodes including electrode 3402, wherein the electrodes are held in place by the electrode holder, and wherein the electrodes are configured to receive electrical and/or electromagnetic signals from the person's brain; and an electronics unit 3403, wherein the electronics unit further comprises a data processor, a data transmitter and/or data receiver, and a power source. It is assumed that the left side of the device is symmetric to the right side, with the possible exception of the electronics unit, unless stated otherwise.

In this example, an electrode-holding ring, crown, headband, halo, or headset completely encircles the lateral circumference of a person's head. In this example, an electrode-holding ring, crown, headband, halo, or headset comprises: a ring which encircles a person's head, wherein an anterior portion of the ring spans across the person's forehead and a posterior portion of the ring portion spans across the back of the person's head; three or more arcuate concave bands (e.g. bands, arms, branches, loops, or sections), wherein the concavities of the concave bands open downward, and wherein the concave bands are connected to (e.g. part of or attached to) the ring; a plurality of sensors (e.g. electrodes) which are held on the person's head by the ring and the concave bands; and an electronics unit which includes a data processor, data transmitter, and power source.

In this example, a concave band has a semicircular or semi-elliptical shape. In an example, a concave band can have a different conic section shape. In this example, the peak of at least one concave band is between 30% and 70% of the way between the top of a person's outer ear (e.g. auricle) and the top of the person's head. In an example, the peak of at least one concave band can be between 40% and 60% of the way between the top of a person's outer ear (e.g. auricle) and the top of the person's head. In this example, there is at least one concave band on each side (right and left) of a person's head. In this example, at least one concave band spans the anterior half of the person's head. In this example, at least one concave band spans the posterior half of the person's head. Example variations discussed elsewhere in this disclosure or in priority-linked disclosures can also be applied to this example where relevant.

Figure 35:
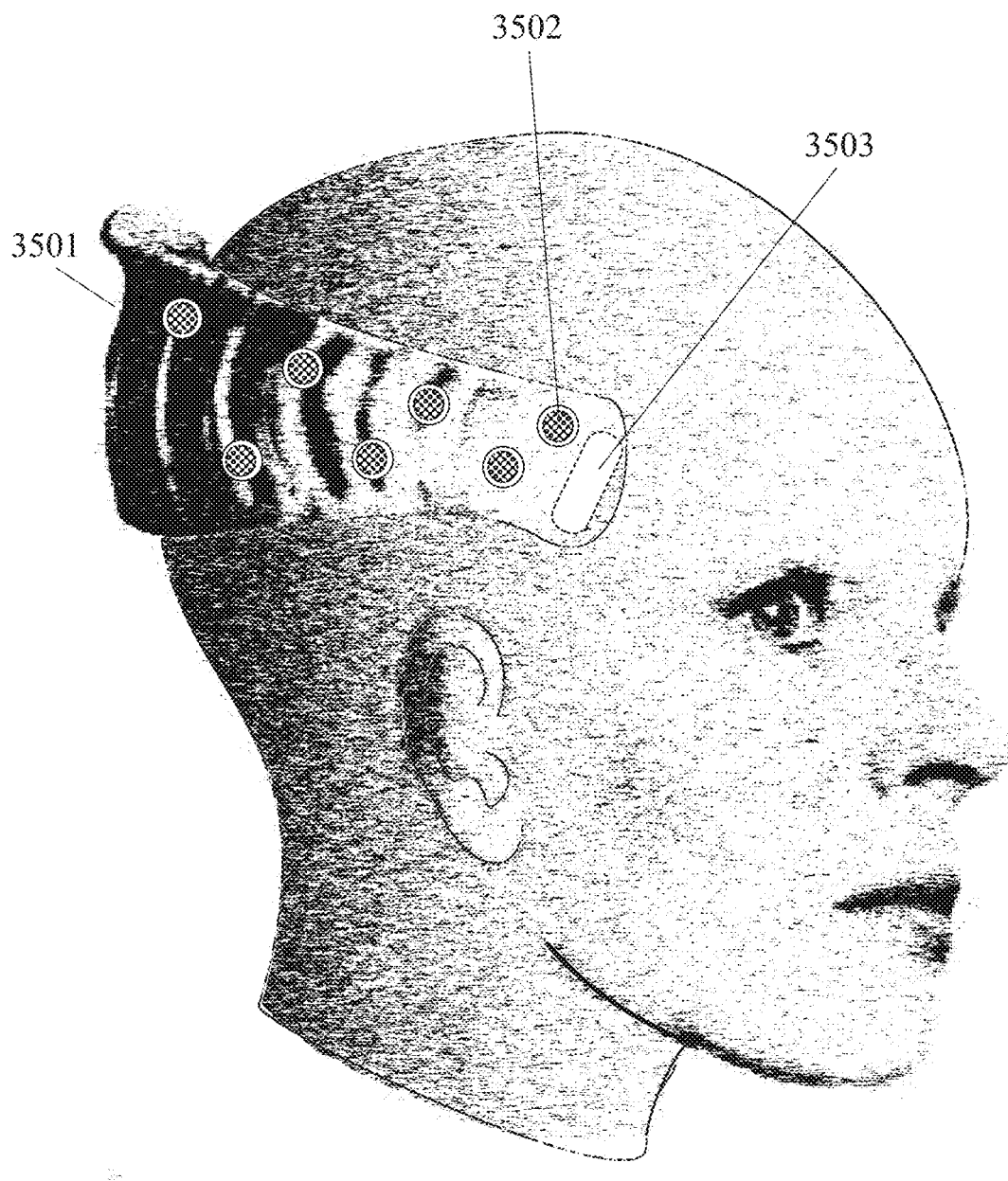
FIG. 35 shows a head-worn EEG device comprising a partial loop which spans the rear half of someone's head.

FIG. 35 shows the right side of a head-worn device for recording brain signals comprising: an arcuate electrode holder 3501, wherein the electrode holder is a headband, halo, or headset which is configured to be worn around at least 40% of the lateral circumference of a sentient being's head; a plurality of electrodes including electrode 3502, wherein the electrodes are held in place by the electrode holder, and wherein the electrodes are configured to receive electrical and/or electromagnetic signals from the sentient being's brain; and an electronics unit 3503, wherein the electronics unit further comprises a data processor, a data transmitter and/or data receiver, and a power source. It is assumed that the left side of the device is symmetric to the right side, with the possible exception of the electronics unit, unless stated otherwise.

In this example, a head-worn device for recording brain signals comprises: a posterior loop which spans the posterior half of a sentient being's head, wherein a posterior portion of the posterior loops is wider and/or thicker than an anterior portion of the posterior loop; a plurality of sensors (e.g. electrodes) which are held on the sentient being's head by the posterior loop; and an electronics unit which includes a data transmitter, a data processor, and a power source. In this example, the device is shown on a sentient being who is bald. In an example, sensors (e.g. electrodes) on the device can further comprise a plurality of protrusions (e.g. teeth, pins, legs, or prongs) to penetrate between strands of hair, just in case the sentient being undergoes a metamorphosis and grows hair to support the plot of the show. In another example, the sentient being may be telepathic, in which case the whole device is rather moot. Example variations discussed elsewhere in this disclosure or in priority-linked disclosures can also be applied to this example where relevant.

I claim:

1. A head-worn device for recording brain signals comprising:
   an arcuate electrode holder, wherein the electrode holder is a headband, halo, or headset;
   wherein the electrode holder is configured to span between 40% and 80% of a circumference of a person's head;

wherein the electrode holder is configured to: start at a location behind an ear; curve upward around the back of the ear; then curve forward to a location on a side of the person's forehead; then curve upward and backward to form an undulation with a posterior-facing concavity; then curve backward to loop around the rear of the person's head; and then continue in a symmetric manner on an opposite side of the person's head, ending at an ear on the opposite side;

a plurality of electrodes, wherein the electrodes are held in place by the electrode holder, and wherein the electrodes are configured to receive electrical and/or electromagnetic signals from the person's brain; and an electronics unit, wherein the electronics unit further comprises a data processor, a data transmitter and/or data receiver, and a power source.

* * * * *